US008129142B2

(12) United States Patent
Mulley et al.

(10) Patent No.: US 8,129,142 B2
(45) Date of Patent: Mar. 6, 2012

(54) MUTATIONS IN ION CHANNELS

(75) Inventors: John Charles Mulley, Firle (AU); Louise Anne Harkin, Northgate (AU); Leanne Michelle Dibbens, College Park (AU); Hilary Anne Phillips, Port Noarlunga (AU); Sarah Elizabeth Heron, Highbury (AU); Samuel Frank Berkovic, Caulfield North (AU); Ingrid Eileen Scheffer, Hawthorn East (AU); Anne Davy, North Adelaide (AU)

(73) Assignee: Bionomics Limited, Thebarton, SA (AU)

( * ) Notice: Subject to any disclaimer, the term of this patent is extended or adjusted under 35 U.S.C. 154(b) by 1031 days.

(21) Appl. No.: 10/567,424

(22) PCT Filed: Aug. 6, 2004

(86) PCT No.: PCT/AU2004/001051
§ 371 (c)(1),
(2), (4) Date: Dec. 9, 2008

(87) PCT Pub. No.: WO2005/014863
PCT Pub. Date: Feb. 17, 2005

(65) Prior Publication Data
US 2009/0081724 A1 Mar. 26, 2009

(30) Foreign Application Priority Data
Aug. 7, 2003 (AU) ................................ 2003904154

(51) Int. Cl.
*C12N 15/12* (2006.01)
*C12N 15/63* (2006.01)
*C12N 5/10* (2006.01)
*C07H 21/00* (2006.01)
*C07K 14/47* (2006.01)

(52) U.S. Cl. ................. 435/69.1; 435/320.1; 435/252.3; 536/23.5; 530/350

(58) Field of Classification Search .................... None
See application file for complete search history.

(56) References Cited

U.S. PATENT DOCUMENTS

| | | | |
|---|---|---|---|
| 4,016,043 | A | 4/1977 | Schuurs et al. |
| 4,172,124 | A | 10/1979 | Koprowski et al. |
| 4,474,893 | A | 10/1984 | Reading |
| 4,971,903 | A | 11/1990 | Hyman |
| 5,331,573 | A | 7/1994 | Balaji et al. |
| 5,579,250 | A | 11/1996 | Balaji et al. |
| 6,331,614 | B1 | 12/2001 | Wong et al. |
| 7,078,515 | B2 | 7/2006 | Wallace et al. |
| 7,282,336 | B2 | 10/2007 | Wallace et al. |
| 7,709,225 | B2 | 5/2010 | Wallace et al. |
| 7,723,027 | B2 | 5/2010 | Petrou et al. |
| 2003/0157525 | A1 | 8/2003 | Mintier et al. |
| 2004/0096886 | A1 | 5/2004 | Rouleau et al. |
| 2004/0110706 | A1 | 6/2004 | Wallace et al. |
| 2004/0214195 | A1 | 10/2004 | Rouleau et al. |
| 2004/0229257 | A1 | 11/2004 | Petrou et al. |
| 2005/0074764 | A1 | 4/2005 | Mulley et al. |
| 2006/0089306 | A1 | 4/2006 | Wallace et al. |
| 2006/0252121 | A1 | 11/2006 | Wallace et al. |
| 2010/0088778 | A1 | 4/2010 | Mulley et al. |

FOREIGN PATENT DOCUMENTS

| | | |
|---|---|---|
| AU | 656247 | 6/1996 |
| WO | WO84/03564 | 9/1984 |
| WO | WO97/02048 | 1/1997 |
| WO | WO 01/38564 | 5/2001 |
| WO | WO01/88125 | 11/2001 |
| WO | WO01/98486 | 12/2001 |
| WO | WO 02/06521 | 1/2002 |
| WO | WO 02/06521 A1 | 1/2002 |
| WO | WO 02/50096 | 6/2002 |
| WO | WO 02/50096 A1 | 6/2002 |
| WO | WO03/008574 | 1/2003 |
| WO | WO 03/008574 A1 | 1/2003 |
| WO | WO 2004/085674 | 10/2004 |
| WO | WO 2004/085674 A | 10/2004 |
| WO | WO 2005/014863 | 2/2005 |

OTHER PUBLICATIONS

Nabbout et al. Jun. 2003 (Neurology 60:1961-1967).*
Breaker et al., "A DNA enzyme with $MG^{2+}$-dependent RNA phosphoesterase activity", *Chemistry & Biology*, 2: 655-660, Oct. 1995.
Cole et al., "Human monoclonal antibodies", *Molecular and Cellular Biochemistry*, 62: 109-120, 1984.
Cote et al., "Generation of human monoclonal antibodies reactive with cellular antigens", *Proceedings of the National Academy of Sciences USA*, 80: 2026-2030, Apr. 1983.
Gamper et al., "Calmodulin mediates $Ca^{2+}$ dependent modulation of M-type $K^+$ channels", *The Journal of General Physiology*, 122: 17-31, Jul. 2003.
Goldman et al., "In vitro and in vivo gene delivery mediated by a synthetic polycationic amino polymer", *Nature Biotechnology*, 15: 462-466, May 1997.
González et al., "Cell-based assays and instrumentation for screening ion-channel targets", *DDT*, 4(9): 431-439, Sep. 1999.
Hamill et al., "Improved patch-clamp techniques for high-resolution current recording from cells and cell-free membrane patches", *European Journal of Physiology*, 391: 85-100, 1981.
Haseloff et al., "Simple RNA enzymes with new and highly specific endoribonuclease activities", *Nature*, 334: 585-591, Aug. 1988.
Heller et al., "Discovery and analysis of inflammatory disease-related genes using cDNA microarrays", *Proceedings of the National Academy of Sciences USA*, 94: 2150-2155, Mar. 1997.

(Continued)

*Primary Examiner* — Daniel E Kolker
(74) *Attorney, Agent, or Firm* — Jenkins, Wilson, Taylor & Hunt, P.A.

(57) ABSTRACT

A method of identifying a subject predisposed to a disorder associated with ion channel dysfunction, comprising ascertaining whether at least one of the genes encoding ion channel subunits in said subject has undergone a mutation event as set forth in one of SEQ ID Numbers: 1-72.

15 Claims, 5 Drawing Sheets

OTHER PUBLICATIONS

Huse et al., "Generation of a large combinatorial library of the immunoglobulin repertoire in phage lambda", *Science*, 246: 1275-1281, Dec. 1989.

Italian League Against Epilepsy Genetic Collaborative Group, "Concordance of clinical forms of epilepsy in families with several affected members", *Epilepsia*, 34(5): 819-826, 1993.

Jentsch Thomas J., "Neuronal KCNQ potassium channels: physiology and role in disease", *Neuroscience*, 1: 21-30, Oct. 2000.

Kasai et al., "Genomic structures of SCN2A and SCN3A- candidate genes for deafness at the DFNA16 locus", *Gene*, 264: 113-122, 2001.

Köhler et al., "Continuous cultures of fused cells secreting antibody of predefined specificity", *Nature*, 256: 495-497, Aug. 1975.

Kozbor et al., "Specific immunoglobulin production and enhanced tumorigenicity following ascites growth of human hybridomas", *Journal of Immunological Methods*, 81: 31-42, 1985.

Ohya et al., "Diverse essential functions revealed by complementing yeast calmodulin mutants", *Science*, 263: 963-966, Feb. 1994.

Orlandi et al., "Cloning immunoglobulin variable domains for expression by the polymerase chain reaction", *Proceedings of the National Academy of Sciences USA*, 86: 3833-3837, May 1989.

Palfi et al., "Differential calmodulin gene expression in the rodent brain", *Life Sciences*, 70: 2829-2855, 2002.

Phillips et al., "CHRNB2 is the second acetylcholine receptor subunit associated with autosomal dominant nocturnal frontal lobe epilepsy", *American Journal of Human Genetics*, 68: 225-231, 2001.

Rickert et al., "B lymphocyte-specific, Cre-mediated mutagenesis in mice", *Nucleic Acids Research*, 25(6): 1317-1318, 1997.

Roger et al., "Epileptic syndromes in infancy, childhood and adolescence", *British Library Cataloguing in Publication Data*, 2: 409-413, 1992.

Scharf et al., "6 heat stress promoters and transcription factors", *Results and Problems in Cell Differentiation*, 20: 125-162, 1994.

Schena et al., "Parallel human genome analysis: microarray-based expression monitoring of 1000 genes", *Proceedings of the National Academy of Sciences USA*, 93: 10614-10619, Oct. 1996.

Schmitt et al., "A recessive C-terminal Jervell and Lange-Nielsen mutation of the KCNQ1 channel impairs subunit assembly", *The EMBO Journal*, 19(3): 332-340, 2000.

Schwake et al., "Surface expression and single channel properties of KCNQ2/KCNQ3, M-type $K^+$ channels involved in epilepsy", *The Journal of Biological Chemistry*, 275(18):13343-13348, 2000.

Schwenk et al., "A cre-transgenic mouse strain for the ubiquitous deletion of loxP-flanked gene segments including deletion in germ cells", *Nucleic Acids Research*, 23(24): 5080-5081, 1995.

Toutenhoofd et al., "The calmodulin multigene family as a unique case of genetic redundancy: multiple levels of regulation to provide spatial and temporal control of calmodulin pools?", *Cell Calcium*, 28(2): 83-96, 2000.

Wallace et al., "Neuronal sodium-channel α1-subunit mutations in generalized epilepsy with febrile seizures plus", *American Journal of Human Genetics*, 68: 859-865, 2001.

Wen et al., "Calmodulin is an auxiliary subunit of KCNQ2/3 potassium channels", *The Journal of Neuroscience*, 22(18): 7991-8001, Sep. 2002.

Winter et al., "Man-made antibodies", *Nature*, 349: 293-299, Jan. 1991.

Wyman et al., "A highly polymorphic locus in human DNA", *Proceedings of the National Academy of Sciences USA*, 77(11): 6754-6758, Nov. 1980.

Yus-Néjera et al., "The identification and characterization of a noncontinuous calmodulin-binding site in noninactivating voltage-dependent KCNQ potassium channels", *The Journal of Biological Chemistry*, 277(32): 28545-28553, 2002.

International Preliminary Report on Patentability, corresponding to PCT application No. PCT/AU2004/00151 dated Feb. 23, 2006.

Abou-Khalil et al. Partial and generalized epilepsy with febrile seizures plus and a novel SCN1A mutation. Neurology, vol. 57, (2001), pp. 2265-2272.

Claes et al. De Novo SCN1A mutations are a major cause of severe myoclonic epilepsy of infancy. Human Mutation, vol. 21, (2003), pp. 615-621.

Escayg et al. A novel SCN1A mutation associated with generalized epilepsy with febrile seizures plus—and prevalence of variants in patients with epilepsy. American Journal of Human Genetics, vol. 68, (2001), pp. 866-873.

Lu et al. Isolation of a human-brain sodium-channel gene encoding two isoforms of the subtype III α-subunit. Journal of Molecular Neuroscience, vol. 10, (1998), pp. 67-70.

Noda et al. Existence of distinct sodium channel messenger RNAs in rat brain. Nature, vol. 320, (1986), pp. 188-192.

Supplementary European Search Report corresponding to an EP application No. EP 04761088 dated May 18, 2007.

Abstracts of Decisions. Decision of a Delegate of the Commissioner of Patents corresponding to an Australian Patent Application No. 18465/01 issued Jan. 29, 2007.

Alekov et al., "A sodium channel mutation causing epilepsy in man exhibits subtle defects in fast inactivation and activation in vitro," Journal of Physiology, vol. 529, No. 3, pp. 533-539 (2000).

Andermann, "Multifactorial Inheritance of Generalized and Focal Epilepsy," Genetic Basis of the Epilepsies, pp. 355-374 (1982).

Annegers, "The Epidemiology of Epilepsy," The Treatment of Epilepsy: Principles and Practice, Chpt. 11, pp. 165-172 (1996).

Baulac et al., "A Second Locus for Familial Generalized Epilepsy with Febrile Seizures Plus Maps to Chromosome 2q21-q33," Am. J. Hum. Genet., vol. 65, pp. 1078-1085 (1999).

Bell and Lathrop, "Multiple loci for multiple sclerosis," Nature Genetics, vol. 13, pp. 377-378 (Aug. 1996).

Bendahhou et al., "Activation and Inactivation of the Voltage-Gated Sodium Channel: Role of Segment S5 Revealed by a Novel Hyperkalaemic Periodic Paralysis Mutation," J. Neurosci., vol. 19, pp. 4762-4771 (1999).

Berkovic et al., "Concepts of absence epilepsies: Discrete syndromes or biological continuum?" Neurology, vol. 37, No. 6, pp. 993-1000 (Jun. 1987).

Berkovic et al., "Familial Epilepsies in Israel: Clinical Syndromes and Modes of Inheritance," Neurology, vol. 54, Suppl. 3, A356, No. P05.063 (Apr. 2000).

Berkovic et al., "The epilepsies: specific syndromes or a neurobiological continuum?" Epileptic Seizures and Syndromes, Chpt. 5, pp. 25-37 (1994).

Bertrand et al., "Properties of neuronal nicotinic acetylcholine receptor mutants from humans suffering from autosomal dominant nocturnal frontal lobe epilepsy," British J. of Pharmacology, vol. 124, pp. 1-10 (1998).

Bievert et al., "A Potassium Channel Mutation in Neonatal Human Epilepsy," Science, vol. 279, pp. 403-406 (Jan. 16, 1998).

Bourgeois, "Chronic Management of Seizures in the Syndromes of Idiopathic Generalized Epilepsy," Epilepsia, 44 (Suppl. 2), pp. 27-32 (2003).

Cannon, "Sodium Channel Gating: No Margin for Error," Neuron, vol. 34, pp. 853-858 (Jun. 13, 2002).

Cavazzuti et al., "Longitudinal Study of Epileptiform EEG Patterns in Normal Children," Epilepsia, vol. 21, pp. 43-55 (1980).

Charlier et al., "A pore mutation in a novel KQT-like potassium channel gene in an idiopathic epilepsy family," Nature Genetics, vol. 18, pp. 53-55 (Jan. 1998).

Chou et al., "The lack of association between febrile convulsions and polymorphisms in SCN1A," Epilepsy Research, vol. 54, pp. 53-57 (2003).

Claes et al., "De Novo Mutations in the Sodium-Channel Gene SCN1A Cause Severe Myoclonic Epilepsy of Infancy," American Journal of Human Genetics, vol. 68, pp. 1327-1332 (2001).

Collins, "Positional cloning moves from perditional to traditional," Nature Genetics, vol. 9, pp. 347-349 (Apr. 1995).

Commission on Classification and Terminology of the International League Against Epilepsy, "Proposal for Revised Classification of Epilepsies and Epileptic Syndromes," Epilepsia, vol. 30, No. 4, pp. 389-399 (1989).

Communication pursuant to Rule 46(1) EPC corresponding to European Application No. 04718885.9-2402 PCT/AU2004000295 dated Jul. 14, 2006.

Database UniProt, "Sodium channel protein type I alpha subunit," XP002313393, retrieved from EBI accession No. UNIPROT: CIN1_HUMAN, Database accession No. P35498. (Abstract).

DePalma, A., "Capturing Proteins Using Antibody Arrays," from Genomics and Proteomics; available online from author at www.adeplama.com, pp. 1-5.

Doose and Baier, "Genetic Aspects of Childhood Epilepsy," Cleveland Clinic Journal of Medicine, vol. 56, Suppl. Part 1, S101-S110 (1989).

Doose and Baier, "Genetic Factors in Epilepsies with Primarily Generalized Minor Seizures," Neuropediatrics, vol. 18, Suppl. I, pp. 1-64 (Feb. 1987).

Dworakowska and Dolowy, "Ion channels-related diseases," ACTA Biochimica Polonica, vol. 47, No. 3, pp. 685-703 (2000).

Escayg et al., "Mutations of SCN1A, encoding a neuronal sodium channel, in two families with GEFS+2," Nature Genetics, vol. 24, pp. 343-345 (Apr. 2000).

European Patent Office Search Report corresponding to European Patent Application No. 07075566.5-2401 dated Oct. 4, 2007.

Examiner's First Report for Australian Patent Application No. 2004200978 dated May 6, 2004.

Finkelstein et al., "Use of denaturing gradient gel electrophoresis for detection of mutation and prospective diagnosis in late onset ornithine transcarbamylase deficiency," Genomics, vol. 7, pp. 167-172 (1990).

Fong et al., "Childhood Absence Epilepsy with Tonic-Clonic Seizures and Electroencephalogram 3-4-Hz Spike and Multispike—Slow Wave Complexes: Linkage to Chromosome 8q24," Am. J. Hum. Genet., vol. 63, pp. 1117-1129 (1998).

Fujiwara et al., "Long-Term Course of Childhood Epilepsy with Intractable Grand Mal Seizures," Jpn. J. Psychiatry Neurol., vol. 46, pp. 297-302 (1992).

Fukuma G., "Mutations of neuronal voltage-gated Na+ channel alpha 1 subunit gene SCN1A in core severe myoclonic epilepsy in infancy (SMEI) and in borderline SMEI (SMEB)," Epilepsia, vol. 45, No. 2, pp. 140-148 (Feb. 2004).

Gardiner, "Impact of our understanding of the genetic aetiology of epilepsy," J. Neurol., vol. 247, pp. 327-334 (2000).

Genbank accession No. AB093548, Oct. 16, 2002.

Genbank accession No. M22253, Oct. 26, 1995.

Genbank accession No. NM_012647, Mar. 21, 2010.

Genbank Accession No. NM_172107, Aug. 5, 2010.

GenBank Locus AF225985, "*Homo sapiens* voltage-gated sodium channel alpha subunit SCN1A (SCN1A) mRNA, complete cds," pp. 1-4 (Feb. 1, 2001).

GenBank Locus NM_006920, "*Homo sapiens* sodium channel, voltage-gated, type I, alpha (SCN1A), mRNA," pp. 1-11 (Nov. 13, 2006).

Gene Card for SCNA1 available via uri: <genecards.org/cgi-bin/carddisp.pl?gene=SCN1A>, Nov. 16, 2006.

GeneCards output for protein-coding SCN1A, available online from www.genecards.org, pp. 1-20, Jul. 23, 2007.

Gennaro et al., "Familial severe myoclonic epilepsy of infancy: truncation of Na$_v$1.1 and genetic heterogeneity," Epileptic Disord., vol. 5, pp. 21-25 (2003).

Geysen H.M. et al., "Cognitive features of continuous antigenic determinants," Journal of Molecular Recognition, vol. 1, pp. 32-41 (1988).

Goldsby et al., "Immunology," Fifth Edition, section "Cross-Reactivity," p. 141 (2003).

Greenberg et al., "Evidence for multiple gene loci in the expression of the common generalized epilepsies," Neurology, vol. 42, Suppl. 5, pp. 56-62 (Apr. 1992).

Greenberg et al., "Juvenile Myoclonic Epilepsy (JME) May be Linked to the BF and HLA Loci on Human Chromosome 6," Am. J. of Medical Genetics, vol. 31, pp. 185-192 (1988).

Greenberg et al., "Segregation Analysis of Juvenile Myoclonic Epilepsy," Genetic Epidemiology, vol. 5, pp. 81-94 (1988).

Guerrini et al., Lamotrigine and seizure aggravation in severe myoclonic epilepsy, Epilepsia, vol. 39s, pp. 508-512 (1998).

Harkin et al., "The Spectrum of SCN1A-Related Infantile Epileptic Encephalopathies," Brain, vol. 130, pp. 843-852 (2007).

Hauser et al., "Incidence of Epilepsy and Unprovoked Seizures in Rochester, Minnesota: 1935-1984," Epilepsia, vol. 34, No. 3, pp. 453-468 (1993).

Hille, "Ionic Channels of Exciteable Membranes," $2^{nd}$ Edition, pp. 423 and 434-444 (1992).

Hirschhorn et al., "A comprehensive review of genetic association studies," Genetics in Medicine, vol. 4, No. 2, pp. 45-61 (2002).

International Search Report for International Application No. PCT/AU2004/000295 dated May 14, 2004.

Interview Summary corresponding to U.S. Appl. No. 11/262,647 dated Dec. 5, 2008.

Interview Summary corresponding to U.S. Appl. No. 10/806,899 dated Nov. 23, 2009.

Interview Summary corresponding to U.S. Appl. No. 10/806,899 dated Oct. 8, 2009.

Interview Summary corresponding to U.S. Appl. No. 10/806,899 dated Nov. 1, 2007.

Janz et al., "Do idiopathic generalized epilepsies share a common susceptibility gene?" Neurology, vol. 42, Suppl 5, pp. 48-55 (Apr. 1992).

Kanai et al., "Effect of localization of missense mutations in SCN1A on epilepsy phenotype severity," Neurology, vol. 63, pp. 329-334 (2004).

Kimura K., "A missense mutation in SCN1A in brothers with severe myoclonic epilepsy in infancy (SMEI) inherited from a father with febrile seizures," Brain Dev., vol. 27, No. 6, pp. 424-430 (Sep. 2005).

Kinzler et al., "Identification of a gene located at chromosome 5q21 that is mutated in colorectal cancers," Science, vol. 251, pp. 1366-1370 (1991).

Kuhn et al., "Movement of voltage sensor S4 in domain 4 is tightly coupled to sodium channel fast inactivation and gating charge immobilization," J. Gen. Physiol., vol. 114, pp. 167-183 (1999).

Lason W., "Neurochemical and pharmacological aspects of cocaine-induced seizures," Polish Journal of Pharmacology, vol. 53, pp. 57-60 (2001).

Lerche et al., "Ion Channels and Epilepsy," Am. J. of Med. Genetics, vol. 106, pp. 146-159 (2001).

Lernmark and Ott, "Sometimes it's hot, sometimes it's not," Nature Genetics, vol. 19, pp. 213-214 (Jul. 1998).

Lo et al., "High Level Expression and Secretion of Fc-X Fusion Proteins in Mammalian Cells," Protein Engineering, vol. 11, pp. 495-500 (1998).

Lopes-Cendes et al., "A New Locus for Generalized Epilepsy with Febrile Seizures Plus Maps to Chromosome 2," Am. J. Hum. Genet., vol. 66, pp. 698-701 (2000).

Lucentini, J., "Gene Asscoiation Studies Typically Wrong," The Scientist, p. 20 (Dec. 20, 2004).

Madia et al., "No evidence of GABRG2 mutations in severe myoclonic epilepsy of infancy," Epilepsy Research, vol. 53, pp. 196-200 (2003).

Malacarne et al., "Lack of SCN1A Mutations in Familial Febrile Seizures," Epelepsia, vol. 43, No. 5, pp. 559-562 (2002).

Maxam et al., "A new method for sequencing DNA," Proceedings of the National Academy of Sciences of the USA, vol. 74, No. 2, pp. 560-564 (1977).

Mazumder et al., "Translations control by the 3'•UTR: the ends specify the means," Trends in Biochemical Sciences, vol. 28, pp. 91-98 (2004).

Modrich, Paul, "Mechanisms and biological effects of mismatch repair," Annual Review of Genetics, vol. 25, pp. 229-253 (1991).

Moran et al., "Skeletal Muscle Sodium Channel Is Affected by an Epileptogenic β1 Subunit Mutation," Biochem. Biophys. Res. Comm., vol. 282, pp. 55-59 (2001).

Moulard et al., "Identification of a New Locus for Generalized Epilepsy with Febrile Seizures Plus (GEFS+) on Chromosome 2q24-q33," Am. J. Hum. Genet., vol. 65, pp. 1396-1400 (1999).

Mulley et al., "SCN1A Mutations and Epilepsy," Human Mutation, vol. 25, pp. 535-542 (2005).

Mulley et al., "Channelopathies as a Genetic Cause of Epilepsy," Current Opinion in Neurology, vol. 16, pp. 171-176 (2003).

Notice of Allowance corresponding to U.S. Appl. No. 10/451,126 (Patent No. 7,078,515) dated Aug. 30, 2005.

Notice of Allowance corresponding to U.S. Appl. No. 11/263,326 (Patent No. 7,282,336) dated Jun. 18, 2007.

Notice of Allowance corresponding to U.S. Appl. No. 11/262,647 dated Dec. 18, 2009.

Notice of Allowance corresponding to U.S. Appl. No. 10/806,899 dated Jan. 4, 2010.

Notification Concerning Transmittal of International Preliminary Report on Patentability for International Application No. PCT/AU2006/000841 dated Jan. 3, 2008.
Official Communication of U.S. Patent and Trademark Office corresponding to U.S. Appl. No. 10/482,834 dated Aug. 7, 2009.
Official Communication of U.S. Patent and Trademark Office corresponding to U.S. Appl. No. 10/482,834 dated Dec. 30, 2008.
Official Communication of U.S. Patent and Trademark Office corresponding to U.S. Appl. No. 10/482,834 dated Apr. 4, 2008.
Official Communication of U.S. Patent and Trademark Office corresponding to U.S. Appl. No. 10/482,834 dated Aug. 2, 2007.
Official Communication of U.S. Patent and Trademark Office corresponding to U.S. Appl. No. 10/806,899 dated Oct. 28, 2009.
Official Communication of U.S. Patent and Trademark Office corresponding to U.S. Appl. No. 10/806,899 dated May 13, 2009.
Official Communication of U.S. Patent and Trademark Office corresponding to U.S. Appl. No. 10/806,899 dated Aug. 19, 2008.
Official Communication of U.S. Patent and Trademark Office corresponding to U.S. Appl. No. 10/806,899 dated Jun. 26, 2007.
Official Communication of U.S. Patent and Trademark Office corresponding to U.S. Appl. No. 10/806,899 dated Nov. 29, 2006.
Official Communication of U.S. Patent and Trademark Office corresponding to U.S. Appl. No. 11/263,326 (Patent No. 7,282,336) dated Oct. 6, 2006.
Official Communication of U.S. Patent and Trademark Office corresponding to U.S. Appl. No. 11/262,647 dated Apr. 22, 2009.
Official Communication of U.S. Patent and Trademark Office corresponding to U.S. Appl. No. 11/262,647 dated Dec. 5, 2008.
Official Communication of U.S. Patent and Trademark Office corresponding to U.S. Appl. No. 11/262,647 dated Feb. 15, 2008.
Official Communication of U.S. Patent and Trademark Office corresponding to U.S. Appl. No. 10/451,126 (Patent No. 7,078,515) dated Jan. 24, 2005.
Ohmori et al., "Significant correlation of the SCN1A mutations and severe myoclonic epilepsy in infancy," Biochemical and Biophysical Research Communications, vol. 295, pp. 17-23 (2002).
Ohtahara et al., "Lennox-Gastaut syndrome: a new vista," Psychiatry Clin. Neurosci., vol. 49, pp. S179-S183 (1995).
Ohtsuka et al., "Long-term prognosis of the Lennox-Gastaut syndrome," Jpn. J. Psychiatry Neurol., vol. 44, pp. 257-264 (1990).
Ohtsuka et al., "Refractory Childhood Epilepsy and Factors Related to Refractoriness," Epilepsia, vol. 41, Suppl. 9, pp. 14-17 (2000).
Okubo et al., "Epileptiform EEG Discharges in Healthy Children: Prevalence, Emotional and Behavioral Correlates, and Genetic Influences," Epilepsia, vol. 35, No. 4, pp. 832-841 (1994).
Orita et al., "Detection of polymorphisms of human DNA by gel electrophoresis as single-strand confirmation polymorphisms," Proceedings of the National Academy of Sciences of the USA, vol. 86, pp. 2766-2770 (1989).
Panayiotopoulos and Obeid, "Juvenile Myoclonic Epilepsy: An Autosomal Recessive Disease," Ann Neurol, vol. 25, pp. 440-443 (1989).
Peiffer et al., "A Locus for Febrile Seizures (FEB3) Maps to Chromosome 2q23-24," Annals of Neurology, vol. 46, No. 4, pp. 671-678 (Oct. 1999).
Phillips et al., "Autosomal Dominant Nocturnal Frontal-Lobe Epilepsy: Genetic Heterogeneity and Evidence for a Second Locus at 15q24," Am. J. Hum. Genet., vol. 63, pp. 1108-1116 (1998).
Phillips et al., "Localization of a gene for autosomal dominant nocturnal frontal lobe epilepsy to chromosome 20q13.2," Nature Genetics, vol. 10, pp. 117-118 (May 1995).
Plummer et al., "Evolution and Diversity of Mammalian Sodium Channel Genes," Genomics, vol. 57, pp. 323-331 (1999).
Plummer et al.,"Exon Organization, Coding Sequence, Physical Mapping, and Polymorphic Intragenic Markers for the Human Neuronal Sodium Channel Gene SCN8A," Genomics, vol. 54, pp. 287-296 (1998).
Reutens and Berkovic, "Idiopathic generalized epilepsy of adolescence: Are the syndromes clinically distinct?" Neurology, vol. 45, pp. 1469-1476 (Aug. 1995).
Risch and Botstein, "A manic depressive history," Nature Genetics, vol. 12, pp. 351-353 (Apr. 1996).

Sanger et al., "DNA sequencing with chain-terminating inhibitors," Proceedings of the National Academy of Sciences of the USA, vol. 74, No. 12, pp. 5463-5467 (1977).
Scheffer and Berkovic, "Generalized epilepsy with febrile seizures plus A genetic disorder with heterogeneous clinical phenotypes," Brain, vol. 120, pp. 479-490 (1997).
Scheffer et al., "Locus for Febrile Seizures," Annals of Neurology, vol. 47, No. 6, pp. 840-841 (Jun. 2000).
Scheffer et al., "The Genetics of Human Epilepsy," TRENDS in Pharmacological Science, vol. 24, No. 8, pp. 428-433 (Aug. 2003).
Sheffield et al., "Attachment of a 40-base-pair G+C-rich sequence (GC-clamp) to genomic DNA fragments by the polymerase chain reaction results," Proceedings of the National Academy of Sciences of the USA, vol. 86, pp. 232-236 (1989).
Singh et al., "A novel potassium channel gene, KCNQ2, is mutated in an inherited epilepsy of newborns," Nature Genetics, vol. 18, pp. 25-29 (Jan. 1998).
Singh et al., "Generalized Epilepsy with Febrile Seizures Plus: a Common Childhood-Onset Onset Genetic Epilepsy Syndrome," Ann. Neurol., vol. 45, pp. 75-81 (1999).
Singh et al., "Severe Myoclonic Epilepsy of Infancy: Extended Spectrum of GEFS?" Epilepsia, vol. 42, No. 7, pp. 837-844 (2001).
Spampanato et al., "Generalized Epilepsy with Febrile Seizures Plus Type 2 Mutation W1204R Alters voltage-Dependent Gating of $Na_v1.1$ Sodium Channels," Neuroscience, vol. 116, pp. 37-48 (2003).
Stafstrom et al., "Epilepsy Genes: The link between molecular dysfunction and pathophysiology", Mental Retardation and Developmental Disabilities Research Reviews, vol. 6, pp. 281-292 (2000).
Steinlein et al., "A missense mutation in the neuronal nicotinic acetylcholine receptor $\alpha 4$ subunit is associated with autosomal dominant nocturnal frontal lobe epilepsy," Nature Genetics, vol. 11, pp. 201-203 (Oct. 1995).
Sugawara et al., "Frequent mutations of SCN1A in severe myoclonic epilepsy in infancy," Neurology, vol. 58, pp. 1122-1124 (2002).
Sugawara, T., "Nav1.1 channels with mutations of severe myoclonic epilepsy in infancy display attenuated currents," Epilepsy Res., vol. 54, Nos. 2-3, pp. 201-207 (May 2003).
Supplementary European Search Report corresponding to Australian Patent No. AU0200910 dated Feb. 17, 2005.
Supplementary Partial European Search Report for Application No. 01271383.0-2406 dated Mar. 12, 2004.
Taylor et al., "Enzymatic methods for mutation scanning," Genetic Analysis: Biomolecular Engineering, vol. 14, pp. 181-186 (1999).
Thisted, "What is a P-value?" available online from www.stat.uchicago.edu, pp. 1-6 (May 25, 1998).
Todd, "Interpretation of results from genetic studies of multifactorial disease," Molecular Medicine, vol. 354, pp. 15-16 (Jul. 1999).
Veggiotti et al., "Generalized Epilepsy with Febrile Seizures plus and Severe Myoclonic Epilepsy in Infancy: a case report of two Italian families," Epileptic Discord, vol. 3, pp. 29-32 (2001).
Wallace et al., "Febrile seizures and generalized epilepsy associated with a mutation in the $Na^+$-channel $\beta 1$ subunit gene SCN1B," Nature Genetics, vol. 19, pp. 366-370 (Aug. 1998).
Wallace et al., "Mutant $GABA_A$ receptor $\gamma 2$-subunit in childhood absence epilepsy and febrile seizures," Nature Genetics, vol. 28, pp. 49-52 (May 2001).
Wallace et al., "Sodium Channel E L-Subunit Mutations in Severe Myoclonic Epilepsy of Infancy and Infantile Spasms," Neurology, vol. 61, pp. 765-769 (Sep. 2003).
Wallace R., "A Plethora of SCN1A Mutations: What Can They Tell Us?" Epilepsy Curro., vol. 5, No. 1, pp. 17-20 (Jan. 2005).
Wartell et al., "Detecting base pair substitutions in DNA fragments by temperature-gradient gel electrophoresis," Nucleic Acids Research, vol. 18, No. 9, pp. 2699-2705 (1990).
Zara et al., "Mapping of genes predisposing to idiopathic generalized epilepsy," Human Molecular Genetics, vol. 4, No. 7, pp. 1201-1207 (1995).
Zara et al., "Mapping of Locus for a Familial Autosomal Recessive Idiopathic Myoclonic Epilepsy of Infancy to Chromosome 16p13," Am. J. Hum. Genet., vol. 66, pp. 1552-1557.

Fujiwara, T. et al., Mutations of sodium channel α submit type 1 (SCN1A) in intractable childhood epilepsies with frequent generalized tonic-clonic seizures, Brain (2003), 126: 531-546.

Nabbout, R. et al., Spectrum of SCN1A mutations in severe myoclonic epilepsy of infancy, Neurology, Jun. (2 of 2) 2003, 60:1961-1967.

International Preliminary Report for Patentability and Written Opinion corresponding PCT Appl. No. PCT/AU2004/001051 dated Aug. 6, 2004.Apr. 25, 2006.

* cited by examiner

SEQUENCE LISTING

```
<160> NUMBER OF SEQ ID NOS: 97

<210> SEQ ID NO 1
<211> LENGTH: 8381
<212> TYPE: DNA
<213> ORGANISM: Homo sapiens

<400> SEQUENCE: 1
atactgcaga ggtctctggt gcatgtgtgt atgtgtgcgt ttgtgtgtgt ttgtgtgtct      60
gtgtgttctg ccccagtgag actgcagccc ttgtaaatac tttgacacct tttgcaagaa     120
ggaatctgaa caattgcaac tgaaggcaca ttgttatcat ctcgtctttg ggtgatgctg     180
```

```
ttcctcactg cagatggata attttccttt taatcaggaa tttcatatgc agaataaatg    240
gtaattaaaa tgtgcaggat gacaagatgg agcaaacagt gcttgtacca ccaggacctg    300
acagcttcaa cttcttcacc agagaatctc ttgcggctat tgaaagacgc attgcagaag    360
aaaaggcaaa gaatcccaaa ccagacaaaa agatgacgac gaaaatggcc caaagccaa     420 atagtgactt ggaagctgga agaaccttca catttattta tggagacatt cctccagaga    480
tggtgtcaga gccctggag gacctggacc cctactatat caataagaaa acttttatag    540
tattgaataa attgaaggcc atcttccggt tcagtgccac ctctgccctg tacattttaa    600
ctcccttcaa tcctcttagg aaaatagcta ttaagatttt ggtacattca ttattcagca    660
tgctaattat gtgcactatt ttgacaaact gtgtgtttat gacaatgagt aaccctcctg    720
attggacaaa gaatgtagaa tacaccttca caggaatata actttttgaa tcacttataa    780
aaattattgc aagggattct tgtttagaag attttacttt ccttcgggat ccatggaact    840
ggctcgattt cactgtcatt acatttgcgt acgtcacaga gtttgtggac ctgggcaatg    900
tctcggcatt gagaacattc agagttctct gagcattgaa gacgatttca gtcattccag    960
gcctgaaaac cattgtggga gccctgatcc agtctgtgaa gaagctctca gatgtaatga   1020
tcctgactgt gttctgtctg agcgtatttg ctctaattgg gctgcagctg ttcatgggca   1080
acctgaggaa taaatgtata caatggcctc ccaccaatgc ttccttggag gaacatagta   1140
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gtttcgacta atgactcagg acttctggga aaatctttat caactgacat   1440
tacgtgctgc tggaaaaacg tacatgatat ttttttgtat tggtcattttc ttgggctcat   1500 tctacctaat aaatttgatc ctggctgtgg tggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga aatcggagga agaaaagaaa acagaaagag cagtctggtg   1800
gggaagagaa agatgaggat gaattccaaa aatctgaatc tgaggacagc atcaggagaa   1860
aaggttttcg cttctccatt gaagggaacc gattgacata tgaaaagagg tactcctccc   1920
cacaccagtc tttgttgagc atccgtggct ccctattttc accaaggcga aatagcagaa   1980 caagccttt cagctttaga gggcgagcaa aggatgtggg atctgagaac gacttcgcag   2040
atgatgagca cagcaccttt gaggataacg agagccgtag agattccttg tttgtgcccc   2100
gacgacacgg agagagacgc aacagcaacc tgagtcagac cagtaggtca tcccggatgc   2160
tggcagtgtt tccagcgaat gggaagatgc acagcactgt ggattgcaat ggtgtggttt   2220
ccttggttgg tggaccttca gttcctacat cgcctgttgg acagcttctg ccagaggtga   2280
taatagataa gccagctact gatgacaatg gaacaaccac tgaaactgaa atgagaaaga   2340
gaaggtcaag ttcttttccac gtttccatgg actttctaga gatccttcc caaaggcaac   2400 gagcaatgag tatagccagc attctaacaa atacagtaga agaacttgaa gaatccaggc   2460
agaaatgccc accctgttgg tataaatttt ccaacatatt cttaatctgg gactgttctc   2520
catattggtt aaaagtgaaa catgttgtca acctggttgt gatggaccca tttgttgacc   2580
```

```
tggccatcac catctgtatt gtcttaaata ctcttttcat ggccatggag cactatccaa    2640
tgacggacca tttcaataat gtgcttacag taggaaactt ggttttcact gggatcttta    2700
cagcagaaat gtttctgaaa attattgcca tggatcctta ctattatttc caagaaggct    2760
ggaatatctt tgacggtttt attgtgacgc ttagcctggt agaacttgga ctcgccaatg    2820
tggaaggatt atctgttctc cgttcatttc gattgctgcg agttttcaag ttggcaaaat    2880
cttggccaac gttaaatatg ctaataaaga tcatcggcaa ttccgtgggg gctctgggaa    2940
atttaaccct cgtcttggcc atcatcgtct tcattttgc cgtggtcggc atgcagctct    3000
ttggtaaaag ctacaaagat tgtgtctgca agatcgccag tgattgtcaa ctcccacgct    3060
ggcacatgaa tgacttcttc cactccttcc tgattgtgtt ccgcgtgctg tgtggggagt    3120
ggatagagac catgtgggac tgtatggagg ttgctggtca agccatgtgc cttactgtct    3180
tcatgatggt catggtgatt ggaaacctag tggtcctgaa tctcttttctg gccttgcttc    3240
tgagctcatt tagtgcagac aaccttgcag ccactgatga tgataatgaa atgaataatc    3300
tccaaattgc tgtggatagg atgcacaaag gagtagctta tgtgaaaaga aaaatatatg    3360
aatttattca acagtccttc attaggaaac aaaagatttt agatgaaatt aaaccacttg    3420
atgatctaaa caacaagaaa gacagttgta tgtccaatca tacaacagaa attgggaaag    3480
atcttgacta tcttaaagat gtaaatgaaa ctacaagtgg tataggaact ggcagcagtg    3540
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca agagaaact gaatgaaagc agtagctcat    3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa acaatggtg gaacctgaga aggacgtgtt    3900
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca tttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agccttatct cgatttgaag    4260
ggatgagggt ggttgtgaat gcccctttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctataccctcg accaggaaac aaatttcaag    4860
gaatggtctt tgacttcgta accagacaag ttttgacat aagcatcatg attctcatct    4920
gtcttaacat ggtcacaatg atggtggaaa cagatgacca gagtgaatat gtgactacca    4980
```

-continued

```
ttttgtcacg catcaatctg gtgttcattg tgctatttac tggagagtgt gtactgaaac   5040
tcatctctct acgccattat tattttacca ttggatggaa tattttttgat tttgtggttg   5100
tcattctctc cattgtaggt atgtttcttg ccgagctgat agaaaagtat ttcgtgtccc   5160
ctaccctgtt ccgagtgatc cgtcttgcta ggattggccg aatcctacgt ctgatcaaag   5220
gagcaaaggg gatccgcacg ctgctctttg ctttgatgat gtcccttcct gcgttgttta   5280
acatcggcct cctactcttc ctagtcatgt tcatctacgc catctttggg atgtccaact   5340
ttgcctatgt taagagggaa gttgggatcg atgacatgtt caactttgag acctttggca   5400
acagcatgat ctgcctattc caaattacaa cctctgctgg ctgggatgga ttgctagcac   5460
ccattctcaa cagtaagcca cccgactgtg accctaataa agttaaccct ggaagctcag   5520
ttaagggaga ctgtgggaac ccatctgttg aattttctt ttttgtcagt tacatcatca   5580
tatccttcct ggttgtggtg aacatgtaca tcgcggtcat cctggagaac ttcagtgttg   5640
ctactgaaga aagtgcagag cctctgagtg aggatgactt tgagatgttc tatgaggttt   5700
gggagaagtt tgatcccgat gcaactcagt tcatggaatt tgaaaaatta tctcagtttg   5760
cagctgcgct tgaaccgcct ctcaatctgc acaaccaaa caaactccag ctcattgcca   5820
tggatttgcc catggtgagt ggtgaccgga tccactgtct tgatatctta tttgcttta   5880
caaagcgggt tctaggagag agtggagaga tggatgctct acgaatacag atggaagagc   5940
gattcatggc ttccaatcct tccaaggtct cctatcagcc aatcactact actttaaaac   6000
gaaaacaaga ggaagtatct gctgtcatta ttcagcgtgc ttacagacgc cacctttaa   6060
agcgaactgt aaaacaagct tcctttacgt acaataaaaa caaaatcaaa ggtggggcta   6120
atcttcttat aaaagaagac atgataattg acagaataaa tgaaaactct attacagaaa   6180
aaactgatct gaccatgtcc actgcagctt gtccaccttc ctatgaccgg gtgacaaagc   6240
caattgtgga aaaacatgag caagaaggca aagatgaaaa agccaaaggg aaataaatga   6300
aaataaataa aaataattgg gtgacaaatt gtttacagcc tgtgaaggtg atgtatttt   6360
atcaacagga ctcctttagg aggtcaatgc caaactgact gttttacac aaatctcctt   6420
aaggtcagtg cctacaataa gacagtgacc ccttgtcagc aaactgtgac tctgtgtaaa   6480
ggggagatga ccttgacagg aggttactgt tctcactacc agctgacact gctgaagata   6540
agatgcacaa tggctagtca gactgtaggg accagtttca aggggtgcaa acctgtgatt   6600
ttggggttgt ttaacatgaa acactttagt gtagtaattg tatccactgt ttgcatttca   6660
actgccacat ttgtcacatt tttatggaat ctgttagtgg attcatcttt ttgttaatcc   6720
atgtgtttat tatatgtgac tatttttgta aacgaagttt ctgttgagaa ataggctaag   6780
gacctctata acaggtatgc cacctggggg gtatggcaac cacatggccc tcccagctac   6840
acaaagtcgt ggtttgcatg agggcatgct gcacttagag atcatgcatg agaaaaagtc   6900
acaagaaaaa caaattctta aatttcacca tatttctggg aggggtaatt gggtgataag   6960
tggaggtgct ttgttgatct tgtttgcga atccagccc ctagaccaag tagattattt   7020
gtgggtaggc cagtaaatct tagcaggtgc aaacttcatt caaatgtttg gagtcataaa   7080
tgttatgttt cttttgttg tattaaaaaa aaaacctgaa tagtgaatat tgcccctcac   7140
cctccaccgc cagaagactg aattgaccaa aattactctt tataaatttc tgctttttcc   7200
tgcactttgt ttagccatct ttgggctctc agcaaggttg acactgtata tgttaatgaa   7260
atgctatta ttatgtaaat agtcatttta ccctgtggtg cacgtttgag caaacaaata   7320
atgacctaag cacagtattt attgcatcaa atatgtacca caagaaatgt agagtgcaag   7380
```

```
ctttacacag gtaataaaat gtattctgta ccatttatag atagtttgga tgctatcaat    7440
gcatgtttat attaccatgc tgctgtatct ggtttctctc actgctcaga atctcattta    7500
tgagaaacca tatgtcagtg gtaaagtcaa ggaaattgtt caacagatct catttattta    7560
agtcattaag caatagtttg cagcacttta acagcttttt ggttattttt acattttaag    7620
tggataacat atggtatata gccagactgt acagacatgt ttaaaaaaac acactgctta    7680
acctattaaa tatgtgttta gaattttata agcaaatata aatactgtaa aaagtcactt    7740
tattttattt ttcagcatta tgtacataaa tatgaagagg aaattatctt caggttgata    7800
tcacaatcac ttttcttact ttctgtccat agtacttttt catgaaagaa atttgctaaa    7860
taagacatga aaacaagact gggtagttgt agatttctgc ttttttaaatt acatttgcta    7920 attttagatt atttcacaat tttaaggagc aaaataggtt cacgattcat atccaaatta    7980
tgctttgcaa ttggaaaagg gtttaaaatt ttatttatat ttctggtagt acctgtacta    8040
actgaattga aggtagtgct tatgttattt ttgttctttt tttctgactt cggtttatgt    8100
tttcatttct ttggagtaat gctgctctag attgttctaa atagaatgtg ggcttcataa    8160
tttttttttc cacaaaaaca gagtagtcaa cttatatagt caattacatc aggacatttt    8220
gtgtttctta cagaagcaaa ccataggctc ctcttttcct taaaactact tagataaact    8280
gtattcgtga actgcatgct ggaaaatgct actattatgc taaataatgc taaccaacat    8340
ttaaaatgtg caaaactaat aaagattaca ttttttattt t                        8381

<210> SEQ ID NO 2
<211> LENGTH: 8381
<212> TYPE: DNA
<213> ORGANISM: Homo sapiens

<400> SEQUENCE: 2
atactgcaga ggtctctggt gcatgtgtgt atgtgtgcgt ttgtgtgtgt ttgtgtgtct      60
gtgtgttctg ccccagtgag actgcagccc ttgtaaatac tttgacacct tttgcaagaa     120
ggaatctgaa caattgcaac tgaaggcaca ttgttatcat ctcgtctttg ggtgatgctg     180
ttcctcactg cagatggata attttccttt taatcaggaa tttcatatgc agaataaatg     240
gtaattaaaa tgtgcaggat gacaagatgg agcaaacagt gcttgtacca ccaggacctg     300
acagcttcaa cttcttcacc agagaatctc ttgcggctat tgaaagacgc attgcagaag     360
aaaaggcaaa gaatcccaaa ccagacaaaa aagatgacga cgaaaatggc ccaaagccaa     420
atagtgactt ggaagctgga aagaaccttc catttattta tggagacatt cctccagaga     480
tggtgtcaga gcccctggag gacctggacc cctactatat caataagaaa acttttatag     540
tattgaataa attgaaggcc atcttccggt tcagtgccac ctctgccctg tacattttaa     600
ctcccttcaa tcctcttagg aaaatagcta ttaagatttt ggtacattca ttattcagca     660
tgctaattat gtgcactatt ttgacaaact gtgtgtttat gacaatgagt aaccctcctg     720
attggacaaa gaatgtagaa tacaccttca caggaatata tactttgaa tcacttataa     780 aaattattgc aaggggattc tgtttagaag attttacttt ccttcgggat ccatggaact     840
ggctcgattt cactgtcatt acatttgcgt acgtcacaga gtttgtggac ctgggcaatg     900
tctcggcatt gagaacattc agagttctcc gagcattgaa gacgatttca gtcattccag     960
gcctgaaaac cattgtggga gccctgatcc agtctgtgaa gaagctctca gatgtaatga    1020
tcctgactgt gttctgtctg agcgtatttg ctcaattgg gctgcagctg ttcatgggca    1080
acctgaggaa taaatgtata caatggcctc ccaccaatgc ttccttggag gaacatagta    1140
```

```
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gtttcgacta atgactcagg acttctgaga aaatctttat caactgacat   1440
tacgtgctgc tgggaaaacg tacatgatat tttttgtatt ggtcattttc ttgggctcat   1500
tctacctaat aaatttgatc ctggctgtgg tggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga aatcggagga agaaaagaaa acagaaagag cagtctggtg   1800
gggaagagaa agatgaggat gaattccaaa aatctgaatc tgaggacagc atcaggagga   1860
aaggttttcg cttctccatt gaagggaacc gattgacata tgaaaagagg tactcctccc   1920
cacaccagtc tttgttgagc atccgtggct ccctattttc accaaggcga aatagcagaa   1980
caagcctttt cagctttaga gggcgagcaa aggatgtggg atctgagaac gacttcgcag   2040
atgatgagca cagcaccttt gaggataacg agagccgtag agattccttg tttgtgcccc   2100
gacgacacgg agagagacgc aacagcaacc tgagtcagac cagtaggtca tcccggatgc   2160
tggcagtgtt tccagcgaat gggaagatgc acagcactgt ggattgcaat ggtgtggttt   2220
ccttggttgg tggaccttca gttcctacat cgcctgttgg acagcttctg ccagaggtga   2280
taatagataa gccagctact gatgacaatg gaacaaccac tgaaactgaa atgagaaaga   2340
gaaggtcaag ttcttttcca cgtttccatg actttctaga agatccttcc caaaggcaac   2400
gagcaatgag tatagccagc attctaacaa atacagtaga agaacttgaa gaatccaggc   2460
agaaatgccc accctgttgg tataaatttt ccaacatatt cttaatctgg gactgttctc   2520
catattggtt aaaagtgaaa catgttgtca acctggttgt gatggaccca tttgttgacc   2580
tggccatcac catctgtatt gtcttaaata ctcttttcat ggccatggag cactatccaa   2640
tgacggacca tttcaataat gtgcttacag taggaaactt ggttttcact gggatcttta   2700
cagcagaaat gtttctgaaa attattgcca tggatcctta ctattatttc caagaaggct   2760
ggaatatctt tgacggtttt attgtgacgc ttagcctggt agaacttgga ctcgccaatg   2820
tggaaggatt atctgttctc cgttcatttc gattgctgcg agttttcaag ttggcaaaat   2880
cttggccaac gttaaatatg ctaataaaga tcatcggcaa ttccgtgggg gctctgggaa   2940
atttaaccct cgtcttggcc atcatcgtct tcatttttgc cgtggtcggc atgcagctct   3000
ttggtaaaag ctacaaagat tgtgtctgca agatcgccag tgattgtcaa ctcccacgct   3060
ggcacatgaa tgacttcttc cactccttcc tgattgtgtt ccgcgtgctg tgtgggagt   3120 ggatagagac catgtgggac tgtatggagg ttgctggtca agccatgtgc cttactgtct   3180
tcatgatggt catggtgatt ggaaacctag tggtcctgaa tctctttctg gccttgcttc   3240
tgagctcatt tagtgcagac aaccttgcag ccactgatga tgataatgaa atgaataatc   3300
tccaaattgc tgtggatagg atgcacaaag gagtagctta tgtgaaaaga aaatatatg   3360 aatttattca acagtccttc attaggaaac aaaagatttt agatgaaatt aaaccacttg   3420
atgatctaaa caacaagaaa gacagttgta tgtccaatca tacaacagaa attgggaaag   3480
atcttgacta tcttaaagat gtaaatggaa ctacaagtgg tataggaact ggcagcagtg   3540
```

```
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca aagagaaact gaatgaaagc agtagctcat    3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa acaatggtg gaacctgaga aggacgtgtt     3900
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca ttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agccttatct cgatttgaag    4260
ggatgagggt ggttgtgaat gcccttttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctatacctcg accagaaaac aaatttcaag    4860
gaatggtctt tgacttcgta accagacaag ttttgacat aagcatcatg attctcatct     4920
gtcttaacat ggtcacaatg atggtggaaa cagatgacca gagtgaatat gtgactacca    4980
ttttgtcacg catcaatctg gtgttcattg tgctatttac tggagagtgt gtactgaaac    5040
tcatctctct acgccattat tattttacca ttggatggaa tatttttgat tttgtggttg    5100
tcattctctc cattgtaggt atgttttctt ccgagctgat agaaaagtat ttcgtgtccc    5160
ctaccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340
ttgcctatgt taagagggaa gttgggatcg atgacatgtt caactttgag accttt ggca   5400
acagcatgat ctgcctattc caaattacaa cctctgctgg ctgggatgga ttgctagcac    5460
ccattctcaa cagtaagcca cccgactgtg accctaataa agttaaccct ggaagctcag    5520
ttaagggaga ctgtgggaac ccatctgttg gaattttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc cacaaccaaa caaactccag ctcattgcca    5820
tggatttgcc catggtgagt ggtgaccgga tccactgtct tgatatctta tttgcttta    5880
caaagcgggt tctaggagag agtggagaga tggatgctct acgaatacag atggaagagc    5940
```

```
gattcatggc ttccaatcct tccaaggtct cctatcagcc aatcactact acttttaaaac    6000 gaaaacaaga ggaagtatct gctgtcatta ttcagcgtgc ttacagacgc caccttttaa    6060
agcgaactgt aaaacaagct tcctttacgt acaataaaaa caaaatcaaa ggtggggcta    6120
atcttcttat aaaagaagac atgataattg acagaataaa tgaaaactct attacagaaa    6180
aaactgatct gaccatgtcc actgcagctt gtccaccttc ctatgaccgg gtgacaaagc    6240
caattgtgga aaaacatgag caagaaggca agatgaaaaa agccaaaggg aaataaatga    6300
aaataaataa aataattgg gtgacaaatt gtttacagcc tgtgaaggtg atgtattttt    6360
atcaacagga ctcctttagg aggtcaatgc caaactgact gttttttacac aaatctcctt    6420 aaggtcagtg cctacaataa gacagtgacc ccttgtcagc aaactgtgac tctgtgtaaa    6480
ggggagatga ccttgacagg aggttactgt tctcactacc agctgacact gctgaagata    6540
agatgcacaa tggctagtca gactgtaggg accagtttca aggggtgcaa acctgtgatt    6600
ttggggttgt ttaacatgaa acactttagt gtagtaattg tatccactgt ttgcatttca    6660
actgccacat ttgtcacatt tttatggaat ctgttagtgg attcatcttt ttgttaatcc    6720
atgtgtttat tatatgtgac tatttttgta aacgaagttt ctgttgagaa ataggctaag    6780
gacctctata acaggtatgc cacctggggg gtatggcaac cacatggccc tcccagctac    6840
acaaagtcgt ggtttgcatg agggcatgct gcacttagag atcatgcatg agaaaaagtc    6900
acaagaaaaa caaattctta aatttcacca tatttctggg aggggtaatt gggtgataag    6960
tggaggtgct ttgttgatct tgttttgcga aatccagccc ctagaccaag tagattattt    7020
gtgggtaggc cagtaaatct tagcaggtgc aaacttcatt caaatgtttg gagtcataaa    7080
tgttatgttt cttttttgttg tattaaaaaa aaaacctgaa tagtgaatat tgcccctcac    7140
cctccaccgc cagaagactg aattgaccaa aattactctt tataaatttc tgcttttcc    7200 tgcactttgt ttagccatct ttgggctctc agcaaggttg acactgtata tgttaatgaa    7260
atgctattta ttatgtaaat agtcattta ccctgtggtg cacgtttgag caaacaaata    7320
atgacctaag cacagtattt attgcatcaa atatgtacca caagaaatgt agagtgcaag    7380
ctttacacag gtaataaaat gtattctgta ccatttatag atagtttgga tgctatcaat    7440
gcatgtttat attaccatgc tgctgtatct ggtttctctc actgctcaga atctcattta    7500
tgagaaacca tatgtcagtg gtaaagtcaa ggaaattgtt caacagatct catttattta    7560
agtcattaag caatagtttg cagcacttta acagcttttt ggttattttt acattttaag    7620
tggataacat atggtatata gccagactgt acagacatgt ttaaaaaaac acactgctta    7680
acctattaaa tatgtgttta gaattttata agcaaatata aatactgtaa aaagtcactt    7740
tattttattt ttcagcatta tgtacataaa tatgaagagg aaattatctt caggttgata    7800
tcacaatcac ttttcttact ttctgtccat agtactttt catgaaagaa atttgctaaa    7860
taagacatga aaacaagact gggtagttgt agatttctgc ttttaaatt acatttgcta    7920 attttagatt atttcacaat tttaaggagc aaaataggtt cacgattcat atccaaatta    7980
tgctttgcaa ttggaaaagg gtttaaaatt ttatttatat ttctggtagt acctgtacta    8040
actgaattga aggtagtgct tatgttattt ttgttctttt tttctgactt cggtttatgt    8100
tttcatttct ttggagtaat gctgctctag attgttctaa atagaatgtg gcttcataa    8160 ttttttttc cacaaaaaca gagtagtcaa cttatatagt caattacatc aggacatttt    8220
gtgtttctta cagaagcaaa ccataggctc ctcttttcct taaaactact tagataaact    8280
gtattcgtga actgcatgct ggaaaatgct actattatgc taaataatgc taaccaacat    8340
```

```
ttaaaatgtg caaaactaat aaagattaca ttttttattt t              8381
```

<210> SEQ ID NO 3
<211> LENGTH: 8381
<212> TYPE: DNA
<213> ORGANISM: Homo sapiens

<400> SEQUENCE: 3

```
atactgcaga ggtctctggt gcatgtgtgt atgtgtgcgt ttgtgtgtgt ttgtgtgtct     60
gtgtgttctg ccccagtgag actgcagccc ttgtaaatac tttgacacct tttgcaagaa    120
ggaatctgaa caattgcaac tgaaggcaca ttgttatcat ctcgtctttg ggtgatgctg    180
ttcctcactg cagatggata attttccttt taatcaggaa tttcatatgc agaataaatg    240
gtaattaaaa tgtgcaggat gacaagatgg agcaaacagt gcttgtacca ccaggacctg    300
acagcttcaa cttcttcacc agagaatctc ttgcggctat tgaaagacgc attgcagaag    360
aaaaggcaaa gaatcccaaa ccagacaaaa aagatgacga cgaaaatggc caaagccaa     420
atagtgactt ggaagctgga aagaaccttc catttattta tggagacatt cctccagaga    480
tggtgtcaga gcccctggag gacctggacc cctactatat caataagaaa acttttatag    540
tattgaataa attgaaggcc atcttccggt tcagtgccac ctctgccctg tacatttaa     600
ctcccttcaa tcctcttagg aaaatagcta ttaagatttt ggtacattca ttattcagca    660
tgctaattat gtgcactatt ttgacaaact gtgtgtttat gacaatgagt aaccctcctg    720
attggacaaa gaatgtagaa tacaccttca caggaatata acttttgaa tcacttataa     780
aaattattgc aaggggattc tgtttagaag atttttacttt ccttcgggat ccatggaact    840
ggctcgattt cactgtcatt acatttgcgt acgtcacaga gtttgtggac ctgggcaatg    900
tctcggcatt gagaacattc agagttctcc gagcattgaa gacgatttca gtcattccag    960
gcctgaaaac cattgtggga gccctgatcc agtctgtgaa gaagctctca gatgtaatga   1020
tcctgactgt gttctgtctg agcgtatttg ctctaattgg gctgcagctg ttcatgggca   1080
acctgaggaa taaatgtata caatggcctc ccaccaatgc ttccttggag gaacatagta   1140
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gtttcgacta atgactcagg acttctggga aaatctttat caactgacat   1440
tacgtgctcc tgggaaaacg tacatgatat ttttgtatt ggtcattttc ttgggctcat    1500
tctacctaat aaatttgatc ctggctgtgg tggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga aatcggagga gaaaagaaa acagaaagag cagtctggtg   1800
gggaagagaa agatgaggat gaattccaaa aatctgaatc tgaggacagc atcaggagga   1860
aaggttttcg cttctccatt gaagggaacc gattgacata tgaaaagagg tactcctccc   1920
cacaccagtc tttgttgagc atccgtggct ccctattttc accaaggcga aatagcagaa   1980
caagcctttt cagctttaga gggcgagcaa aggatgtggg atctgagaac gacttcgcag   2040
atgatgagca cagcaccttt gaggataacg agagccgtag agattccttg tttgtgcccc   2100
```

```
gacgacacgg agagagacgc aacagcaacc tgagtcagac cagtaggtca tcccggatgc   2160
tggcagtgtt tccagcgaat gggaagatgc acagcactgt ggattgcaat ggtgtggttt   2220
ccttggttgg tggaccttca gttcctacat cgcctgttgg acagcttctg ccagaggtga   2280
taatagataa gccagctact gatgacaatg aacaaccac tgaaactgaa atgagaaaga    2340
gaaggtcaag ttcttttccac gtttccatgg actttctaga agatccttcc caaaggcaac  2400
gagcaatgag tatagccagc attctaacaa atacagtaga agaacttgaa gaatccaggc   2460
agaaatgccc accctgttgg tataaattt ccaacatatt cttaatctgg gactgttctc    2520
catattggtt aaaagtgaaa catgttgtca acctggttgt gatggaccca tttgttgacc   2580
tggccatcac catctgtatt gtcttaaata ctcttttcat ggccatggag cactatccaa   2640
tgacggacca tttcaataat gtgcttacag taggaaactt ggttttcact gggatcttta   2700
cagcagaaat gtttctgaaa attattgcca tggatcctta ctattatttc caagaaggct   2760
ggaatatctt tgacggtttt attgtgacgc ttagcctggt agaacttgga ctcgccaatg   2820
tggaaggatt atctgttctc cgttcatttc gattgctgcg agttttcaag ttggcaaaat   2880
cttggccaac gttaaatatg ctaataaaga tcatcggcaa ttccgtgggg gctctgggaa   2940 atttaacccct cgtcttggcc atcatcgtct tcattttgc cgtggtcggc atgcagctct   3000
ttggtaaaag ctacaaagat tgtgtctgca agatcgccag tgattgtcaa ctcccacgct   3060
ggcacatgaa tgacttcttc cactccttcc tgattgtgtt ccgcgtgctg tgtggggagt   3120
ggatagagac catgtgggac tgtatggagg ttgctggtca agccatgtgc cttactgtct   3180
tcatgatggt catggtgatt ggaaacctag tggtcctgaa tctcttttctg gccttgcttc   3240 tgagctcatt tagtgcagac aaccttgcag ccactgatga tgataatgaa atgaataatc   3300
tccaaattgc tgtggatagg atgcacaaag gagtagctta tgtgaaaaga aaaatatatg   3360
aatttattca acagtccttc attaggaaac aaaagattt agatgaaatt aaaccacttg   3420
atgatctaaa caacaagaaa gacagttgta tgtccaatca tacaacagaa attgggaaag   3480
atcttgacta tcttaaagat gtaaatggaa ctacaagtgg tataggaact ggcagcagtg   3540
ttgaaaaata cattattgat gaaagtgatt acatgtcatt cataaacaac cccagtctta   3600
ctgtgactgt accaattgct gtaggagaat ctgactttga aaatttaaac acggaagact   3660
ttagtagtga atcggatctg gaagaaagca aagagaaact gaatgaaagc agtagctcat   3720
cagaaggtag cactgtggac atcggcgcac ctgtagaaga acagcccgta gtggaacctg   3780
aagaaactct tgaaccagaa gcttgtttca ctgaaggctg tgtacaaaga ttcaagtgtt   3840
gtcaaatcaa tgtggaagaa ggcagaggaa aacaatggtg gaacctgaga aggacgtgtt   3900
tccgaatagt tgaacataac tggtttgaga ccttcattgt tttcatgatt ctccttagta   3960
gtggtgctct ggcatttgaa gatatatata ttgatcagcg aaagacgatt aagacgatgt   4020
tggaatatgc tgacaaggtt ttcacttaca tttcattct ggaaatgctt ctaaaatggg    4080
tggcatatgg ctatcaaaca tatttcacca atgcctggtg ttggctggac ttcttaattg   4140
ttgatgtttc attggtcagt ttaacagcaa atgccttggg ttactcagaa cttggagcca   4200
tcaaatctct caggacacta agagctctga gacctctaag agccttatct cgatttgaag   4260
ggatgagggt ggttgtgaat gcccttttag gagcaattcc atccatcatg aatgtgcttc   4320
tggtttgtct tatattctgg ctaattttca gcatcatggg cgtaaatttg tttgctggca   4380
aattctacca ctgtattaac accacaactg tgacaggtt tgacatcgaa gacgtgaata   4440
atcatactga ttgcctaaaa ctaatagaaa gaaatgagac tgctcgatgg aaaaatgtga   4500
```

```
aagtaaactt tgataatgta ggatttgggt atctctcttt gcttcaagtt gccacattca   4560
aaggatggat ggatataatg tatgcagcag ttgattccag aaatgtggaa ctccagccta   4620
agtatgaaaa aagtctgtac atgtatcttt actttgttat tttcatcatc tttgggtcct   4680
tcttcacctt gaacctgttt attggtgtca tcatagataa tttcaaccag cagaaaaga    4740 agtttggagg tcaagacatc tttatgacag aagaacagaa gaaatactat aatgcaatga   4800
aaaaattagg atcgaaaaaa ccgcaaaagc ctatacctcg accaggaaac aaatttcaag   4860
gaatggtctt tgacttcgta accagacaag ttttttgacat aagcatcatg attctcatct   4920
gtcttaacat ggtcacaatg atggtggaaa cagatgacca gagtgaatat gtgactacca   4980
ttttgtcacg catcaatctg gtgttcattg tgctatttac tggagagtgt gtactgaaac   5040
tcatctctct acgccattat tatttttacca ttggatggaa tattttttgat tttgtggttg   5100 tcattctctc cattgtaggt atgtttcttg ccgagctgat agaaaagtat ttcgtgtccc   5160
ctaccctgtt ccgagtgatc cgtcttgcta ggattggccg aatcctacgt ctgatcaaag   5220
gagcaaaggg gatccgcacg ctgctctttg ctttgatgat gtcccttcct gcgttgttta   5280
acatcggcct cctactcttc ctagtcatgt tcatctacgc catctttggg atgtccaact   5340
ttgcctatgt taagagggaa gttgggatcg atgacatgtt caactttgag acctttggca   5400
acagcatgat ctgcctattc caaattacaa cctctgctgg ctgggatgga ttgctagcac   5460
ccattctcaa cagtaagcca cccgactgtg accctaataa agttaaccct ggaagctcag   5520
ttaagggaga ctgtgggaac ccatctgttg gaatttttctt ttttgtcagt tacatcatca   5580
tatccttcct ggttgtggtg aacatgtaca tcgcggtcat cctggagaac ttcagtgttg   5640
ctactgaaga aagtgcagag cctctgagtg aggatgactt tgagatgttc tatgagggttt   5700 gggagaagtt tgatcccgat gcaactcagt tcatggaatt tgaaaaatta tctcagtttg   5760
cagctgcgct tgaaccgcct ctcaatctgc cacaaccaaa caaactccag ctcattgcca   5820
tggatttgcc catggtgagt ggtgaccgga tccactgtct tgatatctta tttgctttta    5880
caaagcgggt tctaggagag agtggagaga tggatgctct acgaatacag atggaagagc   5940
gattcatggc ttccaatcct tccaaggtct cctatcagcc aatcactact actttaaaac   6000
gaaaacaaga ggaagtatct gctgtcatta ttcagcgtgc ttacagacgc cacctttaa    6060 agcgaactgt aaaacaagct tcctttacgt acaataaaaa caaaatcaaa ggtgggcta    6120 atcttcttat aaaagaagac atgataattg acagaataaa tgaaaactct attacagaaa   6180
aaactgatct gaccatgtcc actgcagctt gtccaccttc ctatgaccgg gtgacaaagc   6240
caattgtgga aaaacatgag caagaaggca agatgaaaaa agccaaaggg aaataaatga   6300
aaataaataa aaataattgg gtgacaaatt gtttacagcc tgtgaaggtg atgtattttt   6360
atcaacagga ctcctttagg aggtcaatgc caaactgact gtttttacac aaatctcctt   6420
aaggtcagtg cctacaataa gacagtgacc ccttgtcagc aaactgtgac tctgtgtaaa   6480
ggggagatga ccttgacagg aggttactgt tctcactacc agctgacact gctgaagata   6540
agatgcacaa tggctagtca gactgtaggg accagtttca aggggtgcaa acctgtgatt   6600 ttgggggttgt ttaacatgaa acactttagt gtagtaattg tatccactgt ttgcatttca   6660
actgccacat ttgtcacatt tttatggaat ctgttagtgg attcatcttt ttgttaatcc   6720
atgtgtttat tatatgtgac tatttttgta aacgaagttt ctgttgagaa ataggctaag   6780
gacctctata acaggtatgc cacctggggg gtatggcaac cacatggccc tcccagctac   6840
acaaagtcgt ggtttgcatg agggcatgct gcacttagag atcatgcatg agaaaaagtc   6900
```

| | |
|---|---|
| acaagaaaaa caaattctta aatttcacca tatttctggg aggggtaatt gggtgataag | 6960 |
| tggaggtgct ttgttgatct tgttttgcga aatccagccc ctagaccaag tagattattt | 7020 |
| gtgggtaggc cagtaaatct tagcaggtgc aaacttcatt caaatgtttg gagtcataaa | 7080 |
| tgttatgttt cttttgttg tattaaaaaa aaaacctgaa tagtgaatat tgcccctcac | 7140 |
| cctccaccgc cagaagactg aattgaccaa aattactctt tataaatttc tgcttttcc | 7200 |
| tgcactttgt ttagccatct ttgggctctc agcaaggttg acactgtata tgttaatgaa | 7260 |
| atgctattta ttatgtaaat agtcatttta ccctgtggtg cacgtttgag caaacaaata | 7320 |
| atgacctaag cacagtattt attgcatcaa atatgtacca caagaaatgt agagtgcaag | 7380 |
| ctttacacag gtaataaaat gtattctgta ccatttatag atagtttgga tgctatcaat | 7440 |
| gcatgtttat attaccatgc tgctgtatct ggtttctctc actgctcaga atctcattta | 7500 |
| tgagaaacca tatgtcagtg gtaaagtcaa ggaaattgtt caacagatct catttattta | 7560 |
| agtcattaag caatagtttg cagcacttta acagcttttt ggttattttt acatttaag | 7620 |
| tggataacat atggtatata gccagactgt acagacatgt ttaaaaaac acactgctta | 7680 |
| acctattaaa tatgtgttta gaattttata agcaaatata aatactgtaa aaagtcactt | 7740 |
| tatttattt ttcagcatta tgtacataaa tatgaagagg aaattatctt caggttgata | 7800 |
| tcacaatcac ttttcttact ttctgtccat agtactttt catgaaagaa atttgctaaa | 7860 |
| taagacatga aaacaagact gggtagttgt agatttctgc tttttaaatt acatttgcta | 7920 |
| attttagatt atttcacaat tttaaggagc aaaataggtt cacgattcat atccaaatta | 7980 |
| tgctttgcaa ttggaaaagg gtttaaaatt ttatttatat ttctggtagt acctgtacta | 8040 |
| actgaattga aggtagtgct tatgttattt tgttctttt tttctgactt cggtttatgt | 8100 |
| tttcatttct ttggagtaat gctgctctag attgttctaa atagaatgtg ggcttcataa | 8160 |
| ttttttttc cacaaaaaca gagtagtcaa cttatatagt caattacatc aggacatttt | 8220 |
| gtgtttctta cagaagcaaa ccataggctc ctctttcct taaaactact tagataaact | 8280 |
| gtattcgtga actgcatgct ggaaaatgct actattatgc taaataatgc taaccaacat | 8340 |
| ttaaaatgtg caaaactaat aaagattaca ttttttattt t | 8381 |

<210> SEQ ID NO 4
<211> LENGTH: 8381
<212> TYPE: DNA
<213> ORGANISM: Homo sapiens

<400> SEQUENCE: 4

| | |
|---|---|
| atactgcaga ggtctctggt gcatgtgtgt atgtgtgcgt ttgtgtgtgt ttgtgtgtct | 60 |
| gtgtgttctg ccccagtgag actgcagccc ttgtaaatac tttgacacct tttgcaagaa | 120 |
| ggaatctgaa caattgcaac tgaaggcaca ttgttatcat ctcgtctttg ggtgatgctg | 180 |
| ttcctcactg cagatggata atttccttt taatcaggaa tttcatatgc agaataaatg | 240 |
| gtaattaaaa tgtgcaggat gacaagatgg agcaaacagt gcttgtacca ccaggacctg | 300 |
| acagcttcaa cttcttcacc agagaatctc ttgcggctat tgaaagacgc attgcagaag | 360 |
| aaaaggcaaa gaatcccaaa ccagacaaaa aagatgacga cgaaaatggc ccaaagccaa | 420 |
| atagtgactt ggaagctgga aagaaccttc catttattta tggagacatt cctccagaga | 480 |
| tggtgtcaga gcccctggag gacctggacc cctactatat caataagaaa acttttatag | 540 |
| tattgaataa attgaaggcc atcttccggt tcagtgccac ctctgccctg tacattttaa | 600 |
| ctcccttcaa tcctcttagg aaaatagcta ttaagatttt ggtacattca ttattcagca | 660 |

```
tgctaattat gtgcactatt ttgacaaact gtgtgtttat gacaatgagt aaccctcctg    720
attggacaaa gaatgtagaa tacaccttca caggaatata tacttttgaa tcacttataa    780
aaattattgc aagggattc  tgtttagaag attttacttt ccttcgggat ccatggaact    840
ggctcgattt cactgtcatt acatttgcgt acgtcacaga gtttgtggac ctgggcaatg    900
tctcggcatt gagaacattc agagttctcc gagcattgaa gacgatttca gtcattccag    960
gcctgaaaac cattgtggga gccctgatcc agtctgtgaa gaagctctca gatgtaatga   1020
tcctgactgt gttctgtctg agcgtatttg ctctaattgg gctgcagctg ttcatgggca   1080
acctgaggaa taaatgtata caatggcctc ccaccaatgc ttccttggag gaacatagta   1140
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gtttcgacta atgactcagg acttctggga aaatctttat caactgacat   1440
tacgtgctgc tgggaaaacg tacatgatat ttcttgtatt ggtcattttc ttgggctcat   1500
tctacctaat aaatttgatc ctggctgtgg tggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga aatcggagga agaaaagaaa acagaaagag cagtctggtg   1800
gggaagagaa agatgaggat gaattccaaa aatctgaatc tgaggacagc atcaggagga   1860
aaggttttcg cttctccatt gaagggaacc gattgacata tgaaaagagg tactcctccc   1920
cacaccagtc tttgttgagc atccgtggct ccctattttc accaaggcga aatagcagaa   1980
caagcctttt cagctttaga gggcgagcaa aggatgtggg atctgagaac gacttcgcag   2040
atgatgagca cagcaccttt gaggataacg agagccgtag agattccttg tttgtgcccc   2100
gacgacacgg agagagacgc aacagcaacc tgagtcagac cagtaggtca tcccggatgc   2160
tggcagtgtt tccagcgaat gggaagatgc acagcactgt ggattgcaat ggtgtggttt   2220
ccttggttgg tggaccttca gttcctacat cgcctgttgg acagcttctg ccagaggtga   2280
taatagataa gccagctact gatgacaatg gaacaaccac tgaaactgaa atgagaaaga   2340
gaaggtcaag ttctttccac gtttccatgg actttctaga agatcctcc  caaaggcaac   2400 gagcaatgag tatagccagc attctaacaa atacagtaga agaacttgaa gaatccaggc   2460
agaaatgccc accctgttgg tataaatttt ccaacatatt cttaatctgg gactgttctc   2520
catattggtt aaaagtgaaa catgttgtca acctggttgt gatggaccca tttgttgacc   2580
tggccatcac catctgtatt gtcttaaata ctcttttcat ggccatggag cactatccaa   2640
tgacggacca tttcaataat gtgcttacag taggaaactt ggttttcact gggatcttta   2700
cagcagaaat gttctgaaa  attattgcca tggatcctta ctattatttc caagaaggct   2760
ggaatatctt tgacggtttt attgtgacgc ttagcctggt agaacttgga ctcgccaatg   2820
tggaaggatt atctgttctc cgttcatttc gattgctgcg agttttcaag ttggcaaaat   2880
cttggccaac gttaaatatg ctaataaaga tcatcggcaa ttccgtgggg gctctgggaa   2940
atttaaccct cgtcttggcc atcatcgtct tcatttttgc cgtggtcggc atgcagctct   3000
ttggtaaaag ctacaaagat tgtgtctgca agatcgccag tgattgtcaa ctcccacgct   3060
```

```
ggcacatgaa tgacttcttc cactccttcc tgattgtgtt ccgcgtgctg tgtggggagt      3120
ggatagagac catgtgggac tgtatggagg ttgctggtca agccatgtgc cttactgtct      3180
tcatgatggt catggtgatt ggaaacctag tggtcctgaa tctctttctg gccttgcttc      3240
tgagctcatt tagtgcagac aaccttgcag ccactgatga tgataatgaa atgaataatc      3300
tccaaattgc tgtggatagg atgcacaaag gagtagctta tgtgaaaaga aaaatatatg      3360
aatttattca acagtccttc attaggaaac aaaagatttt agatgaaatt aaaccacttg      3420
atgatctaaa caacaagaaa gacagttgta tgtccaatca tacaacagaa attgggaaag      3480
atcttgacta tcttaaagat gtaaatgaaa ctacaagtgg tataggaact ggcagcagtg      3540
ttgaaaaata cattattgat gaaagtgatt acatgtcatt cataaacaac cccagtctta      3600
ctgtgactgt accaattgct gtaggagaat ctgactttga aaatttaaac acggaagact      3660
ttagtagtga atcggatctg gaagaaagca agagaaact gaatgaaagc agtagctcat      3720
cagaaggtag cactgtggac atcggcgcac ctgtagaaga acagcccgta gtggaacctg      3780
aagaaactct tgaaccagaa gcttgtttca ctgaaggctg tgtacaaaga ttcaagtgtt      3840
gtcaaatcaa tgtggaagaa ggcagaggaa acaatggtg gaacctgaga aggacgtgtt      3900
tccgaatagt tgaacataac tggtttgaga ccttcattgt tttcatgatt ctccttagta      3960
gtggtgctct ggcatttgaa gatatatata ttgatcagcg aaagacgatt aagacgatgt      4020
tggaatatgc tgacaaggtt ttcacttaca ttttcattct ggaaatgctt ctaaaatggg      4080
tggcatatgg ctatcaaaca tatttcacca atgcctggtg ttggctggac ttcttaattg      4140
ttgatgtttc attggtcagt ttaacagcaa atgccttggg ttactcagaa cttggagcca      4200
tcaaatctct caggacacta agagctctga gacctctaag agccttatct cgatttgaag      4260
ggatgagggt ggttgtgaat gcccttttag gagcaattcc atccatcatg aatgtgcttc      4320
tggtttgtct tatattctgg ctaattttca gcatcatggg cgtaaatttg tttgctggca      4380
aattctacca ctgtattaac accacaactg gtgacaggtt tgacatcgaa gacgtgaata      4440
atcatactga ttgcctaaaa ctaatagaaa gaaatgagac tgctcgatgg aaaaatgtga      4500
aagtaaactt tgataatgta ggatttgggt atctctcttt gcttcaagtt gccacattca      4560
aaggatggat ggatataatg tatgcagcag ttgattccag aaatgtggaa ctccagccta      4620
agtatgaaaa aagtctgtac atgtatcttt actttgttat tttcatcatc tttgggtcct      4680
tcttcaccct gaacctgttt attggtgtca tcatagataa tttcaaccag cagaaaaga      4740 agtttggagg tcaagacatc tttatgacag aagaacagaa gaaatactat aatgcaatga      4800
aaaaattagg atcgaaaaaa ccgcaaaagc ctatacctcg accaggaaac aaatttcaag      4860
gaatggtctt tgacttcgta accagacaag tttttgacat aagcatcatg attctcatct      4920
gtcttaacat ggtcacaatg atggtggaaa cagatgacca gagtgaatat gtgactacca      4980
ttttgtcacg catcaatctg gtgttcattg tgctatttac tggagagtgt gtactgaaac      5040
tcatctctct acgccattat tattttacca ttggatggaa tatttttgat tttgtggttg      5100
tcattctctc cattgtaggt atgtttcttg ccgagctgat agaaaagtat ttcgtgtccc      5160
ctaccctgtt ccgagtgatc cgtcttgcta ggattggccg aatcctacgt ctgatcaaag      5220
gagcaaaggg gatccgcacg ctgctctttg ctttgatgat gtcccttcct gcgttgttta      5280
acatcggcct cctactcttc ctagtcatgt tcatctacgc catctttggg atgtccaact      5340
ttgcctatgt taagagggaa gttgggatcg atgacatgtt caactttgag accttttggca      5400 acagcatgat ctgcctattc caaattacaa cctctgctgg ctgggatgga ttgctagcac      5460
```

```
ccattctcaa cagtaagcca cccgactgtg accctaataa agttaaccct ggaagctcag    5520
ttaagggaga ctgtgggaac ccatctgttg gaattttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc acaaccaaa caaactccag ctcattgcca    5820
tggatttgcc catggtgagt ggtgaccgga tccactgtct tgatatctta tttgctttta    5880
caaagcgggt tctaggagag agtggagaga tggatgctct acgaatacag atggaagagc    5940
gattcatggc ttccaatcct tccaaggtct cctatcagcc aatcactact actttaaaac    6000
gaaaacaaga ggaagtatct gctgtcatta ttcagcgtgc ttacagacgc caccttttaa    6060
agcgaactgt aaaacaagct tcctttacgt acaataaaaa caaaatcaaa ggtggggcta    6120
atcttcttat aaaagaagac atgataattg acagaataaa tgaaaactct attacagaaa    6180
aaactgatct gaccatgtcc actgcagctt gtccaccttc ctatgaccgg gtgacaaagc    6240
caattgtgga aaaacatgag caagaaggca aagatgaaaa agccaaaggg aaataaatga    6300
aaataaataa aaataattgg gtgacaaatt gtttacagcc tgtgaaggtg atgtatttt    6360 atcaacagga ctccttagg aggtcaatgc caaactgact gtttttacac aaatctcctt    6420
aaggtcagtg cctacaataa gacagtgacc ccttgtcagc aaactgtgac tctgtgtaaa    6480
ggggagatga ccttgacagg aggttactgt tctcactacc agctgacact gctgaagata    6540
agatgcacaa tggctagtca gactgtaggg accagtttca aggggtgcaa acctgtgatt    6600
ttggggttgt ttaacatgaa acactttagt gtagtaattg tatccactgt ttgcattca    6660 actgccacat ttgtcacatt tttatggaat ctgttagtgg attcatcttt tgttaatcc    6720 atgtgtttat tatatgtgac tattttgta aacgaagttt ctgttgagaa ataggctaag    6780
gacctctata acaggtatgc cacctgggg gtatggcaac cacatggccc tcccagctac    6840
acaaagtcgt ggtttgcatg agggcatgct gcacttagag atcatgcatg agaaaaagtc    6900
acaagaaaaa caaattctta aatttcacca tatttctggg aggggtaatt gggtgataag    6960
tggaggtgct ttgttgatct tgttttgcga aatccagccc ctagaccaag tagattattt    7020
gtgggtaggc cagtaaatct tagcaggtgc aaacttcatt caaatgtttg gagtcataaa    7080
tgttatgttt ctttttgttg tattaaaaaa aaaacctgaa tagtgaatat gcccctcac    7140 cctccaccgc cagaagactg aattgaccaa aattactctt tataaatttc tgcttttcc    7200 tgcactttgt ttagccatct ttgggctctc agcaaggttg acactgtata tgttaatgaa    7260
atgctattta ttatgtaaat agtcatttta ccctgtggtg cacgtttgag caaacaaata    7320
atgacctaag cacagtattt attgcatcaa atatgtacca caagaaatgt agagtgcaag    7380
ctttacacag gtaataaaat gtattctgta ccatttatag atagtttgga tgctatcaat    7440
gcatgtttat attaccatgc tgctgtatct ggtttctctc actgctcaga atctcattta    7500
tgagaaacca tatgtcagtg gtaaagtcaa ggaaattgtt caacagatct catttattta    7560
agtcattaag caatagtttg cagcacttta acagcttttt ggttattttt acattttaag    7620
tggataacat atggtatata gccagactgt acagacatgt ttaaaaaaac acactgctta    7680
acctattaaa tatgtgttta gaattttata agcaaatata aatactgtaa aaagtcactt    7740
tattttattt ttcagcatta tgtacataaa tatgaagagg aaattatctt caggttgata    7800
tcacaatcac tttctttact ttctgtccat agtactttt catgaaagaa atttgctaaa    7860
```

| | |
|---|---:|
| taagacatga aaacaagact gggtagttgt agatttctgc ttttaaatt acatttgcta | 7920 |
| attttagatt atttcacaat tttaaggagc aaaataggtt cacgattcat atccaaatta | 7980 |
| tgctttgcaa ttggaaaagg gtttaaaatt ttatttatat ttctggtagt acctgtacta | 8040 |
| actgaattga aggtagtgct tatgttattt ttgttctttt tttctgactt cggtttatgt | 8100 |
| tttcatttct ttggagtaat gctgctctag attgttctaa atagaatgtg ggcttcataa | 8160 |
| tttttttttc cacaaaaaca gagtagtcaa cttatatagt caattacatc aggacattt | 8220 |
| gtgtttctta cagaagcaaa ccataggctc ctcttttcct taaaactact tagataaact | 8280 |
| gtattcgtga actgcatgct ggaaaatgct actattatgc taaataatgc taaccaacat | 8340 |
| ttaaaatgtg caaaactaat aaagattaca ttttttattt t | 8381 |

```
<210> SEQ ID NO 5
<211> LENGTH: 8381
<212> TYPE: DNA
<213> ORGANISM: Homo sapiens

<400> SEQUENCE: 5
```

| | |
|---|---:|
| atactgcaga ggtctctggt gcatgtgtgt atgtgtgcgt ttgtgtgtgt ttgtgtgtct | 60 |
| gtgtgttctg ccccagtgag actgcagccc ttgtaaatac tttgacacct tttgcaagaa | 120 |
| ggaatctgaa caattgcaac tgaaggcaca ttgttatcat ctcgtctttg ggtgatgctg | 180 |
| ttcctcactg cagatggata atttttccttt taatcaggaa tttcatatgc agaataaatg | 240 |
| gtaattaaaa tgtgcaggat gacaagatgg agcaaacagt gcttgtacca ccaggacctg | 300 |
| acagcttcaa cttcttcacc agagaatctc ttgcggctat tgaaagacgc attgcagaag | 360 |
| aaaaggcaaa gaatcccaaa ccagacaaaa aagatgacga cgaaaatggc ccaaagccaa | 420 |
| atagtgactt ggaagctgga aagaaccttc catttattta tggagacatt cctccagaga | 480 |
| tggtgtcaga gcccctggag gacctggacc cctactatat caataagaaa acttttatag | 540 |
| tattgaataa attgaaggcc atcttccggt tcagtgccac ctctgccctg tacatttaa | 600 |
| ctcccttcaa tcctcttagg aaaatagcta ttaagatttt ggtacattca ttattcagca | 660 |
| tgctaattat gtgcactatt ttgacaaact gtgtgtttat gacaatgagt aaccctcctg | 720 |
| attggacaaa gaatgtagaa tacaccttca caggaatata tactttgaa tcacttataa | 780 |
| aaattattgc aaggggattc tgtttagaag attttacttt ccttcgggat ccatggaact | 840 |
| ggctcgattt cactgtcatt acatttgcgt acgtcacaga gtttgtggac ctgggcaatg | 900 |
| tctcggcatt gagaacattc agagttctcc gagcattgaa gacgattca gtcattccag | 960 |
| gcctgaaaac cattgtggga gccctgatcc agtctgtgaa gaagctctca gatgtaatga | 1020 |
| tcctgactgt gttctgtctg agcgtatttg ctctaattgg gctgcagctg ttcatgggca | 1080 |
| acctgaggaa taaatgtata caatggcctc ccaccaatgc ttccttggag gaacatagta | 1140 |
| tagaaaagaa tataactgtg aattataatg gtacacttat aaatgaaact gtctttgagt | 1200 |
| ttgactggaa gtcatatatt caagattcaa gatatcatta tttcctggag ggttttttag | 1260 |
| atgcactact atgtggaaat agctctgatg caggccaatg tccagaggga tatatgtgtg | 1320 |
| tgaaagctgg tagaaatccc aattatggct acacaagctt tgataccttc agttgggctt | 1380 |
| ttttgtcctt gttcgactac atgactcagg acttctggga aaatctttat caactgacat | 1440 |
| tacgtgctgc tgggaaaacg tacatgatat tttttgtatt ggtcattttc ttgggctcat | 1500 |
| tcaacctaat aaatttgatc ctggctgtgg tggccatggc ctacgaggaa cagaatcagg | 1560 |
| ccaccttgga agaagcagaa cagaaagagg ccgaatttca gcagatgatt gaacagctta | 1620 |

| | |
|---|---|
| aaaagcaaca ggaggcagct cagcaggcag caacggcaac tgcctcagaa cattccagag | 1680 |
| agcccagtgc agcaggcagg ctctcagaca gctcatctga agcctctaag ttgagttcca | 1740 |
| agagtgctaa ggaaagaaga aatcggagga agaaagaaa acagaaagag cagtctggtg | 1800 |
| gggaagagaa agatgaggat gaattccaaa aatctgaatc tgaggacagc atcaggagga | 1860 |
| aaggttttcg cttctccatt gaagggaacc gattgacata tgaaagagg tactcctccc | 1920 |
| cacaccagtc tttgttgagc atccgtggct ccctattttc accaaggcga aatagcagaa | 1980 |
| caagcctttt cagctttaga gggcgagcaa aggatgtggg atctgagaac gacttcgcag | 2040 |
| atgatgagca cagcaccttt gaggataacg agagccgtag agattccttg tttgtgcccc | 2100 |
| gacgacacgg agagagacgc aacagcaacc tgagtcagac cagtaggtca tcccggatgc | 2160 |
| tggcagtgtt tccagcgaat gggaagatgc acagcactgt ggattgcaat ggtgtggttt | 2220 |
| ccttggttgg tggaccttca gttcctacat cgcctgttgg acagcttctg ccagaggtga | 2280 |
| taatagataa gccagctact gatgacaatg gaacaaccac tgaaactgaa atgagaaaga | 2340 |
| gaaggtcaag ttcttcccac gtttccatgg actttctaga agatccttcc caaaggcaac | 2400 |
| gagcaatgag tatagccagc attctaacaa atacagtaga agaacttgaa gaatccaggc | 2460 |
| agaaatgccc accctgttgg tataaatttt ccaacatatt cttaatctgg gactgttctc | 2520 |
| catattggtt aaaagtgaaa catgttgtca acctggttgt gatggaccca tttgttgacc | 2580 |
| tggccatcac catctgtatt gtcttaaata ctcttttcat ggccatggag cactatccaa | 2640 |
| tgacggacca tttcaataat gtgcttacag taggaaactt ggttttcact gggatcttta | 2700 |
| cagcagaaat gtttctgaaa attattgcca tggatcctta ctattatttc caagaaggct | 2760 |
| ggaatatctt tgacggtttt attgtgacgc ttagcctggt agaacttgga ctcgccaatg | 2820 |
| tggaaggatt atctgttctc cgttcatttc gattgctgcg agttttcaag ttggcaaaat | 2880 |
| cttggccaac gttaaatatg ctaataaaga tcatcggcaa ttccgtgggg gctctgggaa | 2940 |
| atttaacccct cgtcttggcc atcatcgtct tcattttgc cgtggtcggc atgcagctct | 3000 |
| ttggtaaaag ctacaaagat tgtgtctgca agatcgccag tgattgtcaa ctcccacgct | 3060 |
| ggcacatgaa tgacttcttc cactccttcc tgattgtgtt ccgcgtgctg tgtgggagt | 3120 |
| ggatagagac catgtgggac tgtatggagg ttgctggtca agccatgtgc cttactgtct | 3180 |
| tcatgatggt catggtgatt ggaaacctag tggtcctgaa tctctttctg gccttgcttc | 3240 |
| tgagctcatt tagtgcagac aaccttgcag ccactgatga tgataatgaa atgaataatc | 3300 |
| tccaaattgc tgtgggatagg atgcacaaag gagtagctta tgtgaaaaga aaatatatg | 3360 |
| aatttattca acagtccttc attaggaaac aaaagatttt agatgaaatt aaaccacttg | 3420 |
| atgatctaaa caacaagaaa gacagttgta tgtccaatca tacaacagaa attgggaaag | 3480 |
| atcttgacta tcttaaagat gtaaatggaa ctacaagtgg tataggaact ggcagcagtg | 3540 |
| ttgaaaaata cattattgat gaaagtgatt acatgtcatt cataaacaac cccagtctta | 3600 |
| ctgtgactgt accaattgct gtaggagaat ctgactttga aaatttaaac acggaagact | 3660 |
| ttagtagtga atcggatctg gaagaaagca aagagaaact gaatgaaagc agtagctcat | 3720 |
| cagaaggtag cactgtggac atcggcgcac ctgtagaaga acagcccgta gtggaacctg | 3780 |
| aagaaactct tgaaccagaa gcttgtttca ctgaaggctg tgtacaaaga ttcaagtgtt | 3840 |
| gtcaaatcaa tgtggaagaa ggcagaggaa acaatggtg gaacctgaga aggacgtgtt | 3900 |
| tccgaatagt tgaacataac tggtttgaga ccttcattgt tttcatgatt ctccttagta | 3960 |
| gtggtgctct ggcatttgaa gatatatata ttgatcagcg aaagacgatt aagacgatgt | 4020 |

-continued

```
tggaatatgc tgacaaggtt ttcacttaca ttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agcctatctc gatttgaag    4260 ggatgagggt ggttgtgaat gccctttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctataccctcg accaggaaac aaatttcaag    4860
gaatggtctt tgacttcgta accagacaag ttttttgacat aagcatcatg attctcatct    4920
gtcttaacat ggtcacaatg atggtggaaa cagatgacca gagtgaatat gtgactacca    4980
ttttgtcacg catcaatctg gtgttcattg tgctatttac tggagagtgt gtactgaaac    5040
tcatctctct acgccattat tattttacca ttggatggaa tattttttgat tttgtggttg    5100 tcattctctc cattgtaggt atgtttcttg ccgagctgat agaaaagtat ttcgtgtccc    5160 ctacccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340 tgcctatgt taagagggaa gttgggatcg atgacatgtt caactttgag accttttggca    5400 acagcatgat ctgcctattc caaattacaa cctctgctgg ctgggatgga ttgctagcac    5460
ccattctcaa cagtaagcca cccgactgtg accctaataa agttaaccct ggaagctcag    5520
ttaagggaga ctgtgggaac ccatctgttg gaattttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc cacaaccaaa caaactccag ctcattgcca    5820
tggatttgcc catggtgagt ggtgaccgga tccactgtct tgatatctta tttgctttta    5880
caaagcgggt tctaggagag agtggagaga tggatgctct acgaatacag atggaagagc    5940
gattcatggc ttccaatcct tccaaggtct cctatcagcc aatcactact actttaaaac    6000
gaaaacaaga ggaagtatct gctgtcatta ttcagcgtgc ttacagacgc cacctttaa    6060 agcgaactgt aaaacaagct tcctttacgt acaataaaaa caaatcaaa ggtgggcta    6120 atcttcttat aaaagaagac atgataattg acagaataaa tgaaaactct attacagaaa    6180
aaactgatct gaccatgtcc actgcagctt gtccacctc ctatgaccgg gtgacaaagc    6240
caattgtgga aaaacatgag caagaaggca agatgaaaa agccaagggg aaataaatga    6300
aaataaataa aaataattgg gtgacaaatt gtttacagcc tgtgaaggtg atgtattttt    6360
atcaacagga ctccttagg aggtcaatgc caaactgact gttttttacac aaatctcctt    6420
```

| | |
|---|---|
| aaggtcagtg cctacaataa gacagtgacc ccttgtcagc aaactgtgac tctgtgtaaa | 6480 |
| ggggagatga ccttgacagg aggttactgt tctcactacc agctgacact gctgaagata | 6540 |
| agatgcacaa tggctagtca gactgtaggg accagtttca aggggtgcaa acctgtgatt | 6600 |
| ttggggttgt ttaacatgaa acactttagt gtagtaattg tatccactgt ttgcatttca | 6660 |
| actgccacat ttgtcacatt tttatggaat ctgttagtgg attcatcttt tgttaatcc | 6720 |
| atgtgtttat tatatgtgac tatttttgta aacgaagttt ctgttgagaa ataggctaag | 6780 |
| gacctctata acaggtatgc cacctggggg gtatggcaac cacatggccc tcccagctac | 6840 |
| acaaagtcgt ggtttgcatg agggcatgct gcacttagag atcatgcatg agaaaaagtc | 6900 |
| acaagaaaaa caaattctta aatttcacca tatttctggg aggggtaatt gggtgataag | 6960 |
| tggaggtgct ttgttgatct tgttttgcga aatccagccc ctagaccaag tagattattt | 7020 |
| gtgggtaggc cagtaaatct tagcaggtgc aaacttcatt caaatgtttg gagtcataaa | 7080 |
| tgttatgttt cttttgttg tattaaaaaa aaaacctgaa tagtgaatat tgcccctcac | 7140 |
| cctccaccgc cagaagactg aattgaccaa aattactctt tataaatttc tgcttttcc | 7200 |
| tgcactttgt ttagccatct ttgggctctc agcaaggttg acactgtata tgttaatgaa | 7260 |
| atgctattta ttatgtaaat agtcatttta ccctgtggtg cacgtttgag caaacaaata | 7320 |
| atgacctaag cacagtattt attgcatcaa atatgtacca caagaaatgt agagtgcaag | 7380 |
| ctttacacag gtaataaaat gtattctgta ccatttatag atagtttgga tgctatcaat | 7440 |
| gcatgtttat attaccatgc tgctgtatct ggtttctctc actgctcaga atctcattta | 7500 |
| tgagaaacca tatgtcagtg gtaaagtcaa ggaaattgtt caacagatct catttattta | 7560 |
| agtcattaag caatagtttg cagcacttta acagctttt ggttattttt acattttaag | 7620 |
| tggataacat atggtatata gccagactgt acagacatgt ttaaaaaaac acactgctta | 7680 |
| acctattaaa tatgtgttta gaattttata agcaaatata aatactgtaa aaagtcactt | 7740 |
| tattttattt ttcagcatta tgtacataaa tatgaagagg aaattatctt caggttgata | 7800 |
| tcacaatcac ttttcttact ttctgtccat agtactttt catgaaagaa atttgctaaa | 7860 |
| taagacatga aaacaagact gggtagttgt agatttctgc ttttttaaatt acatttgcta | 7920 |
| attttagatt atttcacaat tttaaggagc aaaataggtt cacgattcat atccaaatta | 7980 |
| tgctttgcaa ttggaaaagg gtttaaaatt ttatttatat ttctggtagt acctgtacta | 8040 |
| actgaattga aggtagtgct tatgttattt ttgttctttt tttctgactt cggtttatgt | 8100 |
| tttcatttct ttggagtaat gctgctctag attgttctaa atagaatgtg ggcttcataa | 8160 |
| ttttttttc cacaaaaaca gagtagtcaa cttatatagt caattacatc aggacatttt | 8220 |
| gtgtttctta cagaagcaaa ccataggctc ctctttcct taaaactact tagataaact | 8280 |
| gtattcgtga actgcatgct ggaaaatgct actattatgc taaataatgc taaccaacat | 8340 |
| ttaaaatgtg caaaactaat aaagattaca ttttttattt t | 8381 |

<210> SEQ ID NO 6
<211> LENGTH: 8381
<212> TYPE: DNA
<213> ORGANISM: Homo sapiens

<400> SEQUENCE: 6

| | |
|---|---|
| atactgcaga ggtctctggt gcatgtgtgt atgtgtgcgt ttgtgtgtgt ttgtgtgtct | 60 |
| gtgtgttctg ccccagtgag actgcagccc ttgtaaatac tttgacacct tttgcaagaa | 120 |
| ggaatctgaa caattgcaac tgaaggcaca ttgttatcat ctcgtctttg ggtgatgctg | 180 |

```
ttcctcactg cagatggata attttccttt taatcaggaa tttcatatgc agaataaatg    240
gtaattaaaa tgtgcaggat gacaagatgg agcaaacagt gcttgtacca ccaggacctg    300
acagcttcaa cttcttcacc agagaatctc ttgcggctat tgaaagacgc attgcagaag    360
aaaaggcaaa gaatcccaaa ccagacaaaa aagatgacga cgaaaatggc ccaaagccaa    420
atagtgactt ggaagctgga aagaaccttc catttattta tggagacatt cctccagaga    480
tggtgtcaga gccctggag gacctggacc cctactatat caataagaaa acttttatag    540
tattgaataa attgaaggcc atcttccggt tcagtgccac ctctgccctg tacattttaa    600
ctcccttcaa tcctcttagg aaaatagcta ttaagatttt ggtacattca ttattcagca    660
tgctaattat gtgcactatt ttgacaaact gtgtgtttat gacaatgagt aaccctcctg    720
attggacaaa gaatgtagaa tacaccttca caggaatata acttttgaa tcacttataa    780 aaattattgc aagggattc tgtttagaag attttacttt ccttcgggat ccatggaact    840
ggctcgattt cactgtcatt acatttgcgt acgtcacaga gtttgtggac ctgggcaatg    900
tctcggcatt gagaacattc agagttctcc gagcattgaa gacgatttca gtcattccag    960
gcctgaaaac cattgtggga gccctgatcc agtctgtgaa gagctctca gatgtaatga   1020 tcctgactgt gttctgtctg agcgtatttg ctctaattgg gctgcagctg ttcatgggca   1080
acctgaggaa taaatgtata caatggcctc ccaccaatgc ttccttggag gaacatagta   1140
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gttrcgacta atgactcagg acttctggga aaatcttat caactgacat   1440 tacgtgctgc tggaaaacg tacatgatat ttttgtatt ggtcattttc ttgggctcat   1500
tctacctaat aaatttgatc ctggctgtgg aggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga atcggagga agaaaagaaa acagaaagag cagtctggtg   1800
gggaagagaa agatgaggat gaattccaaa aatctgaatc tgaggacagc atcaggagga   1860
aaggttttcg cttctccatt gaagggaacc gattgacata tgaaagagg tactcctccc   1920 cacaccagtc tttgttgagc atccgtggct ccctatttc accaaggcga aatagcagaa   1980
caagcctttt cagctttaga gggcgagcaa aggatgtggg atctgagaac gacttcgcag   2040
atgatgagca cagcaccttt gaggataacg agagccgtag agattccttg tttgtgcccc   2100
gacgacacgg agagagacgc aacagcaacc tgagtcagac cagtaggtca tcccggatgc   2160
tggcagtgtt tccagcgaat gggaagatgc acagcactgt ggattgcaat ggtgtggttt   2220
ccttggttgg tggaccttca gttcctacat cgcctgttgg acagcttctg ccagaggtga   2280
taatagataa gccagctact gatgacaatg gaacaaccac tgaaactgaa atgagaaaga   2340
gaaggtcaag ttcttccac gtttccatgg actttctaga gatccttcc caaaggcaac   2400 gagcaatgag tatagccagc attctaacaa atacagtaga agaacttgaa gaatccaggc   2460
agaaatgccc accctgttgg tataaatttt ccaacatatt cttaatctgg gactgttctc   2520
catattggtt aaaagtgaaa catgttgtca acctggttgt gatggaccca tttgttgacc   2580
```

```
tggccatcac catctgtatt gtcttaaata ctctttctcat ggccatggag cactatccaa    2640
tgacggacca tttcaataat gtgcttacag taggaaactt ggttttcact gggatcttta    2700
cagcagaaat gtttctgaaa attattgcca tggatcctta ctattatttc caagaaggct    2760
ggaatatctt tgacggtttt attgtgacgc ttagcctggt agaacttgga ctcgccaatg    2820
tggaaggatt atctgttctc cgttcatttc gattgctgcg agttttcaag ttggcaaaat    2880
cttggccaac gttaaatatg ctaataaaga tcatcggcaa ttccgtgggg gctctgggaa    2940
atttaaccct cgtcttggcc atcatcgtct tcattttgc cgtggtcggc atgcagctct     3000
ttggtaaaag ctacaaagat tgtgtctgca agatcgccag tgattgtcaa ctcccacgct    3060
ggcacatgaa tgacttcttc cactccttcc tgattgtgtt ccgcgtgctg tgtggggagt    3120
ggatagagac catgtgggac tgtatggagg ttgctggtca agccatgtgc cttactgtct    3180
tcatgatggt catggtgatt ggaaacctag tggtcctgaa tctcttcctg gccttgcttc    3240
tgagctcatt tagtgcagac aaccttgcag ccactgatga tgataatgaa atgaataatc    3300
tccaaattgc tgtggatagg atgcacaaag gagtagctta tgtgaaaaga aaaatatatg    3360
aatttattca acagtccttc attaggaaac aaaagatttt agatgaaatt aaaccacttg    3420
atgatctaaa caacaagaaa gacagttgta tgtccaatca tacaacagaa attgggaaag    3480
atcttgacta tcttaaagat gtaaatgaaa ctacaagtgg tataggaact ggcagcagtg    3540
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca agagaaact gaatgaaagc agtagctcat     3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa acaatggtg gaacctgaga aggacgtgtt     3900
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca tttttcattct ggaaatgctt ctaaaatggg   4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agccttatct cgatttgaag    4260
ggatgagggt ggttgtgaat gccccttttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctataccccg accaggaaac aaatttcaag    4860
gaatggtctt tgacttcgta accagacaag ttttgacat aagcatcatg attctcatct     4920
gtcttaacat ggtcacaatg atggtggaaa cagatgacca gagtgaatat gtgactacca    4980
```

-continued

```
ttttgtcacg catcaatctg gtgttcattg tgctatttac tggagagtgt gtactgaaac    5040
tcatctctct acgccattat tattttacca ttggatggaa tatttttgat tttgtggttg    5100
tcattctctc cattgtaggt atgttcttg ccgagctgat agaaaagtat ttcgtgtccc     5160
ctaccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340
ttgcctatgt taagagggaa gttgggatcg atgacatgtt caactttgag acctttggca    5400
acagcatgat ctgcctattc caaattacaa cctctgctgg ctgggatgga ttgctagcac    5460
ccattctcaa cagtaagcca cccgactgtg accctaataa agttaaccct ggaagctcag    5520
ttaagggaga ctgtgggaac ccatctgttg aattttctt ttttgtcagt acatcatca     5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc acaaccaaa caaactccag ctcattgcca    5820
tggatttgcc catggtgagt ggtgaccgga tccactgtct tgatatctta tttgctttta   5880
caaagcgggg tctaggagag agtggagaga tggatgctct acgaatacag atggaagagc    5940
gattcatggc ttccaatcct tccaaggtct cctatcagcc aatcactact actttaaaac    6000
gaaaacaaga ggaagtatct gctgtcatta ttcagcgtgc ttacagacgc cacctttaa    6060
agcgaactgt aaaacaagct tcctttacgt acaataaaaa caaaatcaaa ggtggggcta    6120
atcttcttat aaaagaagac atgataattg acagaataaa tgaaaactct attacagaaa    6180
aaactgatct gaccatgtcc actgcagctt gtccaccttc ctatgaccgg gtgacaaagc    6240
caattgtgga aaaacatgag caagaaggca aagatgaaaa agccaaaggg aaataaatga    6300
aaataaataa aaataattgg gtgacaaatt gtttacagcc tgtgaaggtg atgtattttt    6360
atcaacagga ctcctttagg aggtcaatgc caaactgact gttttacac aaatctcctt    6420
aaggtcagtg cctacaataa gacagtgacc ccttgtcagc aaactgtgac tctgtgtaaa    6480
ggggagatga ccttgacagg aggttactgt tctcactacc agctgacact gctgaagata    6540
agatgcacaa tggctagtca gactgtaggg accagtttca aggggtgcaa acctgtgatt    6600
ttggggttgt ttaacatgaa acactttagt gtagtaattg tatccactgt ttgcatttca    6660
actgccacat ttgtcacatt tttatggaat ctgttagtgg attcatcttt ttgttaatcc    6720
atgtgtttat tatatgtgac tatttttgta aacgaagttt ctgttgagaa ataggctaag    6780
gacctctata acaggtatgc cacctggggg gtatggcaac cacatggccc tcccagctac    6840
acaaagtcgt ggtttgcatg agggcatgct gcacttagag atcatgcatg agaaaaagtc    6900
acaagaaaaa caaattctta aatttcacca tatttctggg aggggtaatt gggtgataag    6960
tggaggtgct ttgttgatct tgtttttgcga aatccagccc ctagaccaag tagattattt    7020
gtgggtaggc cagtaaatct tagcaggtgc aaacttcatt caaatgtttg gagtcataaa    7080
tgttatgttt cttttttgttg tattaaaaaa aaaacctgaa tagtgaatat tgcccctcac    7140
cctccaccgc cagaagactg aattgaccaa aattactctt tataaatttc tgcttttttcc   7200
tgcactttgt ttagccatct ttgggctctc agcaaggttg acactgtata tgttaatgaa    7260
atgctatttta ttatgtaaat agtcatttta ccctgtggtg cacgtttgag caaacaaata   7320
atgacctaag cacagtattt attgcatcaa atatgtacca caagaaatgt agagtgcaag    7380
```

| | | | | |
|---|---|---|---|---|
| ctttacacag | gtaataaaat | gtattctgta | ccatttatag | atagtttgga tgctatcaat | 7440 |
| gcatgtttat | attaccatgc | tgctgtatct | ggtttctctc | actgctcaga atctcattta | 7500 |
| tgagaaacca | tatgtcagtg | gtaaagtcaa | ggaaattgtt | caacagatct catttattta | 7560 |
| agtcattaag | caatagtttg | cagcacttta | acagctttt | ggttatttt acattttaag | 7620 |
| tggataacat | atggtatata | gccagactgt | acagacatgt | ttaaaaaaac acactgctta | 7680 |
| acctattaaa | tatgtgttta | gaattttata | agcaaatata | aatactgtaa aaagtcactt | 7740 |
| tatttattt | ttcagcatta | tgtacataaa | tatgaagagg | aaattatctt caggttgata | 7800 |
| tcacaatcac | ttttcttact | ttctgtccat | agtactttt | catgaaagaa atttgctaaa | 7860 |
| taagacatga | aaacaagact | gggtagttgt | agatttctgc | tttttaaatt acatttgcta | 7920 |
| attttagatt | atttcacaat | tttaaggagc | aaaataggtt | cacgattcat atccaaatta | 7980 |
| tgctttgcaa | ttggaaaagg | gtttaaaatt | ttatttatat | ttctggtagt acctgtacta | 8040 |
| actgaattga | aggtagtgct | tatgttattt | ttgttctttt | tttctgactt cggtttatgt | 8100 |
| tttcatttct | ttggagtaat | gctgctctag | attgttctaa | atagaatgtg ggcttcataa | 8160 |
| tttttttc | cacaaaaaca | gagtagtcaa | cttatatagt | caattacatc aggacatttt | 8220 |
| gtgtttctta | cagaagcaaa | ccataggctc | ctcttttcct | taaaactact tagataaact | 8280 |
| gtattcgtga | actgcatgct | ggaaaatgct | actattatgc | taaataatgc taaccaacat | 8340 |
| ttaaaatgtg | caaaactaat | aaagattaca | tttttattt | t | 8381 |

<210> SEQ ID NO 7
<211> LENGTH: 8381
<212> TYPE: DNA
<213> ORGANISM: Homo sapiens

<400> SEQUENCE: 7

| | | | | |
|---|---|---|---|---|
| atactgcaga | ggtctctggt | gcatgtgtgt | atgtgtgcgt | ttgtgtgtgt ttgtgtgtct | 60 |
| gtgtgttctg | ccccagtgag | actgcagccc | ttgtaaatac | tttgacacct tttgcaagaa | 120 |
| ggaatctgaa | caattgcaac | tgaaggcaca | ttgttatcat | ctcgtctttg ggtgatgctg | 180 |
| ttcctcactg | cagatggata | attttccttt | taatcaggaa | tttcatatgc agaataaatg | 240 |
| gtaattaaaa | tgtgcaggat | gacaagatgg | agcaaacagt | gcttgtacca ccaggacctg | 300 |
| acagcttcaa | cttcttcacc | agagaatctc | ttgcggctat | tgaaagacgc attgcagaag | 360 |
| aaaaggcaaa | gaatcccaaa | ccagacaaaa | aagatgacga | cgaaaatggc ccaaagccaa | 420 |
| atagtgactt | ggaagctgga | aagaaccttc | catttattta | tggagacatt cctccagaga | 480 |
| tggtgtcaga | gcccctggag | gacctggacc | cctactatat | caataagaaa actttttatag | 540 |
| tattgaataa | attgaaggcc | atcttccggt | tcagtgccac | ctctgccctg tacattttaa | 600 |
| ctcccttcaa | tcctcttagg | aaaatagcta | ttaagatttt | ggtacattca ttattcagca | 660 |
| tgctaattat | gtgcactatt | ttgacaaact | gtgtgtttat | gacaatgagt aaccctcctg | 720 |
| attggacaaa | gaatgtagaa | tacaccttca | caggaatata | tactttgaa tcacttataa | 780 |
| aaattattgc | aaggggattc | tgtttagaag | attttacttt | ccttcgggat ccatggaact | 840 |
| ggctcgattt | cactgtcatt | acatttgcgt | acgtcacaga | gtttgtggac ctgggcaatg | 900 |
| tctcggcatt | gagaacattc | agagttctcc | gagcattgaa | gacgatttca gtcattccag | 960 |
| gcctgaaaac | cattgtggga | gccctgatcc | agtctgtgaa | gaagctctca gatgtaatga | 1020 |
| tcctgactgt | gttctgtctg | agcgtatttg | ctctaattgg | gctgcagctg ttcatgggca | 1080 |
| acctgaggaa | taaatgtata | caatggcctc | ccaccaatgc | ttccttggag gaacatagta | 1140 |

```
tagaaaagaa tataactgtg aattataatg gtacacttat aaatgaaact gtctttgagt      1200
ttgactggaa gtcatatatt caagattcaa gatatcatta tttcctggag ggttttttag      1260
atgcactact atgtggaaat agctctgatg caggccaatg tccagaggga tatatgtgtg      1320
tgaaagctgg tagaaatccc aattatggct acacaagctt tgataccttc agttgggctt      1380
ttttgtcctt gtttcgacta atgactcagg acttctggga aaatctttat caactgacat      1440
tacgtgctgc tgggaaaacg tacatgatat tttttgtatt ggtcattttc ttgggctcat      1500
tctacctaat aaatttgatc ctggctgtgg tggccatggc ctacgaggaa cagaatcagg      1560
ccaccttgga agaagcagaa cagaaagagg ccgaatttca gcagatgatt gaacagctta      1620
aaaagcaaca ggaggcagct cagcaggcag caacggcaac tgcctcagaa cattccagag      1680
agcccagtgc agcaggcagg ctctcagaca gctcatctga agcctctaag ttgagttcca      1740
agagtgctaa ggaaagaaga aatcggagga agaaaagaaa acagaaagag cagtctggtg      1800
gggaagagaa agatgaggat gaattccaaa aatctgaatc tgaggacagc atcaggagga      1860
aaggttttcg cttctccatt gaagggaacc gattgacata tgaaaagagg tactcctccc      1920
cacaccagtc tttgttgagc atccgtggct ccctattttc accaaggcga aatagcagaa      1980
caagcctttt cagctttaga gggcgagcaa aggatgtggg atctgagaac gacttcgcag      2040
atgatgagca cagcaccttt gaggataacg agagccgtag agattccttg tttgtgcccc      2100
gacgacacgg agagagacgc aacagcaacc tgagtcagac cagtaggtca tcccggatgc      2160
tggcagtgtt tccagcgaat gggaagatgc acagcactgt ggattgcaat ggtgtggttt      2220
ccttggttgg tggaccttca gttcctacat cgcctgttgg acagcttctg ccagaggtga      2280
taatagataa gccagctact gatgacaatg gaacaaccac tgaaactgaa atgagaaaga      2340
gaaggtcaag ttctttccac gtttccatgg actttctaga agatccttcc caaaggcaac      2400
gagcaatgag tatagccagc attctaacaa atacagtaga agaacttgaa gaatccaggc      2460
agaaatgccc accctgttgg tataaatttt ccaacatatt cttaatctgg gactgttctc      2520
catattggtt aaaagtgaaa catgttgtca acctggttgt gatggaccca tttgttgacc      2580
tggccatcac catctgtatt gtcttaaata ctcttttcat ggccatggag cactatccaa      2640
tgacggacca tttcaataat gtgcttacag taggaaactt ggttttcact gggatcttta      2700
cagcagaaat gtttctgaaa attattgcca tggatcctta ctattatttc caagaaggct      2760
ggaatatctt tgacggtttt attgtgacgc ttagcctggt agaacttgga ctcgccaatg      2820
tggaaggatt atctgttctc cgttcatttc gattgctgcg agttttcaag ttggcaaaat      2880
cttggccaac gttaaatatg ctaataaaga tcatcggcaa ttccgtgggg gctctgggaa      2940
atttaaccct cgtcttggcc atcatcgtct catttttgc cgtggtcggc atgcagctct      3000
ttggtaaaag ctacaaagat tgtgtctgca agatcgccag tgattgtcaa ctcccacgct      3060
ggcacatgaa tgacttcttc cactccttcc tgattgtgtt ccgcgtgctg tgtgggagt      3120 ggatagagac catgtgggac tgtatggagg ttgctggtca agccatgtgc cttactgtct      3180
tcatgatggt catggtgatt ggaaacctag tggtcctgaa tctctttctg gccttgcttc      3240
tgagctcatt tagtgcagac aaccttgcag ccactgatga tgataatgaa atgaataatc      3300
tccaaattgc tgtggatagg atgcacaaag gagtagctta tgtgaaaaga aaatatatg       3360 aatttattca acagtccttc attaggaaac aaaagatttt agatgaaatt aaaccacttg      3420
atgatctaaa caacaagaaa gacagttgta tgtccaatca tacaacagaa attgggaaag      3480
atcttgacta tcttaaagat gtaaatggaa ctacaagtgg tataggaact ggcagcagtg      3540
```

```
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca aagagaaact gaatgaaagc agtagctcat    3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa acaatggtg gaacctgaga aggacgtgtt    3900
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca ttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agccttatct cgatttgaag    4260
ggatgagggt ggttgtgaat gccctttttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgcttgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctatacctcg accaggaaac aaatttcaag    4860
gaatggtctt tgacttcgta accagacaag ttttttgacat aagcatcatg attctcatct    4920
gtcttaacat ggtcacaatg atggtggaaa cagatgacca gagtgaatat gtgactacca    4980
ttttgtcacg catcaatctg gtgttcattg tgctatttac tggagagtgt gtactgaaac    5040
tcatctctct acgccattat tattttacca ttggatggaa tattttttgat tttgtggttg    5100
tcattctctc cattgtaggt atgtttcttg ccgagctgat agaaaagtat ttcgtgtccc    5160
ctaccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340
ttgcctatgt taagagggaa gttgggatcg atgacatgtt caactttgag acctttggca    5400
acagcatgat ctgcctattc caaattacaa cctctgctgg ctgggatgga ttgctagcac    5460
ccattctcaa cagtaagcca cccgactgtg accctaataa agttaaccct ggaagctcag    5520
ttaagggaga ctgtgggaac ccatctgttg gaattttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc cacaaccaaa caaactccag ctcattgcca    5820
tggatttgcc catggtgagt ggtgaccgga tccactgtct tgatatctta tttgcttta    5880
caaagcgggt tctaggagag agtggagaga tggatgctct acgaatacag atggaagagc    5940
```

```
gattcatggc ttccaatcct tccaaggtct cctatcagcc aatcactact actttaaaac    6000
gaaaacaaga ggaagtatct gctgtcatta ttcagcgtgc ttacagacgc cacctttttaa   6060 agcgaactgt aaaacaagct tcctttacgt acaataaaaa caaaatcaaa ggtggggcta    6120
atcttcttat aaaagaagac atgataattg acagaataaa tgaaaactct attacagaaa    6180
aaactgatct gaccatgtcc actgcagctt gtccaccttc ctatgaccgg gtgacaaagc    6240
caattgtgga aaaacatgag caagaaggca agatgaaaaa agccaaaggg aaataaatga    6300
aaataaataa aataattgg gtgacaaatt gtttacagcc tgtgaaggtg atgtattttt     6360
atcaacagga ctcctttagg aggtcaatgc caaactgact gttttttacac aaatctcctt   6420 aaggtcagtg cctacaataa gacagtgacc ccttgtcagc aaactgtgac tctgtgtaaa    6480
ggggagatga ccttgacagg aggttactgt tctcactacc agctgacact gctgaagata    6540
agatgcacaa tggctagtca gactgtaggg accagtttca aggggtgcaa acctgtgatt    6600
ttggggttgt ttaacatgaa acactttagt gtagtaattg tatccactgt ttgcatttca    6660
actgccacat ttgtcacatt tttatggaat ctgttagtgg attcatcttt ttgttaatcc    6720
atgtgtttat tatatgtgac tatttttgta aacgaagttt ctgttgagaa ataggctaag    6780
gacctctata acaggtatgc cacctggggg gtatggcaac cacatggccc tcccagctac    6840
acaaagtcgt ggtttgcatg agggcatgct gcacttagag atcatgcatg agaaaaagtc    6900
acaagaaaaa caaattctta aatttcacca tatttctggg aggggtaatt gggtgataag    6960
tggaggtgct ttgttgatct tgttttgcga aatccagccc ctagaccaag tagattattt    7020
gtgggtaggc cagtaaatct tagcaggtgc aaacttcatt caaatgtttg gagtcataaa    7080
tgttatgttt cttttttgttg tattaaaaaa aaaacctgaa tagtgaatat tgcccctcac    7140
cctccaccgc cagaagactg aattgaccaa aattactctt tataaatttc tgctttttcc    7200
tgcactttgt ttagccatct ttgggctctc agcaaggttg acactgtata tgttaatgaa    7260 atgctatttta ttatgtaaat agtcatttta ccctgtggtg cacgtttgag caaacaaata   7320
atgacctaag cacagtattt attgcatcaa atatgtacca caagaaatgt agagtgcaag    7380
ctttacacag gtaataaaat gtattctgta ccatttatag atagtttgga tgctatcaat    7440
gcatgtttat attaccatgc tgctgtatct ggtttctctc actgctcaga atctcattta    7500
tgagaaacca tatgtcagtg gtaaagtcaa ggaaattgtt caacagatct catttatttca   7560 agtcattaag caatagtttg cagcactttta acagcttttt ggttattttt acattttaag   7620
tggataacat atggtatata gccagactgt acagacatgt ttaaaaaaac acactgctta    7680
acctattaaa tatgtgttta gaattttata agcaaatata aatactgtaa aaagtcactt    7740 tatttttattt ttcagcatta tgtacataaa tatgaagagg aaattatctt caggttgata   7800
tcacaatcac ttttcttact ttctgtccat agtactttt catgaaagaa atttgctaaa     7860
taagacatga aaacaagact gggtagttgt agatttctgc ttttttaaatt acatttgcta   7920 atttttagatt atttcacaat tttaaggagc aaaataggtt cacgattcat atccaaatta   7980
tgctttgcaa ttggaaaagg gtttaaaatt ttatttatat ttctggtagt acctgtacta    8040
actgaattga aggtagtgct tatgttattt ttgttctttt tttctgactt cggtttatgt    8100
tttcatttct ttggagtaat gctgctctag attgttctaa atagaatgtg gcttcataa     8160 ttttttttc cacaaaaaca gagtagtcaa cttatatagt caattacatc aggacatttt     8220
gtgtttctta cagaagcaaa ccataggctc ctctttttcct taaaactact tagataaact   8280
gtattcgtga actgcatgct ggaaaatgct actattatgc taaataatgc taaccaacat    8340
```
ttaaaatgtg caaaactaat aaagattaca tttttttattt t    8381

<210> SEQ ID NO 8
<211> LENGTH: 8381
<212> TYPE: DNA
<213> ORGANISM: Homo sapiens

<400> SEQUENCE: 8

```
atactgcaga ggtctctggt gcatgtgtgt atgtgtgcgt ttgtgtgtgt ttgtgtgtct     60
gtgtgttctg ccccagtgag actgcagccc ttgtaaatac tttgacacct tttgcaagaa    120
ggaatctgaa caattgcaac tgaaggcaca ttgttatcat ctcgtctttg ggtgatgctg    180
ttcctcactg cagatggata attttccttt taatcaggaa tttcatatgc agaataaatg    240
gtaattaaaa tgtgcaggat gacaagatgg agcaaacagt gcttgtacca ccaggacctg    300
acagcttcaa cttcttcacc agagaatctc ttgcggctat tgaaagacgc attgcagaag    360
aaaaggcaaa gaatcccaaa ccagacaaaa aagatgacga cgaaaatggc ccaaagccaa    420
atagtgactt ggaagctgga aagaaccttc catttattta tggagacatt cctccagaga    480
tggtgtcaga gcccctggag gacctggacc cctactatat caataagaaa acttttatag    540
tattgaataa attgaaggcc atcttccggt tcagtgccac ctctgccctg tacattttaa    600
ctccccttcaa tcctcttagg aaaatagcta ttaagatttt ggtacattca ttattcagca    660
tgctaattat gtgcactatt ttgacaaact gtgtgtttat gacaatgagt aaccctcctg    720
attggacaaa gaatgtagaa tacaccttca caggaatata cttttttgaa tcacttataa    780
aaattattgc aagggggattc tgtttagaag attttacttt ccttcgggat ccatggaact    840
ggctcgattt cactgtcatt acatttgcgt acgtcacaga gtttgtggac ctgggcaatg    900
tctcggcatt gagaacattc agagttctcc gagcattgaa gacgatttca gtcattccag    960
gcctgaaaac cattgtggga gccctgatcc agtctgtgaa gaagctctca gatgtaatga   1020
tcctgactgt gttctgtctg agcgtatttg ctctaattgg gctgcagctg ttcatgggca   1080
acctgaggaa taaatgtata caatggcctc ccaccaatgc ttccttggag gaacatagta   1140
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gtttcgacta atgactcagg acttctggga aaatctttat caactgacat   1440
tacgtgctgc tgggaaaacg tacatgatat ttttttgtatt ggtcatttc ttgggctcat   1500
tctacctaat aaatttgatc ctggctgtgg tggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga aatcggagga gaaaagaaa acagaaagag cagtctggtg   1800
gggaagagaa agatgaggat gaattccaaa aatctgaatc tgaggacagc atcaggagga   1860
aaggttttcg cttctccatt gaagggaacc gattgacata tgaaaagagg tactcctccc   1920
cacaccagtc tttgttgagc atccgtggct ccctatttc accaaggcga aatagcagaa   1980
caagccttt cagctttaga gggcgagcaa aggatgtggg atctgagaac gacttcgcag   2040
atgatgagca cagcaccttt gaggataacg agagccgtag agattccttg tttgtgcccc   2100
```

```
gacgacacgg agagagacgc aacagcaacc tgagtcagac cagtaggtca tcccggatgc    2160
tggcagtgtt tccagcgaat gggaagatgc acagcactgt ggattgcaat ggtgtggttt    2220
ccttggttgg tggaccttca gttcctacat cgcctgttgg acagcttctg ccagaggtga    2280
taatagataa gccagctact gatgacaatg aacaaccac tgaaactgaa atgagaaaga     2340
gaaggtcaag ttcttccac gtttccatgg actttctaga agatccttcc caaaggcaac    2400
gagcaatgag tatagccagc attctaacaa atacagtaga agaacttgaa gaatccaggc    2460
agaaatgccc accctgttgg tataaatttt ccaacatatt cttaatctgg gactgttctc    2520
catattggtt aaaagtgaaa catgttgtca acctggttgt gatggaccca tttgttgacc    2580
tggccatcac catctgtatt gtcttaaata ctcttttcat ggccatggag cactatccaa    2640
tgacggacca tttcaataat gtgcttacag taggaaactt ggttttcact gggatcttta    2700
cagcagaaat gtttctgaaa attattgcca tggatcctta ctattatttc caagaaggct    2760
ggaatatctt tgacggtttt attgtgacgc ttagcctggt agaacttgga ctcgccaatg    2820
tggaaggatt atctgttctc cgttcatttc gattgctgcg agttttcaag ttggcaaaat    2880
cttggccaac gttaaatatg ctaataaaga tcatcggcaa ttccgtgggg gctctgggaa    2940 atttaacccct cgtcttggcc atcatcgtct tcattttttgc cgtggtcggc atgcagctct    3000
ttggtaaaag ctacaaagat tgtgtctgca agatcgccag tgattgtcaa ctcccacgct    3060
ggcacatgaa tgacttcttc cactccttcc tgattgtgtt ccgcgtgctg tgtggggagt    3120
ggatagagac catgtgggac tgtatggagg ttgctggtca agccatgtgc cttactgtct    3180
tcatgatggt catggtgatt ggaaacctag tggtcctgaa tctcttctg gccttgcttc     3240 tgagctcatt tagtgcagac aaccttgcag ccactgatga tgataatgaa atgaataatc    3300
tccaaattgc tgtggatagg atgcacaaag gagtagctta tgtgaaaaga aaaatatatg    3360
aatttattca acagtccttc attaggaaac aaaagatttt agatgaaatt aaaccacttg    3420
atgatctaaa caacaagaaa gacagttgta tgtccaatca tacaacagaa attgggaaag    3480
atcttgacta tcttaaagat gtaaatggaa ctacaagtgg tataggaact ggcagcagtg    3540
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca aagagaaact gaatgaaagc agtagctcat    3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa aacaatggtg gaacctgaga aggacgtgtt    3900
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca ttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agccttatct cgatttgaag    4260
ggatgagggt ggttgtgaat gcccttttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
```

```
aagtaaactt tgataatgta ggatttgggt atctctcttt gcttcaagtt gccacattca   4560
aaggatggat ggatataatg tatgcagcag ttgattccag aaatgtggaa ctccagccta   4620
agtatgaaaa aagtctgtac atgtatcttt actttgttat tttcatcatc tttgggtcct   4680
tcttcacctt gaacctgttt attggtgtca tcatagataa tttcaaccag cagaaaaga   4740 agtttggagg tcaagacatc tttatgacag aagaacagaa gaaatactat aatgcaatga   4800
aaaaattagg atcgaaaaaa ccgcaaaagc ctatacctcg accaggaaac aaatttcaag   4860
gaatggtctt tgacttcgta accagacaag ttttgacat aagcatcatg attctcatct    4920
gtcttaacat ggtcacaatg atggtggaaa cagatgacca gagtgaatat gtgactacca   4980
ttttgtcacg catcaatctg tgttcattg tgctatttac tggagagtgt gtactgaaac    5040
tcatctctct acgccattat tatttacca ttggatggaa tattttgat tttgtggttg      5100 tcattctctc cattgtaggt atgtttcttg ccgagctgat agaaaagtat tcgtgtccc    5160 ctaccctgtt ccgagtgatc cgtcttgcta ggattggccg aatcctacgt ctgatcaaag   5220
gagcaagggg atccgcacg ctgctctttg ctttgatgat gtccttcct gcgttgttta    5280 acatcggcct cctactcttc ctagtcatgt tcatctacgc catctttggg atgtccaact   5340
ttgcctatgt taagagggaa gttgggatcg atgacatgtt caactttgag accttttggca  5400 acagcatgat ctgcctattc caaattacaa cctctgctgg ctgggatgga ttgctagcac   5460
ccattctcaa cagtaagcca cccgactgtg accctaataa agttaaccct ggaagctcag   5520
ttaagggaga ctgtgggaac ccatctgttg gaatttctct tttgtcagt tacatcatca    5580 tatccttcct ggttgtggtg aacacgtaca tcgcggtcat cctggagaac ttcagtgttg   5640
ctactgaaga aagtgcagag cctctgagtg aggatgactt tgagatgttc tatgaggttt   5700
gggagaagtt tgatcccgat gcaactcagt tcatggaatt tgaaaaatta tctcagtttg   5760
cagctgcgct tgaaccgcct ctcaatctgc cacaaccaaa caaactccag ctcattgcca   5820
tggatttgcc catggtgagt ggtgaccgga tccactgtct tgatatctta tttgcttta    5880 caaagcgggt tctaggagag agtggagaga tggatgctct acgaatacag atggaagagc   5940
gattcatggc ttccaatcct tccaaggtct cctatcagcc aatcactact actttaaaac   6000
gaaaacaaga ggaagtatct gctgtcatta ttcagcgtgc ttacagacgc cacctttta    6060 agcgaactgt aaaacaagct tcctttacgt acaataaaaa caaatcaaa ggtgggcta    6120 atcttcttat aaaagaagac atgataattg acagaataaa tgaaaactct attacagaaa   6180
aaactgatct gaccatgtcc actgcagctt gtccaccttc ctatgaccgg gtgacaaagc   6240
caattgtgga aaaacatgag caagaaggca agatgaaaa agccaaaggg aaataaatga   6300
aaataaataa aaataattgg gtgacaaatt gtttacagcc tgtgaaggtg atgtattttt    6360
atcaacagga ctcctttagg aggtcaatgc caaactgact gtttttacac aaatctcctt   6420
aaggtcagtg cctacaataa gacagtgacc ccttgtcagc aaactgtgac tctgtgtaaa   6480
ggggagatga ccttgacagg aggttactgt tctcactacc agctgacact gctgaagata   6540
agatgcacaa tggctagtca gactgtaggg accagtttca aggggtgcaa acctgtgatt   6600 ttgggttgt ttaacatgaa acactttagt gtagtaattg tatccactgt ttgcatttca    6660
actgccacat ttgtcacatt tttatggaat ctgttagtgg attcatcttt ttgttaatcc   6720
atgtgtttat tatatgtgac tattttgta aacgaagttt ctgttgagaa ataggctaag     6780
gacctctata acaggtatgc cacctggggg gtatggcaac cacatggccc tcccagctac   6840
acaaagtcgt ggtttgcatg agggcatgct gcacttagag atcatgcatg agaaaaagtc   6900
```

-continued

| | |
|---|---|
| acaagaaaaa caaattctta aatttcacca tatttctggg aggggtaatt gggtgataag | 6960 |
| tggaggtgct ttgttgatct tgttttgcga aatccagccc ctagaccaag tagattattt | 7020 |
| gtgggtaggc cagtaaatct tagcaggtgc aaacttcatt caaatgtttg gagtcataaa | 7080 |
| tgttatgttt cttttgttg tattaaaaaa aaaacctgaa tagtgaatat tgcccctcac | 7140 |
| cctccaccgc cagaagactg aattgaccaa aattactctt tataaatttc tgcttttcc | 7200 |
| tgcactttgt ttagccatct ttgggctctc agcaaggttg acactgtata tgttaatgaa | 7260 |
| atgctattta ttatgtaaat agtcatttta ccctgtggtg cacgtttgag caaacaaata | 7320 |
| atgacctaag cacagtattt attgcatcaa atatgtacca caagaaatgt agagtgcaag | 7380 |
| ctttacacag gtaataaaat gtattctgta ccatttatag atagtttgga tgctatcaat | 7440 |
| gcatgtttat attaccatgc tgctgtatct ggtttctctc actgctcaga atctcattta | 7500 |
| tgagaaacca tatgtcagtg gtaaagtcaa ggaaattgtt caacagatct catttattta | 7560 |
| agtcattaag caatagtttg cagcacttta acagcttttt ggttattttt acatttaag | 7620 |
| tggataacat atggtatata gccagactgt acagacatgt ttaaaaaaac acactgctta | 7680 |
| acctattaaa tatgtgttta gaattttata agcaaatata aatactgtaa aaagtcactt | 7740 |
| tatttatt ttcagcatta tgtacataaa tatgaagagg aaattatctt caggttgata | 7800 |
| tcacaatcac ttttcttact ttctgtccat agtactttt catgaaagaa atttgctaaa | 7860 |
| taagacatga aaacaagact gggtagttgt agatttctgc ttttaaatt acatttgcta | 7920 |
| attttagatt atttcacaat tttaaggagc aaaataggtt cacgattcat atccaaatta | 7980 |
| tgctttgcaa ttggaaaagg gtttaaaatt ttatttatat ttctggtagt acctgtacta | 8040 |
| actgaattga aggtagtgct tatgttattt ttgttctttt tttctgactt cggtttatgt | 8100 |
| tttcatttct ttggagtaat gctgctctag attgttctaa atagaatgtg ggcttcataa | 8160 |
| ttttttttc cacaaaaaca gagtagtcaa cttatatagt caattacatc aggacatttt | 8220 |
| gtgtttctta cagaagcaaa ccataggctc ctctttcct taaaactact tagataaact | 8280 |
| gtattcgtga actgcatgct ggaaaatgct actattatgc taaataatgc taaccaacat | 8340 |
| ttaaaatgtg caaaactaat aaagattaca tttttatttt t | 8381 |

<210> SEQ ID NO 9
<211> LENGTH: 8381
<212> TYPE: DNA
<213> ORGANISM: Homo sapiens

<400> SEQUENCE: 9

| | |
|---|---|
| atactgcaga ggtctctggt gcatgtgtgt atgtgtgcgt ttgtgtgtgt ttgtgtgtct | 60 |
| gtgtgttctg ccccagtgag actgcagccc ttgtaaatac tttgacacct tttgcaagaa | 120 |
| ggaatctgaa caattgcaac tgaaggcaca ttgttatcat ctcgtctttg ggtgatgctg | 180 |
| ttcctcactg cagatggata attttccttt taatcaggaa tttcatatgc agaataaatg | 240 |
| gtaattaaaa tgtgcaggat gacaagatgg agcaaacagt gcttgtacca ccaggacctg | 300 |
| acagcttcaa cttcttcacc agagaatctc ttgcggctat tgaaagacgc attgcagaag | 360 |
| aaaaggcaaa gaatcccaaa ccagacaaaa aagatgacga cgaaaatggc ccaaagccaa | 420 |
| atagtgactt ggaagctgga aagaaccttc catttattta tggagacatt cctccagaga | 480 |
| tggtgtcaga gcccctggag gacctggacc cctactatat caataagaaa acttttatag | 540 |
| tattgaataa attgaaggcc atcttccggt tcagtgccac ctctgccctg tacattttaa | 600 |
| ctcccttcaa tcctcttagg aaaatagcta ttaagatttt ggtacattca ttattcagca | 660 |

-continued

```
tgctaattat gtgcactatt ttgacaaact gtgtgtttat gacaatgagt aaccctcctg    720
attggacaaa gaatgtagaa tacaccttca caggaatata tacttttgaa tcacttataa    780
aaattattgc aagggqattc tgtttagaag attttacttt ccttcgggat ccatggaact    840
ggctcgattt cactgtcatt acatttgcgt acgtcacaga gtttgtggac ctgggcaatg    900
tctcggcatt gagaacattc agagttctcc gagcattgaa gacgatttca gtcattccag    960
gcctgaaaac cattgtggga gccctgatcc agtctgtgaa gaagctctca gatgtaatga   1020
tcctgactgt gttctgtctg agcgtatttg ctctaattgg gctgcagctg ttcatgggca   1080
acctgaggaa taaatgtata caatggcctc ccaccaatgc ttccttggag gaacatagta   1140
tagaaaagaa tataactgtg aattataatg gtacacttat aaatgaaact gtctttgagt   1200
ttgactggaa gtcatatatt caagattcaa gatatcatta tttcctggag ggttttttag   1260
atgcactact atgtggaaat agctctgatg caggccaatg tccagaggga tatatgtgtg   1320
tgaaagctgg tagaaatccc aattatggct acacaagctt tgataccttc agttgggctt   1380
ttttgtcctt gtttcgacta atgactcagg acttctggga aaatctttat caactgacat   1440
tacgtgctgc tgggaaaacg tacatgatat ttttttgtatt ggtcatttc ttgggctcat   1500 tctacctaat aaatttgatc ctggctgtgg tggccatggc ctacgaggaa cagaatcagg   1560
ccaccttgga agaagcagaa cagaaagagg ccgaatttca gcagatgatt gaacagctta   1620
aaaagcaaca ggaggcagct cagcaggcag caacggcaac tgcctcagaa cattccagag   1680
agcccagtgc agcaggcagg ctctcagaca gctcatctga agcctctaag ttgagttcca   1740
agagtgctaa ggaaagaaga aatcggagga agaaaagaaa acagaaagag cagtctggtg   1800
gggaagagaa agatgaggat gaattccaaa aatctgaatc tgaggacagc atcaggagga   1860
aaggttttcg cttctccatt gaagggaacc gattgacata tgaaaagagg tactcctccc   1920
cacaccagtc tttgttgagc atccgtggct ccctattttc accaaggcga aatagcagaa   1980
caagcctttt cagctttaga gggcgagcaa aggatgtggg atctgagaac gacttcgcag   2040
atgatgagca cagcaccttt gaggataacg agagccgtag agattccttg tttgtgcccc   2100
gacgacacgg agagagacgc aacagcaacc tgagtcagac cagtaggtca tcccggatgc   2160
tggcagtgtt tccagcgaat gggaagatgc acagcactgt ggattgcaat ggtgtggttt   2220
ccttggttgg tggaccttca gttcctacat cgcctgttgg acagcttctg ccagaggtga   2280
taatagataa gccagctact gatgacaatg gaacaaccac tgaaactgaa atgagaaaga   2340
gaaggtcaag ttctttccac gtttccatgg actttctaga gatccttcc caaaggcaac   2400 gagcaatgag tatagccagc attctaacaa atacagtaga gaacttgaa gaatccaggc   2460 agaaatgccc accctgttgg tataaatttt ccaacatatt cttaatctgg gactgttctc   2520
catattggtt aaaagtgaaa catgttgtca acctggttgt gatggaccca tttgttgacc   2580
tggccatcac catctgtatt gtcttaaata ctctttcat ggccatggag cactatccaa   2640
tgacggacca tttcaataat gtgcttacag taggaaactt ggttttcact gggatcttta   2700
cagcagaaat gttctgaaa attattgcca tggatcctta ctattatttc caagaaggct   2760
ggaatatctt tgacggtttt attgtgacgc ttagcctggt agaacttgga ctcgccaatg   2820
tggaaggatt atctgttctc cgttcatttc gattgctgcg agttttcaag ttggcaaaat   2880
cttggccaac gttaaatatg ctaataaaga tcatcggcaa ttccgtgggg gctctgggaa   2940
atttaaccct cgtcttggcc atcatcgtct tcattttgc cgtggtcggc atgcagctct   3000
ttggtaaaag ctacaaagat tgtgtctgca agatcgccag tgattgtcaa ctcccacgct   3060
```

```
ggcacatgaa tgacttcttc cactccttcc tgattgtgtt ccgcgtgctg tgtggggagt      3120
ggatagagac catgtgggac tgtatggagg ttgctggtca agccatgtgc cttactgtct      3180
tcatgatggt catggtgatt ggaaacctag tggtcctgaa tctctttctg gccttgcttc      3240
tgagctcatt tagtgcagac aaccttgcag ccactgatga tgataatgaa atgaataatc      3300
tccaaattgc tgtggatagg atgcacaaag gagtagctta tgtgaaaaga aaaatatatg      3360
aatttattca acagtccttc attaggaaac aaaagatttt agatgaaatt aaaccacttg      3420
atgatctaaa caacaagaaa gacagttgta tgtccaatca tacaacagaa attgggaaag      3480
atcttgacta tcttaaagat gtaaatgaaa ctacaagtgg tataggaact ggcagcagtg      3540
ttgaaaaata cattattgat gaaagtgatt acatgtcatt cataaacaac cccagtctta      3600
ctgtgactgt accaattgct gtaggagaat ctgactttga aaatttaaac acggaagact      3660
ttagtagtga atcggatctg gaagaaagca agagaaact gaatgaaagc agtagctcat      3720
cagaaggtag cactgtggac atcggcgcac ctgtagaaga acagcccgta gtggaacctg      3780
aagaaactct tgaaccagaa gcttgtttca ctgaaggctg tgtacaaaga ttcaagtgtt      3840
gtcaaatcaa tgtggaagaa ggcagaggaa acaatggtg gaacctgaga aggacgtgtt      3900
tccgaatagt tgaacataac tggtttgaga ccttcattgt tttcatgatt ctccttagta      3960
gtggtgctct ggcatttgaa gatatatata ttgatcagcg aaagacgatt aagacgatgt      4020
tggaatatgc tgacaaggtt ttcacttaca ttttcattct ggaaatgctt ctaaaatggg      4080
tggcatatgg ctatcaaaca tatttcacca atgcctggtg ttggctggac ttcttaattg      4140
ttgatgtttc attggtcagt ttaacagcaa atgccttggg ttactcagaa cttggagcca      4200
tcaaatctct caggacacta agagctctga gacctctaag agcttatct cgatttgaag      4260 ggatgagggt ggttgtgaat gccctttag gagcaattcc atccatcatg aatgtgcttc      4320
tggtttgtct tatattctgg ctaatttttca gcatcatggg cgtaaatttg tttgctggca      4380
aattctacca ctgtattaac accacaactg gtgacaggtt tgacatcgaa gacgtgaata      4440
atcatactga ttgcctaaaa ctaatagaaa gaaatgagac tgctcgatgg aaaaatgtga      4500
aagtaaactt tgataatgta ggatttgggt atctctcttt gcttcaagtt gccacattca      4560
aaggatggat ggatataatg tatgcagcag ttgattccag aaatgtggaa ctccagccta      4620
agtatgaaaa aagtctgtac atgtatcttt actttgttat tttcatcatc tttgggtcct      4680 tcttcaccctt gaacctgttt attggtgtca tcatagataa tttcaaccag cagaaaaaga      4740
agtttggagg tcaagacatc tttatgacag aagaacagaa gaaatactat aatgcaatga      4800
aaaaattagg atcgaaaaaa ccgcaaaagc ctatacctcg accaggaaac aaatttcaag      4860
gaatggtctt tgacttcgta accagacaag tttttgacat aagcatcatg attctcatct      4920
gtcttaacat ggtcacaatg atggtggaaa cagatgacca gagtgaatat gtgactacca      4980
ttttgtcacg catcaatctg gtgttcattg tgctatttac tggagagtgt gtactgaaac      5040
tcatctctct acgccattat tattttacca ttggatggaa tatttttgat tttgtggttg      5100
tcattctctc cattgtaggt atgtttcttg ccgagctgat agaaagtat ttcgtgtccc      5160 ctaccctgtt ccgagtgatc cgtcttgcta ggattggccg aatcctacgt ctgatcaaag      5220
gagcaagggg gatccgcacg ctgctctttg ctttgatgat gtcccttcct gcgttgttta      5280
acatcggcct cctactcttc ctagtcatgt tcatctacgc catctttggg atgtccaact      5340
ttgcctatgt taagagggaa gttgggatcg atgacatgtt caactttgag accttggca      5400 acagcatgat ctgcctattc caaattacaa cctctgctgg ctgggatgga ttgctagcac      5460
```

-continued

```
ccattctcaa cagtaagcca cccgactgtg accctaataa agttaaccct ggaagctcag    5520
ttaagggaga ctgtgggaac ccatctgttg gaatttttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc acaaccaaa caaactccag ctcattgcca    5820
tggatttgcc catggtgagt ggtgaccgga tccactgtct tgatatctta tttgctttta    5880
caaagcgggt tctaggagag agtggagaga tggatgctct acgaatacag atggaagagt    5940
gattcatggc ttccaatcct tccaaggtct cctatcagcc aatcactact actttaaaac    6000
gaaaacaaga ggaagtatct gctgtcatta ttcagcgtgc ttacagacgc cacctttaa    6060 agcgaactgt aaaacaagct tcctttacgt acaataaaaa caaaatcaaa ggtggggcta    6120
atcttcttat aaaagaagac atgataattg acagaataaa tgaaaactct attacagaaa    6180
aaactgatct gaccatgtcc actgcagctt gtccaccttc ctatgaccgg gtgacaaagc    6240
caattgtgga aaaacatgag caagaaggca aagatgaaaa agccaaaggg aaataaatga    6300
aaataaataa aaataattgg gtgacaaatt gtttacagcc tgtgaaggtg atgtatttt    6360 atcaacagga ctcctttagg aggtcaatgc caaactgact gttttacac aaatctcctt    6420 aaggtcagtg cctacaataa gacagtgacc ccttgtcagc aaactgtgac tctgtgtaaa    6480
ggggagatga ccttgacagg aggttactgt tctcactacc agctgacact gctgaagata    6540
agatgcacaa tggctagtca gactgtaggg accagtttca aggggtgcaa acctgtgatt    6600
ttggggttgt ttaacatgaa acactttagt gtagtaattg tatccactgt ttgcatttca    6660
actgccacat ttgtcacatt tttatggaat ctgttagtgg attcatcttt ttgttaatcc    6720
atgtgtttat tatatgtgac tatttttgta aacgaagttt ctgttgagaa ataggctaag    6780
gacctctata acaggtatgc cacctggggg gtatggcaac cacatggccc tcccagctac    6840
acaaagtcgt ggtttgcatg agggcatgct gcacttagag atcatgcatg agaaaaagtc    6900
acaagaaaaa caaattctta aatttcacca tatttctggg aggggtaatt gggtgataag    6960
tggaggtgct ttgttgatct tgttttgcga aatccagccc ctagaccaag tagattattt    7020
gtgggtaggc cagtaaatct tagcaggtgc aaacttcatt caaatgtttg gagtcataaa    7080
tgttatgttt ctttttgttg tattaaaaaa aaaacctgaa tagtgaatat tgcccctcac    7140
cctccaccgc cagaagactg aattgaccaa aattactctt tataaatttc tgcttttcc    7200 tgcactttgt ttagccatct ttgggctctc agcaaggttg acactgtata tgttaatgaa    7260
atgctattta ttatgtaaat agtcatttta ccctgtggtg cacgtttgag caaacaaata    7320
atgacctaag cacagtattt attgcatcaa atatgtacca caagaaatgt agagtgcaag    7380
ctttacacag gtaataaaat gtattctgta ccatttatag atagtttgga tgctatcaat    7440
gcatgtttat attaccatgc tgctgtatct ggtttctctc actgctcaga atctcattta    7500
tgagaaacca tatgtcagtg gtaaagtcaa ggaaattgtt caacagatct catttattta    7560
agtcattaag caatagtttg cagcacttta acagcttttt ggttattttt acattttaag    7620
tggataacat atggtatata gccagactgt acagacatgt ttaaaaaaac acactgctta    7680
acctattaaa tatgtgttta gaattttata agcaaatata aatactgtaa aaagtcactt    7740
tattttattt ttcagcatta tgtacataaa tatgaagagg aaattatctt caggttgata    7800
tcacaatcac ttttcttact ttctgtccat agtacttttt catgaaagaa atttgctaaa    7860
```

| | |
|---|---:|
| taagacatga aaacaagact gggtagttgt agatttctgc ttttaaatt acatttgcta | 7920 |
| attttagatt atttcacaat tttaaggagc aaaataggtt cacgattcat atccaaatta | 7980 |
| tgctttgcaa ttggaaaagg gtttaaaatt ttatttatat ttctggtagt acctgtacta | 8040 |
| actgaattga aggtagtgct tatgttattt ttgttctttt tttctgactt cggtttatgt | 8100 |
| tttcatttct ttggagtaat gctgctctag attgttctaa atagaatgtg ggcttcataa | 8160 |
| ttttttttc cacaaaaaca gagtagtcaa cttatatagt caattacatc aggacatttt | 8220 |
| gtgtttctta cagaagcaaa ccataggctc ctcttttcct taaaactact tagataaact | 8280 |
| gtattcgtga actgcatgct ggaaaatgct actattatgc taaataatgc taaccaacat | 8340 |
| ttaaaatgtg caaaactaat aaagattaca ttttttattt t | 8381 |

<210> SEQ ID NO 10
<211> LENGTH: 1414
<212> TYPE: DNA
<213> ORGANISM: Homo sapiens
<400> SEQUENCE: 10

| | |
|---|---:|
| gctcccgggg acattctaac cgccgccagg tcccgccgcc tctcgccccg ctattaatac | 60 |
| cggcggcccg ggaggggggc gcagcacgcg ccgcgcagcc atggggaggc tgctggcctt | 120 |
| agtggtcggc gcggcactgg tgtcctcagc ctgcgggggc tgcgtggagg tggactcgga | 180 |
| gaccgaggcc gtgtatggga tgaccttcaa aattctttgc atctcctgca agcgccgcag | 240 |
| cgagaccaac gctgagacct tcaccgagtg gaccttccgc cagaagggca ctgaggagtt | 300 |
| tgtcaagatc ctgcgctatg agaatgaggt gttgcagctg gaggaggatg agcacttcga | 360 |
| gggccgcgtg gtgtggaatg gcagccgggg caccaaagac ctgcaggatc tgtctatctt | 420 |
| catcaccaat gtcacctaca accactcggg cgactacgag tgccacgtct accgcctgct | 480 |
| cttcttcgaa aactacgagc acaacaccag cgtcgtcaag aagatccaca ttgaggtagt | 540 |
| ggacaaagcc aacagagaca tggcatccat cgtgtctgag atcatgatgt atgtgctcat | 600 |
| tgtggtgttg accatatggc tcgtggcaga gatgatttac tgctacaaga agatcgctgc | 660 |
| cgccacggag actgctgcac aggagaatgc ctcggaatac ctggccatca cctctgaaag | 720 |
| caaagagaac tgcacgggcg tccaggtggc cgaatagccc tggccctggg ccccgcctca | 780 |
| aggaagagcc agccgtaatg gggactctcc aggcaccgcc tgcccccagc gtggggtgg | 840 |
| ccactcctgg gccccagaaa gcctcagagt cctgccgacg gagccactgg ggtgggaggg | 900 |
| ggcaggggc ttggctcgca ccccactttt cgcctcctcc agctcctgcc ccgcggccg | 960 |
| cgcaccgcca tgcatgatgg gtaaagcaat actgccgctg ccccaccct gcttctgctg | 1020 |
| cctgtttggg gagggggcg gtgaggtggg ggcagcggcc ccgcacccct cctccttgct | 1080 |
| gatttgcaca cattggccgc ttcagacacg cacttctggg gccagcccct cccgcctcc | 1140 |
| tccctgcctg gcgcaggggg tcgcgatgat gggctggagc agtttggggc aggggttct | 1200 |
| gggacccact ccgactcccc ctccccggca tcatttcccc tcccgcttcc tccggctgga | 1260 |
| cctggggtcc cccctccctg taatgcactc ctgcccggc caacctcgc cctctctcac | 1320 |
| cagccttgaa ctgtggccac ctagaaaggg gcccattcag cctcgtctct ttacagaagt | 1380 |
| agttttgttc atgaaataaa gactcttgga cttg | 1414 |

<210> SEQ ID NO 11
<211> LENGTH: 6328
<212> TYPE: DNA
<213> ORGANISM: Homo sapiens

<400> SEQUENCE: 11

```
ttcttggtgc cagcttatca atcccaaact ctgggtgtaa agattctac agggcacttt      60
cttatgcaag gagctaaaca gtgattaaag gagcaggatg aaaagatggc acagtcagtg    120
ctggtaccgc caggacctga cagcttccgc ttctttacca gggaatccct tgctgctatt    180
gaacaacgca ttgcagaaga gaaagctaag agacccaaac aggaacgcaa ggatgaggat    240
gatgaaaatg gcccaaagcc aaacagtgac ttggaagcag aaaatctct tccatttatt     300
tatggagaca ttcctccaga gatggtgtca gtgccctgg aggatctgga cccctactat     360
atcaataaga aaacgtttat agtattgaat aaagggaaag caatctctcg attcagtgcc    420
accccctgccc tttacatttt aactcccttc aaccctatta gaaaattagc tattaagatt   480
ttggtacatt ctttattcaa tatgctcatt atgtgcacga ttcttaccaa ctgtgtattt    540
atgaccatga gtaaccctcc agactggaca aagaatgtgg agtataccttt acaggaatt    600
tatactttttg aatcacttat taaaatactt gcaaggggct tttgtttaga agatttcaca   660
ttttttacggg atccatggaa ttggttggat ttcacagtca ttactttttgc atatgtgaca  720
gagtttgtgg acctgggcaa tgtctcagcg ttgagaacat tcagagttct ccaagcattg    780
aaaacaattt cagtcattcc aggcctgaag accattgtgg gggccctgat ccagtcagtg    840
aagaagcttt ctgatgtcat gatcttgact gtgttctgtc taagcgtgtt tgcgctaata    900
ggattgcagt tgttcatggg caacctacga aataaatgtt tgcaatggcc tccagataat    960
tcttcctttg aaataaatat cacttccttc tttaacaatt cattggatgg gaatggtact   1020
actttcaata ggacagtgag catatttaac tgggatgaat atattgagga taaaagtcac   1080
ttttattttt tagaggggca aaatgatgct ctgcttttgtg caacagctc agatgcaggc   1140
cagtgtcctg aaggatacat ctgtgtgaag gctggtagaa accccaacta tggctacacg   1200
agctttgaca ccctttagttg ggcctttttg tccttatttc gtctcatgac tcaagacttc   1260
tgggaaaacc tttatcaact gacactacgt gctgctggga aaacgtacat gatatttttt   1320
gtgctggtca ttttcttggg ctcattctat ctaataaatt tgatcttggc tgtggtggcc   1380
atggcctatg aggaacagaa tcaggccaca ttggaagagg ctgaacagaa ggaagctgaa   1440
tttcagcaga tgctcgaaca gttgaaaaag caacaagaag aagctcaggc ggcagctgca   1500
gccgcatctg ctgaatcaag agacttcagt ggtgctggtg ggataggagt ttttcagag    1560
agttcttcag tagcatctaa gttgagctcc aaaagtgaaa aagagctgaa aaacagaaga   1620
aagaaaaaga acagaaaga acagtctgga gaagaagaga aaatgacag agtcctaaaa    1680
tcggaatctg aagacagcat aagaagaaaa ggtttccgtt tttccttgga aggaagtagg   1740
ctgacatatg aaaagagatt ttcttctcca caccagtcct tactgagcat ccgtggctcc   1800
cttttctctc caagacgcaa cagtagggcg agccttttca gcttcagagg tcgagcaaag   1860
gacattggct ctgagaatga ctttgctgat gatgagcaca gcacctttga ggacaatgac   1920
agccgaagag actctctgtt cgtgccgcac agacatggag aacggcgcca cagcaatgtc   1980
agccaggcca gccgtgcctc cagggtgctc cccatcctgc ccatgaatgg gaagatgcat   2040
agcgctgtgg actgcaatgg tgtggtctcc ctggtcgggg cccttctac cctcacatct    2100
gctgggcagc tcctaccaga gggcacaact actgaaacag aaataagaaa gagacggtcc   2160
agttcttatc atgtttccat ggatttattg gaagatccta catcaaggca agagcaatg    2220
agtatagcca gtattttgac caacaccatg aagaacttg aagaatccag acagaaatgc   2280
ccaccatgct ggtataaatt tgctaatatg tgtttgattt gggactgttg taaaccatgg   2340
```

```
ttaaaggtga acaccttgt caacctggtt gtaatggacc catttgttga cctggccatc    2400
accatctgca ttgtcttaaa tacactcttc atggctatgg agcactatcc catgacggag    2460
cagttcagca gtgtactgtc tgttggaaac ctggtcttca cagggatctt cacagcagaa    2520
atgtttctca agataattgc catggatcca tattattact ttcaagaagg ctggaatatt    2580
tttgatggtt ttattgtgag ccttagttta atggaacttg gtttggcaaa tgtggaagga    2640
ttgtcagttc tccgatcatt ccggctgctc cgagttttca agttggcaaa atcttggcca    2700
actctaaata tgctaattaa gatcattggc aattctgtgg gggctctagg aaacctcacc    2760
ttggtattgg ccatcatcgt cttcattttt gctgtggtcg gcatgcagct ctttggtaag    2820
agctacaaag aatgtgtctg caagatttcc aatgattgtg aactcccacg ctggcacatg    2880
catgactttt tccactcctt cctgatcgtg ttccgcgtgc tgtgtggaga gtggatagag    2940
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct ttgttaggaa gcagaaagct ttagatgaaa ttaaaccgct tgaagatcta    3240
aataataaaa aagacagctg tatttccaac cataccacca tagaaatagg caaagacctc    3300
aattatctca aagacggaaa tggaactact agtggcatag gcagcagtgt agaaaaatat    3360
gtcgtggatg aaagtgatta catgtcattt ataaacaacc ctagcctcac tgtgacagta    3420
ccaattgctg ttgagagaatc tgactttgaa aatttaaata ctgaagaatt cagcagcgag    3480
tcagatatgg aggaaagcaa agagaagcta atgcaacta gttcatctga aggcagcacg    3540
gttgatattg gagctcccgc cgagggagaa cagcctgagg ttgaacctga ggaatcccct    3600
gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780
gcctttgaag atatatacat tgagcagcga aaaaccatta gaccatgtt agaatatgct    3840 gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc ggtttgaagg aatgagggtt    4080
gttgtaaatg ctctttttagg agccattcca tctatcatga atgtacttct ggtttgtctg    4140
atcttttggc taatattcag tatcatggga gtgaatctct tgctggcaa gttttaccat    4200 tgtattaatt acaccactgg agagatgttt gatgtaagcg tggtcaacaa ctacagtgag    4260
tgcaaagctc tcattgagag caatcaaact gccaggtgga aaatgtgaa agtaaacttt    4320 gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatcttta ttttgtcatc tttattattt ttggttcatt cttttacctt    4500
aatcttttca ttggtgtcat catagataac ttcaaccaac agaaaagaa gtttggaggt    4560 caagacattt ttatgacaga agaacagaag aaatactaca atgcaatgaa aaaactgggt    4620
tcaaagaaac cacaaaaacc catacctcga cctgctaaca aattccaagg aatggtctttt    4680 gattttgtaa ccaaacaagt ctttgatatc agcatcatga tcctcatctg ccttaacatg    4740
```

```
gtcaccatga tggtggaaac cgatgaccag agtcaagaaa tgacaaacat tctgtactgg      4800
attaatctgg tgtttattgt tctgttcact ggagaatgtg tgctgaaact gatctctctt      4860
cgttactact atttcactat tggatggaat attttttgatt ttgtggtggt cattctctcc     4920
attgtaggaa tgtttctggc tgaactgata gaaaagtatt ttgtgtcccc tacccctgttc    4980 cgagtgatcc gtcttgccag gattggccga atcctacgtc tgatcaaagg agcaaagggg      5040
atccgcacgc tgctctttgc tttgatgatg tcccttcctg cgttgtttaa catcggcctc      5100 cttctttttcc tggtcatgtt catctacgcc atctttggga tgtccaattt tgcctatgtt    5160
aagagggaag ttgggatcga tgacatgttc aactttgaga cctttggcaa cagcatgatc      5220
tgcctgttcc aaattacaac ctctgctggc tgggatggat tgctagcacc tattcttaat      5280
agtggacctc cagactgtga ccctgacaaa gatcaccctg gaagctcagt taaaggagac      5340
tgtgggaacc catctgttgg gattttcttt tttgtcagtt acatcatcat atccttcctg      5400
gttgtgctga acatgtacat cgcggtcatc ctggagaact tcagtgttgc tactgaagaa      5460
agtgcagagc ctctgagtga ggatgacttt gagatgttct atgaggtttg ggagaagttt      5520
gatcccgatg cgacccagtt tatagagttt gccaaacttt ctgattttgc agatgccctg      5580
gatcctcctc ttctcatagc aaaacccaac aaagtccagc tcattgccat ggatctgccc      5640
atggtgagtg gtgaccggat ccactgtctt gacatcttat ttgcttttac aaagcgtgtt     5700
ttgggtgaga gtggagagat ggatgccctt cgaatacaga tggaagagcg attcatggca      5760
tcaaacccct ccaaagtctc ttatgagccc attacgacca cgttgaaacg caaacaagag      5820
gaggtgtctg ctattattat ccagagggct tacagacgct acctcttgaa gcaaaaagtt      5880
aaaaaggtat caagtatata caagaaagac aaaggcaaag aatgtgatgg aacacccatc      5940
aaagaagata ctctcattga taaactgaat gagaattcaa ctccagagaa aaccgatatg      6000
acgccttcca ccacgtctcc accctcgtat gatagtgtga ccaaaccaga aaagaaaaa      6060 tttgaaaaag acaaatcaga aaggaagac aaagggaaag atatcaggga agtaaaaag      6120 taaaagaaa ccaagaattt tccatttgt gatcaattgt ttacagcccg tgatggtgat       6180
gtgtttgtgt caacaggact cccacaggag gtctatgcca aactgactgt ttttacaaat    6240
gtatacttaa ggtcagtgcc tataacaaga cagagacctc tggtcagcaa actggaactc     6300
agtaaactgg agaaatagta tcgatggg                                        6328
```

<210> SEQ ID NO 12  
<211> LENGTH: 6328  
<212> TYPE: DNA  
<213> ORGANISM: Homo sapiens

<400> SEQUENCE: 12

```
ttcttggtgc cagcttatca atcccaaact ctgggtgtaa aagattctac agggcacttt       60
cttatgcaag gagctaaaca gtgattaaag gagcaggatg aaaagatggc acagtcagtg      120
ctggtaccgc caggacctga cagcttccgc ttctttacca gggaatccct tgctgctatt      180
gaacaacgca ttgcagaaga gaaagctaag agacccaaac aggaacgcaa ggatgaggat      240
gatgaaaatg gcccaaagcc aaacagtgac ttggaagcag gaaaatctct tccatttatt      300
tatgagacat tcctccaga gatggtgtca gtgcccctgg aggatctgga cccctactat      360
atcaataaga aaacgtttat agtattgaat aaagggaaag caatctctcg attcagtgcc      420 accccctgccc tttacatttt aactcccttc aaccctatta gaaaattagc tattaagatt      480
ttggtacatt cctttattcaa tatgctcatt atgtgcacga ttcttaccaa ctgtgtattt      540
```

```
atgaccatga gtaaccctcc agactggaca agaatgtgg  agtataccTt  tacaggaatt    600
tatactttTg  aatcacttat taaaatactt gcaaggggct tttgtttaga agatttcaca    660
tttttacggg  atccatggaa ttggttggat ttcacagtca ttacttttgc atatgtgaca    720
gagtttgtgg  acctgggcaa tgtctcagcg ttgagaacat tcagagttct ccgagcattg    780
aaaacaattt  cagtcattcc aggcctgaag accattgtgg gggccctgat ccagtcagtg    840
aagaagcttt  ctgatgtcat gatcttgact gtgttctgtc taagcgtgtt tgcgctaata    900
ggattgcagt  tgttcatggg caacctacga ataaatgtt  tgcaatggcc tccagataat    960
tcttcctttg  aaataaatat cacttccttc tttaacaatt cattggatgg gaatggtact   1020
actttcaata  ggacagtgag catatttaac tgggatgaat atattgagga taaaagtcac   1080
ttttatTttt  tagaggggca aaatgatgct ctgctttgtg caacagctc  agatgcaggc   1140
cagtgtcctg  aaggatacat ctgtgtgaag gctggtagaa accccaacta tggctacacg   1200
agctttgaca  ccttTagttg ggccttTttg tccttatttc gtctcatgac tcaagacttc   1260
tgggaaaacc  tttatcaact gacactacgt gctgctggga aaacgtacat gatatttTtt   1320
gtgctggtca  ttttcttggg ctcattctat ctaataaatt tgatcttggc tgtggtggcc   1380
atggcctatg  aggaacagaa tcaggccaca ttggaagagg ctgaacagaa ggaagctgaa   1440
tttcagcaga  tgctcgaaca gttgaaaaag caacaagaag aagctcaggc ggcagctgca   1500
gccgcatctg  ctgaatcaag agacttcagt ggtgctggtg ggataggagt ttTttcagag   1560
agttcTtcag  tagcatctaa gttgagctcc aaaagtgaaa aagagctgaa aaacagaaga   1620
aagaaaaaga  aacagaaaga acagtctgga gaagaagaga aaaatgacag agtcctaaaa   1680
tcggaatctg  aagacagcat aagaagaaaa ggtttccgtt tttccttgga aggaagtagg   1740
ctgacatatg  aaaagagatt tcttctccca caccagtcct tactgagcat ccgtggctcc   1800
ctttctctc   caagacgcaa cagtagggcg agccttttca gcttcagagg tcgagcaaag   1860
gacattggct  ctgagaatga ctttgctgat gatgagcaca gcacctttga ggacaatgac   1920
agccgaagag  actctctgtt cgtgccgcac agacatggag aacggcgcca cagcaatgtc   1980
agccaggcca  gccgtgcctc cagggtgctc cccatcctgc ccatgaatgg gaagatgcat   2040
agcgctgtgg  actgcaatgg tgtggtctcc ctggtcgggg gcccttctac cctcacatct   2100
gctgggcagc  tcctaccaga gggcacaact actgaaacag aaataagaaa gagacggtcc   2160
agttcTtatc  atgtttccat ggatttattg gaagatccta catcaaggca agagcaatg    2220
agtatagcca  gtatTttgac caacaccatg aagaacttg  aagaatccag acagaaatgc   2280
ccaccatgct  ggtataaatt tgctaatatg tgtttgattt gggactgttg taaaccatgg   2340
ttaaaggtga  acaccttgt  caacctggtt gtaatgacc  catttgttga cctggccatc   2400
accatctgca  ttgtcttaaa tacactcttc atggctatgg agcactatcc catgacggag   2460
cagtTcagca  gtgtactgtc tgttggaaac ctggtcttca cagggatctt cacagcagaa   2520
atgtttctca  agataattgc catggatcca tattattact ttcaagaagg ctggaatatt   2580
tttgatggtt  ttattgtgag ccttagttta atggaacttg gtttggcaaa tgtggaagga   2640
ttgtcagttc  tccgatcatt ccggctgctc cgagttttca gttggcaaa  atcttggcca   2700
actctaaata  tgctaattaa gatcattggc aattctgtgg gggctctagg aaacctcacc   2760
ttggtattgg  ccatcatcat cttcattttt gctgtggtcg gcatgcagct ctttggtaag   2820
agctacaaag  aatgtgtctg caagatttcc aatgattgtg aactcccacg ctggcacatg   2880
catgactttt  tccactcctt cctgatcgtg ttccgcgtgc tgtgtggaga gtggatagag   2940
```

```
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct ttgttaggaa gcagaaagct ttagatgaaa ttaaaccgct gaagatcta     3240 aataataaaa aagacagctg tatttccaac cataccacca tagaaatagg caaagacctc    3300
aattatctca aagacggaaa tggaactact agtggcatag gcagcagtgt agaaaaatat    3360
gtcgtggatg aaagtgatta catgtcattt ataaacaacc ctagcctcac tgtgacagta    3420
ccaattgctg ttggagaatc tgactttgaa aatttaaata ctgaagaatt cagcagcgag    3480
tcagatatgg aggaaagcaa agagaagcta atgcaacta gttcatctga aggcagcacg     3540
gttgatattg gagctcccgc cgagggagaa cagcctgagg ttgaacctga ggaatccctt    3600
gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780 gccttttgaag atatatacat tgagcagcga aaaaccatta agaccatgtt agaatatgct    3840
gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc ggtttgaagg aatgagggtt    4080
gttgtaaatg ctcttttagg agccattcca tctatcatga atgtacttct ggtttgtctg    4140
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatctttta ttttgtcatc tttattattt ttggttcatt cttttacctt    4500 aatctttca ttggtgtcat catagataac ttcaaccaac agaaaagaa gtttggaggt      4560 caagacattt ttatgacaga agaacagaag aaatactaca atgcaatgaa aaaactgggt    4620
tcaaagaaac cacaaaaacc catacctcga cctgctaaca aattccaagg aatggtctttt   4680 gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt ttgtggtggt cattctctcc    4920
attgtaggaa tgtttctggc tgaactgata gaaaagtatt ttgtgtccc tacctgtttc    4980 cgagtgatcc gtcttgccag gattggccga atcctacgtc tgatcaaagg agcaaagggg    5040
atccgcacgc tgctctttgc tttgatgatg tccttcctg cgttgtttaa catcggcctc    5100 cttctttcc tggtcatgtt catctacgcc atctttggga tgtccaattt tgcctatgtt     5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
```

```
tgtgggaacc catctgttgg gattttcttt tttgtcagtt acatcatcat atccttcctg    5400
gttgtgctga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtggagagat ggatgccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaagtt    5880 aaaaaggtat caagtatata caagaaagac aaaggcaaag aatgtgatgg aacacccatc    5940
aaagaagata ctctcattga taaactgaat gagaattcaa ctccagagaa aaccgatatg    6000
acgccttcca ccacgtctcc accctcgtat gatagtgtga ccaaaccaga aaagaaaaa     6060 tttgaaaaag acaaatcaga aaggaagac  aaagggaaag atatcaggga aagtaaaaag    6120 taaaagaaa  ccaagaattt tccattttgt gatcaattgt ttacagcccg tgatggtgat    6180
gtgtttgtgt caacaggact cccacaggag gtctatgcca aactgactgt ttttacaaat    6240
gtatacttaa ggtcagtgcc tataacaaga cagagacctc tggtcagcaa actggaactc    6300
agtaaactgg agaaatagta tcgatggg                                       6328

<210> SEQ ID NO 13
<211> LENGTH: 6328
<212> TYPE: DNA
<213> ORGANISM: Homo sapiens

<400> SEQUENCE: 13
ttcttggtgc cagcttatca atcccaaact ctgggtgtaa aagattctac agggcacttt      60
cttatgcaag gagctaaaca gtgattaaag gagcaggatg aaaagatggc acagtcagtg     120
ctggtaccgc caggacctga cagcttccgc ttctttacca gggaatccct tgctgctatt     180
gaacaacgca ttgcagaaga gaaagctaag agacccaaac aggaacgcaa ggatgaggat     240
gatgaaaatg gcccaaagcc aaacagtgac ttggaagcag gaaaatctct tccatttatt     300 tatgagagaca ttcctccaga gatggtgtca gtgcccctgg aggatctgga cccctactat    360
atcaataaga aaacgtttat agtattgaat aaagggaaag caatctctcg attcagtgcc     420 accccctgccc tttacatttt aactcccttc aaccctatta gaaaattagc tattaagatt    480
ttggtacatt cttttattca tatgctcatt atgtgcacga ttcttaccaa ctgtgtattt     540
atgaccatga gtaaccctcc agactggaca agaatgtgg  agtataccct tacaggaatt    600 tatactttg  aatcacttat taaaatactt gcaaggggct tttgtttaga agatttcaca    660
tttttacggg atccatggaa ttggttggat ttcacagtca ttacttttgc atatgtgaca    720
gagtttgtgg acctgggcaa tgtctcagcg ttgagaacat tcagagttct ccgagcattg    780
aaaacaattt cagtcattcc aggcctgaag accattgtgg gggccctgat ccagtcagtg    840
aagaagcttt ctgatgtcat gatcttgact gtgttctgtc taagcgtgtt tgcgctaata    900
ggattgcagt tgttcatggg caacctacga aataaatgtt tgcaatggcc tccagataat    960
tcttcctttg aaataaatat cacttccttc tttaacaatt cattggatgg gaatggtact   1020
actttcaata ggacagtgag catatttaac tgggatgaat atattgagga taaagtcac    1080 tttttatttt tagagggca aaatgatgct ctgctttgtg gcaacagctc agatgcaggc    1140
```

```
cagtgtcctg aaggatacat ctgtgtgaag gctggtagaa accccaacta tggctacacg    1200
agctttgaca cctttagttg ggccttttttg tccttatttc gtctcatgac tcaagacttc    1260
tgggaaaacc tttatcaact gacactacgt gctgctggga aaacgtacat gatattttt     1320 gtgctggtca ttttcttggg ctcattctat ctaataaatt tgatcttggc tgtggtggcc    1380
atggcctatg aggaacagaa tcaggccaca ttggaagagg ctgaacagaa ggaagctgaa    1440
tttcagcaga tgctcgaaca gttgaaaaag caacaagaag aagctcaggc ggcagctgca    1500
gccgcatctg ctgaatcaag agacttcagt ggtgctggtg ggataggagt tttttcagag    1560
agttcttcag tagcatctaa gttgagctcc aaaagtgaaa aagagctgaa aacagaaga    1620 aagaaaaaga acagaaaga acagtctgga gaagaagaga aaatgacag agtcctaaaa    1680 tcggaatctg aagacagcat aagaagaaaa ggtttccgtt tttccttgga aggaagtagg    1740
ctgacatatg aaaagagatt tcttctcca caccagtcct tactgagcat ccgtggctcc    1800 ctttctctc caagacgcaa cagtagggcg agccttttca gcttcagagg tcgagcaaag    1860
gacattggct ctgagaatga ctttgctgat gatgagcaca gcacctttga ggacaatgac    1920
agccgaagag actctctgtt cgtgccgcac agacatggag aacggcgcca cagcaatgtc    1980
agccaggcca gccgtgcctc cagggtgctc cccatcctgc ccatgaatgg gaagatgcat    2040
agcgctgtgg actgcaatgg tgtggtctcc ctggtcgggg gccttctac cctcacatct    2100 gctgggcagc tcctaccaga gggcacaact actgaaacag aaataagaaa gagacggtcc    2160
agttcttatc atgttccat ggatttattg gaagatccta catcaaggca aagagcaatg    2220
agtatagcca gtatttgac caacaccatg gaagaacttg aagaatccag acagaaatgc    2280
ccaccatgct ggtataaatt tgctaatatg tgtttgattt gggactgttg taaaccatgg    2340
ttaaaggtga acaccttgt caacctggtt gtaatggacc catttgttga cctggccatc    2400
accatctgca ttgtcttaaa tacactcttc atggctatgg agcactatcc catgacggag    2460
cagttcagca gtgtactgtc tgttggaaac ctggtcttca cagggatctt cacagcagaa    2520
atgtttctca agataattgc catggatcca tattattact ttcaagaagg ctggaatatt    2580
tttgatggtt ttattgtgag ccttagttta atggaacttg gtttggcaaa tgtggaagga    2640
ttgtcagttc tccgatcatt ccggctgctc cgagttttca gttggcaaaa tcttggcca    2700 actctaaata tgctaattaa gatcattggc aattctgtgg gggctctagg aaacctcacc    2760
ttggtattgg ccatcatcgt cttcattttt gctgtggtcg gcatgcagct ctttggtaag    2820
agctacaaag aatgtgtctg caagatttcc aatgattgtg aactcccacg ctggcacatg    2880
catgactttt tccactcctt cctgatcgtg ttccgcgtgc tgtgtggaga gtggatagag    2940
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tatccagatt    3120
gctgtgggaa ggatgcagaa aggaatcgat tttgttaaaa gaaaaatacg tgaatttatt    3180
cagaaagcct tgttaggaa gcagaaagct ttagatgaaa ttaaaccgct tgaagatcta    3240
aataataaaa aagacagctg tatttccaac cataccacca tagaaatagg caaagacctc    3300
aattatctca aagacggaaa tggaactact agtggcatag cagcagtgt agaaaaatat    3360 gtcgtggatg aaagtgatta catgtcattt ataaacaacc ctagcctcac tgtgacagta    3420
ccaattgctg ttgagaatc tgactttgaa aatttaaata ctgaagaatt cagcagcgag    3480
tcagatatgg aggaaagcaa agagaagcta atgcaacta gttcatctga aggcagcacg    3540
```

```
gttgatattg gagctcccgc cgagggagaa cagcctgagg ttgaacctga ggaatccctt    3600
gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780
gcctttgaag atatatacat tgagcagcga aaaaccatta agaccatgtt agaatatgct    3840
gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc ggtttgaagg aatgagggtt    4080
gttgtaaatg ctcttttagg agccattcca tctatcatga atgtacttct ggtttgtctg    4140
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatcttta ttttgtcatc tttattattt ttggttcatt ctttaccttg    4500
aatcttttca ttggtgtcat catagataac ttcaaccaac agaaaagaa gtttggaggt    4560 caagacattt ttatgacaga agaacagaag aaatactaca atgcaatgaa aaaactgggt    4620
tcaaagaaac cacaaaaacc catacctcga cctgctaaca aattccaagg aatggtcttt    4680
gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt ttgtggtggt cattctctcc    4920
attgtaggaa tgtttctggc tgaactgata gaaaagtatt ttgtgtcccc taccctgttc    4980
cgagtgatcc gtcttgccag gattggccga atcctacgtc tgatcaaagg agcaaagggg    5040
atccgcacgc tgctctttgc tttgatgatg tcccttcctg cgttgtttaa catcggcctc    5100 cttctttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
tgtgggaacc catctgttgg gattttcttt tttgtcagtt acatcatcat atccttcctg    5400
gttgtgctga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtgagagat ggatgccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaaagtt    5880
aaaaaggtat caagtatata caagaaagac aaaggcaaag aatgtgatgg aacacccatc    5940
```

```
aaagaagata ctctcattga taaactgaat gagaattcaa ctccagagaa aaccgatatg    6000
acgccttcca ccacgtctcc accctcgtat gatagtgtga ccaaaccaga aaagaaaaa     6060 tttgaaaaag acaaatcaga aaggaagac  aagggaaag  atatcaggga aagtaaaaag    6120 taaaagaaa  ccaagaattt tccattttgt gatcaattgt ttacagcccg tgatggtgat    6180
gtgtttgtgt caacaggact cccacaggag gtctatgcca aactgactgt ttttacaaat    6240
gtatacttaa ggtcagtgcc tataacaaga cagagacctc tggtcagcaa actggaactc    6300
agtaaactgg agaaatagta tcgatggg                                       6328

<210> SEQ ID NO 14
<211> LENGTH: 6328
<212> TYPE: DNA
<213> ORGANISM: Homo sapiens

<400> SEQUENCE: 14
ttcttggtgc cagcttatca atcccaaact ctgggtgtaa aagattctac agggcacttt      60
cttatgcaag gagctaaaca gtgattaaag gagcaggatg aaaagatggc acagtcagtg     120
ctggtaccgc caggacctga cagcttccgc ttctttacca gggaatccct tgctgctatt     180
gaacaacgca ttgcagaaga gaaagctaag agacccaaac aggaacgcaa ggatgaggat     240
gatgaaaatg gcccaaagcc aaacagtgac ttggaagcag gaaaatctct tccatttatt     300
tatggagaca ttcctccaga gatggtgtca gtgcccctgg aggatctgga cccctactat     360
atcaataaga aaacgtttat agtattgaat aaagggaaag caatctctcg attcagtgcc     420 accccctgccc tttacatttt aactcccttc aaccctatta gaaaattagc tattaagatt     480
ttggtacatt ctttattcaa tatgctcatt atgtgcacga ttcttaccaa ctgtgtatt     540 atgaccatga gtaaccctcc agactggaca aagaatgtgg agtataccct tacaggaatt     600
tatacttttg aatcacttat taaaatactt gcaaggggct tttgtttaga agattttaca     660
tttttacggg atccatggaa ttggttggat ttcacagtca ttacttttgc atatgtgaca     720
gagtttgtgg acctgggcaa tgtctcagcg ttgagaacat tcagagttct ccgagcattg     780
aaaacaattt cagtcattcc aggcctgaag accattgtgg gggccctgat ccagtcagtg     840
aagaagcttt ctgatgtcat gatcttgact gtgttctgtc taagcgtgtt tgcgctaata     900
ggattgcagt tgttcatggg caacctacga aataaatgtt tgcaatggcc tccagataat     960
tcttcctttg aaataaatat cacttccttc tttaacaatt cattggatgg gaatggtact    1020
actttcaata ggacagtgag catatttaac tgggatgaat atattgagga taaaagtcac    1080
ttttattttt tagaggggca aaatgatgct ctgctttgtg gcaacagctc agatgcaggc    1140
cagtgtcctg aaggatacat ctgtgtgaag gctggtagaa accccaacta tggctacacg    1200
agctttgaca cctttagttg ggcctttttg tccttatttc gtctcatgac tcaagacttc    1260
tgggaaaacc tttatcaact gacactacgt gctgctggga aaacgtacat gatatttttt    1320
gtgctggtca ttttcttggg ctcattctat ctaataaatt tgatcttggc tgtggtggcc    1380
atggcctatg aggaacagaa tcaggccaca ttggaagagg ctgaacgaaa ggaagctgaa    1440
tttcagcaga tgctcgaaca gttgaaaaag caacaagaag aagctcaggc ggcagctgca    1500
gccgcatctg ctgaatcaag agacttcagt ggtgctggtg ggataggagt tttttcagag    1560
agttcttcag tagcatctaa gttgagctcc aaaagtgaaa aagagctgaa aaacagaaga    1620
aagaaaaaga acagaaaga  acagtctgga gaagaagaga aaaatgacag agtcctaaaa    1680
tcggaatctg aagacagcat aagaagaaaa ggtttccgtt tttccttgga aggaagtagg    1740
```

```
ctgacatatg aaaagagatt ttcttctcca caccagtcct tactgagcat ccgtggctcc    1800
cttttctctc caagacgcaa cagtagggcg agccttttca gcttcagagg tcgagcaaag    1860
gacattggct ctgagaatga ctttgctgat gatgagcaca gcacctttga ggacaatgac    1920
agccgaagag actctctgtt cgtgccgcac agacatggag aacggcgcca cagcaatgtc    1980
agccaggcca gccgtgcctc cagggtgctc cccatcctgc ccatgaatgg aagatgcat     2040 agcgctgtgg actgcaatgg tgtggtctcc ctggtcgggg gccttctac cctcacatct     2100 gctgggcagc tcctaccaga gggcacaact actgaaacag aaataagaaa gagacggtcc    2160
agttcttatc atgtttccat ggatttattg gaagatccta catcaaggca aagagcaatg    2220
agtatagcca gtattttgac caacaccatg aagaacttg aagaatccag acagaaatgc     2280
ccaccatgct ggtataaatt tgctaatatg tgtttgattt gggactgttg taaaccatgg    2340
ttaaaggtga acaccttgt caacctggtt gtaatggacc catttgttga cctggccatc     2400
accatctgca ttgtcttaaa tacactcttc atggctatgg agcactatcc catgacggag    2460
cagttcagca gtgtactgtc tgttggaaac ctggtcttca cagggatctt cacagcagaa    2520
atgtttctca agataattgc catggatcca tattattact ttcaagaagg ctggaatatt    2580
tttgatggtt ttattgtgag ccttagttta atggaacttg gtttggcaaa tgtggaagga    2640
ttgtcagttc tccgatcatt ccggctgctc cgagttttca agttggcaaa atcttggcca    2700
actctaaata tgctaattaa gatcattggc aattctgtgg gggctctagg aaacctcacc    2760
ttggtattgg ccatcatcgt cttcattttt gctgtggtcg gcatgcagct ctttggtaag    2820
agctacaaag aatgtgtctg caagatttcc aatgattgtg aactcccacg ctggcacatg    2880
catgactttt tccactcctt cctgatcgtg ttccgcgtgc tgtgtggaga gtggatagag    2940
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct tgttaggaa gcagaaagct ttagatgaaa ttaaaccgct tgaagatcta    3240
aataataaaa aagacagctg tatttccaac cataccacca tagaaatagg caaagacctc    3300
aattatctca aagacggaaa tggaactact agtggcatag cagcagtgt agaaaaatat    3360 gtcgtggatg aaagtgatta catgtcattt ataaacaacc ctagcctcac tgtgacagta    3420
ccaattgctg ttgagaatc tgactttgaa aatttaaata ctgaagaatt cagcagcgag    3480
tcagatatgg aggaaagcaa agagaagcta aatgcaacta gttcatctga aggcagcacg    3540
gttgatattg gagctcccgc cgagggagaa cagcctgagg ttgaacctga ggaatccctt    3600
gaacctgaag cctgttttac agaagactgt gtacggaagt tcaagtgttg tcagataagc    3660
atagaagaag gcaaagggaa actctggtgg aatttgagga aagcatgcta taagatagtg    3720
gagcacaatt ggttcgaaac cttcattgtc ttcatgattc tgctgagcag tggggctctg    3780
gcctttgaag atatatacat tgagcagcga aaaaccatta gaccatgtt agaatatgct    3840 gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttgtgccat caaatccctc    4020 agaacactaa gagctctgag gccactgaga gctttgtccc ggtttgaagg aatgagggtt    4080
gttgtaaatg ctcttttagg agccattcca tctatcatga atgtacttct ggtttgtctg    4140
```

```
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatcttta ttttgtcatc tttattattt ttggttcatt ctttaccttg    4500
aatcttttca ttggtgtcat catagataac ttcaaccaac agaaaagaa gtttggaggt    4560
caagacattt ttatgacaga agaacagaag aaatactaca atgcaatgaa aaaactgggt    4620
tcaaagaaac cacaaaaacc catacctcga cctgctaaca aattccaagg aatggtcttt    4680
gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt ttgtggtggt cattctctcc    4920
attgtaggaa tgtttctggc tgaactgata gaaaagtatt ttgtgtcccc taccctgttc    4980
cgagtgatcc gtcttgccag gattggccga atcctacgtc tgatcaaagg agcaaagggg    5040
atccgcacgc tgctctttgc tttgatgatg tcccttcctg cgttgtttaa catcggcctc    5100
cttcttttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
tgtgggaacc catctgttgg gattttctt tttgtcagtt acatcatcat atccttcctg    5400
gttgtgctga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtgagagat ggatgccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaaagtt    5880
aaaaaggtat caagtatata caagaaagac aaaggcaaag aatgtgatgg aacacccatc    5940
aaagaagata ctctcattga taaactgaat gagaattcaa ctccagagaa aaccgatatg    6000
acgccttcca ccacgtctcc accctcgtat gatagtgtga ccaaaccaga aaagaaaaa    6060
tttgaaaaag acaaatcaga aaaggaagac aaagggaaag atatcaggga aagtaaaaag    6120
taaaaagaaa ccaagaattt tccattttgt gatcaattgt ttacagcccg tgatggtgat    6180
gtgtttgtgt caacaggact cccacaggag gtctatgcca aactgactgt ttttacaaat    6240
gtatacttaa ggtcagtgcc tataacaaga cagagacctc tggtcagcaa actgaactc    6300
agtaaactgg agaaatagta tcgatggg                                        6328

<210> SEQ ID NO 15
<211> LENGTH: 6328
<212> TYPE: DNA
<213> ORGANISM: Homo sapiens
```

<400> SEQUENCE: 15

```
ttcttggtgc cagcttatca atcccaaact ctgggtgtaa agattctac agggcacttt      60
cttatgcaag gagctaaaca gtgattaaag gagcaggatg aaaagatggc acagtcagtg    120
ctggtaccgc caggacctga cagcttccgc ttctttacca gggaatccct tgctgctatt    180
gaacaacgca ttgcagaaga gaaagctaag agacccaaac aggaacgcaa ggatgaggat    240
gatgaaaatg gcccaaagcc aaacagtgac ttggaagcag aaaatctct tccatttatt     300
tatggagaca ttcctccaga gatggtgtca gtgccctgg aggatctgga cccctactat     360
atcaataaga aaacgtttat agtattgaat aaagggaaag caatctctcg attcagtgcc    420
acccctgccc tttacatttt aactcccttc aaccctatta gaaaattagc tattaagatt    480
ttggtacatt ctttattcaa tatgctcatt atgtgcacga ttcttaccaa ctgtgtattt    540
atgaccatga gtaaccctcc agactggaca aagaatgtgg agtatacctt tacaggaatt    600
tatacttttg aatcacttat taaaatactt gcaaggggct tttgtttaga agatttcaca    660
tttttacggg atccatggaa ttggttggat ttcacagtca ttacttttgc atatgtgaca    720
gagtttgtgg acctgggcaa tgtctcagcg ttgagaacat tcagagttct ccgagcattg    780
aaaacaattt cagtcattcc aggcctgaag accattgtgg gggccctgat ccagtcagtg    840
aagaagcttt ctgatgtcat gatcttgact gtgttctgtc taagcgtgtt tgcgctaata    900
ggattgcagt tgttcatggg caacctacga aataaatgtt tgcaatggcc tccagataat    960
tcttcctttg aaataaatat cacttccttc tttaacaatt cattggatgg gaatggtact   1020
actttcaata ggacagtgag catatttaac tgggatgaat atattgagga taaaagtcac   1080
ttttattttt tagaggggca aaatgatgct ctgctttgtg caacagctc agatgcaggc   1140
cagtgtcctg aaggatacat ctgtgtgaag gctggtagaa accccaacta tggctacacg   1200
agctttgaca cctttagttg ggcctttttg tccttatttc gtctcatgac tcaagacttc   1260
tgggaaaacc tttatcaact gacactacgt gctgctggga aaacgtacat gatatttttt   1320
gtgctggtca ttttcttggg ctcattctat ctaataaatt tgatcttggc tgtggtggcc   1380
atggcctatg aggaacagaa tcaggccaca ttggaagagg ctgaacagaa ggaagctgaa   1440
tttcagcaga tgctcgaaca gttgaaaaag caacaagaag aagctcaggc ggcagctgca   1500
gccgcatctg ctgaatcaag agacttcagt ggtgctggtg ggataggagt tttttcagag   1560
agttcttcag tagcatctaa gttgagctcc aaaagtgaaa aagagctgaa aaacagaaga   1620
aagaaaaaga acagaaaga acagtctgga gaagaagaga aaaatgacag agtcctaaaa   1680
tcggaatctg aagacagcat aagaagaaaa ggtttccgtt tttccttgga aggaagtagg   1740
ctgacatatg aaaagagatt ttcttctcca caccagtcct tactgagcat ccgtggctcc   1800
cttttctctc caagacgcaa cagtagggcg agccttttca gcttcagagg tcgagcaaag   1860
gacattggct ctgagaatga ctttgctgat gatgagcaca gcacctttga ggacaatgac   1920
agccgaagag actctctgtt cgtgccgcac agacatggag aacggcgcca cagcaatgtc   1980
agccaggcca gccgtgcctc cagggtgctc cccatcctgc ccatgaatgg gaagatgcat   2040
agcgctgtgg actgcaatgg tgtggtctcc ctggtcgggg gcccttctac cctcacatct   2100
gctgggcagc tcctaccaga gggcacaact actgaaacag aaataagaaa gagacggtcc   2160
agttcttatc atgtttccat ggatttattg gaagatccta catcaaggca agagcaatg   2220
agtatagcca gtattttgac caacaccatg aagaacttg aagaatccag acagaaatgc   2280
ccaccatgct ggtataaatt tgctaatatg tgtttgattt gggactgttg taaaccatgg   2340
```

```
ttaaaggtga acaccttgt caacctggtt gtaatggacc catttgttga cctggccatc    2400
accatctgca ttgtcttaaa tacactcttc atggctatgg agcactatcc catgacggag    2460
cagttcagca gtgtactgtc tgttggaaac ctggtcttca cagggatctt cacagcagaa    2520
atgtttctca agataattgc catggatcca tattattact ttcaagaagg ctggaatatt    2580
tttgatggtt ttattgtgag ccttagttta atggaacttg gtttggcaaa tgtggaagga    2640
ttgtcagttc tccgatcatt ccggctgctc cgagttttca agttggcaaa atcttggcca    2700
actctaaata tgctaattaa gatcattggc aattctgtgg gggctctagg aaacctcacc    2760
ttggtattgg ccatcatcgt cttcattttt gctgtggtcg gcatgcagct ctttggtaag    2820
agctacaaag aatgtgtctg caagatttcc aatgattgtg aactcccacg ctggcacatg    2880
catgactttt tccactcctt cctgatcgtg ttccgcgtgc tgtgtggaga gtggatagag    2940
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct ttgttaggaa gcagaaagct ttagatgaaa ttaaaccgct tgaagatcta    3240
aataataaaa aagacagctg tatttccaac cataccacca tagaaatagg caaagacctc    3300
aattatctca aagacggaaa tggaactact agtggcatag gcagcagtgt agaaaaatat    3360
gtcgtggatg aaagtgatta catgtcattt ataaacaacc ctagcctcac tgtgacagta    3420
ccaattgctg ttgagaatc tgactttgaa aatttaaata ctgaagaatt cagcagcgag    3480
tcagatatgg aggaaagcaa agagaagcta aatgcaacta gttcatctga aggcagcacg    3540
gttgatattg gagctcccgc cgagggagaa cagcctgagg ttgaacctga ggaatccctt    3600
gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780
gcctttgaag atatatacat tgagcagcga aaaaccatta gaccatgtt agaatatgct    3840 gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc agtttgaagg aatgagggtt    4080
gttgtaaatg ctcttttagg agccattcca tctatcatga atgtacttct ggtttgtctg    4140
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatctta ttttgtcatc tttattattt ttggttcatt cttttacttg    4500
aatcttttca ttggtgtcat catagataac ttcaaccaac agaaaagaa gtttggaggt    4560 caagacattt ttatgacaga agaacagaag aaatactaca tgcaatgaa aaaactgggt    4620 tcaaagaaac cacaaaaacc catacctcga cctgctaaca aattccaagg aatggtctt    4680 gattttgtaa ccaaacaagt ctttgatatc agcatcatga tcctcatctg ccttaacatg    4740
```

-continued

| | |
|---|---|
| gtcaccatga tggtggaaac cgatgaccag agtcaagaaa tgacaaacat tctgtactgg | 4800 |
| attaatctgg tgtttattgt tctgttcact ggagaatgtg tgctgaaact gatctctctt | 4860 |
| cgttactact atttcactat tggatggaat attttttgatt ttgtggtggt cattctctcc | 4920 |
| attgtaggaa tgtttctggc tgaactgata gaaaagtatt ttgtgtcccc tacccctgttc | 4980 |
| cgagtgatcc gtcttgccag gattggccga atcctacgtc tgatcaaagg agcaaagggg | 5040 |
| atccgcacgc tgctctttgc tttgatgatg tcccttcctg cgttgtttaa catcggcctc | 5100 |
| cttcttttcc tggtcatgtt catctacgcc atctttggga tgtccaattt tgcctatgtt | 5160 |
| aagagggaag ttgggatcga tgacatgttc aactttgaga cctttggcaa cagcatgatc | 5220 |
| tgcctgttcc aaattacaac ctctgctggc tgggatggat tgctagcacc tattcttaat | 5280 |
| agtggacctc cagactgtga ccctgacaaa gatcaccctg gaagctcagt taaaggagac | 5340 |
| tgtgggaacc catctgttgg gattttctttt ttttgtcagtt acatcatcat atccttcctg | 5400 |
| gttgtgctga acatgtacat cgcggtcatc ctggagaact tcagtgttgc tactgaagaa | 5460 |
| agtgcagagc ctctgagtga ggatgacttt gagatgttct atgaggtttg ggagaagttt | 5520 |
| gatcccgatg cgacccagtt tatagagttt gccaaacttt ctgattttgc agatgccctg | 5580 |
| gatcctcctc ttctcatagc aaaacccaac aaagtccagc tcattgccat ggatctgccc | 5640 |
| atggtgagtg tgaccggat ccactgtctt gacatcttat ttgcttttac aaagcgtgtt | 5700 |
| ttgggtgaga gtggagagat ggatgccctt cgaatacaga tggaagagcg attcatggca | 5760 |
| tcaaaccccct ccaaagtctc ttatgagccc attacgacca cgttgaaacg caaacaagag | 5820 |
| gaggtgtctg ctattattat ccagagggct tacagacgct acctcttgaa gcaaaaagtt | 5880 |
| aaaaaggtat caagtatata caagaaagac aaaggcaaag aatgtgatgg aacacccatc | 5940 |
| aaagaagata ctctcattga taaactgaat gagaattcaa ctccagagaa aaccgatatg | 6000 |
| acgccttcca ccacgtctcc accctcgtat gatagtgtga ccaaaccaga aaagaaaaa | 6060 |
| tttgaaaaag acaaatcaga aaggaagac aaagggaaag atatcaggga aagtaaaaag | 6120 |
| taaaaagaaa ccaagaattt tccattttgt gatcaattgt ttacagcccg tgatggtgat | 6180 |
| gtgtttgtgt caacaggact cccacaggag gtctatgcca aactgactgt ttttacaaat | 6240 |
| gtatacttaa ggtcagtgcc tataacaaga cagagacctc tggtcagcaa actggaactc | 6300 |
| agtaaactgg agaaatagta tcgatggg | 6328 |

<210> SEQ ID NO 16
<211> LENGTH: 6328
<212> TYPE: DNA
<213> ORGANISM: Homo sapiens

<400> SEQUENCE: 16

| | |
|---|---|
| ttcttggtgc cagcttatca atcccaaact ctgggtgtaa aagattctac agggcacttt | 60 |
| cttatgcaag gagctaaaca gtgattaaag gagcaggatg aaaagatggc acagtcagtg | 120 |
| ctggtaccgc caggacctga cagcttccgc ttctttacca gggaatccct tgctgctatt | 180 |
| gaacaacgca ttgcagaaga gaaagctaag agacccaaac aggaacgcaa ggatgaggat | 240 |
| gatgaaaatg gcccaaagcc aaacagtgac ttggaagcag gaaaatctct tccatttatt | 300 |
| tatggagaca ttcctccaga gatggtgtca gtgcccctgg aggatctgga ccctactat | 360 |
| atcaataaga aaacgtttat agtattgaat aaagggaaag caatctctcg attcagtgcc | 420 |
| acccctgccc tttacatttt aactcccttc aaccctatta gaaaattagc tattaagatt | 480 |
| ttggtacatt cttttattcaa tatgctcatt atgtgcacga ttcttaccaa ctgtgtattt | 540 |

```
atgaccatga gtaaccctcc agactggaca agaatgtgg  agtataccdt tacaggaatt   600
tatacttttg aatcacttat taaaatactt gcaaggggct tttgtttaga agatttcaca   660
tttttacggg atccatggaa ttggttggat ttcacagtca ttacttttgc atatgtgaca   720
gagtttgtgg acctgggcaa tgtctcagcg ttgagaacat tcagagttct ccgagcattg   780
aaaacaattt cagtcattcc aggcctgaag accattgtgg gggccctgat ccagtcagtg   840
aagaagcttt ctgatgtcat gatcttgact gtgttctgtc taagcgtgtt tgcgctaata   900
ggattgcagt tgttcatggg caacctacga ataaatgtt  tgcaatggcc tccagataat   960
tcttcctttg aaataaatat cacttccttc tttaacaatt cattggatgg gaatggtact  1020
actttcaata ggacagtgag catatttaac tgggatgaat atattgagga taaaagtcac  1080
ttttattttt tagaggggca aaatgatgct ctgctttgtg gcaacagctc agatgcaggc  1140
cagtgtcctg aaggatacat ctgtgtgaag gctggtagaa accccaacta tggctacacg  1200
agctttgaca cctttagttg ggcctttttg tccttatttc gtctcatgac tcaagacttc  1260
tgggaaaacc tttatcaact gacactacgt gctgctggga aaacgtacat gatatttttt  1320
gtgctggtca ttttcttggg ctcattctat ctaataaatt tgatcttggc tgtggtggcc  1380
atggcctatg aggaacagaa tcaggccaca ttggaagagg ctgaacagaa ggaagctgaa  1440
tttcagcaga tgctcgaaca gttgaaaaag caacaagaag aagctcaggc ggcagctgca  1500
gccgcatctg ctgaatcaag agacttcagt ggtgctggtg ggataggagt tttttcagag  1560
agttcttcag tagcatctaa gttgagctcc aaaagtgaaa aagagctgaa aaacagaaga  1620
aagaaaaaga aacagaaaga acagtctgga gaagaagaga aaaatgacag agtcctaaaa  1680
tcggaatctg aagacagcat aagaagaaaa ggtttccgtt tttccttgga aggaagtagg  1740
ctgacatatg aaaagagatt ttcttctcca caccagtcct tactgagcat ccgtggctcc  1800
cttttctctc caagacgcaa cagtagggcg agccttttca gcttcagagg tcgagcaaag  1860
gacattggct ctgagaatga ctttgctgac gatgagcaca gcacctttga ggacaatgac  1920
agccgaagag actctctgtt cgtgccgcac agacatggag aacggcgcca cagcaatgtc  1980
agccaggcca gccgtgcctc cagggtgctc cccatcctgc ccatgaatgg gaagatgcat  2040
agcgctgtgg actgcaatgg tgtggtctcc ctggtcgggg gcccttctac cctcacatct  2100
gctgggcagc tcctaccaga gggcacaact actgaaacag aaataagaaa gagacggtcc  2160
agttcttatc atgtttccat ggatttattg gaagatccta tcatcaaggca aagagcaatg  2220 agtatagcca gtattttgac caacaccatg aagaacttg  aagaatccag acagaaatgc  2280
ccaccatgct ggtataaatt tgctaatatg tgtttgattt gggactgttg taaaccatgg  2340
ttaaaggtga acaccttgt  caacctggtt gtaatgacc  catttgttga cctggccatc  2400
accatctgca ttgtcttaaa tacactcttc atggctatgg agcactatcc catgacggag  2460
cagttcagca gtgtactgtc tgttggaaac ctggtcttca gggatcttt  cacagcagaa  2520 atgtttctca agataattgc catggatcca tattattact ttcaagaagg ctggaatatt  2580
tttgatggtt ttattgtgag ccttagttta atggaacttg gtttggcaaa tgtgaagga   2640 ttgtcagttc tccgatcatt ccggctgctc cgagttttca agttggcaaa atcttggcca  2700
actctaaata tgctaattaa gatcattggc aattctgtgg gggctctagg aaacctcacc  2760
ttggtattgg ccatcatcgt cttcattttt gctgtggtcg gcatgcagct ctttggtaag  2820
agctacaaag aatgtgtctg caagatttcc aatgattgtg aactcccacg ctggcacatg  2880
catgactttt tccactcctt cctgatcgtg ttccgcgtgc tgtgtggaga gtggatagag  2940
```

```
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct ttgttaggaa gcagaaagct ttagatgaaa ttaaaccgct gaagatcta     3240 aataataaaa aagacagctg tatttccaac cataccacca tagaaatagg caagacctc     3300 aattatctca aagacggaaa tggaactact agtggcatag gcagcagtgt agaaaaatat    3360
gtcgtggatg aaagtgatta catgtcattt ataaacaacc ctagcctcac tgtgacagta    3420
ccaattgctg ttggagaatc tgactttgaa aatttaaata ctgaagaatt cagcagcgag    3480
tcagatatgg aggaaagcaa agagaagcta atgcaacta gttcatctga aggcagcacg      3540
gttgatattg gagctcccgc cgagggagaa cagcctgagg ttgaacctga ggaatccctt    3600
gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780
gcctttgaag atatatacat tgagcagcga aaaaccatta agaccatgtt agaatatgct    3840
gacaaggttt tcacttacat attcattctg gaaatgctgc taaagtgggg tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc ggtttgaagg aatgagggtt    4080
gttgtaaatg ctctttttagg agccattcca tctatcatga atgtacttct ggtttgtctg    4140
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatctttta ttttgtcatc tttattattt ttggttcatt cttttacttg     4500
aatcttttca ttggtgtcat catagataac ttcaaccaac agaaaagaa gtttggaggt     4560 caagacattt ttatgacaga agaacagaag aaatactaca atgcaatgaa aaaactgggt    4620
tcaaagaaac cacaaaaacc catacctcga cctgctaaca aattccaagg aatggtctttt    4680 gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt ttgtggtggt cattctctcc    4920
attgtaggaa tgtttctggc tgaactgata gaaaagtatt ttgtgtcccc taccctgttc    4980
cgagtgatcc gtcttgccag gattggccga atcctacgtc tgatcaaagg agcaaagggg    5040
atccgcacgc tgctctttgc tttgatgatg tcccttcctg cgttgtttaa catcggcctc    5100
cttcttttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
```

| | |
|---|---|
| tgtgggaacc catctgttgg gattttcttt tttgtcagtt acatcatcat atccttcctg | 5400 |
| gttgtgctga acatgtacat cgcggtcatc ctggagaact tcagtgttgc tactgaagaa | 5460 |
| agtgcagagc ctctgagtga ggatgacttt gagatgttct atgaggtttg ggagaagttt | 5520 |
| gatcccgatg cgacccagtt tatagagttt gccaaacttt ctgattttgc agatgccctg | 5580 |
| gatcctcctc ttctcatagc aaaacccaac aaagtccagc tcattgccat ggatctgccc | 5640 |
| atggtgagtg gtgaccggat ccactgtctt gacatcttat ttgcttttac aaagcgtgtt | 5700 |
| ttgggtgaga gtggagagat ggatgccctt cgaatacaga tggaagagcg attcatggca | 5760 |
| tcaaacccct ccaaagtctc ttatgagccc attacgacca cgttgaaacg caaacaagag | 5820 |
| gaggtgtctg ctattattat ccagagggct tacagacgct acctcttgaa gcaaaaagtt | 5880 |
| aaaaaggtat caagtatata caagaaagac aaaggcaaag aatgtgatgg aacacccatc | 5940 |
| aaagaagata ctctcattga taaactgaat gagaattcaa ctccagagaa aaccgatatg | 6000 |
| acgccttcca ccacgtctcc accctcgtat gatagtgtga ccaaaccaga aaagaaaaa | 6060 |
| tttgaaaaag acaaatcaga aaggaagac aaagggaaag atatcaggga aagtaaaaag | 6120 |
| taaaagaaa ccaagaattt tccattttgt gatcaattgt ttacagcccg tgatggtgat | 6180 |
| gtgtttgtgt caacaggact cccacaggag gtctatgcca aactgactgt ttttacaaat | 6240 |
| gtatacttaa ggtcagtgcc tataacaaga cagagacctc tggtcagcaa actggaactc | 6300 |
| agtaaactgg agaaatagta tcgatggg | 6328 |

<210> SEQ ID NO 17
<211> LENGTH: 6328
<212> TYPE: DNA
<213> ORGANISM: Homo sapiens

<400> SEQUENCE: 17

| | |
|---|---|
| ttcttggtgc cagcttatca atcccaaact ctgggtgtaa aagattctac agggcacttt | 60 |
| cttatgcaag gagctaaaca gtgattaaag gagcaggatg aaaagatggc acagtcagtg | 120 |
| ctggtaccgc caggacctga cagcttccgc ttctttacca gggaatccct tgctgctatt | 180 |
| gaacaacgca ttgcagaaga gaaagctaag agacccaaac aggaacgcaa ggatgaggat | 240 |
| gatgaaaatg cccaaagcc aaacagtgac ttggaagcag gaaaatctct tccatttatt | 300 |
| tatgagacga ttcctccaga gatggtgtca gtgcccctgg aggatctgga ccctactat | 360 |
| atcaataaga aaacgtttat agtattgaat aaagggaaag caatctctcg attcagtgcc | 420 |
| accctgccc tttacatttt aactcccttc aaccctatta gaaaattagc tattaagatt | 480 |
| ttggtacatt ctttattcaa tatgctcatt atgtgcacga ttcttaccaa ctgtgtattt | 540 |
| atgaccatga gtaaccctcc agactggaca agaatgtgg agtatacctt tacaggaatt | 600 |
| tatactttg aatcacttat taaaatactt gcaaggggct tttgtttaga agatttcaca | 660 |
| tttttacggg atccatggaa ttggttggat ttcacagtca ttacttttgc atatgtgaca | 720 |
| gagtttgtgg acctgggcaa tgtctcagcg ttgagaacat tcagagttct ccgagcattg | 780 |
| aaaacaattt cagtcattcc aggcctgaag accattgtgg gggccctgat ccagtcagtg | 840 |
| aagaagcttt ctgatgtcat gatcttgact gtgttctgtc taagcgtgtt tgcgctaata | 900 |
| ggattgcagt tgttcatggg caacctacga aataaatgtt tgcaatggcc tccagataat | 960 |
| tcttcctttg aaataaatat cacttccttc tttaacaatt cattggatgg gaatggtact | 1020 |
| actttcaata ggacagtgag catatttaac tgggatgaat atattgagga taaaagtcac | 1080 |
| ttttattttt tagaggggca aaatgatgct ctgcttttgtg gcaacagctc agatgcaggc | 1140 |

```
cagtgtcctg aaggatacat ctgtgtgaag gctggtagaa accccaacta tggctacacg    1200
agctttgaca cctttagttg ggccttttg tccttatttc gtctcatgac tcaagacttc    1260
tgggaaaacc tttatcaact gacactacgt gctgctggga aaacgtacat gatattttt    1320 gtgctggtca ttttcttggg ctcattctat ctaataaatt tgatcttggc tgtggtggcc    1380
atggcctatg aggaacagaa tcaggccaca ttggaagagg ctgaacagaa ggaagctgaa    1440
tttcagcaga tgctcgaaca gttgaaaaag caacaagaag aagctcaggc ggcagctgca    1500
gccgcatctg ctgaatcaag agacttcagt ggtgctggtg ggataggagt tttttcagag    1560
agttcttcag tagcatctaa gttgagctcc aaaagtgaaa aagagctgaa aaacagaaga    1620
aagaaaaaga aacagaaaga acagtctgga gaagaagaga aaaatgacag agtcctaaaa    1680
tcggaatctg aagacagcat aagaagaaaa ggtttccgtt tttccttgga aggaagtagg    1740
ctgacatatg aaaagagatt tcttctcca caccagtcct tactgagcat ccgtggctcc    1800
cttttctctc caagacgcaa cagtagggcg agccttttca gcttcagagg tcgagcaaag    1860
gacattggct ctgagaatga ctttgctgat gatgagcaca gcacctttga ggacaatgac    1920
agccgaagag actctctgtt cgtgccgcac agacatggag aacggcgcca cagcaatgtc    1980
agccaggcca gccgtgcctc cagggtgctc cccatcctgc ccatgaatgg gaagatgcat    2040
agcgctgtgg actgcaatgg tgtggtctcc ctggtcgggg gccttctac cctcacatct    2100 gctgggcagc tcctaccaga gggcacaact actgaaacag aaataagaaa gagacggtcc    2160
agttcttatc atgtttccat ggatttattg gaagatccta catcaaggca agagcaatg    2220 agtatagcca gtattttgac caacaccatg aagaacttg aagaatccag acagaaatgc    2280
ccaccatgct ggtataaatt tgctaatatg tgtttgattt gggactgttg taaaccatgg    2340
ttaaaggtga acaccttgt caacctggtt gtaatggacc catttgttga cctggccatc    2400
accatctgca ttgtcttaaa tacactcttc atggctatgg agcactatcc catgacggag    2460
cagttcagca gtgtactgtc tgttggaaac ctggtcttca cagggatctt cacagcagaa    2520
atgtttctca agataattgc catggatcca tattattact ttcaagaagg ctggaatatt    2580
tttgatggtt ttattgtgag ccttagttta atggaacttg gtttggcaaa tgtggaagga    2640
ttgtcagttc tccgatcatt ccggctgctc cgagttttca gttggcaaa tcttggcca    2700 actctaaata tgctaattaa gatcattggc aattctgtgg gggctctagg aaacctcacc    2760
ttggtattgg ccatcatcgt cttcattttt gctgtggtcg gcatgcagct ctttggtaag    2820
agctacaaag aatgtgtctg caagatttcc aatgattgtg aactcccacg ctggcacatg    2880
catgactttt tccactcctt cctgatcgtg ttccgcgtgc tgtgtggaga gtggatagag    2940
accatgtggg actgtatgga ggtcgctggc caaaccatgt gccttactgt cttcatgatg    3000
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct tgttaggaa gcagaaagct ttagatgaaa ttaaaccgct tgaagatcta    3240
aataataaaa aagacagctg tatttccaac cataccacca tagaaatagg caaagacctc    3300
aattatctca aagacggaaa tggaactact agtggcatag cagcagtgt agaaaaatat    3360 gtcgtggatg aaagtgatta catgtcattt ataaacaacc ctagcctcac tgtgacagta    3420
ccaattgctg ttgagaatc tgactttgaa aatttaaata ctgaagaatt cagcagcgag    3480
tcagatatgg aggaaagcaa agagaagcta atgcaacta gttcatctga aggcagcacg    3540
```

```
gttgatattg gagctcccgc cgagggagaa cagcctgagg ttgaacctga ggaatccctt    3600
gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780
gcctttgaag atatatacat tgagcagcga aaaaccatta agaccatgtt agaatatgct    3840
gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc ggtttgaagg aatgagggtt    4080
gttgtaaatg ctcttttagg agccattcca tctatcatga atgtacttct ggtttgtctg    4140
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat acaacccaa gtatgaagac    4440 aacctgtaca tgtatcttta ttttgtcatc tttattattt ttggttcatt ctttaccttg    4500
aatcttttca ttggtgtcat catagataac ttcaaccaac agaaaagaa gtttggaggt    4560 caagacattt ttatgacaga agaacagaag aaatactaca atgcaatgaa aaaactgggt    4620
tcaaagaaac cacaaaaacc catacctcga cctgctaaca aattccaagg aatggtcttt    4680
gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt tgtggtggt cattctctcc    4920 attgtaggaa tgtttctggc tgaactgata gaaaagtatt ttgtgtcccc taccctgttc    4980
cgagtgatcc gtcttgccag gattggccga atcctacgtc tgaacaaagg agcaaagggg    5040
atccgcacgc tgctctttgc tttgatgatg tcccttcctg cgttgtttaa catcggcctc    5100 cttctttttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat gctagcacc tattcttaat    5280 agtggacctc cagactgtga ccctgacaaa gatcaccctg gaagctcagt taaaggagac    5340
tgtgggaacc catctgttgg gattttcttt tttgtcagtt acatcatcat atccttcctg    5400
gttgtgctga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtgagagat ggatgccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaagtt    5880 aaaaaggtat caagtatata caagaaagac aaaggcaaag aatgtgatgg aacacccatc    5940
```

```
aaagaagata ctctcattga taaactgaat gagaattcaa ctccagagaa aaccgatatg    6000
acgccttcca ccacgtctcc accctcgtat gatagtgtga ccaaaccaga aaagaaaaa     6060 tttgaaaaag acaaatcaga aaggaagac aaagggaaag atatcaggga aagtaaaaag     6120 taaaagaaa ccaagaattt tccattttgt gatcaattgt ttacagcccg tgatggtgat     6180
gtgtttgtgt caacaggact cccacaggag gtctatgcca aactgactgt ttttacaaat    6240
gtatacttaa ggtcagtgcc tataacaaga cagagacctc tggtcagcaa actggaactc    6300
agtaaactgg agaaatagta tcgatggg                                       6328
```

<210> SEQ ID NO 18
<211> LENGTH: 385
<212> TYPE: DNA
<213> ORGANISM: Homo sapiens

<400> SEQUENCE: 18

```
ttcaatatat tttttaaaag ccatgcaaat acttcagccc tttcaaagaa agatacagtc      60
tcttcaggtg ctatgttaaa atcatttctc ttcaatataa caggcagcaa cggcaactgc     120
ctcagaacat tccagagagc ccagtgcagc aggcaggctc tcagacagct catctgaagc    180
ctctaagttg agttccaaga gtgctaagga aagaagaaat cggaggaaga aaagaaaaca    240
gaaagagcag tctggtgggg aagagaaaga tgaggatgaa ttccaaaaat ctgaatctga    300
ggacagcatc aggaggaaag gttttcgctt ctccattgaa gggaaccgat tgacatatga    360
aaagaggtac tcctccccac accag                                          385
```

<210> SEQ ID NO 19
<211> LENGTH: 238
<212> TYPE: DNA
<213> ORGANISM: Homo sapiens

<400> SEQUENCE: 19

```
gtggaactcc agcctaagta tgaagaaagt ctgtacatgt atctttactt tgttattttc     60
atcatctttg ggtccttctt caccttgaac ctgtttattg gtgtcatcat agataatttc    120
aaccagcaga aaaagaagat aagtatttct aatattttct ctcccactga aatagaaaat    180
tattccttgg agtgttttct ctgccaaatg agtacttgaa tttagaaaca aatggga       238
```

<210> SEQ ID NO 20
<211> LENGTH: 373
<212> TYPE: DNA
<213> ORGANISM: Homo sapiens

<400> SEQUENCE: 20

```
gcctgaagac cattgtgggg gccctgatcc agtcagtgaa gaagctttct gatgtcatga     60
tcttgactgt gttctgtcta agcgtgtttg cgctaatagg attgcagttg ttcatgggca    120
acctacgaaa taaatgtttg caatggcctc cagataattc ttcctttgaa ataaatatca    180
cttccttctt taacaattca ttggatggga atggtactac tttcaatagg acagtgagca    240
tatttaactg ggatgaatat attgaggata aagtaagat atactctata aaccattaag     300
ttgtttagtt ctctaaatat taaatattat ataaaatgga aattatctca atttagatgt    360
gaatcaagtg act                                                       373
```

<210> SEQ ID NO 21
<211> LENGTH: 274
<212> TYPE: DNA
<213> ORGANISM: Homo sapiens -continued

```
<400> SEQUENCE: 21
taggcacctg ataagagctt gcatcgtttc cttttttaag aaatcgtcaa ttagagactg      60
tttctgatca taaaatttaa tagaattttt tgacttacag gcctttgaag atatatacat     120
tgagcagcga aaaaccatta agaccatgtt agaatatgct gacaaggttt tcacttacat     180
attcattctg gaaatgctgc taaagtgggt tgcatatggt tttcaagtgt attttaccaa     240
tgcctggtgc tggctagact tcctgattgt tgat                                 274

<210> SEQ ID NO 22
<211> LENGTH: 154
<212> TYPE: DNA
<213> ORGANISM: Homo sapiens

<400> SEQUENCE: 22
gtattgaata catgtcaaat agaatttttga tcaattattc aatttatttt ctaaaattat     60
aattttgggg aaaaagaaaa tgatatgact tttcttacag gccacgttta agggatggat    120
ggatattatg tatgcagctg ttgattcacg aaat                                 154

<210> SEQ ID NO 23
<211> LENGTH: 219
<212> TYPE: DNA
<213> ORGANISM: Homo sapiens

<400> SEQUENCE: 23
ttacagggca atatttataa ataatggttt tactttttctc ttaaaatatt cttaatatat     60
attctaagtt ttatttttatg tgttgtgttt tcttttttcag acgtttatag tattgaataa    120
agggaaagca atctctcgat tcagtgccac ccctgcccctt tacattttaa ctcccttcaa    180
ccctattaga aaattagcta ttaagatttt ggtacattc                           219

<210> SEQ ID NO 24
<211> LENGTH: 242
<212> TYPE: DNA
<213> ORGANISM: Homo sapiens

<400> SEQUENCE: 24
gtgcctgtat aaaacagaca ttggcatata ttaaaacagg aaaaccaatt agcagacttg      60
ccgttattga cttcctttct ttcctctaac ctaattacag ccagtgtcct gaaggataca    120
tctgtgtgaa ggctggtaga aaccccaact atggctacac gagctttgac acctttagtt    180
gggccttttt gtccttattt cgtctcatga ctcaagactt ctgggaaaac ctttatcaac    240
tg                                                                   242

<210> SEQ ID NO 25
<211> LENGTH: 388
<212> TYPE: DNA
<213> ORGANISM: Homo sapiens

<400> SEQUENCE: 25
gcggcagctg cagccgcatc tgctgaatca agagacttca gtggtgctgg tgggatagga     60
gttttttcag agagttcttc agtagcatct aagttgagct ccaaaagtga aaagagctg     120 aaaaacagaa gaaagaaaaa gaaacagaaa gaacagtctg gagaagaaga gaaaatgac    180 agagtcctaa aatcggaatc tgaagacagc ataagaagaa aaggtttccg ttttttccttg    240 gaaggaagta ggctgacata tgaaaagaga ttttcttctc cacaccaggt aaaaatatta    300
aattacatga attgtgttct cataaatttt ttaaaagaat atgccagaat ttaatggaga    360
```

```
gaaaaccgcc ttccacctgg atggcaca                                        388
```

<210> SEQ ID NO 26
<211> LENGTH: 445
<212> TYPE: DNA
<213> ORGANISM: Homo sapiens

<400> SEQUENCE: 26

```
aagtcaatga ctatgacaca atgaatcaaa ttctgttttt cagaatgcca gctcttaact     60
ctcttcatct cattttgtt tcttttcttg ttattcatag tccttactga gcatccgtgg    120
ctcccttttc tctccaagac gcaacagtag ggcgagcctt ttcagcttca gaggtcgagc    180
aaaggacatt ggctctgaga atgactttgc tgatgatgag cacagcacct ttgaggacaa    240
tgacagccga agagactctc tgttcgtgcc gcacagacat ggagaacggc gcccacagcaa   300
tgtcagccag gccagccgtg cctccagggt gctccccatc ctgcccatga atgggaagat    360
gcatagcgct gtggactgca atggtgtggt ctccctggtc gggggcccctt ctaccctcac   420
atctgctggg cagctcctac cagag                                          445
```

<210> SEQ ID NO 27
<211> LENGTH: 221
<212> TYPE: DNA
<213> ORGANISM: Homo sapiens

<400> SEQUENCE: 27

```
aaatgcatac agaagatggg ggggggcat acctaattaa ttttttatatt tagattaaag     60
aaaataatta aatgtgtttt tttgtgggat tgattttcag aagctaaatg caactagttc    120
atctgaaggc agcacggttg atattggagc tcccgccgag ggagaacagc ctgaggttga    180
acctgaggaa tcccttgaac ctgaagcctg ttttacagaa g                        221
```

<210> SEQ ID NO 28
<211> LENGTH: 221
<212> TYPE: DNA
<213> ORGANISM: Homo sapiens

<400> SEQUENCE: 28

```
aaaatgcata cagaagatgg gggggggcac acctaattaa ttttttatatt tagattaaag    60
aaaataatta aatgtgtttt tttgtgggat tgattttcag aagctaaatg caactagttc    120
atctgaaggc agcacggttg atattggagc tcccgccgag ggagaacagc ctgaggttga    180
acctgaggaa tcccttgaac ctgaagcctg ttttacagaa g                        221
```

<210> SEQ ID NO 29
<211> LENGTH: 221
<212> TYPE: DNA
<213> ORGANISM: Homo sapiens

<400> SEQUENCE: 29

```
aatgcataca gaagatgggg ggggggcac acctaattaa ttttttatatt tagattaaag     60
aaaataatta aatgtgtttt tttgtgggat tgattttcag aagctaaatg caactagttc    120
atctgaaggc agcacggttg atattggagc tcccgccgag ggagaacagc ctgaggttga    180
acctgaggaa tcccttgaac ctgaagcctg ttttacagaa g                        221
```

<210> SEQ ID NO 30
<211> LENGTH: 1679
<212> TYPE: DNA
<213> ORGANISM: Homo sapiens

```
<400> SEQUENCE: 30
gggagctgtg gcgcggagcg gcccctctgc tgcgtctgcc ctcgttttgt ctcacgactc      60
acactcagtg ctccattccc caagagttcg cgttccccgc gcggcggtcg agaggcggct     120
gcccgcggtc ccgcgcgggc gcggggcgat ggcggcgcgg gggtcagggc cccgcgcgct     180
ccgcctgctg ctcttggtcc agctggtcgc ggggcgctg cggtctagcc gggcgcggcg     240
ggcggcgcgc agaggattat ctgaaccttc ttctattgca aaacatgaag atagtttgct     300
taaggattta tttcaagact acgaaagatg ggttcgtcct gtggaacacc tgaatgacaa     360
aataaaaata aaatttggac ttgcaatatc tcaattggtg gatgtggatg agaaaaatca     420
gttaatgaca acaaacgtct ggttgaaaca ggaatggata gatgtaaaat taagatggaa     480
ccctgatgac tatggtggaa taaaagttat acgtgttcct tcagactctt cgtgacacc      540 agacatcatt ttgtttgata atgcagatgg acgttttgaa gggaccagta cgaaaacagt     600
catcaggtac aatggcactg tcacctggac tccaccggca aactcaaaa gttcctgtac      660 catagatgtc acgttttcc catttgacct tcagaactgt tccatgaaat tggttcttg       720 gacttatgat ggatcacagg ttgatataat tctagaggac caagatgtag acaagagaga     780 ttttttgat aatggagaat gggagattgt gagtgcaaca gggagcaaag gaaacagaac       840
cgacagctgt tgctggtatc cgtatgtcac ttactcattt gtaatcaagc gcctgcctct     900 ctttatacc ttgttcctta taatacctg tattgggctc tcattttaa ctgtacttgt         960 cttctatctt ccttcaaatg aaggtgaaaa gatttgtctc tgcacttcag tacttgtgtc    1020
tttgactgtc ttccttctgg ttattgaaga gatcatacca tcatcttcaa aagtcatacc    1080
tctaattgga gagtatctgg tatttaccat gattttgtg acactgtcaa ttatggtaac     1140
cgtcttcgct atcaacattc atcatcgttc ttcctcaaca cataatgcca tggcgccttt    1200
ggtccgcaag atatttcttc acacgcttcc caaactgctt tcgatgagaa gtcatgtaga    1260
caggtacttc actcagaaag aggaaactga gagtggtagt ggaccaaaat cttctagaaa    1320
cacattggaa gctgcgctcg attctattcg ctacattaca acacacatca tgaaggaaaa    1380
tgatgtccgt gaggttgttg aagattggaa attcatagcc caggttcttg atcggatgtt    1440
tctgtggact tttcttttcg tttcaattgt tggatctctt gggcttttg ttcctgttat      1500 ttataaatgg gcaaatatat taataccagt tcatattgga aatgcaaata agtgaagcct    1560
cccaagggac tgaagtatac atttagttaa cacacatata tctgatggca cctataaaat    1620
tatgaaaatg taagttatgt gttaaattta gtgcaagctt aacagacta agttgctaa     1679

<210> SEQ ID NO 31
<211> LENGTH: 2664
<212> TYPE: DNA
<213> ORGANISM: Homo sapiens

<400> SEQUENCE: 31
gagagaacag cgtgagcctg tgtgcttgtg tgctgagccc tcatcccctc ctggggccag      60
gcttgggttt cacctgcaga atcgcttgtg ctgggctgcc tggctgtcc tcagtggcac     120 ctgcatgaag ccgttctggc tgccagagct ggacagcccc aggaaaaccc acctctctgc    180
agagcttgcc cagctgtccc cgggaagcca atgcctctc atgtaagtct tctgctcgac    240 gggtgtctc ctaaaccctc actcttcagc ctctgtttga ccatgaaatg aagtgactga     300
gctctattct gtacctgcca ctctatttct ggggtgactt ttgtcagctg cccagaatct    360
ccaagccagg ctggttctct gcatcctttc aatgacctgt tttcttctgt aaccacaggt    420
```

```
tcggtggtga gaggaagcct cgcagaatcc agcagaatcc tcacagaatc cagcagcagc    480
tctgctgggg acatggtcca tggtgcaacc cacagcaaag ccctgacctg acctcctgat    540
gctcaggaga agccatgggc ccctcctgtc ctgtgttcct gtccttcaca aagctcagcc    600
tgtggtggct ccttctgacc ccagcaggtg agaggaagct aagcgccca ctcccaggg     660
ctcctggaga cccactctcc tctcccagtc ccacggcatt gccgcaggga ggctcgcata    720
ccgagactga ggaccggctc ttcaaacacc tcttccgggg ctacaaccgc tgggcgcgcc    780
cggtgcccaa cacttcagac gtggtgattg tgcgctttgg actgtccatc gctcagctca    840
tcgatgtgga tgagaagaac caaatgatga ccaccaacgt ctggctaaaa caggagtgga    900
gcgactacaa actgcgctgg aaccccactg attttggcaa catcacatct ctcagggtcc    960
cttctgagat gatctggatc cccgacattg ttctctacaa caatgcagat ggggagtttg   1020
cagtgaccca catgaccaag gcccacctct ctccacggg cactgtgcac tgggtgcccc    1080
cggccatcta caagagctcc tgcagcatcg acgtcacctt cttcccctc gaccagcaga   1140
actgcaagat gaagtttggc tcctggactt atgacaaggc caagatcgac ctggagcaga   1200
tggagcagac tgtggacctg aaggactact gggagagcgg cgagtgggcc atcgtcaatg   1260
ccacgggcac ctacaacagc aagaagtacg actgctgcgc cgagatctac cccgacgtca   1320
cctacgcctt cgtcatccgg cggctgccgc tcttctacac catcaacctc atcatcccct   1380
gcctgctcat ctcctgcctc actgtgctgg tcttctacct gcctccgac tgcggcgaga   1440
agatcacgct gtgcatttcg gtgctgctgt cactcaccgt cttcctgctg ctcatcactg   1500
agatcatccc gtccacctcg ctggtcatcc cgctcatcgg cgagtacctg ctgttcacca   1560
tgatcttcgt caccctgtcc atcgtcatca ccgtcttcgt gctcaatgtg caccaccgct   1620
cccccagcac ccacaccatg ccccactggg tgcgggggc ccttctgggc tgtgtgcccc    1680
ggtggcttct gatgaaccgg ccccaccac ccgtggagct ctgccacccc ctacgcctga    1740
agctcagccc ctcttatcac tggctggaga gcaacgtgga tgccgaggag agggaggtgg   1800
tggtggagga ggaggacaga tgggcatgtg caggtcatgt ggcccctct gtgggcaccc   1860
tctgcagcca cggccacctg cactctgggg cctcaggtcc caaggctgag gctctgctgc   1920
aggagggtga gctgctgcta tcaccccaca tgcagaaggc actggaaggt gtgcactaca   1980
ttgccgacca cctgcggtct gaggatgctg actcttcggt gaaggaggac tggaagtatg   2040
ttgccatggt catcgacagg atcttcctct ggctgtttat catcgtctgc ttcctgggga   2100
ccatcggcct ctttctgcct ccgttcctag ctggaatgat ctgactgcac ctccctcgag   2160
ctggctccca gggcaaaggg gagggttctt ggatgtggaa gggctttgaa caatgtttag   2220
atttggagat gagcccaaag tgccagggag aacagccagg tgaggtggga ggttggagag   2280
ccaggtgagg tctctctaag tcaggctggg gttgaagttt ggagtctgtc cgagtttgca   2340
gggtgctgag ctgtatggtc cagcagggga gtaataaggg ctcttccgga aggggaggaa   2400
gcgggaggca ggcctgcacc tgatgtggag gtacaggcag atcttcccta ccggggaggg   2460
atggatggtt ggatacaggt ggctgggcta ttccatccat ctggaagcac atttgagcct   2520
ccaggcttct ccttgacgtc attcctctcc ttccttgctg caaaatggct ctgcaccagc   2580
cggccccag gaggtctggc agagctgaga gccatggcct gcaggggctc catatgtccc    2640
tacgcgtgca gcaggcaaac aaga                                          2664
```

<210> SEQ ID NO 32
<211> LENGTH: 3020
<212> TYPE: DNA

<213> ORGANISM: Homo sapiens

<400> SEQUENCE: 32

| | | | | | |
|---|---|---|---|---|---|
| gtcctcccgc | gggtccgagg | gcgctggaaa | cccagcggcg | gcgaagcgga | gaggagcccc | 60 |
| gcgcgtctcc | gcccgcacgg | ctccaggtct | ggggtctgcg | ctggagccgc | gcggggagag | 120 |
| gccgtctctg | cgaccgccgc | gcccgctccc | gaccgtccgg | gtccgcggcc | agcccggcca | 180 |
| ccagccatgg | gctctggccc | gctctcgctg | ccctggcgc | tgtcgccgcc | gcggctgctg | 240 |
| ctgctgctgc | tgctgtctct | gctgccagtg | gccagggcct | cagaggctga | gcaccatcta | 300 |
| tttgagcggc | tgtttgaaga | ttacaatgag | atcatccggc | tgtagccaa | cgtgtctgac | 360 |
| ccagtcatca | tccatttcga | ggtgtccatg | tctcagctgg | tgaaggtgga | tgaagtaaac | 420 |
| cagatcatga | gaccaacct | gtggctcaag | caaatctgga | atgactacaa | gctgaagtgg | 480 |
| aaccctctg | actatggtgg | ggcagagttc | atgcgtgtcc | ctgcacagaa | gatctggaag | 540 |
| ccagacattg | tgctgtataa | caatgctgtt | ggggatttcc | aggtggacga | caagaccaaa | 600 |
| gccttactca | agtacactgg | ggaggtgact | tggatacctc | cggccatctt | taagagctcc | 660 |
| tgtaaaatcg | acgtgaccta | cttcccgttt | gattaccaaa | actgtaccat | gaagttcggt | 720 |
| tcctggtcct | acgataaggc | gaaaatcgat | ctggtcctga | tcggctcttc | catgaacctc | 780 |
| aaggactatt | gggagagcgg | cgagtgggcc | atcatcaaag | ccccaggcta | caaacacgac | 840 |
| atcaagtaca | actgctgcga | ggagatctac | cccgacatca | catactcgct | gtacatccgg | 900 |
| cgcctgcct | tgttctacac | catcaacctc | atcatcccct | gcctgctcat | ctccttcctc | 960 |
| actgtgctcg | tcttctacct | gccctccgac | tgcggtgaga | aggtgaccct | gtgcatttct | 1020 |
| gtcctcctct | ccctgacggt | gtttctcctg | gtgatcactg | agaccatccc | ttccacctcg | 1080 |
| ctggtcatcc | ccctgattgg | agagtacctc | ctgttcacca | tgattttgt | aaccttgtcc | 1140 |
| atcgtcatca | ccgtcttcgt | gctcaacgtg | cactacagaa | ccccgacgac | acacacaatg | 1200 |
| ccctcatggg | tgaagactgt | attcttgaac | ctgctcccca | gggtcatgtt | catgaccagg | 1260 |
| ccaacaagca | acgagggcaa | cgctcagaag | ccgaggcccc | tctacggtgc | cgagctctca | 1320 |
| aatctgaatt | gcttcagccg | cgcagagtcc | aaaggctgca | aggagggcta | cccctgccag | 1380 |
| gacgggatgt | gtggttactg | ccaccaccgc | aggataaaaa | tctccaattt | cagtgctaac | 1440 |
| ctcacgagaa | gctctagttc | tgaatctgtt | gatgctgtgc | tgtccctctc | tgctttgtca | 1500 |
| ccagaaatca | agaagccat | ccaaagtgtc | aagtatattg | ctgaaaatat | gaaagcacaa | 1560 |
| aatgaagcca | aagagattca | agatgattgg | aagtatgttg | ccatggtgat | tgatcgtatt | 1620 |
| tttctgtggg | ttttcacccct | ggtgtgcatt | ctagggacag | caggattgtt | tctgcaaccc | 1680 |
| ctgatggcca | gggaagatgc | ataagcacta | agctgtgtgc | ctgcctggga | gacttccttg | 1740 |
| tgtcagggca | ggaggaggct | gcttcctagt | aagaacgtac | tttctgttat | caagctacca | 1800 |
| gctttgtttt | tggcatttcg | aggtttactt | attttccact | tatcttggaa | tcatgcaaaa | 1860 |
| aaaaaaatgt | caagagtatt | tattaccgat | aaatgaacat | ttaactagcc | ttttggtat | 1920 |
| ggtaaagaga | tgtcaaaatg | tgattctatg | tgattagtat | gctatgctat | ggaatataca | 1980 |
| tgtaaaaatg | tttcctttta | gttgttgaaa | caaaactgga | tagaaaaatg | ctgttcagaa | 2040 |
| atatgaaaag | tcattcagtt | atcactacag | atctcccagt | aattttttctt | atttagccca | 2100 |
| taatctcttt | gaaggtttat | actaattcag | caatccccca | tcgttaccca | tttcttacca | 2160 |
| tgcatttctc | gttctttact | gggtctaaag | ggctatgcct | ccatttcaga | gagcttcaac | 2220 |
| tacttctctt | gcatacttct | aaattatact | atgagaaatc | atgcctagtt | attcattgtt | 2280 |

| | |
|---|---|
| aatataactg tcttagtaca ccataaactg ggtggattat aaacaacaga aacttctcag | 2340 |
| ttttggaggt tgggaggtcc aaggtcaagg caccagcaaa tttggtgtct ggtgagggtc | 2400 |
| ctcttcctca aagggtgcct tctagctgtg tcctcacatg actgaaggga ctagctatct | 2460 |
| ctgtggggtc tattttataa gggcactaac cccattcatg agagcagagc ccccatggcc | 2520 |
| taatcacctt tccaaggccc caccttctat ctaagacaat cacgctggga ataggtttca | 2580 |
| acatatgaat tggggagga cacatttgga ccacagcatg aacctttaga cagggtttc | 2640 |
| tcagccttag cactacggac attttgggct ggataaatat gtgttggtac agaatggggg | 2700 |
| tatcctgtgc attgtaggat ctttagcagt accctagcct caactcacta gatgccaatg | 2760 |
| acataccttg cttcttcacc agttatgata accaagaatg tctccattgt taaatgtccc | 2820 |
| cttaggagca aaattgcccc tggttgagaa acattgcttt agacaaattg ttaagagtat | 2880 |
| catgtactac acttctgaaa cttaacgtga tcatcaccac tgacagatga ttcacagaga | 2940 |
| gagactgttt gaatcttgtc tcactagttt ttcctgtgca aaaataaaat ggacagaatt | 3000 |
| gcaaaaaaaa aaaaaaaaa | 3020 |

<210> SEQ ID NO 33
<211> LENGTH: 2664
<212> TYPE: DNA
<213> ORGANISM: Homo sapiens

<400> SEQUENCE: 33

| | |
|---|---|
| gagagaacag cgtgagcctg tgtgcttgtg tgctgagccc tcatcccctc ctggggccag | 60 |
| gcttgggttt cacctgcaga atcgcttgtg ctgggctgcc tgggctgtcc tcagtggcac | 120 |
| ctgcatgaag ccgttctggc tgccagagct ggacagcccc aggaaaaccc acctctctgc | 180 |
| agagcttgcc cagctgtccc cgggaagcca atgcctctc atgtaagtct tctgctcgac | 240 |
| ggggtgtctc ctaaaccctc actcttcagc ctctgtttga ccatgaaatg aagtgactga | 300 |
| gctctattct gtacctgcca ctctatttct ggggtgactt ttgtcagctg cccagaatct | 360 |
| ccaagccagg ctggttctct gcatcctttc aatgacctgt tttcttctgt aaccacaggt | 420 |
| tcggtggtga gaggaagcct cgcagaatcc agcagaatcc tcacagaatc cagcagcagc | 480 |
| tctgctgggg acatggtcca tggtgcaacc cacagcaaag ccctgacctg acctcctgat | 540 |
| gctcaggaga agccatgggc ccctcctgtc ctgtgttcct gtccttcaca aagctcagcc | 600 |
| tgtggtggct ccttctgacc cagcaggtg gagaggaagc taagcgccca cctcccaggg | 660 |
| ctcctggaga cccactctcc tctcccagtc ccacggcatt gccgcaggga ggctcgcata | 720 |
| ccgagactga ggaccggctc ttcaaacacc tcttccgggg ctacaaccgc tgggcgcgcc | 780 |
| cggtgcccaa cacttcagac gtggtgattg tgcgctttgg actgtccatc gctcagctca | 840 |
| tcgatgtgga tgagaagaac caaatgatga ccaccaacgt ctggctaaaa caggagtgga | 900 |
| gcgattacaa actgcgctgg aaccccgctg atttggcaa catcacatct ctcagggtcc | 960 |
| cttctgagat gatctggatc cccgacattg ttctctacaa caatgcagat ggggagttg | 1020 |
| cagtgaccca catgaccaag gcccacctct ctccacgggg cactgtgcac tgggtgcccc | 1080 |
| cggccatcta caagagctcc tgcagcatcg acgtcacctt cttccccttc gaccagcaga | 1140 |
| actgcaagat gaagtttggc tcctggactt atgacaaggc caagatcgac ctggagcaga | 1200 |
| tggagcagac tgtggacctg aaggactact gggagagcgg cgagtgggcc atcgtcaatg | 1260 |
| ccacgggcac ctacaacagc aagaagtacg actgctgcgc cgagatctac cccgacgtca | 1320 |
| cctacgcctt cgtcatccgg cggctgccgc tcttctacac catcaacctc atcatcccct | 1380 |

```
gcctgctcat ctcctgcctc actgtgctgg tcttctacct gccctccgac tgcggcgaga    1440
agatcacgct gtgcatttcg gtgctgctgt cactcaccgt cttcctgctg ctcatcactg    1500
agatcatccc gtccacctcg ctggtcatcc cgctcatcgg cgagtacctg ctgttcacca    1560
tgatcttcgt caccctgtcc atcgtcatca ccgtcttcgt gctcaatgtg caccaccgct    1620
cccccagcac ccacaccatg ccccactggg tgcgggggc ccttctgggc tgtgtgcccc    1680
ggtggcttct gatgaaccgg cccccaccac ccgtggagct ctgccacccc ctacgcctga    1740
agctcagccc ctcttatcac tggctggaga gcaacgtgga tgccgaggag agggaggtgg    1800
tggtggagga ggaggacaga tgggcatgtg caggtcatgt ggcccctct gtgggcaccc    1860 tctgcagcca cggccacctg cactctgggg cctcaggtcc caaggctgag gctctgctgc    1920
aggagggtga gctgctgcta tcaccccaca tgcagaaggc actggaaggt gtgcactaca    1980
ttgccgacca cctgcggtct gaggatgctg actcttcggt gaaggaggac tggaagtatg    2040
ttgccatggt catcgacagg atcttcctct ggctgtttat catcgtctgc ttcctgggga    2100
ccatcggcct ctttctgcct ccgttcctag ctggaatgat ctgactgcac ctccctcgag    2160
ctggctccca gggcaaaggg gagggttctt ggatgtggaa gggctttgaa caatgtttag    2220
atttggagat gagcccaaag tgccagggag aacagccagg tgaggtggga ggttggagag    2280
ccaggtgagg tctctctaag tcaggctggg gttgaagttt ggagtctgtc cgagtttgca    2340
gggtgctgag ctgtatggtc cagcagggga gtaataaggg ctcttccgga aggggaggaa    2400 gcggaggca ggcctgcacc tgatgtggag gtacaggcag atcttcccta ccggggaggg    2460
atggatggtt ggatacaggt ggctgggcta ttccatccat ctggaagcac atttgagcct    2520
ccaggcttct ccttgacgtc attcctctcc ttccttgctg caaaatggct ctgcaccagc    2580
cggcccccag gaggtctggc agagctgaga gccatggcct gcagggctc catatgtccc    2640 tacgcgtgca gcaggcaaac aaga                                           2664

<210> SEQ ID NO 34
<211> LENGTH: 2664
<212> TYPE: DNA
<213> ORGANISM: Homo sapiens

<400> SEQUENCE: 34
gagagaacag cgtgagcctg tgtgcttgtg tgctgagccc tcatcccctc ctggggccag      60
gcttgggttt cacctgcaga atcgcttgtg ctgggctgcc tgggctgtcc tcagtggcac     120
ctgcatgaag ccgttctggc tgccagagct ggacagcccc aggaaaaccc acctctctgc     180
agagcttgcc cagctgtccc cgggaagcca aatgcctctc atgtaagtct tctgctcgac     240
ggggtgtctc ctaaaccctc actcttcagc ctctgtttga ccatgaaatg aagtgactga     300
gctctattct gtacctgcca ctctatttct ggggtgactt ttgtcagctg cccagaatct     360
ccaagccagg ctggttctct gcatccttc aatgacctgt tttcttctgt aaccacaggt      420
tcggtggtga gaggaagcct cgcagaatcc agcagaatcc tcacagaatc cagcagcagc     480
tctgctgggg acatggtcca tggtgcaacc cacagcaaag ccctgacctg acctcctgat     540
gctcaggaga agccatgggc ccctcctgtc ctgtgttcct gtccttcaca aagctcagcc     600
tgtggtggct ccttctgacc ccagcaggtg agaggaagc taagcgccca cctcccaggg     660
ctcctggaga cccactctcc tctcccagtc ccacggcatt gccgcaggga ggctcgcata     720
ccgagactga ggaccggctc ttcaaacacc tcttccgggg ctacaaccgc tgggcgcgcc     780
cggtgcccaa cacttcagac gtggtgattg tgcgctttgg actgtccatc gctcagctca     840
```

| | | |
|---|---|---|
| tcgatgtgga tgagaagaac caaatgatga ccaccaacgt ctggctaaaa caggagtgga | 900 | |
| gcgactacaa actgcgctgg aaccccgctg attttggcaa catcacatct ctcagggtcc | 960 | |
| cttctgagat gatctggatc cccgacattg ttctctacaa caatgcagat ggggagtttg | 1020 | |
| cagtgaccca catgaccaag gcccacctct tctccacggg cactgtgcac tgggtgcccc | 1080 | |
| cggccatcta caagagctcc tgcagcatcg acgtcacctt cttcccttc gaccagcaga | 1140 | |
| actgcaagat gaagtttggc tcctggactt atgacaaggc caagatcgac ctggagcaga | 1200 | |
| tggagcagac tgtggacctg aaggactact gggagagcgg cgagtgggcc atcgtcaatg | 1260 | |
| ccacgggcac ctacaacagc aagaagtacg actgctgcgc cgagatctac cccgacgtca | 1320 | |
| cctatgcctt cgtcatccgg cggctgccgc tcttctacac catcaacctc atcatcccct | 1380 | |
| gcctgctcat ctcctgcctc actgtgctgg tcttctacct gccctccgac tgcggcgaga | 1440 | |
| agatcacgct gtgcatttcg gtgctgctgt cactcaccgt cttcctgctg ctcatcactg | 1500 | |
| agatcatccc gtccacctcg ctggtcatcc cgctcatcgg cgagtacctg ctgttcacca | 1560 | |
| tgatcttcgt caccctgtcc atcgtcatca ccgtcttcgt gctcaatgtg caccaccgct | 1620 | |
| cccccagcac ccacaccatg ccccactggg tgcggggggc ccttctgggc tgtgtgcccc | 1680 | |
| ggtggcttct gatgaaccgg cccccaccac ccgtggagct ctgccacccc ctacgcctga | 1740 | |
| agctcagccc ctcttatcac tggctggaga gcaacgtgga tgccgaggag agggaggtgg | 1800 | |
| tggtggagga ggaggacaga tgggcatgtg caggtcatgt ggcccctct gtgggcaccc | 1860 | |
| tctgcagcca cggccacctg cactctgggg cctcaggtcc caaggctgag gctctgctgc | 1920 | |
| aggagggtga gctgctgcta tcaccccaca tgcagaaggc actggaaggt gtgcactaca | 1980 | |
| ttgccgacca cctgcggtct gaggatgctg actcttcggt gaaggaggac tggaagtatg | 2040 | |
| ttgccatggt catcgacagg atcttcctct ggctgtttat catcgtctgc ttcctgggga | 2100 | |
| ccatcggcct cttttctgcct ccgttcctag ctggaatgat ctgactgcac ctccctcgag | 2160 | |
| ctggctccca gggcaaaggg gagggttctt ggatgtggaa gggctttgaa caatgtttag | 2220 | |
| atttggagat gagcccaaag tgccaggag aacagccagg tgaggtggga ggttggagag | 2280 | |
| ccaggtgagg tctctctaag tcaggctggg gttgaagttt ggagtctgtc cgagtttgca | 2340 | |
| gggtgctgag ctgtatggtc cagcagggga gtaataaggg ctcttccgga aggggaggaa | 2400 | |
| gcgggaggca ggcctgcacc tgatgtggag gtacaggcag atcttcccta ccggggaggg | 2460 | |
| atggatggtt ggatacaggt ggctgggcta ttccatccat ctggaagcac atttgagcct | 2520 | |
| ccaggcttct ccttgacgtc attcctctcc ttccttgctg caaaatggct ctgcaccagc | 2580 | |
| cggcccccag gaggtctggc agagctgaga ccatggcct gcagggctc catatgtccc | 2640 | |
| tacgcgtgca gcaggcaaac aaga | 2664 | |

<210> SEQ ID NO 35
<211> LENGTH: 3020
<212> TYPE: DNA
<213> ORGANISM: Homo sapiens

<400> SEQUENCE: 35

| | | |
|---|---|---|
| gtcctcccgc gggtccgagg gcgctggaaa cccagcggcg gcgaagcgga gaggagcccc | 60 | |
| gcgcgtctcc gcccgcacgg ctccaggtct ggggtctgcg ctggagccgc gcggggagag | 120 | |
| gccgtctctg cgaccgccgc gcccgctccc gaccgtccgg gtccgcggcc agcccggcca | 180 | |
| ccagccatgg gctctggccc gctctcgctg cccctggcgc tgtcgccgcc gcggctgctg | 240 | |
| ctgctgctgc tgctgtctct gctgccagtg gccagggcct cagaggctga gcaccgtcta | 300 | |

```
tttgagcggc tgtttgaaga ttacaatgag atcatccggc ctgtggccaa cgtgtctgac    360
ccagtcatca tccatttcga ggtgtccatg tctcagctgg tgaaggtgga tgaagtaaac    420
cagatcatgg agaccaacct gtggctcaag caaatctgga atgactacaa gctgaagtgg    480
aacccctctg actatggtgg ggcagagttc atgcgtgtcc ctgcacagaa gatctggaag    540
ccagacattg tgctgtataa caatgctgtt ggggatttcc aggtggacga caagaccaaa    600
gccttactca agtacactgg ggaggtgact tggatacctc cggccatctt taagagctcc    660
tgtaaaatcg acgtgaccta cttcccgttt gattaccaaa actgtaccat gaagttcggt    720
tcctggtcct acgataaggc gaaaatcgat ctggtcctga tcggctcttc catgaacctc    780
aaggactatt gggagagcgg cgagtgggcc atcatcaaag ccccaggcta caaacacgac    840
atcaagtaca actgctgcga ggagatctac cccgacatca catactcgct gtacatccgg    900
cgcctgccct tgttctacac catcaacctc atcatcccct gcctgctcat ctccttcctc    960
actgtgctcg tcttctacct gccctccgac tgcggtgaga aggtgaccct gtgcatttct   1020
gtcctcctct ccctgacggt gtttctcctg gtgatcactg agaccatccc ttccacctcg   1080
ctggtcatcc ccctgattgg agagtacctc ctgttcacca tgattttgt aaccttgtcc   1140 atcgtcatca ccgtcttcgt gctcaacgtg cactacagaa ccccgacgac acacacaatg   1200
ccctcatggg tgaagactgt attcttgaac ctgctcccca gggtcatgtt catgaccagg   1260
ccaacaagca acgagggcaa cgctcagaag ccgaggcccc tctacggtgc cgagctctca   1320
aatctgaatt gcttcagccg cgcagagtcc aaaggctgca aggagggcta cccctgccag   1380
gacgggatgt gtggttactg ccaccaccgc aggataaaaa tctccaattt cagtgctaac   1440
ctcacgagaa gctctagttc tgaatctgtt gatgctgtgc tgtccctctc tgctttgtca   1500
ccagaaatca agaagccat ccaaagtgtc aagtatattg ctgaaaatat gaaagcacaa   1560
aatgaagcca aagagattca agatgattgg aagtatgttg ccatggtgat tgatcgtatt   1620
tttctgtggg ttttcacccct ggtgtgcatt ctagggacag caggattgtt tctgcaaccc   1680
ctgatggcca gggaagatgc ataagcacta agctgtgtgc ctgcctggga gacttccttg   1740
tgtcagggca ggaggaggct gcttcctagt aagaactac tttctgttat caagctacca   1800
gctttgtttt tggcatttcg aggtttactt attttccact tatcttggaa tcatgcaaaa   1860
aaaaaaatgt caagagtatt tattaccgat aaatgaacat ttaactagcc ttttggtat   1920 ggtaaagaga tgtcaaaatg tgattctatg tgattagtat gctatgctat ggaatataca   1980
tgtaaaaatg tttccttta gttgttgaaa caaaactgga tagaaaaatg ctgttcagaa   2040
atatgaaaag tcattcagtt atcactacag atctcccagt aattttctt atttagccca   2100 taatctcttt gaaggttat actaattcag caatcccca tcgttaccca tttcttacca   2160
tgcatttctc gttctttact gggtctaaag gctatgcctt ccatttcaga gagcttcaac   2220
tacttctctt gcatacttct aaattatact atgagaaatc atgcctagtt attcattgtt   2280
aatataactg tcttagtaca ccataaactg ggtggattat aaacaacaga aacttctcag   2340
ttttggaggt tgggaggtcc aaggtcaagg caccagcaaa tttggtgtct ggtgagggtc   2400
ctcttcctca aggggtgcct tctagctgtg tcctcacatg actgaaggga ctagctatct   2460
ctgtggggtc tattttataa gggcactaac cccattcatg agagcagagc ccccatggcc   2520
taatcacctt tccaaggccc caccttctat ctaagacaat cacgctggga ataggtttca   2580
acatatgaat tgggggagga cacatttgga ccacagcatg aacctttaga acagggttc   2640 tcagccttag cactacggac attttgggct ggataaatat gtgttggtac agaatggggg   2700
```

-continued

```
tatcctgtgc attgtaggat ctttagcagt accctagcct caactcacta gatgccaatg      2760
acataccttg cttcttcacc agttatgata accaagaatg tctccattgt taaatgtccc      2820
cttaggagca aaattgcccc tggttgagaa acattgcttt agacaaattg ttaagagtat      2880
catgtactac acttctgaaa cttaacgtga tcatcaccac tgacagatga ttcacagaga      2940
gagactgttt gaatcttgtc tcactagttt ttcctgtgca aaaataaaat ggacagaatt      3000
gcaaaaaaaa aaaaaaaaaa                                                  3020

<210> SEQ ID NO 36
<211> LENGTH: 3020
<212> TYPE: DNA
<213> ORGANISM: Homo sapiens

<400> SEQUENCE: 36
gtcctcccgc gggtccgagg gcgctggaaa cccagcggcg gcgaagcgga gaggagcccc        60
gcgcgtctcc gcccgcacgg ctccaggtct ggggtctgcg ctggagccgc gcggggagag       120
gccgtctctg cgaccgccgc gcccgctccc gaccgtccgg gtccgcggcc agcccggcca       180
ccagccatgg gctctggccc gctctcgctg cccctggcgc tgtcgccgcc gcggctgctg       240
ctgctgctgc tgctgtctct gctgccagtg gccagggcct cagaggctga gcaccgtcta       300
tttgagcggc tgtttgaaga ttacaatgag atcatccggc tgtagccaa cgtgtctgac       360 ccagtcatca tccatttcga ggtgtccatg tctcagctgg tgaaggtgga tgaagtaaac       420
cagatcatgg agaccaacct gtggctcaag caaatctgga atgactacaa gctgaaatgg       480 aaccctctg actatggtgg ggcagagttc atgcgtgtcc ctgcacagaa gatctggaag       540
ccagacattg tgctgtataa caatgctgtt ggggatttcc aggtggacga caagaccaaa       600
gccttactca agtacactgg ggaggtgact tggatacctc cggccatctt taagagctcc       660
tgtaaaatcg acgtgaccta cttcccgttt gattaccaaa actgtaccat gaagttcggt       720
tcctggtcct acgataaggc gaaaatcgat ctggtcctga tcggctcttc catgaacctc       780
aaggactatt gggagagcgg cgagtgggcc atcatcaaag ccccaggcta caaacacgac       840
atcaagtaca actgctgcga ggagatctac cccgacatca catactcgct gtacatccgg       900
cgcctgccct tgttctacac catcaacctc atcatcccct gcctgctcat ctccttcctc       960
actgtgctcg tcttctacct gccctccgac tgcggtgaga aggtgaccct gtgcatttct      1020
gtcctcctct ccctgacggt gtttctcctg gtgatcactg agaccatccc ttccacctcg      1080
ctggtcatcc ccctgattgg agagtacctc ctgttcacca tgattttttgt aaccttgtcc      1140 atcgtcatca ccgtcttcgt gctcaacgtg cactacagaa ccccgacgac acacacaatg      1200
ccctcatggg tgaagactgt attcttgaac ctgctcccca gggtcatgtt catgaccagg      1260
ccaacaagca acgagggcaa cgctcagaag ccgaggcccc tctacggtgc cgagctctca      1320
aatctgaatt gcttcagccg cgcagagtcc aaaggctgca aggagggcta cccctgccag      1380
gacgggatgt gtggttactg ccaccaccgc aggataaaaa tctccaattt cagtgctaac      1440
ctcacgagaa gctctagttc tgaatctgtt gatgctgtgc tgtccctctc tgctttgtca      1500
ccagaaatca agaagccat ccaaagtgtc aagtatattg ctgaaaatat gaaagcacaa      1560
aatgaagcca agagattca agatgattgg aagtatgttg ccatggtgat tgatcgtatt      1620
tttctgtggg ttttcacccct ggtgtgcatt ctagggacag caggattgtt tctgcaaccc      1680
ctgatggcca gggaagatgc ataagcacta agctgtgtgc ctgcctggga gacttccttg      1740
tgtcagggca ggaggaggct gcttcctagt aagaacgtac tttctgttat caagctacca      1800
```

-continued

```
gctttgtttt tggcatttcg aggtttactt attttccact tatcttggaa tcatgcaaaa    1860
aaaaaaatgt caagagtatt tattaccgat aaatgaacat ttaactagcc ttttttggtat    1920 ggtaaagaga tgtcaaaatg tgattctatg tgattagtat gctatgctat ggaatataca    1980
tgtaaaaatg tttccttta gttgttgaaa caaaactgga tagaaaaatg ctgttcagaa    2040
atatgaaaag tcattcagtt atcactacag atctcccagt aattttttctt atttagccca    2100 taatctcttt gaaggtttat actaattcag caatccccca tcgttaccca tttcttacca    2160
tgcatttctc gttctttact gggtctaaag ggctatgcct ccatttcaga gagcttcaac    2220
tacttctctt gcatacttct aaattatact atgagaaatc atgcctagtt attcattgtt    2280
aatataactg tcttagtaca ccataaactg ggtggattat aaacaacaga aacttctcag    2340 tttttggaggt tgggaggtcc aaggtcaagg caccagcaaa tttggtgtct ggtgagggtc    2400
ctcttcctca aagggtgcct tctagctgtg tcctcacatg actaaggga ctagctatct    2460 ctgtggggtc tattttataa gggcactaac cccattcatg agagcagagc ccccatggcc    2520
taatcacctt tccaaggccc caccttctat ctaagacaat cacgctggga ataggtttca    2580
acatatgaat tgggggagga cacatttgga ccacagcatg aacctttaga cagggtttc    2640 tcagccttag cactacggac attttgggct ggataaatat gtgttggtac agaatggggg    2700
tatcctgtgc attgtaggat ctttagcagt accctagcct caactcacta gatgccaatg    2760
acataccttg cttcttcacc agttatgata accaagaatg tctccattgt taaatgtccc    2820
cttaggagca aaattgcccc tggttgagaa acattgcttt agacaaattg ttaagagtat    2880
catgtactac acttctgaaa cttaacgtga tcatcaccac tgacagatga ttcacagaga    2940
gagactgttt gaatcttgtc tcactagttt ttcctgtgca aaaataaaat ggacagaatt    3000
gcaaaaaaaa aaaaaaaaa                                                3020
```

<210> SEQ ID NO 37
<211> LENGTH: 3020
<212> TYPE: DNA
<213> ORGANISM: Homo sapiens

<400> SEQUENCE: 37

```
gtcctcccgc gggtccgagg gcgctggaaa cccagcggcg gcgaagcgga gaggagcccc     60
gcgcgtctcc gcccgcacgg ctccaggtct ggggtctgcg ctggagccgc gcggggagag    120
gccgtctctg cgaccgccgc gcccgctccc gaccgtccgg gtccgcggcc agcccggcca    180
ccagccatgg gctctggccc gctctcgctg cccctggcgc tgtcgccgcc gcggctgctg    240
ctgctgctgc tgctgtctct gctgccagtg gccagggcct cagaggctga gcaccgtcta    300
tttgagcggg tgtttgaaga ttacaatgag atcatccggc ctgtagccaa cgtgtctgac    360
ccagtcatca tccatttcga ggtgtccatg tctcagctgg tgaaggtgga tgaagtaaac    420
cagatcatgg agaccaacct gtggctcaag caaatctgga atgactacaa gctgaagtgg    480
aacccctctg actatggtgg ggcagagttc atgcgtgtcc ctgcacagaa aatctggaag    540
ccagacattg tgctgtataa caatgctgtt gggatttcc aggtggacga caagaccaaa    600
gccttactca agtacactgg ggaggtgact tggataccctc cggccatctt taagagctcc    660
tgtaaaatcg acgtgaccta cttcccgttt gattaccaaa actgtaccat gaagttcggt    720
tcctggtcct acgataaggc gaaaatcgat ctggtcctga tcggctcttc catgaacctc    780
aaggactatt gggagagcgg cgagtgggcc atcatcaaag ccccaggcta caaacacgac    840
atcaagtaca actgctgcga ggagatctac cccgacatca catactcgct gtacatccgg    900
```

-continued

```
cgcctgccct tgttctacac catcaacctc atcatcccct gcctgctcat ctccttcctc     960
actgtgctcg tcttctacct gccctccgac tgcggtgaga aggtgaccct gtgcatttct    1020
gtcctcctct ccctgacggt gtttctcctg gtgatcactg agaccatccc ttccacctcg    1080
ctggtcatcc ccctgattgg agagtaccte ctgttcacca tgattttgt aaccttgtcc     1140 atcgtcatca ccgtcttcgt gctcaacgtg cactacagaa ccccgacgac acacacaatg    1200
ccctcatggg tgaagactgt attccttgaac ctgctcccca gggtcatgtt catgaccagg   1260
ccaacaagca acgagggcaa cgctcagaag ccgaggcccc tctacggtgc cgagctctca    1320
aatctgaatt gcttcagccg cgcagagtcc aaaggctgca aggagggcta cccctgccag    1380
gacgggatgt gtggttactg ccaccaccgc aggataaaaa tctccaattt cagtgctaac    1440
ctcacgagaa gctctagttc tgaatctgtt gatgctgtgc tgtccctctc tgctttgtca    1500
ccagaaatca agaagccat ccaaagtgtc aagtatattg ctgaaaatat gaaagcacaa     1560
aatgaagcca agagattca agatgattgg aagtatgttg ccatggtgat tgatcgtatt     1620
tttctgtggg ttttcacccct ggtgtgcatt ctagggacag caggattgtt tctgcaaccc   1680
ctgatggcca gggaagatgc ataagcacta agctgtgtgc ctgcctggga gacttccttg    1740
tgtcagggca ggaggaggct gcttcctagt aagaacgtac tttctgttat caagctacca    1800
gctttgtttt tggcatttcg aggtttactt attttccact tatctggaa tcatgcaaaa     1860 aaaaaaatgt caagagtatt tattaccgat aaatgaacat ttaactagcc tttttggtat    1920
ggtaaagaga tgtcaaaatg tgattctatg tgattagtat gctatgctat ggaatataca    1980
tgtaaaaatg tttccttta gttgttgaaa caaaactgga tagaaaatg ctgttcagaa      2040 atatgaaaag tcattcagtt atcactacag atctcccagt aatttttctt atttagccca    2100
taatctcttt gaaggtttat actaattcag caatccccca tcgttaccca tttcttacca    2160
tgcatttctc gttctttact gggtctaaag ggctatgcct ccatttcaga gagcttcaac    2220
tacttctctt gcatacttct aaattatact atgagaaatc atgcctagtt attcattgtt    2280
aatataactg tcttagtaca ccataaactg ggtggattat aaacaacaga aacttctcag    2340
ttttggaggt tgggaggtcc aaggtcaagg caccagcaaa tttggtgtct ggtgagggtc    2400
ctcttcctca aagggtgcct tctagctgtg tcctcacatg actgaaggga ctagctatct    2460 ctgtgggggtc tatttataa gggcactaac cccattcatg agagcagagc ccccatggcc    2520
taatcacctt tccaaggccc caccttctat ctaagacaat cacgctggga ataggtttca    2580
acatatgaat tgggggagga cacatttgga ccacagcatg aacctttaga acagggtttc    2640
tcagccttag cactacggac attttgggct ggataaatat gtgttggtac agaatggggg    2700
tatcctgtgc attgtaggat ctttagcagt accctagcct caactcacta gatgccaatg    2760
acataccttg cttcttcacc agttatgata accaagaatg tctccattgt taaatgtccc    2820
cttaggagca aaattgcccc tggttgagaa acattgcttt agacaaattg ttaagagtat    2880
catgtactac acttctgaaa cttaacgtga tcatcaccac tgacagatga ttcacagaga    2940
gagactgttt gaatcttgtc tcactagttt ttcctgtgca aaaataaaat ggacagaatt    3000
gcaaaaaaaa aaaaaaaaaa                                                3020
```

<210> SEQ ID NO 38
<211> LENGTH: 210
<212> TYPE: DNA
<213> ORGANISM: Homo sapiens

<400> SEQUENCE: 38

```
gggctgcttg gcccaattct gggcatcccc ggggtgtgct agctttgccc taggctgctc    60
cctggaagcg aggttgacac aacttcttcc ccacacacag gagtggagcg actacaaact   120
gcgctggaac cccgctgatt ttggcaacat cacatctctc agggtcccct ctgagatgat   180
ctggatcccc gacattgttc tctacaacaa                                    210

<210> SEQ ID NO 39
<211> LENGTH: 210
<212> TYPE: DNA
<213> ORGANISM: Homo sapiens

<400> SEQUENCE: 39
agcaggggtg gggagtcacc aagatgggtg gtgccacggg aagtaaaacc aggctgattc    60
ttttaccgtc tccttctccc tccctgcttc cttcccgag atctggaatg actacaagct    120
gaagtggaac ccctctgact atggtggggc agagttcatg cgtgtccctg cacagaagat   180
ctggaagcca gacattgtgc tgtataacaa                                    210

<210> SEQ ID NO 40
<211> LENGTH: 210
<212> TYPE: DNA
<213> ORGANISM: Homo sapiens

<400> SEQUENCE: 40
atctggaatg actacaagct gaagtggaac ccctctgact atggtggggc agagttcatg    60
cgtgtccctg cacagaagat ctggaagcca gacattgtgc tgtataacaa gtaaggtcct   120
ggggggccca cgccctctca gggctgtcag cctgggctct gggttttttgg cccactgtgc   180 ttaaaacctg gccttccttg gccttttcca                                    210

<210> SEQ ID NO 41
<211> LENGTH: 7438
<212> TYPE: DNA
<213> ORGANISM: Homo sapiens

<400> SEQUENCE: 41
gctgagcctg agcccgaccc ggggcgcctc ccgccaggca ccatggtgca gaagtcgcgc    60
aacggcggcg tataccccgg cccgagcggg gagaagaagc tgaaggtggg cttcgtgggg   120
ctggaccccg cgcgcccga ctccaccccgg gacggggcgc tgctgatcgc cggctccgag   180
gcccccaagc gcggcagcat cctcagcaaa cctcgcgcgg gcggcgcggg cgccgggaag   240 ccccccaag cgcaacgcct tctaccgcaa gctgcagaat ttcctctaca acgtgctgga   300
gcggccgcgc ggctgggcgt tcatctacca cgcctacgtg ttcctcctgg ttttctcctg   360
cctcgtgctg tctgtgtttt ccaccatcaa ggagtatgag aagagctcgg agggggccct   420
ctacatcctg gaaatcgtga ctatcgtggt gtttggcgtg gagtacttcg tgcggatctg   480
ggccgcaggc tgctgctgcc ggtaccgtgg ctggaggggg cggctcaagt ttgcccggaa   540
accgttctgt gtgattgaca tcatggtgct catcgcctcc attgcggtgc tggccgccgg   600
ctcccagggc aacgtctttg ccacatctgc gctccggagc ctgcgcttcc tgcagattct   660
gcggatgatc cgcatggacc ggcggggagg cacctggaag ctgctgggct ctgtggtcta   720
tgcccacagc aaggagctgg tcactgcctg gtacatcggc ttccttttgtc tcatcctggc   780 ctcgttcctg gtgtacttgg cagagaaggg ggagaacgac cactttgaca cctacgcgga   840
tgcactctgg tggggcctga tcacgctgac caccattggc tacggggaca gtacccccca   900
gacctggaac ggcaggctcc ttgcggcaac cttcaccctc atcggtgtct ccttcttcgc   960
```

```
gctgcctgca ggcatcttgg ggtctgggtt tgccctgaag gttcaggagc agcacaggca   1020
gaagcacttt gagaagaggc ggaacccggc agcaggcctg atccagtcgg cctggagatt   1080
ctacgccacc aacctctcgc gcacagacct gcactccacg tggcagtact acgagcgaac   1140
ggtcaccgtg cccatgtaca gttcgcaaac tcaaacctac ggggcctcca gacttatccc   1200
cccgctgaac cagctggagc tgctgaggaa cctcaagagt aaatctggac tcgctttcag   1260
gaaggacccc ccgccggagc cgtctccaag ccagaaggtc agtttgaaag atcgtgtctt   1320
ctccagcccc cgaggcgtgg ctgccaaggg aaggggtcc ccgcaggccc agactgtgag   1380
gcggtcaccc agcgccgacc agagcctcga ggacagcccc agcaaggtgc ccaagagctg   1440
gagcttcggg gaccgcagcc gggcacgcca ggctttccgc atcaagggtg ccgcgtcacg   1500
gcagaactca gaagaagcaa gcctccccgg agaggacatt gtggatgaca gagctgccc   1560 ctgcgagttt gtgaccgagg acctgacccc gggcctcaaa gtcagcatca gagccgtgtg   1620
tgtcatgcgg ttcctggtgt ccaagcgaa gttcaaggag agcctgcggc cctacgacgt   1680
gatggacgtc atcgagcagt actcagccgg ccacctggac atgctgtccc gaattaagag   1740
cctgcagtcc agagtggacc agatcgtggg gcggggccca gcgatcacgg acaaggaccg   1800
caccaagggc ccggccgagg cggagctgcc cgaggacccc agcatgatgg gacggctcgg   1860
gaaggtggag aagcaggtct tgtccatgga aagaagctg gacttcctgg tgaatatcta   1920
catgcagcgg atgggcatcc ccccgacaga gaccgaggcc tactttgggg ccaaagagcc   1980
ggagccggcg ccgccgtacc acagcccgga agacagccgg gagcatgtcg acaggcacgg   2040
ctgcattgtc aagatcgtgc gctccagcag ctccacgggc cagaagaact ctcggcgcc   2100 cccggccgcg ccccctgtcc agtgtccgcc ctccacctcc tggcagccac agagccaccc   2160
gcgccagggc cacggcacct cccccgtggg ggaccacggc tccctggtgc gcatcccgcc   2220
gccgcctgcc cacgagcggt cgctgtccgc ctacggcggg ggcaaccgcg ccagcatgga   2280
gttcctgcgg caggaggaca ccccgggctg caggcccccc gaggggaccc tgcgggacag   2340
cgacacgtcc atctccatcc cgtccgtgga ccacgaggag ctggagcgtt ccttcagcgg   2400
cttcagcatc tcccagtcca aggagaacct ggatgctctc aacagctgct acgcggccgt   2460
ggcgccttgt gccaaagtca ggccctacat tgcggaggga gagtcagaca ccgactccga   2520
cctctgtacc ccgtgcgggc ccccgccacg ctcggccacc ggcgagggtc cctttggtga   2580
cgtgggctgg gccgggccca ggaagtgagg cggcgctggg ccagtggacc cgcccgcggc   2640
cctcctcagc acggtgcctc cgaggttttg aggcggaac cctctggggc cttttctta    2700 cagtaactga gtgtggcggg aagggtgggc cctggagggg cccatgtggg ctgaaggatg   2760
ggggctcctg gcagtgacct tttacaaaag ttattttcca acaggcact cccaggccct    2820 gtcgccattg aggtgcctcc gctgggctgt ctcctcaccc ctccctgtgc tggagcctgt   2880
cccaaaaagg tgccaactgg gaggcctcgg aagccactgt ccaggctccc actgcctgtc   2940
tgctctgttc ccaaaggcag cgtgtgtggc ctcgggccct gcggtggcat gaagcatccc   3000
ttctggtgtg ggcatcgcta cgtgttttgg gggcagcgtt tcacggcggt gcccttgctg   3060
tctcccttgg gctggctcga gcctggggtc catgtccctt tgccgtcccg tcatggggca   3120
gggaatccat agcggggccc acaggcaggg gtatgagtgc gtcccaccca acgcagcacc   3180
agccccggcc accgctcccc gtgtcccag ttccgtctca gctacctgga ctccaggacc    3240
ctggagaagg gagacctggc agtggaggga ggctgtgctg tgtgtccccc tgcaggtgtg   3300
accccgcctg ctctttcctc cccgccagg tgtggccccg cctgctcttt cctcccccac    3360
```

```
cagtatggcc ccacctgctc tttcctcccc ccccaaggtg tggccccacc tgttctttcc    3420
tcccctgccg aggtgtgacc ccacctgctc tttcctccct cccagtatgg ccccacctgc    3480
tctttcctcc cccgaggtga ggccccgcct gctctttcct cccatgggag ccgctgaggc    3540
gtgcgcacct gggcacaggt tggggctctg caggatgagg aagacaggcc aatcccttcc    3600
ctcccagaag ctggccgccc agcaggaggg actgaggcca gactcatgtc cagcaaggaa    3660
cgtgtggtgt gtccctggg aagtctctgg gccctgggaa gagggaaggt gcacgtcctg     3720
ggatggttgc ggggccctgt tttgggagac aaaggggtag agggtctgtc ttgggccccc    3780
ccagactcta gcccgagcag tgcagccacc tactgcccca cctcagagaa gtgcagcggg    3840
aaggaggctg gaggtggtgc ggcgctgcct cgggtgtctg cgtgaatgag cgtggccaag    3900
gaccagtgcc acctcatggc aaagagctcc cgcagtgttt gttagagtgc acatcctacg    3960
tgcccactgg cacacacacg tgctcacata catgtccgcg tacaggcgta cacatgcacg    4020
cttgcacaca tgcacacaga ccacatagca cacatgtgca ctgaccacac ctgtatagac    4080
catgcacagt acacatacgt gcatacacat gcctgcatac aggcatacac atgcacgctt    4140
acatgtacac gtgcacagat cacacacatg cacacacgtg tagctcacac acagtataca    4200
catacacaag tgcacagacc acacacagca ctaacacatg cacacacaaa gtgcataggc    4260
cacacagcac atgcacacag gtgcacagac cacacagcac acacaagtgc acagagcaca    4320
ctgcacacat gcacacacac acgcgtgcat gcacactcct cgcacttcca gccttggagc    4380
ccttctgtct ctggtctttc tctttgaccc tgctgagtgt aagctgcctg ggagggggct    4440
acaaggagta attgtggctt taggggtcgt ggtgatgctg gaatgtcaag cgccgtcgtg    4500
gggtatccga ctgtccggc tcctggtccg cagtggcaga gcgccaggca gagccaatca     4560
gggtctcgtg ctgcccttcc cccccacagc ctggcagcca tccagaggag gggctctacc    4620
agatgccaag gtgccccggt gtctgtatgg gtgtccggtt gggtcctgtg tttggtctgc    4680
cctggaggtg gctgggccct cctgggatgg gtggctcagc ctcgaatccc aggccccagc    4740
ccaggcaggt gctgctgcct gttgtggttt cctggcccag cttctccttc tccctctgca    4800
taaaatcaca gtccgtgagt cttccagctg ccaccacggc tgggacacgc tggggagggg    4860
ctcctcccat gcctcctgca cacagccgtc tgagcagggc aggtgccaac accccccacc    4920
ggagacacgc tgccctcag cgatgcccct acctttggg gggcctcgtc tcaagccccc      4980
ccttggaggc tgaaatcacc ccaggcactg tgagggcttc tccaggggga cacccttga     5040 gctgtgggtc tgatcacccc aagtcccgca cacggaggag aggcacagcc agggcgtgtg    5100
gtttaatgtt tgccccttcg gggctggagg tctcagtgtt tctagattcc agaccctgct    5160
gccagagaga cctgctgccg gagagaaggg gaggaggact ccagctgggc tcggtccccc    5220
acagtcaggg accccccataa aggacacccc cttctctcta gaaagagctg gctctcagc    5280 tatttctagt tgcttcccag aagccgagga gcagaaggag ctgtgagagc tttgcagaaa    5340
cgcccttgtc cccgccctcc tgagctatga atgccgtaca gagcagaggc tggggcattg    5400
gcaagatcac aggttgatgc tgcacagccc cattgacaca aaccctcaaa gcagacgtga    5460
gagggacggt tcacaaagct tggacctgcc gtggagggtg cccggcagac gtggcgtgag    5520
agggacggct cacgaggctt ggacctgctg tggagggtgc ccagcagacg tggtgtgaga    5580
ggaacggctc acgagacttg gacctggtgg agggtgccca gcagacgtgg tgtgagaggg    5640
acggctcaca gggcttggac cggagagaga tggctcatga gacttggacc tgccgtggag    5700
ggtgcccagc agacgtggta tgagagggat ggctcacgag gcttggacct ggtggagggt    5760
```

| | |
|---|---:|
| gcccggcaga cgtgtgagag ggacggttca caaggcttgg acctgccatg gagggtgccc | 5820 |
| agcagacgtg gtgtgagagg gacagctcac gaggcttgga cctgccgtgg agggtgccca | 5880 |
| gcaggggggct gagctctgag gggtgggtgc tcagtgcacg ggtgccccca gtgtcctctg | 5940 |
| atcctgtccg gtgcctcccc caaccccac acccatgcag aactcccagg tcacatgcac | 6000 |
| gtatgtccag ggcatggggg tggcgtgaag aggcctggtc agggccttta ggggctgcag | 6060 |
| gacggaatgg ccacctgggg agcctgtgtg gctgtgccgg gcagccatcc tgcattccca | 6120 |
| cccagcgcgc agtctccacc tcggccccag caaagcgcta agcagccgga gagacagcca | 6180 |
| gggcggcttc ctgaaggatg tgggatggtg gactccgggg tcgagggaat acgcaggttc | 6240 |
| ctgtcctccg ggagacctag agaagctgca cacccaggag cttccatga cccgggagca | 6300 |
| tgagtgaatg gggggttcca gtttgctgaa ctttgctgtc ttgtaagggt gggggctgac | 6360 |
| ggccgaccct gggaggaggt gacaccgcag ggggaggttg tgggcaacgg tggaggagga | 6420 |
| gagacgggag gggaccattt gggatggagg ggcctcttca gagttttaaa aggcgtttgt | 6480 |
| ggggtggagt tgagtgtgct ctgggcttgg acacttgccg tggtgcccct ggctggccga | 6540 |
| ggagactggc tctggccagg gccccgtcct gagaggtcct cagcgtctga ctctcggcca | 6600 |
| ggcgccagca aggaggggcc ggtccccggg gctaccaggc aggcacgtgc acatcgccat | 6660 |
| cgccacacgc caactccgcc tgggttttac aaagtcgttg ccttaatgca tgtgacagg | 6720 |
| aactccctga ggtcgcccca tgccccctgg ctgtgccagg tacggacgcc ctggaccctg | 6780 |
| cgaacaggtg gggcgggcga ggggcccaag ggacgggctc cagagacacg cgcagggcag | 6840 |
| gaggggtctc acggaggggt ctcgcactga ggcgcccaga gctggtggtc ccgctggacg | 6900 |
| ccatccctct gcccgggatc cacacggccc acgtgtgccc gccatgcccg cgccccacgc | 6960 |
| cattgcagtc ttccatcctc tggccgtgac ggtggctgca gcttccccat ttgcgccgtt | 7020 |
| gcctctggct gtctgcactt tgttcatgc tccaaagaac atttcataat gccttcagta | 7080 |
| ccgacgtaca cttctgacca ttttgtatgt gtccttgtgc cgtagtgacc aggccttttt | 7140 |
| ttggtggatg tgttaccccg cacacttcaa tctcaacttt gtgcaccgtc catttttctag | 7200 |
| ggatagacgc ccagggaatg aactctagtt ttctaacaga ttagctgaga tattaactta | 7260 |
| ctcacacgga caggttgatg ccagagccgt aagaatgcgc cagtgcgggt ttgcggggga | 7320 |
| cttcgggtgt ggggtcctgc ggccgcgatg gccgtggaag gttctgggga tccctgctgc | 7380 |
| cacggggacg agttcggacg ccaggtggac ctgtgcactc agtaaaacgc agtgattc | 7438 |

<210> SEQ ID NO 42
<211> LENGTH: 7437
<212> TYPE: DNA
<213> ORGANISM: Homo sapiens

<400> SEQUENCE: 42

| | |
|---|---:|
| gctgagcctg agcccgaccc ggggcgcctc ccgccaggca ccgtggtgca gaagtcgcgc | 60 |
| aacggcggcg tatacccccgg cccgagcggg gagaagaagc tgaaggtggg cttcgtgggg | 120 |
| ctggaccccg gcgcgcccga ctccaccccgg gacgggcgc tgctgatcgc cggctccgag | 180 |
| gcccccaagc gcggcagcat cctcagcaaa cctcgcgcgg gcggcgcggg cgccgggaag | 240 |
| ccccccaagc gcaacgcctt ctaccgcaag ctgcagaatt tcctctacaa cgtgctggag | 300 |
| cggccgcgcg gctgggcgtt catctaccac gcctacgtgt tcctcctggt tttctcctgc | 360 |
| ctcgtgctgt ctgtgttttc caccatcaag gagtatgaga agagctcgga gggggccctc | 420 |
| tacatcctgg aaatcgtgac tatcgtggtg tttggcgtgg agtacttcgt gcggatctgg | 480 |

```
gccgcaggct gctgctgccg gtaccgtggc tggaggggc ggctcaagtt tgcccggaaa    540
ccgttctgtg tgattgacat catggtgctc atcgcctcca ttgcggtgct ggccgccggc    600
tcccagggca acgtctttgc cacatctgcg ctccggagcc tgcgcttcct gcagattctg    660
cggatgatcc gcatggaccg gcggggaggc acctggaagc tgctgggctc tgtggtctat    720
gcccacagca aggagctggt cactgcctgg tacatcggct cctttgtct catcctggcc     780 tcgttcctgg tgtacttggc agagaagggg agaacgacc actttgacac ctacgcggat    840
gcactctggt ggggcctgat cacgctgacc accattggct acggggacaa gtaccccag    900 acctggaacg gcaggctcct tgcggcaacc ttcaccctca tcgtgtgctc cttcttcgcg    960
ctgcctgcag gcatcttggg gtctgggttt gccctgaagg ttcaggagca gcacaggcag   1020
aagcactttg agaagaggcg gaacccggca gcaggcctga tccagtcggc ctggagattc   1080
tacgccacca acctctcgcg cacagacctg cactccacgt ggcagtacta cgagcgaacg   1140
gtcaccgtgc ccatgtacag ttcgcaaact caaacctacg ggcctccag acttatcccc    1200 ccgctgaacc agctggagct gctgaggaac ctcaagagta atctggact cgctttcagg   1260 aaggaccccc cgccggagcc gtctccaagc cagaaggtca gtttgaaaga tcgtgtcttc   1320
tccagccccc gaggcgtggc tgccaagggg aagggtccc cgcaggccca gactgtgagg   1380
cggtcaccca gcgccgacca gagcctcgag gacagcccca gcaaggtgcc caagagctgg   1440
agcttcgggg accgcagccg ggcacgccag gctttccgca tcaagggtgc cgcgtcacgg   1500
cagaactcag aagaagcaag cctccccgga gaggacattg tggatgacaa gagctgcccc   1560
tgcgagtttg tgaccgagga cctgaccccg ggcctcaaag tcagcatcag agccgtgtgt   1620 gtcatgcgcgt tcctggtgtc caagcggaag ttcaaggaga gcctgcggcc ctacgacgtg   1680
atggacgtca tcgagcagta tcagccggcc cacctggaca tgctgtcccg aattaagagc   1740
ctgcagtcca gagtggacca gatcgtgggg cggggcccag cgatcacgga caaggaccgc   1800
accaagggcc cggccgaggc ggagctgccc gaggacccca gcatgatggg acggctcggg   1860
aaggtggaga agcaggtctt gtccatggag aagaagctgg acttcctggt gaatatctac   1920
atgcagcgga tgggcatccc cccgacagag accgaggcct actttgggc aaagagccg   1980 gagccggcgc cgccgtacca cagcccggaa gacagccggg agcatgtcga caggcacggc   2040
tgcattgtca agatcgtgcg ctccagcagc tccacgggcc agaagaactt ctcggcgccc   2100
ccggccgcgc ccctgtcca gtgtccgccc tccacctcct ggcagccaca gagccacccg   2160
cgccagggcc acggcacctc ccccgtgggg gaccacggct ccctggtgcg catcccgccc   2220
ccgcctgccc acgagcggtc gctgtccgcc tacgcggggg gcaaccgcgc cagcatggag   2280
ttcctgcggc aggaggacac cccgggctgc aggcccccg aggggaccct gcgggacagc   2340
gacacgtcca tctccatccc gtccgtggac cacgaggagc tggagcgttc cttcagcggc   2400
ttcagcatct cccagtccaa ggagaacctg gatgctctca acagctgcta cgcggccgtg   2460
gcgccttgtg ccaaagtcag gccctacatt gcggagggag agtcagacac cgactccgac   2520
ctctgtaccc cgtgcgggcc cccgccacgc tcggccaccg cgagggtcc ctttggtgac   2580 gtgggctggg ccgggcccag gaagtgaggc ggcgctgggc cagtggaccc gcccgcggcc   2640
ctcctcagca cggtgcctcc gaggttttga ggcgggaacc ctctggggcc cttttcttac   2700
agtaactgag tgtggcggga agggtgggcc ctggaggggc ccatgtgggc tgaaggatgg   2760
gggctcctgg cagtgacctt ttacaaaagt tattttccaa cagggcactc ccaggccctg   2820
tcgccattga ggtgcctccg ctgggctgtc tcctcacccc tccctgtgct ggagcctgtc   2880
```

-continued

```
ccaaaaaggt gccaactggg aggcctcgga agccactgtc caggctccca ctgcctgtct    2940
gctctgttcc caaaggcagc gtgtgtggcc tcgggccctg cggtggcatg aagcatccct    3000
tctggtgtgg gcatcgctac gtgttttggg ggcagcgttt cacggcggtg cccttgctgt    3060
ctcccttggg ctggctcgag cctggggtcc atgtcccttt gccgtccgt catggggcag     3120 ggaatccata gcggggccca caggcagggg tatgagtgcg tcccacccaa cgcagcacca    3180
gccccggcca ccgctcccg tgtccccagt tccgtctcag ctacctggac tccaggaccc     3240
tggagaaggg agacctggca gtggagggag gctgtgctgt gtgtccccct gcaggtgtga    3300
ccccgcctgc tctttcctcc cccgccaggt gtggccccgc ctgctctttc ctcccccacc    3360
agtatggccc cacctgctct ttcctccccc cccaaggtgt ggccccacct gttctttcct    3420
cccctgccga ggtgtgaccc cacctgctct ttcctccctc ccagtatggc cccacctgct    3480
ctttcctccc ccgaggtgag gccccgcctg ctctttcctc ccatgggagc cgctgaggcg    3540
tgcgcacctg ggcacaggtt ggggctctgc aggatgagga agacaggcca atcccttccc    3600
tcccagaagc tggccgccca gcaggaggga ctgaggccag actcatgtcc agcaaggaac    3660
gtgtggtgtg tcccctggga agtctctggg ccctgggaag agggaaggtg cacgtcctgg    3720
gatggttgcg gggccctgtt ttgggagaca aaggggtaga gggtctgtct tgggcccccc    3780
cagactctag cccgagcagt gcagccacct actgccccac ctcagagaag tgcagcggga    3840
aggaggctgg aggtggtgcg gcgctgcctc gggtgtctgc gtgaatgagc gtggccaagg    3900
accagtgcca cctcatggca aagagctccc gcagtgtttg ttagagtgca catcctacgt    3960
gcccactggc acacacacgt gctcacatac atgtccgcgt acaggcgtac acatgcacgc    4020
ttgcacacat gcacacagac cacatagcac acatgtgcac tgaccacacc tgtatagacc    4080
atgcacagta cacatacgtg catacacatg cctgcataca ggcatacaca tgcacgctta    4140
catgtacacg tgcacagatc acacacatgc acacacgtgt agctcacaca cagtatacac    4200
atacacaagt gcacagacca cacacagcac taacacatgc acacacaaag tgcataggcc    4260
acacagcaca tgcacacagg tgcacagacc acacagcaca cacaagtgca cagagcacac    4320
tgcacacatg cacacacaca cgcgtgcatg cacactcctc gcacttccag ccttggagcc    4380
cttctgtctc tggtctttct ctttgaccct gctgagtgta agctgcctgg ggagggcta    4440 caaggagtaa ttgtggcttt aggggtcgtg gtgatgctgg aatgtcaagc gccgtcgtgg    4500
ggtatccgac tgtccgggct cctggtccgc agtggcagag cgccaggcag agccaatcag    4560
ggtctcgtgt gcccttccc ccccacagcc tggcagccat ccagaggagg ggctctacca    4620
gatgccaagg tgccccggtg tctgtatggg tgtccggttg ggtcctgtgt ttggtctgcc    4680
ctggaggtgc ctgggccctc ctgggatggg tggctcagcc tcgaatccca ggccccagcc    4740
caggcaggtg ctgctgcctg ttgtggtttc ctggcccagc ttctccttct ccctctgcat    4800
aaaatcacag tccgtgagtc ttccagctgc caccacggct gggacacgct gggggagggc    4860
tcctcccatg cctcctgcac acagccgtct gagcagggca ggtgccaaca cccccaccg    4920 gagacacgct gccctcagc gatgccccta ccttttgggg ggcctcgtct caagcccccc     4980
cttggaggct gaaatcaccc caggcactgt gagggcttct ccaggggac acccttgag     5040 ctgtgggtct gatcacccca gtcccgcac acgaggaga ggcacagcca gggcgtgtgg    5100
tttaatgttt gccccttcgg ggctggaggt ctcagtgttt ctagattcca gaccctgctg    5160
ccagagagac ctgctgccgg agagaagggg aggaggactc cagctgggct cggtcccccca   5220 cagtcaggga cccccataaa ggacaccccc ttctctctag aaagagctgg gctctcagct    5280
```

```
atttctagtt gcttcccaga agccgaggag cagaaggagc tgtgagagct ttgcagaaac   5340
gcccttgtcc ccgcccctcct gagctatgaa tgccgtacag agcagaggct ggggcattgg   5400
caagatcaca ggttgatgct gcacagcccc attgacacaa accctcaaag cagacgtgag   5460
agggacggtt cacaaagctt ggacctgccg tggaggtgc ccggcagacg tggcgtgaga   5520
gggacggctc acgaggcttg gacctgctgt ggagggtgcc cagcagacgt ggtgtgagag   5580
gaacggctca cgagacttgg acctggtgga gggtgcccag cagacgtggt gtgagggga   5640 cggctcacag ggcttggacc ggagagagat ggctcatgag acttggacct gccgtggagg   5700
gtgcccagca gacgtggtat gagagggatg gctcacgagg cttggacctg gtggagggtg   5760
cccggcagac gtgtgagagg gacggttcac aaggcttgga cctgccatgg agggtgccca   5820
gcagacgtgg tgtgagaggg acagctcacg aggcttggac ctgccgtgga gggtgcccag   5880
cagggggctg agctctgagg ggtgggtgct cagtgcacgg gtgcccccag tgtcctctga   5940
tcctgtccgg tgcctccccc aaccccccaca cccatgcaga actcccaggt cacatgcacg   6000
tatgtccagg gcatgggggt ggcgtgaaga ggcctggtca gggcctttag gggctgcagg   6060
acggaatggc cacctgggga gcctgtgtgg ctgtgccggg cagccatcct gcattcccac   6120
ccagcgcgca gtctccacct cggccccagc aaagcgctaa gcagccggag agacagccag   6180
ggcggcttcc tgaaggatgt gggatggtgg actccgggt cgagggaata cgcaggttcc   6240
tgtcctccgg gagacctaga gaagctgcac acccaggagc tttccatgac ccgggagcat   6300
gagtgaatgg ggggttccag tttgctgaac tttgctgtct tgtaagggtg ggggctgacg   6360
gccgaccctg ggaggaggtg acaccgcagg gggaggttgt gggcaacggt ggaggaggag   6420
agacgggagg ggaccatttg ggatggaggg gcctcttcag agttttaaaa ggcgtttgtg   6480
gggtggagtt gagtgtgctc tgggcttgga cacttgccgt ggtgcccctg gctggccgag   6540
gagactggct ctggccaggg ccccgtcctg agaggtcctc agcgtctgac tctcggccag   6600
gcgccagcaa ggaggggccg gtcccgggg ctaccaggca ggcacgtgca catcgccatc   6660
gccacacgcc aactccgcct gggttttaca aagtcgttgc cttaatgcat gtggacagga   6720
actccctgag gtcgccccat gcccctgge tgtgccaggt acggacgccc tggaccctgc   6780
gaacaggtgg ggcgggcgag gggcccaagg gacgggctcc agagacacgc gcagggcagg   6840
aggggtctca cggagggtc tcgcactgag gcgcccagag ctggtggtcc cgctggacgc   6900
catccctctg cccgggatcc acacggccca cgtgtgcccg ccatgcccgc gccccacgcc   6960
attgcagtct tccatcctct ggccgtgacg gtggctgcag cttccccatt gcgccgttg   7020 cctctggctg tctgcacttt tgttcatgct ccaaagaaca tttcataatg ccttcagtac   7080
cgacgtacac ttctgaccat tttgtatgtg tccttgtgcc gtagtgacca ggcctttttt   7140
tggtggatgt gttaccccgc acacttcaat ctcaactttg tgcaccgtcc attttctagg   7200
gatagacgcc cagggaatga actctagttt tctaacagat tagctgagat attaacttac   7260
tcacacggac aggttgatgc cagagccgta agaatgcgcc agtgcgggtt tgcgggggac   7320
ttcgggtgtg gggtcctgcg gccgcgatgg ccgtggaagg ttctggggat ccctgctgcc   7380
acggggacga gttcggacgc caggtggacc tgtgcactca gtaaaacgca gtgattc      7437
```

<210> SEQ ID NO 43
<211> LENGTH: 7437
<212> TYPE: DNA
<213> ORGANISM: Homo sapiens

<400> SEQUENCE: 43

```
gctgagcctg agcccgaccc ggggcgcctc ccgccaggca ccacggtgca gaagtcgcgc    60
aacggcggcg tataccccgg cccgagcggg gagaagaagc tgaaggtggg cttcgtgggg   120
ctggaccccg gcgcgcccga ctccacccgg gacggggcgc tgctgatcgc cggctccgag   180
gcccccaagc gcggcagcat cctcagcaaa cctcgcgcgg gcggcgcggg cgccgggaag   240
cccccaagc gcaacgcctt ctaccgcaag ctgcagaatt cctctacaa cgtgctggag    300
cggccgcgcg gctgggcgtt catctaccac gcctacgtgt cctcctggt tttctcctgc   360
ctcgtgctgt ctgtgttttc caccatcaag gagtatgaga gagctcgga ggggccctc    420
tacatcctgg aaatcgtgac tatcgtggtg tttggcgtgg agtacttcgt gcggatctgg   480
gccgcaggct gctgctgccg gtaccgtggc tggaggggc ggctcaagtt tgcccggaaa   540
ccgttctgtg tgattgacat catggtgctc atcgcctcca ttgcggtgct ggccgccggc   600
tcccagggca acgtctttgc cacatctgcg ctccggagcc tgcgcttcct gcagattctg   660
cggatgatcc gcatggaccg gcggggaggc acctggaagc tgctgggctc tgtggtctat   720
gcccacagca aggagctggt cactgcctgg tacatcggct tcctttgtct catcctggcc   780
tcgttcctgg tgtacttggc agagaagggg gagaacgacc actttgacac ctacgcggat   840
gcactctggt ggggcctgat cacgctgacc accattggct acggggacaa gtaccccag    900
acctggaacg gcaggctcct tgcggcaacc ttcacctca tcggtgtctc cttcttcgcg    960
ctgcctgcag gcatcttggg gtctgggttt gccctgaagg ttcaggagca gcacaggcag  1020
aagcactttg agaagaggcg gaacccggca gcaggcctga tccagtcggc ctggagattc  1080
tacgccacca acctctcgcg cacagacctg cactccacgt ggcagtacta cgagcgaacg  1140
gtcaccgtgc ccatgtacag ttcgcaaact caaacctacg gggcctccag acttatcccc  1200
ccgctgaacc agctggagct gctgaggaac ctcaagagta aatctggact cgcttttcagg 1260
aaggaccccc cgccggagcc gtctccaagc cagaaggtca gtttgaaaga tcgtgtcttc  1320
tccagccccc gaggcgtggc tgccaagggg aaggggtccc cgcaggccca gactgtgagg  1380
cggtcaccca gcgccgacca gagcctcgag gacagcccca gcaaggtgcc caagagctgg  1440
agcttcgggg accgcagccg ggcacgccag gctttccgca tcaagggtgc cgcgtcacgg  1500
cagaactcag aagaagcaag cctccccgga gaggacattg tggatgacaa gagctgcccc  1560
tgcgagtttg tgaccgagga cctgacccccg ggcctcaaag tcagcatcag agccgtgtgt  1620
gtcatgcggt tcctggtgtc caagcggaag ttcaaggaga gcctgcggcc ctacgacgtg  1680
atggacgtca tcgagcagta tcagccggc cacctgtgaca tgctgtcccg aattaagagc  1740
ctgcagtcca gagtggacca gatcgtgggg cggggcccag cgatcacgga caaggaccgc  1800
accaagggcc cggccgaggc ggagctgccc gaggacccca gcatgatggg acggctcggg  1860
aaggtggaga gcaggtcttg tccatggag aagaagctgg acttcctggt gaatatctac  1920
atgcagcgga tgggcatccc cccgacagag accgaggcct actttggggc caaagagccg  1980
gagccggcgc cgccgtacca cagcccggaa cacagccggg agcatgtcga caggcacggc  2040
tgcattgtca agatcgtgcg ctccagcagc tccacgggcc agaagaactt ctcggcgccc  2100
ccggccgcgc ccctgtccca gtgtccgccc tccacctcct ggcagccaca gagccacccg  2160
cgccagggcc acggcacctc ccccgtgggg gaccacggct ccctggtgcg catcccgccg  2220
ccgcctgccc acgagcggtc gctgtccgcc tacggcgggg gcaaccgcgc cagcatggag  2280
ttcctgcggc aggaggacac cccgggctgc aggcccccg aggggaccct gcgggacagc  2340
gacacgtcca tctccatccc gtccgtggac cacgaggagc tggagcgttc cttcagcggc  2400
```

```
ttcagcatct cccagtccaa ggagaacctg gatgctctca acagctgcta cgcggccgtg    2460
gcgccttgtg ccaaagtcag gccctacatt gcggagggag agtcagacac cgactccgac    2520
ctctgtaccc cgtgcgggcc cccgccacgc tcggccaccg gcgagggtcc ctttggtgac    2580
gtgggctggg ccgggcccag gaagtgaggc ggcgctgggc cagtggaccc gcccgcggcc    2640
ctcctcagca cggtgcctcc gaggttttga ggcgggaacc ctctggggcc cttttcttac    2700
agtaactgag tgtggcggga agggtgggcc ctggaggggc ccatgtgggc tgaaggatgg    2760
gggctcctgg cagtgacctt ttacaaaagt tattttccaa cagggcactc ccaggccctg    2820
tcgccattga ggtgcctccg ctgggctgtc tcctcacccc tccctgtgct ggagcctgtc    2880 ccaaaaggt gccaactggg aggcctcgga agccactgtc caggctccca ctgcctgtct    2940
gctctgttcc caaaggcagc gtgtgtggcc tcgggccctg cggtggcatg aagcatccct    3000
tctggtgtgg gcatcgctac gtgttttggg ggcagcgttt cacggcggtg cccttgctgt    3060
ctcccttggg ctggctcgag cctggggtcc atgtcccttt gccgtcccgt catggggcag    3120
ggaatccata gcggggccca caggcagggg tatgagtgcg tcccacccaa cgcagcacca    3180
gccccggcca ccgctccccg tgtccccagt tccgtctcag ctacctggac tccaggaccc    3240
tggagaaggg agacctggca gtggagggag gctgtgctgt gtgtcccct gcaggtgtga    3300 ccccgcctgc tctttcctcc cccgccaggt gtggccccgc ctgctctttc ctcccccacc    3360
agtatggccc cacctgctct ttcctccccc cccaaggtgt ggccccacct gttctttcct    3420
cccctgccga ggtgtgaccc cacctgctct ttcctccctc ccagtatggc cccacctgct    3480 cttttcctccc ccgaggtgag gccccgcctg ctctttcctc ccatgggagc cgctgaggcg    3540
tgcgcacctg gcacaggtt ggggctctgc aggatgagga agacaggcca atcccttccc    3600
tcccagaagc tggccgccca gcaggaggga ctgaggccag actcatgtcc agcaaggaac    3660
gtgtggtgtg tccctggga agtctctggg ccctgggaag agggaaggtg cacgtcctgg    3720
gatggttgcg gggccctgtt ttgggagaca aaggggtaga gggtctgtct tgggcccccc    3780
cagactctag cccgagcagt gcagccacct actgccccac ctcagagaag tgcagcggga    3840
aggaggctgg aggtggtgcg gcgctgcctc gggtgtctgc gtgaatgagc gtggccaagg    3900
accagtgcca cctcatggca aagagctccc gcagtgtttg ttagagtgca catcctacgt    3960
gcccactggc acacacacgt gctcacatac atgtccgcgt acaggcgtac acatgcacgc    4020
ttgcacacat gcacacagac cacatagcac acatgtgcac tgaccacacc tgtatagacc    4080
atgcacagta cacatacgtg catacacatg cctgcataca ggcatacaca tgcacgctta    4140
catgtacacg tgcacagatc acacacatgc acacgtgt agctcacaca cagtatacac    4200
atacacaagt gcacagacca cacacagcac taacacatgc acacaaag tgcataggcc    4260 acacagcaca tgcacacagg tgcacagacc acacagcaca cacaagtgca cagagcacac    4320
tgcacacatg cacacacaca cgcgtgcatg cacactcctc gcacttccag ccttggagcc    4380
cttctgtctc tggtctttct cttttgaccct gctgagtgta agctgcctgg ggaggggcta    4440
caaggagtaa ttgtggcttt aggggtcgtg gtgatgctgg aatgtcaagc gccgtcgtgg    4500
ggtatccgac tgtccgggct cctggtccgc agtggcagag cgccaggcag agccaatcag    4560
ggtctcgtgc tgcccttccc ccccacagcc tggcagccat ccagaggagg ggctctacca    4620
gatgccaagg tgccccggtg tctgtatggg tgtccggttg ggtcctgtgt ttggtctgcc    4680
ctggaggtgg ctgggccctc ctgggatggg tggctcagcc tcgaatccca ggccccagcc    4740
caggcaggtg ctgctgcctg ttgtggtttc ctggcccagc ttctccttct ccctctgcat    4800
```

```
aaaatcacag tccgtgagtc ttccagctgc caccacggct gggacacgct gggggagggc    4860
tcctcccatg cctcctgcac acagccgtct gagcagggca ggtgccaaca ccccccaccg    4920
gagacacgct gccccctcagc gatgccccta ccttttgggg ggcctcgtct caagcccccc    4980
cttggaggct gaaatcaccc caggcactgt gagggcttct ccaggggac  acccttgag    5040 ctgtgggtct gatcacccca gtcccgcac  acggaggaga ggcacagcca gggcgtgtgg    5100
tttaatgttt gccccttcgg ggctggaggt ctcagtgttt ctagattcca gaccctgctg    5160
ccagagagac ctgctgccgg agagaagggg aggaggactc cagctgggct cggtccccca    5220
cagtcaggga cccccataaa ggacaccccc ttctctctag aaagagctgg gctctcagct    5280
atttctagtt gcttcccaga agccgaggag cagaaggagc tgtgagagct ttgcagaaac    5340
gcccttgtcc ccgccctcct gagctatgaa tgccgtacag agcagaggct ggggcattgg    5400
caagatcaca ggttgatgct gcacagcccc attgacacaa accctcaaag cagacgtgag    5460
agggacggtt cacaaagctt ggacctgccg tggagggtgc ccggcagacg tggcgtgaga    5520
gggacggctc acgaggcttg gacctgctgt ggagggtgcc cagcagacgt ggtgtgagag    5580
gaacggctca cgagacttgg acctggtgga gggtgcccag cagacgtggt gtgagggga    5640 cggctcacag ggcttggacc ggagagagat ggctcatgag acttggacct gccgtggagg    5700
gtgcccagca gacgtggtat gagagggatg gctcacgagg cttggacctg gtgagggtg    5760 cccggcagac gtgtgagagg gacggttcac aaggcttgga cctgccatgg agggtgccca    5820
gcagacgtgg tgtgagaggg acagctcacg aggcttggac ctgccgtgga gggtgcccag    5880 caggggggctg agctctgagg ggtgggtgct cagtgcacgg gtgcccccag tgtcctctga    5940
tcctgtccgg tgcctccccc aaccccccaca cccatgcaga actcccaggt cacatgcacg    6000
tatgtccagg gcatggggt  ggcgtgaaga ggcctggtca gggcctttag gggctgcagg    6060
acggaatggc cacctgggga gcctgtgtgg ctgtgccggg cagccatcct gcattcccac    6120
ccagcgcgca gtctccacct cggccccagc aaagcgctaa gcagccggag agacagccag    6180
ggcggcttcc tgaaggatgt gggatggtgg actccggggt cgagggaata cgcaggttcc    6240
tgtcctccgg gagacctaga gaagctgcac acccaggagc tttccatgac ccgggagcat    6300
gagtgaatgg ggggttccag tttgctgaac tttgctgtct tgtaagggtg ggggctgacg    6360
gccgaccctg gaggaggtg  acaccgcagg gggaggttgt gggcaacggt ggaggaggag    6420
agacgggagg ggaccatttg ggatggaggg gcctcttcag agttttaaaa ggcgtttgtg    6480
gggtggagtt gagtgtgctc tgggcttgga cacttgccgt ggtgccctg  gctggccgag    6540 gagactggct ctggccaggg cccgtcctg  agaggtcctc agcgtctgac tctcggccag    6600
gcgccagcaa ggaggggccg gtcccgggg  ctaccaggca ggcacgtgca catcgccatc    6660
gccacacgcc aactccgcct gggttttaca aagtcgttgc cttaatgcat gtggacagga    6720
actccctgag gtcgccccat gcccctggc  tgtgccaggt acggacgccc tggaccctgc    6780
gaacaggtgg ggcgggcgag gggcccaagg gacgggctcc agagacacgc gcagggcagg    6840 agggtctca  cggaggggtc tcgcactgag gcgcccagag ctggtggtcc cgctggacgc    6900
catccctctg cccgggatcc acacggccca cgtgtgcccg ccatgcccgc gccccacgcc    6960
attgcagtct tccatcctct ggccgtgacg gtggctgcag cttccccatt tgcgccgttg    7020
cctctggctg tctgcacttt tgttcatgct ccaaagaaca tttcataatg ccttcagtac    7080
cgacgtacac ttctgaccat tttgtatgtg tccttgtgcc gtagtgacca ggcctttttt    7140
tggtggatgt gttaccccgc acacttcaat ctcaactttg tgcaccgtcc attttctagg    7200
```

-continued

| | |
|---|---|
| gatagacgcc cagggaatga actctagttt tctaacagat tagctgagat attaacttac | 7260 |
| tcacacggac aggttgatgc cagagccgta agaatgcgcc agtgcgggtt tgcgggggac | 7320 |
| ttcgggtgtg gggtcctgcg gccgcgatgg ccgtggaagg ttctggggat ccctgctgcc | 7380 |
| acggggacga gttcggacgc caggtggacc tgtgcactca gtaaaacgca gtgattc | 7437 |

<210> SEQ ID NO 44
<211> LENGTH: 7437
<212> TYPE: DNA
<213> ORGANISM: Homo sapiens

<400> SEQUENCE: 44

| | |
|---|---|
| gctgagcctg agcccgaccc ggggcgcctc ccgccaggca ccatggtgca gaagtcgcgc | 60 |
| aacggcggcg tatacccggg cccgagcggg gagaagaagc tgaaggtggg cttcgtgggg | 120 |
| ctggaccccg gcgcgcccga ctccacccgg gacggggcgc tgctgatcgc cggctccgag | 180 |
| gcccccaagc gcggcagcat cctcagcaaa cctcgcgcgg gcggcgcggg cgccgggaag | 240 |
| cccccaagc gcaacgcctt ctaccgcaag ctgcagaatt tcctctacaa cgtgctggag | 300 |
| cggccgcgcg gctgggcgtt catctaccac gcctacgtgt cctcctggt tttctcctgc | 360 |
| ctcgtgctgt ctgtgttttc caccatcaag gagtatgaga agagctcgga gggggccctc | 420 |
| tacatcctgg aaatcgtgac tatcgtggtg tttggcgtgg agtacttcgt gcggatctgg | 480 |
| gccgcaggct gctgctgccg gtaccgtggc tggagggggc ggctcaagtt tgcccggaaa | 540 |
| ccgttctgtg tgattgacat catggtgctc atcgcctcca ttgcggtgct ggccgccggc | 600 |
| tcccagggca acgtctttgc cacatctgcg ctccggagcc tgcgcttcct gcagattctg | 660 |
| cggatgatcc gcatggaccg gcggggaggc acctggaagc tgctgggctc tgtggtctat | 720 |
| gcccacagca aggagctggt cactgcctgg tacatcggct tcctttgtct catcctggcc | 780 |
| tcgttcctgg tgtacttggc agagaagggg gagaacgacc actttgacac ctacgcggat | 840 |
| gcactctggt ggggcctgat cacgctgacc accattggct acggggacaa gtaccccag | 900 |
| acctggaacg gcaggctcct tgcggcaacc ttcacccctca tcggtgtctc cttcttcgcg | 960 |
| ctgcctgcag gcatcttggg gtctgggttt gccctgaagg ttcaggagca gcacaggcag | 1020 |
| aagcactttg agaagaggcg gaacccggca gcaggcctga tccagtcggc ctggagattc | 1080 |
| tacgccacca acctctcggg cacagacctg cactccacgt ggcagtacta cgagcgaacg | 1140 |
| gtcaccgtgc ccatgtacag ttcgcaaact caaacctacg ggcctccag acttatcccc | 1200 |
| ccgctgaacc agctggagct gctgaggaac ctcaagagta atctggact cgcttttcagg | 1260 |
| aaggaccccc cgccggagcc gtctccaagc cagaaggtca gtttgaaaga tcgtgtcttc | 1320 |
| tccagccccc gaggcgtggc tgccaagggg aaggggtccc cgcaggccca gactgtgagg | 1380 |
| cggtcaccca cgcgccgacca gagcctcgag gacagcccca gcaaggtgcc caagagctgg | 1440 |
| agcttcgggg accgcagccg ggcacgccag gctttccgca tcaagggtgc cgcgtcacgg | 1500 |
| cagaactcag aagaagcaag cctccccgga gaggacattg tggatgacaa gagctgcccc | 1560 |
| tgcgagtttg tgaccgagga cctgaccccg ggcctcaaag tcagcatcag agccgtgtgt | 1620 |
| gtcatgcggt tcctggtgtc caagcggaag ttcaaggaga gcctgcggcc ctacgacgtg | 1680 |
| atggacgtca tcgagcagta tcagccggca cacctgaca tgctgtcccg aattaagagc | 1740 |
| ctgcagtcca gagtggacca gatcgtgggg cggggcccag cgatcacgga caaggaccgc | 1800 |
| accaagggcc cggccgaggc ggagctgccc gaggacccca gcatgatggg acggctcggg | 1860 |
| aaggtggaga agcaggtctt gtccatggag aagaagctgg acttcctggt gaatatctac | 1920 |

-continued

| | |
|---|---|
| atgcagcgga tgggcatccc cccgacagag accgaggcct actttggggc caaagagccg | 1980 |
| gagccggcgc cgccgtacca cagcccggaa gacagccggg agcatgtcga caggcacggc | 2040 |
| tgcattgtca agatcgtgcg ctccagcagc tccacgggcc agaagaactt ctcggcgccc | 2100 |
| ccggccgcgc ccctgtcca gtgtccgcc tccacctcct ggcagccaca gagccacccg | 2160 |
| cgccagggcc acggcacctc ccccgtgggg gaccacggct ccctggtgcg catcccgccg | 2220 |
| ccgcctgccc acgagcggtc gctgtccgcc tacggcgggg gcaaccgcgc cagcatggag | 2280 |
| ttcctgcggc aggaggacac cccgggctgc aggcccccg aggggaccct gcgggacagc | 2340 |
| gacacgtcca tctccatccc gtccgtggac cacgaggagc tggagcgttc cttcagcggc | 2400 |
| ttcagcatct cccagtccaa ggagaacctg gatgctctca acagctgcta cgcggccgtg | 2460 |
| gcgccttgtg ccaaagtcag gccctacatt gcggagggag agtcagacac cgactccgac | 2520 |
| ctctgtaccc cgtgcgggcc cccgccacgc tcggccaccg gcgagggtcc ctttggtgac | 2580 |
| gtgggctggg ccgggcccag gaagtgaggc ggcgctgggc cagtggaccc gcccgcggcc | 2640 |
| ctcctcagca cggtgcctcc gaggttttga ggcgggaacc ctctggggcc cttttcttac | 2700 |
| agtaactgag tgtggcggga agggtgggcc ctggagggc ccatgtgggc tgaaggatgg | 2760 |
| gggctcctgg cagtgacctt ttacaaaagt tattttccaa cagggcactc ccaggccctg | 2820 |
| tcgccattga ggtgcctccg ctgggctgtc tcctcacccc tccctgtgct ggagcctgtc | 2880 |
| ccaaaaggt gccaactggg aggcctcgga agccactgtc caggctccca ctgcctgtct | 2940 |
| gctctgttcc caaaggcagc gtgtgtggcc tcgggccctg cggtggcatg aagcatccct | 3000 |
| tctggtgtgg gcatcgctac gtgttttggg ggcagcgttt cacggcggtg cccttgctgt | 3060 |
| ctcccttggg ctggctcgag cctggggtcc atgtcccttt gccgtcccgt catggggcag | 3120 |
| ggaatccata gcgggcccca caggcagggg tatgagtgcg tcccacccaa cgcagcacca | 3180 |
| gccccggcca ccgctcccg tgtccccagt tccgtctcag ctacctggac tccaggaccc | 3240 |
| tggagaaggg agacctggca gtggagggag gctgtgctgt gtgtcccct gcaggtgtga | 3300 |
| ccccgcctgc tctttcctcc cccgccaggt gtggcccgc ctgctctttc ctcccccacc | 3360 |
| agtatggccc cacctgctct ttcctccccc cccaaggtgt ggcccacct gttctttcct | 3420 |
| cccctgccga ggtgtgaccc cacctgtctc ttcctccctc ccagtatggc cccacctgct | 3480 |
| cttttcctccc ccgaggtgag gccccgcctg ctctttcctc ccatgggagc cgctgaggcg | 3540 |
| tgcgcacctg ggcacaggtt ggggctctgc aggatgagga agacaggcca atcccttccc | 3600 |
| tcccagaagc tggccgccca gcaggaggga ctgaggccag actcatgtcc agcaaggaac | 3660 |
| gtgtggtgtg tcccctggga agtctctggg ccctgggaag agggaaggtg cacgtcctgg | 3720 |
| gatggttgcg gggccctgtt ttgggagaca aaggggtaga gggtctgtct tgggcccccc | 3780 |
| cagactctag cccgagcagt gcagccacct actgccccac ctcagagaag tgcagcggga | 3840 |
| aggaggctga aggtggtgcg gcgctgcctc gggtgtctgc gtgaatgagc gtggccaagg | 3900 |
| accagtgcca cctcatggca aagagctccc gcagtgtttg ttagagtgca catcctacgt | 3960 |
| gcccactggc acacacgt gctcacatac atgtccgcgt acaggcgtac acatgcacgc | 4020 |
| ttgcacacat gcacacagac cacatagcac acatgtgcac tgaccacacc tgtatagacc | 4080 |
| atgcacagta cacatacgtg catacacatg cctgcataca ggcatacaca tgcacgctta | 4140 |
| catgtacacg tgcacagatc acacacatgc acacgtgt agctcacaca cagtatacac | 4200 |
| atacacaagt gcacagacca cacacagcac taacacatgc acacaaaag tgcataggcc | 4260 |
| acacagcaca tgcacacagg tgcacagacc acacagcaca cacaagtgca cagagcacac | 4320 |

```
tgcacacatg cacacacaca cgcgtgcatg cacactcctc gcacttccag ccttggagcc    4380
cttctgtctc tggtctttct ctttgaccct gctgagtgta agctgcctgg ggaggggcta    4440
caaggagtaa ttgtggcttt aggggtcgtg gtgatgctgg aatgtcaagc gccgtcgtgg    4500
ggtatccgac tgtccgggct cctggtccgc agtggcagag cgccaggcag agccaatcag    4560
ggtctcgtgc tgcccttccc ccccacagcc tggcagccat ccagaggagg ggctctacca    4620
gatgccaagg tgcccggtg tctgtatggg tgtccggttg ggtcctgtgt ttggtctgcc    4680
ctggaggtgg ctgggccctc ctgggatggg tggctcagcc tcgaatccca ggccccagcc    4740
caggcaggtg ctgctgcctg ttgtggtttc ctggcccagc ttctccttct ccctctgcat    4800
aaaatcacag tccgtgagtc ttccagctgc caccacggct gggacacgct gggggagggc    4860
tcctcccatg cctcctgcac acagccgtct gagcagggca ggtgccaaca ccccccaccg    4920
gagacacgct gccctcagc gatgcccta ccttttgggg ggcctcgtct caagcccccc    4980
cttggaggct gaaatcaccc caggcactgt gagggcttct ccagggggac acccctttgag    5040 ctgtgggtct gatcacccca gtcccgcac acggaggaga ggcacagcca gggcgtgtgg    5100
tttaatgttt gcccttcgg ggctggaggt ctcagtgttt ctagattcca gaccctgctg    5160
ccagagagac ctgctgccgg agagaagggg aggaggactc cagctgggct cggtccccca    5220
cagtcaggga cccccataaa ggacacccc ttctctctag aaagagctgg gctctcagct    5280
atttctagtt gcttcccaga agccgaggag cagaaggagc tgtgagagct ttgcagaaac    5340
gcccttgtcc ccgccctcct gagctatgaa tgccgtacag agcagaggct ggggcattgg    5400
caagatcaca ggttgatgct gcacagcccc attgacacaa accctcaaag cagacgtgag    5460
agggacggtt cacaaagctt ggacctgccg tggagggtgc ccggcagacg tggcgtgaga    5520
gggacggctc acgaggcttg gacctgctgt ggagggtgcc cagcagacgt ggtgtgagag    5580
gaacggctca cgagacttgg acctggtgga gggtgcccag cagacgtggt gtgagggga    5640 cggctcacag ggcttggacc ggagagagat ggctcatgag acttggacct gccgtggagg    5700
gtgcccagca gacgtggtat gagagggatg gctcacgagg cttggacctg gtggagggtg    5760
cccggcagac gtgtgagagg gacggttcac aaggcttgga cctgccatgg agggtgccca    5820
gcagacgtgg tgtgagaggg acagctcacg aggcttggac ctgccgtgga gggtgcccag    5880 caggggctg agctctgagg ggtgggtgct cagtgcacgg gtgcccccag tgtcctctga    5940
tcctgtccgg tgcctccccc aacccccaca cccatgcaga actcccaggt cacatgcacg    6000
tatgtccagg gcatggggt ggcgtgaaga ggcctggtca gggccttag gggctgcagg    6060 acggaatggc cacctgggga gcctgtgtgg ctgtgccggg cagccatcct gcattcccac    6120
ccagcgcgca gtcccacct cggccccagc aaagcgctaa gcagccggag agacagccag    6180
ggcggcttcc tgaaggatgt gggatggtgg actccggggt cgagggaata cgcaggttcc    6240
tgtcctccgg gagacctaga gaagctgcac acccaggagc tttccatgac ccgggagcat    6300
gagtgaatgg ggggttccag tttgctgaac tttgctgtct tgtaagggtg ggggctgacg    6360
gccgaccctg gaggaggtg acaccgcagg gggaggttgt gggcaacggt ggaggaggag    6420
agacgggagg ggaccatttg ggatggaggg gcctcttcag agttttaaaa ggcgtttgtg    6480
gggtggagtt gagtgtgctc tgggcttgga cacttgccgt ggtgcccctg gctgccgag    6540 gagactggct ctgccaggg cccgtcctg agaggtcctc agcgtctgac tctcggccag    6600
gcgccagcaa ggaggggccg gtccccgggg ctaccaggca ggcacgtgca catcgccatc    6660
gccacacgcc aactccgcct gggttttaca aagtcgttgc cttaatgcat gtggacagga    6720
```

| | |
|---|---|
| actccctgag gtcgccccat gcccctggc tgtgccaggt acggacgccc tggaccctgc | 6780 |
| gaacaggtgg ggcgggcgag gggcccaagg gacgggctcc agagacacgc gcagggcagg | 6840 |
| aggggtctca cggaggggtc tcgcactgag gcgcccagag ctggtggtcc cgctggacgc | 6900 |
| catccctctg cccgggatcc acacggccca cgtgtgcccg ccatgcccgc gccccacgcc | 6960 |
| attgcagtct ccatcctct ggccgtgacg gtggctgcag cttccccatt tgcgccgttg | 7020 |
| cctctggctg tctgcacttt tgttcatgct ccaaagaaca tttcataatg ccttcagtac | 7080 |
| cgacgtacac ttctgaccat tttgtatgtg tccttgtgcc gtagtgacca ggcctttttt | 7140 |
| tggtggatgt gttaccccgc acacttcaat ctcaactttg tgcaccgtcc attttctagg | 7200 |
| gatagacgcc cagggaatga actctagttt tctaacagat tagctgagat attaacttac | 7260 |
| tcacacggac aggttgatgc cagagccgta agaatgcgcc agtgcgggtt tgcggggac | 7320 |
| ttcgggtgtg gggtcctgcg gccgcgatgg ccgtggaagg ttctggggat ccctgctgcc | 7380 |
| acggggacga gttcggacgc caggtggacc tgtgcactca gtaaaacgca gtgattc | 7437 |

<210> SEQ ID NO 45
<211> LENGTH: 7437
<212> TYPE: DNA
<213> ORGANISM: Homo sapiens

<400> SEQUENCE: 45

| | |
|---|---|
| gctgagcctg agcccgaccc ggggcgcctc ccgccaggca ccatggtgca gaagtcgcgc | 60 |
| aacggcggcg tatacccgg cccgagcggg gagaagaagc tgaaggtggg cttcgtgggg | 120 |
| ctggaccccg gcgcgcccga ctccaccgg gacggggcgc tgctgatcgc cggctccgag | 180 |
| gcccccaagc gcggcagcat cctcagcaaa cctcgcgcgg gcggcgcggg cgccgggaag | 240 |
| cccccaagc gcaacgcctt ctaccgcaag ctgcagaatt tcctctacaa cgtgctggag | 300 |
| cggccgcgcg gctgggcgtt catctaccac gcctacgtgt tcctcctggt tttctcctgc | 360 |
| ctcgtgctgt ctgtgttttc caccatcaag gagtatgaga gagctcgga ggggggccctc | 420 |
| tacatcctgg aaatcgtgac tatcgtggtg tttggcgtgg agtacttcgt gcggatctgg | 480 |
| gccgcaggct gctgctgccg gtaccgtggc tggaggggggc ggctcaagtt tgcccggaaa | 540 |
| ccgttctgtg tgattgacat catggtgctc atcgcctcca ttgcggtgct ggccgccggc | 600 |
| tcccagggca acgtctttgc cacatctgcg ctccggagcc tgcgcttcct gcagattctg | 660 |
| cggatgatcc gcatggaccg gcggggaggc acctggaagc tgctgggctc tgtggtctat | 720 |
| gcccacagca aggagctggt cactgcctgg tacatcggct tcctttgtct catcctggcc | 780 |
| tcgttcctgg tgtacttggc agagaagggg gagaacgacc actttgacac ctacgcggat | 840 |
| gcactctggt ggggcctgat cacgctgacc accattggct acgggacaa gtaccccag | 900 |
| acctggaacg gcaggctcct tgcggcaacc ttcacccctca tcggtgtctc cttcttcgcg | 960 |
| ctgcctgcag gcatcttggg gtctgggttt gccctgaagg ttcaggagca gcacaggcag | 1020 |
| aagcactttg agaagaggcg gaacccggca gcaggcctga tccagtcggc ctggagattc | 1080 |
| tacgccacca acctctcgcg cacagacctg cactccacgt ggcagtacta cgagcgaacg | 1140 |
| gtcaccgtgc ccatgtacag ttcgcaaact caaacctacg gggcctccag acttatcccc | 1200 |
| ccgctgaacc agctggagct gctgaggaac ctcaagagta atctggact cgcttttcagg | 1260 |
| aaggaccccc cgccggagcc gtctccaagc cagaaggtca gtttgaaaga tcgtgtcttc | 1320 |
| tccagcccct gaggcgtggc tgccaagggg aaggggtccc cgcaggccca gactgtgagg | 1380 |
| cggtcaccca gcgccgacca gagcctcgag gacagcccca gcaaggtgcc caagagctgg | 1440 |

```
agcttcgggg accgcagccg ggcacgccag gctttccgca tcaagggtgc cgcgtcacgg    1500
cagaactcag aagaagcaag cctccccgga gaggacattg tggatgacaa gagctgcccc    1560
tgcgagtttg tgaccgagga cctgaccccg ggcctcaaag tcagcatcag agccgtgtgt    1620
gtcatgcggt tcctggtgtc caagcggaag ttcaaggaga gcctgcgcc ctacgacgtg     1680
atggacgtca tcgagcagta tcagccggc cacctggaca tgctgtcccg aattaagagc     1740
ctgcagtcca gagtggacca gatcgtgggg cggggcccag cgatcacgga caaggaccgc    1800
accaagggcc cggccgaggc ggagctgccc gaggacccca gcatgatggg acggctcggg    1860
aaggtggaga agcaggtctt gtccatggag aagaagctgg acttcctggt gaatatctac    1920
atgcagcgga tgggcatccc cccgacagag accgaggcct actttggggc caaagagccg    1980
gagccggcgc cgccgtacca cagcccggaa gacagccggg agcatgtcga caggcacggc    2040
tgcattgtca agatcgtgcg ctccagcagc tccacgggcc agaagaactt ctcggcgccc    2100
ccggccgcgc cccctgtcca gtgtccgccc tccaccctcct ggcagccaca gagccacccg    2160
cgccagggcc acggcacctc ccccgtgggg gaccacggct ccctggtgcg catcccgccg    2220
ccgcctgccc acgagcggtc gctgtccgcc tacggcgggg caaccgcgc cagcatggag    2280
ttcctgcggc aggaggacac cccgggctgc aggcccccg aggggaccct gcgggacagc    2340
gacacgtcca tctccatccc gtccgtggac cacgaggagc tggagcgttc cttcagcggc    2400
ttcagcatct cccagtccaa ggagaacctg gatgctctca cagctgcta cgcggccgtg    2460
gcgccttgtg ccaaagtcag gccctacatt gcggagggag agtcagacac cgactccgac    2520
ctctgtaccc cgtgcgggcc cccgccacgc tcggccaccg gcgagggtcc ctttggtgac    2580
gtgggctggg ccgggcccag gaagtgaggc ggcgctgggc cagtggaccc gcccgcggcc    2640
ctcctcagca cggtgcctcc gaggttttga ggcgggaacc ctctggggcc cttttcttac    2700
agtaactgag tgtggcggga aggtggcc ctggagggc ccatgtgggc tgaaggatgg       2760
gggctcctgg cagtgacctt ttacaaaagt tattttccaa cagggcactc ccaggccctg    2820
tcgccattga ggtgcctccg ctgggctgtc cctcacccc tccctgtgct ggagcctgtc     2880
ccaaaaaggt gccaactggg aggcctcgga agccactgtc caggctccca ctgcctgtct    2940
gctctgttcc caaaggcagc gtgtgtggcc tcgggccctg cggtggcatg aagcatccct    3000
tctggtgtgg gcatcgctac gtgttttggg ggcagcgttt cacggcggtg cccttgctgt    3060
ctcccttggg ctggctcgag cctggggtcc atgtcccttt gccgtccgt catggggcag     3120
ggaatccata gcggggccca caggcagggg tatgagtgcg tcccacccaa cgcagcacca    3180
gccccggcca ccgctccccg tgtccccagt tccgtctcag ctacctggac tccaggaccc    3240
tggagaaggg agacctggca gtggagggag gctgtgctgt gtgtcccct gcaggtgtga     3300
ccccgcctgc tctttcctcc cccgccaggt gtggcccgc ctgctctttc ctcccccacc     3360
agtatggccc cacctgctct ttcctccccc ccaaggtgt ggccccacct gttctttcct     3420
cccctgccga ggtgtgaccc cacctgctct ttcctccctc ccagtatggc cccacctgct    3480
ctttcctccc ccgaggtgag gccccgcctg ctctttcctc ccatgggagc cgctgaggcg    3540
tgcgcacctg ggcacaggtt ggggctctgc aggatgagga agacaggcca atcccttccc    3600
tcccagaagc tggccgccca gcaggaggga ctgaggccag actcatgtcc agcaaggaac    3660
gtgtggtgtg tcccctggga agtctctggg ccctgggaag agggaaggtg cacgtcctgg    3720
gatggttgcg gggccctgtt ttgggagaca aaggggtaga gggtctgtct tgggcccccc    3780
cagactctag cccgagcagt gcagccacct actgccccac ctcagagaag tgcagcggga    3840
```

```
aggaggctgg aggtggtgcg gcgctgcctc gggtgtctgc gtgaatgagc gtggccaagg   3900
accagtgcca cctcatggca aagagctccc gcagtgtttg ttagagtgca catcctacgt   3960
gcccactggc acacacacgt gctcacatac atgtccgcgt acaggcgtac acatgcacgc   4020
ttgcacacat gcacacagac cacatagcac acatgtgcac tgaccacacc tgtatagacc   4080
atgcacagta cacatacgtg catacacatg cctgcataca ggcatacaca tgcacgctta   4140
catgtacacg tgcacagatc acacacatgc acacacgtgt agctcacaca cagtatacac   4200
atacacaagt gcacagacca cacacagcac taacacatgc acacacaaag tgcataggcc   4260
acacagcaca tgcacacagg tgcacagacc acacagcaca cacaagtgca cagagcacac   4320
tgcacacatg cacacacaca cgcgtgcatg cacactcctc gcacttccag ccttggagcc   4380
cttctgtctc tggtctttct ctttgaccct gctgagtgta agctgcctgg ggaggggcta   4440
caaggagtaa ttgtggcttt aggggtcgtg gtgatgctgg aatgtcaagc gccgtcgtgg   4500
ggtatccgac tgtccgggct cctggtccga agtggcagag cgccaggcag agccaatcag   4560
ggtctcgtgc tgcccttccc ccccacagcc tggcagccat ccagaggagg ggctctacca   4620
gatgccaagg tgccccggtg tctgtatggg tgtccggttg ggtcctgtgt ttggtctgcc   4680
ctggaggtgg ctgggccctc ctgggatggg tggctcagcc tcgaatccca ggccccagcc   4740
caggcaggtg ctgctgcctg ttgtggtttc ctggcccagc ttctccttct ccctctgcat   4800
aaaatcacag tccgtgagtc ttccagctgc caccacggct gggacacgct gggggagggc   4860
tcctcccatg cctcctgcac acagccgtct gagcagggca ggtgccaaca ccccccaccg   4920
gagacacgct gcccctcagc gatgccccta ccttttgggg ggcctcgtct caagcccccc   4980
cttggaggct gaaatcaccc caggcactgt gagggcttct ccaggggggac accctttgag   5040
ctgtgggtct gatcaccccca agtcccgcac acggaggaga ggcacagcca gggcgtgtgg   5100
tttaatgttt gcccccttcgg ggctggaggt ctcagtgttt ctagattcca gaccctgctg   5160
ccagagagac ctgctgccgg agagaagggg aggaggactc cagctgggct cggtccccca   5220
cagtcaggga cccccataaa ggacaccccc ttctctctag aaagagctgg gctctcagct   5280
atttctagtt gcttcccaga agccgaggag cagaaggagc tgtgagagct ttgcagaaac   5340
gcccttgtcc ccgccctcct gagctatgaa tgccgtacag agcagaggct ggggcattgg   5400
caagatcaca ggttgatgct gcacagcccc attgacacaa accctcaaag cagacgtgag   5460
agggacggtt cacaaagctt ggacctgccg tggagggtgc ccggcagacg tggcgtgaga   5520
gggacggctc acgaggcttg gacctgctgt ggagggtgcc cagcagacgt ggtgtgagag   5580
gaacggctca cgagacttgg acctggtgga gggtgcccag cagacgtggt gtgagaggga   5640
cggctcacag ggcttggacc ggagagagat ggctcatgag acttggacct gccgtggagg   5700
gtgcccagca gacgtggtat gagagggatg gctcacgagg cttggacctg gtggagggtg   5760
cccggcagac gtgtgagagg gacggttcac aaggcttgga cctgccatgg agggtgccca   5820
gcagacgtgg tgtgagaggg acagctcacg aggcttggac ctgccgtgga gggtgcccag   5880
caggggctg agctctgagg ggtgggtgct cagtgcacgg gtgcccccag tgtcctctga   5940
tcctgtccgg tgcctccccc aaccccccaca cccatgcaga actcccaggt cacatgcacg   6000
tatgtccagg gcatggggt ggcgtgaaga ggcctggtca gggcctttag gggctgcagg   6060
acggaatggc caccctgggga gcctgtgtgg ctgtgccggg cagccatcct gcattcccac   6120
ccagcgcgca gtctccacct cggccccagc aaagcgctaa gcagccggag agacagccag   6180
ggcggcttcc tgaaggatgt gggatggtgg actccgggga tcgagggaata cgcaggttcc   6240
```

-continued

```
tgtcctccgg gagacctaga gaagctgcac acccaggagc tttccatgac ccgggagcat      6300
gagtgaatgg ggggttccag tttgctgaac tttgctgtct tgtaagggtg ggggctgacg      6360
gccgaccctg ggaggaggtg acaccgcagg gggaggttgt gggcaacggt ggaggaggag      6420
agacgggagg ggaccatttg ggatggaggg gcctcttcag agttttaaaa ggcgtttgtg      6480
gggtggagtt gagtgtgctc tgggcttgga cacttgccgt ggtgcccctg gctggccgag      6540
gagactggct ctggccaggg ccccgtcctg agaggtcctc agcgtctgac tctcggccag      6600
gcgccagcaa ggaggggccg gtccccgggg ctaccaggca ggcacgtgca catcgccatc      6660
gccacacgcc aactccgcct gggttttaca aagtcgttgc cttaatgcat gtggacagga      6720
actccctgag gtcgccccat gccccctggc tgtgccaggt acggacgccc tggaccctgc      6780
gaacaggtgg ggcgggcgag gggcccaagg gacgggctcc agagacacgc gcagggcagg      6840
aggggtctca cggaggggtc tcgcactgag gcgcccagag ctggtggtcc cgctggacgc      6900
catccctctg cccgggatcc acacggccca cgtgtgcccg ccatgcccgc gccccacgcc      6960
attgcagtct tccatcctct ggccgtgacg gtggctgcag cttccccatt tgcgccgttg      7020 cctctgctg tctgcacttt tgttcatgct ccaaagaaca tttcataatg ccttcagtac      7080
cgacgtacac ttctgaccat tttgtatgtg tccttgtgcc gtagtgacca ggccttttt      7140 tggtggatgt gttaccccgc acacttcaat ctcaactttg tgcaccgtcc attttctagg      7200
gatagacgcc cagggaatga actctagttt tctaacagat tagctgagat attaacttac      7260
tcacacggac aggttgatgc cagagccgta agaatgcgcc agtgcgggtt tgcggggac      7320 ttcgggtgtg gggtcctgcg gccgcgatgg ccgtggaagg ttctggggat ccctgctgcc      7380
acggggacga gttcggacgc caggtggacc tgtgcactca gtaaaacgca gtgattc        7437
```

<210> SEQ ID NO 46
<211> LENGTH: 7437
<212> TYPE: DNA
<213> ORGANISM: Homo sapiens

<400> SEQUENCE: 46

```
gctgagcctg agcccgaccc ggggcgcctc ccgccaggca ccatggtgca gaagtcgcgc        60
aacggcggcg tataccccgg cccgagcggg gagaagaagc tgaaggtggg cttcgtgggg       120
ctggaccccg cgcgcccga ctccaccccgg gacggggcgc tgctgatcgc cggctccgag       180
gcccccaagc gcggcagcat cctcagcaaa cctcgcgcgg gcggcgcggg cgccgggaag       240
ccccccaagc gcaacgcctt ctaccgcaag ctgcagaatt tcctctacaa cgtgctggag       300
cggccgcgcg gctgggcgtt catctaccac gcctacgtgt tcctcctggt tttctcctgc       360
ctcgtgctgt ctgtgttttc caccatcaag gagtatgaga gagctcgga gggggccctc       420 tacatcctgg aaatcgtgac tatcgtggtg tttggcgtgg agtacttcgt gcggatctgg       480
gccgcaggct gctgctgccg gtaccgtggc tggagggggc ggctcaagtt tgcccggaaa       540
ccgttctgtg tgattgacat catggtgctc atcgcctcca ttgcggtgct ggccgccggc       600
tcccagggca acgtctttgc cacatctgcg ctccggagcc tgcgcttcct gcagattctg       660
cggatgatcc gcatggaccg gcggggaggc acctggaagc tgctgggctc tgtggtctat       720
gcccacagca aggagctggt cactgcctgg tacatcggct tcctttgtct catcctggcc       780
tcgttcctgg tgtacttggc agagaagggg gagaacgacc actttgacac ctacgcggat       840
gcactctggt ggggcctgat cacgctgacc accattggct acgggdacaa gtaccccag       900 acctggaacg gcaggctcct tgcggcaacc ttcacccctca tcggtgtctc cttcttcgcg       960
```

```
ctgcctgcag gcatcttggg gtctgggttt gccctgaagg ttcaggagca gcacaggcag      1020
aagcactttg agaagaggcg gaacccggca gcaggcctga tccagtcggc ctggagattc      1080
tacgccacca acctctcgcg cacagacctg cactccacgt ggcagtacta cgagcgaacg      1140
gtcaccgtgc ccatgtacag ttcgcaaact caaacctacg ggcctccag acttatcccc       1200 ccgctgaacc agctggagct gctgaggaac ctcaagagta aatctggact cgctttcagg      1260
aaggaccccc cgccggagcc gtctccaagc cagaaggtca gtttgaaaga tcgtgtcttc      1320
tccagccccc gaggcgtggc tgccaagggg aaggggtccc cgcaggccca gactgtgagg      1380
cggtcaccca gcgccgacca gagcctcgag gacagcccca gcaaggtgcc caagagctgg      1440
agcttcgggg accgcagccg ggcacgccag gctttccgca tcaagggtgc cgcgtcacgg      1500
cagaactcag aagaagcaag cctccccgga gaggacattg tggatgacaa gagctgcccc      1560
tgcgagtttg tgaccgagga cctgaccccg ggcctcaaag tcagcatcag agccgtgtgt      1620
gtcatgcggt tcctggtgtc caagcggaag ttcaaggaga gcctgcggcc ctacgacgtg      1680
atggacgtca tcgagcagta ctcagccggc cacctggaca tgctgtcccg aattaagagc      1740
ctgcagtcca gtgtggacca gatcgtgggg cggggcccag cgatcacgga caaggaccgc      1800
accaagggcc cggccgaggc ggagctgccc gaggacccca gcatgatggg acggctcggg      1860
aaggtggaga agcaggtctt gtccatggag aagaagctgg acttcctggt gaatatctac      1920
atgcagcgga tgggcatccc cccgacagag accgaggcct actttggggc caaagagccg      1980
gagccggcgc cgccgtacca cagcccgaaa gacagccggg agcatgtcga caggcacggc      2040
tgcattgtca agatcgtgcg ctccagcagc tccacgggcc agaagaactt ctcggcgccc      2100
ccggccgcgc ccctgtcca gtgtccgccc tccacctcct ggcagccaca gagccacccg      2160
cgccagggcc acggcacctc ccccgtgggg gaccacggct ccctggtgcg catcccgccg      2220
ccgcctgccc acgagcggtc gctgtccgcc tacggcgggg caaccgcgc cagcatggag      2280 ttcctgcggc aggaggacac cccgggctgc aggcccccg aggggaccct gcgggacagc       2340
gacacgtcca tctccatccc gtccgtggac cacgaggagc tggagcgttc cttcagcggc      2400
ttcagcatct cccagtccaa ggagaacctg gatgctctca cagctgcta cgcggccgtg       2460 gcgccttgtg ccaaagtcag gccctacatt gcggagggag agtcagacac cgactccgac      2520
ctctgtaccc cgtgcgggcc cccgccacgc tcggccaccg gcgagggtcc ctttggtgac      2580
gtgggctggg ccgggcccag gaagtgaggc ggcgctgggc cagtggaccc gcccgcggcc      2640
ctcctcagca cggtgcctcc gaggttttga ggcgggaacc ctctggggcc cttttcttac      2700
agtaactgag tgtggcggga agggtgggcc ctggaggggc ccatgtgggc tgaaggatgg      2760
gggctcctgg cagtgacctt ttacaaaagt tattttccaa cagggcactc ccaggccctg      2820
tcgccattga ggtgcctccg ctgggctgtc tcctcacccc tccctgtgct ggagcctgtc      2880
ccaaaaaggt gccaactggg aggcctcgga agccactgtc caggctccca ctgcctgtct      2940
gctctgttcc caaaggcagc gtgtgtggcc tcgggccctg cggtggcatg aagcatccct      3000
tctggtgtgg gcatcgctac gtgttttggg ggcagcgttt cacggcggtg cccttgctgt      3060
ctcccttggg ctggctcgag cctggggtcc atgtcccttt gccgtcccgt catggggcag      3120
ggaatccata gcgggcccca caggcagggg tatgagtgcg tcccacccaa cgcagcacca      3180
gccccggcca ccgctccccg tgtccccagt tccgtctcag ctacctggac tccaggaccc      3240
tggagaaggg agacctggca gtggagggag gctgtgctgt gtgtcccctt gcaggtgtga      3300
ccccgcctgc tctttcctcc cccgccaggt gtggcccgc ctgctctttc ctccccccacc       3360
```

```
agtatggccc cacctgctct ttcctccccc cccaaggtgt ggccccacct gttctttcct    3420
cccctgccga ggtgtgaccc cacctgctct ttcctccctc ccagtatggc cccacctgct    3480
ctttcctccc ccgaggtgag gccccgcctg ctctttcctc ccatgggagc cgctgaggcg    3540
tgcgcacctg ggcacaggtt ggggctctgc aggatgagga agacaggcca atcccttccc    3600
tcccagaagc tggccgccca gcaggaggga ctgaggccag actcatgtcc agcaaggaac    3660
gtgtggtgtg tccctggga agtctctggg ccctgggaag agggaaggtg cacgtcctgg    3720
gatggttgcg gggccctgtt ttgggagaca aaggggtaga gggtctgtct tgggcccccc    3780
cagactctag cccgagcagt gcagccacct actgccccac ctcagagaag tgcagcggga    3840
aggaggctgg aggtggtgcg gcgctgcctc gggtgtctgc gtgaatgagc gtggccaagg    3900
accagtgcca cctcatggca aagagctccc gcagtgtttg ttagagtgca catcctacgt    3960
gcccactggc acacacacgt gctcacatac atgtccgcgt acaggcgtac acatgcacgc    4020
ttgcacacat gcacacagac cacatagcac acatgtgcac tgaccacacc tgtatagacc    4080
atgcacagta cacatacgtg catacacatg cctgcataca ggcatacaca tgcacgctta    4140
catgtacacg tgcacagatc acacacatgc acacacgtgt agctcacaca cagtatacac    4200
atacacaagt gcacagacca cacacagcac taacacatgc acacacaaag tgcataggcc    4260
acacagcaca tgcacacagg tgcacagacc acacagcaca cacaagtgca cagagcacac    4320
tgcacacatg cacacacaca cgcgtgcatg cacactcctc gcacttccag ccttggagcc    4380
cttctgtctc tggtctttct ctttgaccct gctgagtgta agctgcctgg ggagggcta    4440 caaggagtaa ttgtggcttt aggggtcgtg gtgatgctgg aatgtcaagc gccgtcgtgg    4500
ggtatccgac tgtccgggct cctggtccgc agtggcagag cgccaggcag agccaatcag    4560
ggtctcgtgc tgcccttccc ccccacagcc tggcagccat ccagaggagg ggctctacca    4620
gatgccaagg tgcccggtg tctgtatggg tgtccggttg ggtcctgtgt ttggtctgcc    4680
ctggaggtgg ctgggccctc ctgggatggg tggctcagcc tcgaatccca ggccccagcc    4740
caggcaggtg ctgctgcctg ttgtggtttc ctggcccagc ttctccttct ccctctgcat    4800
aaaatcacag tccgtgagtc ttccagctgc caccacggct gggacacgct gggggagggc    4860
tcctcccatg cctcctgcac acagccgtct gagcagggca ggtgccaaca ccccccaccg    4920
gagacacgct gccctcagc gatgccccta ccttttgggg ggcctcgtct caagcccccc    4980
cttggaggct gaaatcaccc caggcactgt gagggcttct ccaggggac accctttgag    5040 ctgtgggtct gatcacccca gtccccgcac acggaggaga ggcacagcca gggcgtgtgg    5100
tttaatgttt gccccttcgg ggctggaggt ctcagtgttt ctagattcca gaccctgctg    5160
ccagagagac ctgctgccgg agagaagggg aggaggactc cagctgggct cggtcccccca    5220 cagtcaggga cccccataaa ggacaccccc ttctctctag aaagagctgg gctctcagct    5280
atttctagtt gcttcccaga agccgaggag cagaaggagc tgtgagagct ttgcagaaac    5340
gcccttgtcc ccgccctcct gagctatgaa tgccgtacag agcagaggct ggggcattgg    5400
caagatcaca ggttgatgct gcacagcccc attgacacaa accctcaaag cagacgtgag    5460
agggacggtt cacaaagctt ggacctgccg tgagggtgc ccggcagacg tggcgtgaga    5520
gggacggctc acgaggcttg gacctgctgt ggagggtgcc cagcagacgt ggtgtgagag    5580
gaacggctca cgagacttgg acctggtgga gggtgcccag cagacgtggt gtgagaggga    5640
cggctcacag gcttggacc ggagagagat ggctcatgag acttggacct gccgtggagg    5700
gtgcccagca gacgtggtat gagagggatg gctcacgagg cttggacctg gtggagggtg    5760
```

-continued

| | |
|---|---|
| cccggcagac gtgtgagagg gacggttcac aaggcttgga cctgccatgg agggtgccca | 5820 |
| gcagacgtgg tgtgagaggg acagctcacg aggcttggac ctgccgtgga gggtgcccag | 5880 |
| caggggggctg agctctgagg ggtgggtgct cagtgcacgg gtgcccccag tgtcctctga | 5940 |
| tcctgtccgg tgcctccccc aaccccccaca cccatgcaga actcccaggt cacatgcacg | 6000 |
| tatgtccagg gcatgggggt ggcgtgaaga ggcctggtca gggcctttag gggctgcagg | 6060 |
| acggaatggc cacctgggga gcctgtgtgg ctgtgccggg cagccatcct gcattcccac | 6120 |
| ccagcgcgca gtctccacct cggccccagc aaagcgctaa gcagccggag agacagccag | 6180 |
| ggcggcttcc tgaaggatgt gggatggtgg actccggggt cgaggaata cgcaggttcc | 6240 |
| tgtcctccgg gagacctaga gaagctgcac acccaggagc tttccatgac ccgggagcat | 6300 |
| gagtgaatgg ggggttccag tttgctgaac tttgctgtct tgtaagggtg ggggctgacg | 6360 |
| gccgaccctg ggaggaggtg acaccgcagg gggaggttgt gggcaacggt ggaggaggag | 6420 |
| agacgggagg ggaccatttg ggatggaggg gcctcttcag agttttaaaa ggcgtttgtg | 6480 |
| gggtggagtt gagtgtgctc tgggcttgga cacttgccgt ggtgcccctg gctggccgag | 6540 |
| gagactggct ctggccaggg ccccgtcctg agaggtcctc agcgtctgac tctcggccag | 6600 |
| gcgccagcaa ggaggggccg gtccccgggg ctaccaggca ggcacgtgca catcgccatc | 6660 |
| gccacacgcc aactccgcct gggttttaca aagtcgttgc cttaatgcat gtggacagga | 6720 |
| actccctgag gtcgccccat gcccctggc tgtgccaggt acggacgccc tggaccctgc | 6780 |
| gaacaggtgg ggcgggcgag gggcccaagg gacgggctcc agagacacgc gcagggcagg | 6840 |
| aggggtctca cggaggggtc tcgcactgag gcgcccagag ctggtggtcc cgctggacgc | 6900 |
| catccctctg cccgggatcc acacggccca cgtgtgcccg ccatgcccgc gccccacgcc | 6960 |
| attgcagtct tccatcctct ggccgtgacg gtggctgcag cttccccatt tgcgccgttg | 7020 |
| cctctggctg tctgcacttt tgttcatgct ccaaagaaca tttcataatg ccttcagtac | 7080 |
| cgacgtacac ttctgaccat tttgtatgtg tccttgtgcc gtagtgacca ggcctttttt | 7140 |
| tggtggatgt gttaccccgc acacttcaat ctcaactttg tgcaccgtcc attttctagg | 7200 |
| gatagacgcc cagggaatga actctagttt tctaacagat tagctgagat attaacttac | 7260 |
| tcacacggac aggttgatgc cagagccgta agaatgcgcc agtgcgggtt tgcggggac | 7320 |
| ttcgggtgtg gggtcctgcg gccgcgatgg ccgtggaagg ttctggggat ccctgctgcc | 7380 |
| acggggacga gttcggacgc caggtggacc tgtgcactca gtaaaacgca gtgattc | 7437 |

<210> SEQ ID NO 47
<211> LENGTH: 7437
<212> TYPE: DNA
<213> ORGANISM: Homo sapiens

<400> SEQUENCE: 47

| | |
|---|---|
| gctgagcctg agcccgaccc ggggcgcctc ccgccaggca ccatggtgca gaagtcgcgc | 60 |
| aacggcggcg tataccccgg cccgagcggg gagaagaagc tgaaggtggg cttcgtgggg | 120 |
| ctggaccccg gcgcgcccga ctccaccccgg gacggggcgc tgctgatcgc cggctccgag | 180 |
| gccccccaagc gcggcagcat cctcagcaaa cctcgcgcgg gcggcgcggg cgccgggaag | 240 |
| ccccccaagc gcaacgcctt ctaccgcaag ctgcagaatt tcctctacaa cgtgctggag | 300 |
| cggccgcgcg gctgggcgtt catctaccac gcctacgtgt tcctcctggt tttctcctgc | 360 |
| ctcgtgctgt ctgtgttttc caccatcaag gagtatgaga agagctcgga gggggccctc | 420 |
| tacatcctgg aaatcgtgac tatcgtggtg tttggcgtgg agtacttcgt gcggatctgg | 480 |

```
gccgcaggct gctgctgccg gtaccgtggc tggaggggc ggctcaagtt tgcccggaaa    540
ccgttctgtg tgattgacat catggtgctc atcgcctcca ttgcggtgct ggccgccggc    600
tcccagggca acgtctttgc cacatctgcg ctccggagcc tgcgcttcct gcagattctg    660
cggatgatcc gcatggaccg gcggggaggc acctggaagc tgctgggctc tgtggtctat    720
gcccacagca aggagctggt cactgcctgg tacatcggct cctttgtct catcctggcc    780
tcgttcctgg tgtacttggc agagaagggg gagaacgacc actttgacac ctacgcggat    840
gcactctggt ggggcctgat cacgctgacc accattggct acggggacaa gtaccccag    900
acctggaacg gcaggctcct tgcggcaacc ttcaccctca tcggtgtctc cttcttcgcg    960
ctgcctgcag gcatcttggg gtctgggttt gccctgaagg ttcaggagca gcacaggcag   1020
aagcactttg agaagaggcg gaacccggca gcaggcctga tccagtcggc ctggagattc   1080
tacgccacca acctctcgcg cacagacctg cactccacgt ggcagtacta cgagcgaacg   1140
gtcaccgtgc ccatgtacag ttcgcaaact caaacctacg ggcctccag acttatcccc   1200
ccgctgaacc agctggagct gctgaggaac ctcaagagta atctggact cgctttcagg   1260
aaggaccccc cgccggagcc gtctccaagc cagaaggtca gtttgaaaga tcgtgtcttc   1320
tccagccccc gaggcgtggc tgccaagggg aagggtccc cgcaggccca gactgtgagg   1380
cggtcaccca cgccgaccca gagcctcgag gacagcccca gcaaggtgcc caagagctgg   1440
agcttcgggg accgcagccg ggcacgccag gctttccgca tcaagggtgc cgcgtcacgg   1500
cagaactcag aagaagcaag cctccccgga gaggacattg tggatgacaa gagctgcccc   1560
tgcgagtttg tgaccgagga cctgaccccg ggcctcaaag tcagcatcag agccgtgtgt   1620
gtcatgcgt tcctggtgtc caagcggaag ttcaaggaga gcctgcggcc ctacgacgtg   1680
atggacgtca tcgagcagta tcagccggc cacctggaca tgctgtcccg aattaagagc   1740
ctgcagtcca gagtggacca gatcgtgggg cggggcccag cgatcacgga caaggaccgc   1800
accaagggcc cggccgaggc ggagctgccc gaggacccca gcatgatggg acggctcggg   1860
aaggtggaga agcaggtctt gtccatggag aagaagcggg acttcctggt gaatatctac   1920
atgcagcgga tgggcatccc cccgacagag accgaggcct actttgggc aaagagccg   1980
gagccggcgc cgccgtacca cagcccggaa gacagccggg agcatgtcga caggcacggc   2040
tgcattgtca gatcgtgcg ctccagcagc tccacgggcc agaagaactt ctcggcgccc   2100
ccggccgcgc ccctgtccca gtgtccgccc tccacctcct ggcagccaca gagccacccg   2160
cgccagggcc acggcacctc cccgtgggg gaccacggct ccctggtgcg catcccgccc   2220
ccgcctgccc acgagcggtc gctgtccgcc tacggcgggg gcaaccgcgc cagcatggag   2280
ttcctgcggc aggaggacac cccgggctgc aggcccccg aggggaccct gcgggacagc   2340
gacacgtcca tctccatccc gtccgtggac cacgaggagc tggagcgttc cttcagcggc   2400
ttcagcatct cccagtccaa ggagaacctg atgctctca acagctgcta cgcggccgtg   2460
gcgccttgtg ccaaagtcag gccctacatt gcggagggag agtcagacac cgactccgac   2520
ctctgtacc cgtgcgggcc cccgccacgc tcggccaccg gcgagggtcc ctttggtgac   2580
gtgggctggg ccgggcccag gaagtgaggc ggcgctgggc cagtggaccc gccgcggcc   2640
ctcctcagca cggtgcctcc gaggttttga ggcgggaacc ctctgggcc cttttcttac   2700
agtaactgag tgtggcggga agggtgggcc ctggaggggc ccatgtgggc tgaaggatgg   2760
gggctcctgg cagtgacctt ttacaaaagt tattttccaa cagggcactc ccaggccctg   2820
tcgccattga ggtgcctccg ctgggctgtc tcctcacccc tccctgtgct ggagcctgtc   2880
```

```
ccaaaaaggt gccaactggg aggcctcgga agccactgtc caggctccca ctgcctgtct    2940
gctctgttcc caaaggcagc gtgtgtggcc tcgggccctg cggtggcatg aagcatccct    3000
tctggtgtgg gcatcgctac gtgttttggg ggcagcgttt cacggcggtg cccttgctgt    3060
ctcccttggg ctggctcgag cctggggtcc atgtccettt gccgtccgt catggggcag     3120
ggaatccata gcggggccca caggcagggg tatgagtgcg tcccacccaa cgcagcacca    3180
gccccggcca ccgctcccg tgtcccagt tccgtctcag ctacctggac tccaggaccc      3240
tggagaaggg agacctggca gtggagggag gctgtgctgt gtgtccccct gcaggtgtga    3300
ccccgcctgc tctttcctcc cccgccaggt gtggccccgc ctgctctttc ctccccccacc   3360
agtatggccc cacctgctct ttcctccccc cccaaggtgt ggccccacct gttctttcct    3420
cccctgccga ggtgtgaccc cacctgctct ttcctccctc ccagtatggc cccacctgct    3480
ctttcctccc ccgaggtgag gccccgcctg ctctttcctc ccatgggagc cgctgaggcg    3540
tgcgcacctg gcacaggtt ggggctctgc aggatgagga agacaggcca atcccttccc     3600
tcccagaagc tggccgccca gcaggaggga ctgaggccag actcatgtcc agcaaggaac    3660
gtgtggtgtg tccctggga agtctctggg ccctgggaag agggaaggtg cacgtcctgg     3720
gatggttgcg gggccctgtt ttgggagaca aaggggtaga gggtctgtct tgggcccccc    3780
cagactctag cccgagcagt gcagccacct actgccccac ctcagagaag tgcagcggga    3840
aggaggctgg aggtggtgcg gcgctgcctc gggtgtctgc gtgaatgagc gtggccaagg    3900
accagtgcca cctcatggca aagagctccc gcagtgtttg ttagagtgca catcctacgt    3960
gcccactggc acacacacgt gctcacatac atgtccgcgt acaggcgtac acatgcacgc    4020
ttgcacacat gcacacagac cacatagcac acatgtgcac tgaccacacc tgtatagacc    4080
atgcacagta cacatacgtg catacacatg cctgcataca ggcatacaca tgcacgctta    4140
catgtacacg tgcacagatc acacacatgc acacacgtgt agctcacaca cagtatacac    4200
atacacaagt gcacagacca cacacagcac taacacatgc acacacaaag tgcataggcc    4260
acacagcaca tgcacacagg tgcacagacc acacagcaca cacaagtgca cagagcacac    4320
tgcacacatg cacacacaca cgcgtgcatg cacactcctc gcacttccag ccttggagcc    4380
cttctgtctc tggtctttct cttgaccct gctgagtgta agctgcctgg ggaggggcta     4440
caaggagtaa ttgtggcttt agggtcgtg gtgatgctgg aatgtcaagc gccgtcgtgg     4500
ggtatccgac tgtccgggct cctggtccgc agtggcagag cgccaggcag agccaatcag    4560
ggtctcgtgc tgcccttccc ccccacagcc tggcagccat ccagaggagg ggctctacca    4620
gatgccaagg tgccccggtg tctgtatggg tgtccggttg ggtcctgtgt ttggtctgcc    4680
ctggaggtgc ctgggccctc ctgggatggg tggctcagcc tcgaatccca ggccccagcc    4740
caggcaggtg ctgctgcctg ttgtggtttc ctggcccagc ttctccttct ccctctgcat    4800
aaaatcacag tccgtgagtc ttccagctgc caccacggct gggacacgct gggggagggc    4860
tcctcccatg cctcctgcac acagccgtct gagcagggca ggtgccaaca cccccccaccg    4920
gagacacgct gccctcagc gatgcccta ccttttgggg ggcctcgtct caagcccccc       4980
cttggaggct gaaatcaccc caggcactgt gagggcttct ccaggggac acccttgag      5040
ctgtgggtct gatcacccca gtccgcac acgaggaga gcacagcca gggcgtgtgg        5100
tttaatgttt gccccttcgg ggctggaggt ctcagtgttt ctagattcca gaccctgctg    5160
ccagagagac ctgctgccgg agagaagggg aggaggactc cagctgggct cggtccccca    5220
cagtcaggga cccccataaa ggacaccccc ttctctctag aaagagctgg gctctcagct    5280
```

```
atttctagtt gcttcccaga agccgaggag cagaaggagc tgtgagagct ttgcagaaac    5340
gcccttgtcc ccgccctcct gagctatgaa tgccgtacag agcagaggct ggggcattgg    5400
caagatcaca ggttgatgct gcacagcccc attgacacaa accctcaaag cagacgtgag    5460
agggacggtt cacaaagctt ggacctgccg tggaggtgcc ccggcagacg tggcgtgaga    5520
gggacggctc acgaggcttg gacctgctgt ggagggtgcc cagcagacgt ggtgtgagag    5580
gaacggctca cgagacttgg acctggtgga gggtgcccag cagacgtggt gtgagggga    5640 cggctcacag ggcttggacc ggagagagat ggctcatgag acttggacct gccgtggagg    5700
gtgcccagca gacgtggtat gagagggatg gctcacgagg cttggacctg gtggagggtg    5760
cccggcagac gtgtgagagg gacggttcac aaggcttgga cctgccatgg agggtgccca    5820
gcagacgtgg tgtgagaggg acagctcacg aggcttggac ctgccgtgga gggtgcccag    5880
cagggggctg agctctgagg ggtgggtgct cagtgcacgg gtgcccccag tgtcctctga    5940
tcctgtccgg tgcctccccc aacccccaca cccatgcaga actcccaggt cacatgcacg    6000
tatgtccagg gcatgggggt ggcgtgaaga ggcctggtca gggcctttag gggctgcagg    6060
acggaatggc cacctgggga gcctgtgtgg ctgtgccggg cagccatcct gcattcccac    6120
ccagcgcgca gtctccacct cggccccagc aaagcgctaa gcagccggag agacagccag    6180
ggcggcttcc tgaaggatgt gggatggtgg actccggggt cgagggaata cgcaggttcc    6240
tgtcctccgg gagacctaga gaagctgcac acccaggagc tttccatgac ccgggagcat    6300
gagtgaatgg ggggttccag tttgctgaac tttgctgtct tgtaagggtg ggggctgacg    6360
gccgaccctg ggaggaggtg acaccgcagg gggaggttgt gggcaacggt ggaggaggag    6420
agacgggagg ggaccatttg ggatggaggg gcctcttcag agtttttaaaa ggcgtttgtg    6480 gggtggagtt gagtgtgctc tgggcttgga cacttgccgt ggtgcccctg gctggccgag    6540
gagactggct ctggccaggg ccccgtcctg agaggtcctc agcgtctgac tctcggccag    6600
gcgccagcaa ggaggggccg gtccccgggg ctaccaggca ggcacgtgca catcgccatc    6660
gccacacgcc aactccgcct gggttttaca aagtcgttgc cttaatgcat gtggacagga    6720
actccctgag gtcgccccat gccccctggc tgtgccaggt acggacgccc tggaccctgc    6780
gaacaggtgg ggcgggcgag gggcccaagg gacgggctcc agagacacgc gcagggcagg    6840
aggggtctca cggaggggtc tcgcactgag gcgcccagag ctggtggtcc cgctggacgc    6900
catccctctg cccgggatcc acacggccca cgtgtgcccg ccatgcccgc gccccacgcc    6960
attgcagtct tccatcctct ggccgtgacg gtggctgcag cttccccatt gcgccgttg    7020 cctctggctg tctgcacttt tgttcatgct ccaaagaaca tttcataatg ccttcagtac    7080
cgacgtacac ttctgaccat tttgtatgtg tccttgtgcc gtagtgacca ggcctttttt    7140
tggtggatgt gttaccccgc acacttcaat ctcaactttg tgcaccgtcc atttctagg    7200 gatagacgcc cagggaatga actctagttt tctaacagat tagctgagat attaacttac    7260
tcacacggac aggttgatgc cagagccgta agaatgcgcc agtgcgggtt tgcgggggac    7320
ttcgggtgtg gggtcctgcg gccgcgatgg ccgtggaagg ttctggggat ccctgctgcc    7380
acggggacga gttcggacgc caggtggacc tgtgcactca gtaaaacgca gtgattc       7437

<210> SEQ ID NO 48
<211> LENGTH: 169
<212> TYPE: DNA
<213> ORGANISM: Homo sapiens

<400> SEQUENCE: 48
```

```
acttatcccc ccgctgaacc agctggagct gctgaggaac ctcaagagta aatctggact      60
cgctttcagg tcagctgggg agctccaggt ggggcgggtg ggcgtctcag tcctgggggc     120
cccagctgcc cacagaagac acgccaggac agtgccccag ggactccag                 169

<210> SEQ ID NO 49
<211> LENGTH: 203
<212> TYPE: DNA
<213> ORGANISM: Homo sapiens

<400> SEQUENCE: 49
atgccgggac aggtgacccc atggcggaag acaggggcta tgggaatgac ttccccatcg      60
aagacatgat ccccaccctg aaggccgcca tccgagccgt caggtaatgc ccccacggtc     120
ccacctgtgc ctgtgtgcct cccccactcc agctcaactc ccacaggaag gggcttataa     180
aattatcttg cactttggga agg                                             203

<210> SEQ ID NO 50
<211> LENGTH: 232
<212> TYPE: DNA
<213> ORGANISM: Homo sapiens

<400> SEQUENCE: 50
aattctacaa ttccgtctct ataaaaaaaa attcaaggag actttgaggc cttacgatgt      60
gaaggatgtg attgagcagt attctgccgg gcatctcgac atgctttcca ggataaagta     120
ccttcagacg aggtgagaca gtcacatctg gagggactgc actcccctca aagccctatg     180
aaccttagag tttaaggtga gaggtattca gaaataattc aaaatgcagg ga             232

<210> SEQ ID NO 51
<211> LENGTH: 1925
<212> TYPE: DNA
<213> ORGANISM: Homo sapiens

<400> SEQUENCE: 51
ggtccattcg ggaattactg cccagcagcc gactaagttg cattccttga atcttcgcag      60
aaaagacaat tcttttaatc agagttagta atgtggacag tacaaaatcg agagagtctg     120
gggcttctct ctttcccgtgt gatgattacc atggtctgtt gtgcacacag caccaatgaa     180
cccagcaaca tgccatacgt gaaagagaca gtggacagat tgctcaaagg atatgacatt     240
cgcttgcggc cggacttcgg agggcccccc gtcgacgttg ggatgcggat cgatgtcgcc     300
agcatagaca tggtctccga agtgaatatg gattatacac tcaccatgta tttccagcag     360
tcttggaaag acaaaaggct ttcttattct ggaatcccac tgaacctcac cctagacaat     420
agggtagctg accaactctg ggtaccagac acctactttc tgaatgacaa gaatcatttt     480
gtgcatgggg tcacagtgaa aaatcgaatg attcgactgc atcctgatgg aacagttctc     540
tatggactcc gaatcacaac cacagctgca tgtatgatgg atcttcgaag atatccattg     600
gatgagcaga actgcaccct ggagatcgaa agttatggct ataccactga tgacattgaa     660
ttttactgga tggaggaga agggcagtc actggtgtta ataaaatcga acttcctcaa     720
ttttcaattg ttgactacaa gatggtgtct aagaaggtgg agttcacaac aggagcgtat     780
ccacgactgt cactaagttt tcgtctaaag agaaacattg gttacttcat tttgcaaacc     840
tacatgcctt ctacactgat tacaattctg tcctgggtgt cttttttggat caactatgat     900 gcatctgcag ccagagtcgc actaggaatc acgacagtgc ttacaatgac aaccatcagc     960
acccacctca gggagaccct gccaaagatc ccttatgtca aagcgattga tatttatctg    1020
```

| | | | | |
|---|---|---|---|---|
| atgggttgct | ttgtgtttgt | gttcctggct | ctgctggagt atgcctttgt | aaattacatc | 1080 |
| ttctttggga | aaggccctca | gaaaaaggga | gctagcaaac aagaccagag | tgccaatgag | 1140 |
| aagaataaac | tggagatgaa | taaagtccag | gtcgacgccc acggtaacat | tctcctcagc | 1200 |
| accctggaaa | tccggaatga | gacgagtggc | tcggaagtgc tcacgagcgt | gagcgacccc | 1260 |
| aaggccacca | tgtactccta | tgacagcgcc | agcatccagt accgcaagcc | cctgagcagc | 1320 |
| cgcgaggcct | acgggcgcgc | cctggaccgg | cacggggtac ccagcaaggg | gcgcatccgc | 1380 |
| aggcgtgcct | cccagctcaa | agtcaagatc | cccgacttga ctgatgtgaa | ttccatagac | 1440 |
| aagtggtccc | gaatgttttt | ccccatcacc | ttttctcttt ttaatgtcgt | ctattggctt | 1500 |
| tactatgtac | actgaggtct | gttctaatgg | ttccatttag actactttcc | tcttctattg | 1560 |
| tttttaacc | ttacaggtcc | ccaacagcga | tactgctgtt tctcgaggta | agagattcag | 1620 |
| ccatccaatt | ggttttaggt | cttgcatatc | agttttatta ctgcaccatg | tttacttcaa | 1680 |
| aaagacaaaa | caaaaaaaaa | attattttc | cagtctaccg tggtccaggt | tatcagctct | 1740 |
| ttaagagctc | tattaattgc | catgtttaca | aacaaacaca aagagagaag | ttagacaggt | 1800 |
| agatctttag | cagtcttttc | tagtttccct | ggatttcact gatttatttt | ttagggaaaa | 1860 |
| tgaaaagagg | accttgctgt | ccgcctgcac | tgcttcctgg taaactataa | caaacttatg | 1920 |
| ctgcc | | | | | 1925 |

<210> SEQ ID NO 52
<211> LENGTH: 1925
<212> TYPE: DNA
<213> ORGANISM: Homo sapiens

<400> SEQUENCE: 52

| | | | | |
|---|---|---|---|---|
| ggtccattcg | ggaattactg | cccagcagcc | gactaagttg cattccttga | atcttcgcag | 60 |
| aaaagacaat | tcttttaatc | agagttagta | atgtggacag tacaaaatcg | agagagtctg | 120 |
| gggcttctct | ctttccctgt | gatgattacc | atggtctgtt gtgcacacag | caccaatgaa | 180 |
| cccagcaaca | tgccatacgt | gaaagagaca | gtggacagat tgctcaaagg | atatgacatt | 240 |
| cgcttgcggc | cggacttcgg | agggcccccc | gtcgacgttg gatgcggat | cgatgtcgcc | 300 |
| agcatagaca | tggtctccga | agtgaatatg | gattataccc tcaccatgta | tttccagcag | 360 |
| tcttggaaag | acaaaaggct | tcttattct | ggaatcccac tgaacctcac | cctagacaat | 420 |
| agggtagctg | accaactctg | ggtaccagac | acctactttc tgaatgacaa | gaaatcattt | 480 |
| gtgcatgggt | tcagagtgaa | aaatcgaatg | attcgactgc atcctgatgg | aacagttctc | 540 |
| tatggactcc | gaatcacaac | cacagctgca | tgtatgatgg atcttcgaag | atatccactg | 600 |
| gatgagcaga | actgcaccct | ggagatcgaa | agttatggct ataccactga | tgacattgaa | 660 |
| ttttactgga | atggaggaga | aggggcagtc | actggtgtta ataaaatcga | acttcctcaa | 720 |
| ttttcaattg | ttgactacaa | gatggtgtct | aagaaggtgg agttcacaac | aggagcgtat | 780 |
| ccacgactgt | cactaagttt | tcgtctaaag | agaaacattg gttacttcat | tttgcaaacc | 840 |
| tacatgcctt | ctacactgat | tacaattctg | tcctgggtgt cttttttggat | caactatgat | 900 |
| gcatctgcag | ccagagtcgc | actaggaatc | acgacagtgc ttacaatgac | aaccatcagc | 960 |
| acccacctca | gggagaccct | gccaaagatc | ccttatgtca aagcgattga | tatttatctg | 1020 |
| atgggttgct | ttgtgtttgt | gttcctggct | ctgctggagt atgcctttgt | aaattacatc | 1080 |
| ttctttggga | aaggccctca | gaaaaaggga | gctagcaaac aagaccagag | tgccaatgag | 1140 |
| aagaataaac | tggagatgaa | taaagtccag | gtcgacgccc acggtaacat | tctcctcagc | 1200 |

-continued

| | |
|---|---|
| accctggaaa tccggaatga gacgagtggc tcggaagtgc tcacgagcgt gagcgacccc | 1260 |
| aaggccacca tgtactccta tgacagcgcc agcatccagt accgcaagcc cctgagcagc | 1320 |
| cgcgaggcct acgggcgcgc cctggaccgg cacggggtac ccagcaaggg gcgcatccgc | 1380 |
| aggcgtgcct cccagctcaa agtcaagatc cccgacttaa ctgatgtgaa ttccatagac | 1440 |
| aagtggtccc gaatgttttt ccccatcacc ttttctcttt ttaatgtcgt ctattggctt | 1500 |
| tactatgtac actgaggtct gttctaatgg ttccatttag actactttcc tcttctattg | 1560 |
| ttttttaacc ttacaggtcc ccaacagcga tactgctgtt tctcgaggta agagattcag | 1620 |
| ccatccaatt ggttttaggt cttgcatatc agttttatta ctgcaccatg tttacttcaa | 1680 |
| aaagacaaaa caaaaaaaaa attatttttc cagtctaccg tggtccaggt tatcagctct | 1740 |
| ttaagagctc tattaattgc catgtttaca aacaaacaca aagagagaag ttagacaggt | 1800 |
| agatctttag cagtcttttc tagtttccct ggatttcact gatttatttt ttagggaaaa | 1860 |
| tgaaaagagg accttgctgt ccgcctgcac tgcttcctgg taaactataa caaacttatg | 1920 |
| ctgcc | 1925 |

<210> SEQ ID NO 53
<211> LENGTH: 1925
<212> TYPE: DNA
<213> ORGANISM: Homo sapiens

<400> SEQUENCE: 53

| | |
|---|---|
| ggtccattcg ggaattactg cccagcagcc gactaagttg cattccttga atcttcgcag | 60 |
| aaaagacaat tcttttaatc agagttagta atgtggacag tacaaaatcg agagagtctg | 120 |
| gggcttctct ctttccctgt gatgattacc atggtctgtt gtgcacacag caccaatgaa | 180 |
| cccagcaaca tgccatacgt gaaagagaca gtggacagat tgctcaaagg atatgacatt | 240 |
| cgcttgcggc cggacttcgg agggccccccc gtcgacgttg ggatgcggat cgatgtcgcc | 300 |
| agcatagaca tggtctccga agtgaatatg gattatacac tcaccatgta tttccagcag | 360 |
| tcttggaaag acaaaaggct ttcttattct ggaatcccac tgaacctcac cctagacaat | 420 |
| agggtagctg accaactctg ggtaccagac acctactttc tgaatgacaa gaaatcattt | 480 |
| gtgcatgggg tcacagtgaa aaatcgaatg attcgactgc atcctgatgg aacagttctc | 540 |
| tatggactcc gaatcacaac cacagctgca tgtatgatgg atcttcgaag atatccactg | 600 |
| gatgagcaga actgcaccct ggagatcgaa agttatggct ataccactga tgacattgaa | 660 |
| ttttactgga atggaggaga aggggcagtc actggtgtta ataaaatcga acttcctcaa | 720 |
| ttttcaattg ttgactacaa gatggtgtct aagaaggtgg agttcacaac aggagcgtat | 780 |
| ccacgactgt cactaagttt tcgtctaaag agaaacattg gttacttcat tttgcaaacc | 840 |
| tacatgcctt ctacactgat tacaattctg tcctgggtgt cttttttggat caactatgat | 900 |
| gcatctgcag ccagagtcgc actaggaatc acgacagtgc ttacaatgac aaccatcagc | 960 |
| acccacctca gggagaccct gccaaagatc ccttatgtca aagcgattga tatttatctg | 1020 |
| atgggttgct ttgtgtttgt gttcctggct ctgctggagt atgcttttgt aaattacatc | 1080 |
| ttctttggga aaggccctca gaaaaaggga gctagcaaac aagaccagag tgccaatgag | 1140 |
| aagaataaac tggagatgaa taagtccag gtcgacgccc acgtaacat tctcctcagc | 1200 |
| accctggaaa tccggaatga gacgagtggc tcggaagtgc tcacgagcgt gagcgacccc | 1260 |
| aaggccacca tgtactccta tgacagcgcc agcatccagt accgcaagcc cctgagcagc | 1320 |
| cgcgaggcct acgggcgcgc cctggaccgg cacggggtac ccagcaaggg gcgcatccgc | 1380 |

| | |
|---|---:|
| aggcgtgcct cccagctcaa agtcaagatc cccgacttga ctgatgtgaa ttccatagac | 1440 |
| aagtggtccc gaatgttttt ccccatcacc ttttctcttt ttaatgtcgt ctattggctt | 1500 |
| tactatgtac actgaggtct gttctaatgg ttccatttag actactttcc tcttctattg | 1560 |
| tttttaacc ttacaggtcc ccaacagcga tactgctgtt tctcgaggta agagattcag | 1620 |
| ccatccaatt ggttttaggt cttgcatatc agttttatta ctgcaccatg tttacttcaa | 1680 |
| aaagacaaaa caaaaaaaaa attatttttc cagtctaccg tggtccaggt tatcagctct | 1740 |
| ttaagagctc tattaattgc catgtttaca acaaacaca agagagaag ttagacaggt | 1800 |
| agatctttag cagtctttc tagtttccct ggatttcact gatttatttt ttagggaaaa | 1860 |
| tgaaaagagg accttgctgt ccgcctgcac tgcttcctgg taaactataa caaacttatg | 1920 |
| ctgcc | 1925 |

<210> SEQ ID NO 54
<211> LENGTH: 1536
<212> TYPE: DNA
<213> ORGANISM: Homo sapiens

<400> SEQUENCE: 54

| | |
|---|---:|
| tgaattcgtg agatggcgag ctccacggca ccatggcccc gaagctgctg ctcctcctct | 60 |
| gcctgttctc gggcttgcac gcgcggtcca gaaaggtgga agaggatgaa tatgaagatt | 120 |
| catcatcaaa ccaaaagtgg gtcttggctc caaaatccca agacaccgac gtgactctta | 180 |
| ttctcaacaa gttgctaaga gagtatgata aaaagctgag gccagatatt ggaataaaac | 240 |
| cgaccgtaat tgacgttgac attatgtta acagcattgg tcctgtgtca tcaataaaca | 300 |
| tggaatacca aattgacata ttttttgctc agacctggac agatagtcgc cttcgattca | 360 |
| acagcacaat gaaaattctt actctgaaca gcaacatggt ggggttaatc tggatcccag | 420 |
| acaccatctt ccgcaattct aaaaccgcag aggctcactg gatcaccaca cccaatcagc | 480 |
| tcctccggat ttggaatgac gggaaaatcc tttacacttt gaggctcacc atcaatgctg | 540 |
| agtgccagct gcagctgcac aacttcccca tggacgaaca ctcctgcccg ctgattttct | 600 |
| ccagctatgg ctatcccaaa gaagaaatga tttatagatg gagaaaaaat tcagtggagg | 660 |
| cagctgacca gaaatcatgg cggctttatc agtttgactt catgggcctc agaaacacca | 720 |
| cagaaatcgt gacaacgtct gcaggtgatt atgttgtcat gactatatat tttgaattga | 780 |
| gtagaagaat gggatacttc accattcaga catacattcc ctgtatactg actgtggttt | 840 |
| tatcctgggt gtcattttgg atcaaaaaag atgctacgcc agcaagaaca gcattaggca | 900 |
| tcaccacggt gctgaccatg accaccctga gcaccatcgc caggaagtcc ttgccacgcg | 960 |
| tgtcctacgt gaccgccatg gaccttttg tgactgtgtg cttcctgttt gtcttcgccg | 1020 |
| cgctgacgga gtatgccacc ctcaactact attccagctg tagaaaacca accaccacga | 1080 |
| aaagacaaac atcgttacta catccagatt cctcaagatg gattcctgag cgaataagcc | 1140 |
| tacaagcccc ttccaactat tccctcctgg acatgaggcc accaccacct gcgatgatca | 1200 |
| ctttaaacaa ttccgtttac tggcaggaat ttgaagatac ctgtgtctat gagtgtctgg | 1260 |
| atggcaaaga ctgtcagagc ttcttctgct gctatgaaga atgtaaatca ggatcctgga | 1320 |
| ggaaagggcg tattcacata gacatcttgg agctggactc gtactcccgg gtcttttttcc | 1380 |
| ccacgtcctt cctgctcttt aacctggtct actgggttgg atacctgtat ctctaagtgt | 1440 |
| tgctcagagt gaagagtgaa gagcatttgg tacacacttg accttctgtc gtccccagac | 1500 |
| cagtagtgac caatcgggag tagcaaggaa ggacac | 1536 |

<210> SEQ ID NO 55
<211> LENGTH: 1843
<212> TYPE: DNA
<213> ORGANISM: Homo sapiens

<400> SEQUENCE: 55

| | | | | | |
|---|---|---|---|---|---|
| gcacaattca | gaggtaacag | cgcctgcgtt | ttctccatga | taacatagac | aaacagttgc | 60 |
| ctccaaagct | gcagattgga | tattgggaag | caaatttggg | tgtgaaatct | tcagcaaagg | 120 |
| agcacgcaga | gtccatgatg | gctcagacca | agtgagtgag | aggcagagcg | agggcgcccc | 180 |
| tctgctctgg | cgcgcccgga | ctcggactcg | cagactcgcg | ctggctccag | tctctccacg | 240 |
| attctctctc | ccagactttt | ccccggtctt | aagagatcct | gtgtccagag | ggggccttag | 300 |
| ctgctccagc | ccgcgatgag | gaaaagtcca | ggtctgtctg | actgtctttg | ggcctggatc | 360 |
| ctccttctga | gcacactgac | tggaagaagc | tatggacagc | cgtcattaca | agatgaactt | 420 |
| aaagacaata | ccactgtctt | caccaggatt | ttggacagac | tcctagatgg | ttatgacaat | 480 |
| cgcctgagac | caggattggg | agagcgtgta | accgaagtga | agactgatat | cttcgtcacc | 540 |
| agtttcggac | ccgtttcaga | ccatgatatg | gaatatacaa | tagatgtatt | tttccgtcaa | 600 |
| agctggaagg | atgaaaggtt | aaaatttaaa | ggacctatga | cagtcctccg | gttaaataac | 660 |
| ctaatggcaa | gtaaaatccg | gactccggac | acattttcc | acaatggaaa | gaagtcagtg | 720 |
| gcccacaaca | tgaccatgcc | caacaaactc | ctgcggatca | cagaggatgg | caccttgctg | 780 |
| tacaccatga | ggctgacagt | gagagctgaa | tgtccgatgc | atttggagga | cttccctatg | 840 |
| gatgcccatg | cttgcccact | aaaatttgga | agttatgctt | atacaagagc | agaagttgtt | 900 |
| tatgaatgga | ccagagagcc | agcacgctca | gtggttgtag | cagaagatgg | atcacgtcta | 960 |
| aaccagtatg | accttcttgg | acaaacagta | gactctggaa | ttgtccagtc | aagtacagga | 1020 |
| gaatatgttg | ttatgaccac | tcatttccac | ttgaagagaa | agattggcta | ctttgttatt | 1080 |
| caaacatacc | tgccatgcat | aatgacatg | attctctcac | aagtctcctt | ctggctcaac | 1140 |
| agagagtctg | taccagcaag | aactgtcttt | ggagtaacaa | ctgtgctcac | catgacaaca | 1200 |
| ttgagcatca | gtgccagaaa | ctccctccct | aaggtggctt | atgcaacagc | tatggattgg | 1260 |
| tttattgccg | tgtgctatgc | ctttgtgttc | tcagctctga | ttgagtttgc | cacagtaaac | 1320 |
| tatttcacta | agagaggtta | tgcatgggat | ggcaaaagtg | tggttccaga | aaagccaaag | 1380 |
| aaagtaaagg | atcctcttat | taagaaaaac | aacacttacg | ctccaacagc | aaccagctac | 1440 |
| acccctaatt | tggccagggg | cgacccgggc | ttagccacca | ttgctaaaag | tgcaaccata | 1500 |
| gaacctaaag | aggtcaagcc | cgaaacaaaa | ccaccagaac | ccaagaaaac | ctttaacagt | 1560 |
| gtcagcaaaa | ttgaccgact | gtcaagaata | gccttcccgc | tgctatttgg | aatcttaac | 1620 |
| ttagtctact | gggctacgta | tttaaacaga | gagcctcagc | taaaagcccc | cacaccacat | 1680 |
| caatagatct | tttactcaca | ttctgttgtt | cagttcctct | gcactgggaa | tttatttatg | 1740 |
| ttctcaacgc | agtaattccc | atctgccttt | attgcctctg | tcttaaagaa | tttgaaagtt | 1800 |
| tccttatttt | cataattcat | ttaagacaag | agacccctgt | ctg | | 1843 |

<210> SEQ ID NO 56
<211> LENGTH: 1843
<212> TYPE: DNA
<213> ORGANISM: Homo sapiens

<400> SEQUENCE: 56

| | | | | | |
|---|---|---|---|---|---|
| gcacaattca | gaggtaacag | cgcctgcgtt | ttctccatga | taacatagac | aaacagttgc | 60 |

-continued

```
ctccaaagct gcagattgga tattgggaag caaatttggg tgtgaaatct tcagcaaagg    120
agcacgcaga gtccatgatg gctcagacca agtgagtgag aggcagagcg aggacgcccc    180
tctgctctgg cgcgcccgga ctcggactcg cagactcgcg ctggctccag tctctccacg    240
attctctctc ccagactttt ccccggtctt aagagatcct gtgttcagag ggggccttag    300
ctgctccagc ccgcgatgag gaaaagtcca ggtctgtctg actgtctttg ggcctggatc    360
ctccttctga gcacactgac tggaagaagc tatggacagc cgtcattaca agatgaactt    420
aaagacaata ccactgtctt caccaggatt ttggacagac tcctagatgg ttatgacaat    480
cgcctgagac aggattggg agagcgtgta accgaagtga agactgatat cttcgtcacc    540
agtttcggac ccgtttcaga ccatgatatg aaatatacaa tagatgtatt tttccgtcaa    600
agctggaagg atgaaaggtt aaaatttaaa ggacctatga cagtcctccg gttaaataac    660
ctaatggcaa gtaaaatccg gactccggac acattttcc acaatggaaa gaagtcagtg    720
gcccacaaca tgaccatgcc caacaaactc ctgcggatca cagaggatgg caccttgctg    780
tacaccatga ggctgacagt gagagctgaa tgtccgatgc atttggagga cttccctatg    840
gatgcccatg cttgcccact aaaatttgga agttatgctt atacaagagc agaagttgtt    900
tatgaatgga ccagagagcc agcacgctca gtggttgtag cagaagatgg atcacgtcta    960
aaccagtatg accttcttgg acaaacagta gactctggaa ttgtccagtc aagtacagga    1020
gaatatgttg ttatgaccac tcatttccac ttgaagagaa agattggcta ctttgttatt    1080
caaacatacc tgccatgcat aatgacagtg attctctcac aagtctcctt ctggctcaac    1140
agagagtctg taccagcaag aactgtcttt ggagtaacaa ctgtgctcac catgacaaca    1200
ttgagcatca gtgccagaaa ctccctccct aaggtggctt atgcaacagc tatggattgg    1260
tttattgccg tgtgctatgc ctttgtgttc tcagctctga ttgagtttgc cacagtaaac    1320
tatttcacta agagaggtta tgcatgggat ggcaaaagtg tggttccaga aaagccaaag    1380
aaagtaaagg atcctcttat taagaaaaac aacacttacg ctccaacagc aaccagctac    1440
acccctaatt tggccagggg cgacccgggc ttagccacca ttgctaaaag tgcaaccata    1500
gaacctaaag aggtcaagcc cgaaacaaaa ccaccagaaac ccaagaaaac ctttaacagt    1560
gtcagcaaaa ttgaccgact gtcaagaata gccttcccgc tgctatttgg aatctttaac    1620
ttagtctact gggctacgta tttaaacaga gagcctcagc taaaagcccc cacaccacat    1680
caatagatct tttactcaca ttctgttgtt cagttcctct gcactgggaa tttatttatg    1740
ttctcaacgc agtaattccc atctgccttt attgcctctg tcttaaagaa tttgaaagtt    1800
tccttatttt cataattcat ttaagacaag agacccctgt ctg                      1843
```

<210> SEQ ID NO 57
<211> LENGTH: 2189
<212> TYPE: DNA
<213> ORGANISM: Homo sapiens

<400> SEQUENCE: 57

```
cctagcgctc ctctccggct tccaccagcc catcgctcca cgctctcttg gctgctgcag     60
tctcggtctc tctctctctc tctctctctc tctctctctc tctctctctc tctctctctc    120
tctctctctc tctctcccaa gtttcctatc tcgtcaagat cagggcaaaa gaagaaaaca    180
ccgaattctg cttgccgttt cagagcggcg gtgatgaaga caaaattgaa catctacaac    240
atcgagttcc tgcttttgt tttcttggtg tgggaccctg ccaggttggt gctggctaac    300
atccaagaag atgaggctaa aaataacatt accatcttta cgagaattct tgacagactt    360
```

-continued

| | |
|---|---|
| ctggatggtt acgataatcg gcttagacca ggactgggag acagtattac tgaagtcttc | 420 |
| actaacatct acgtgaccag ttttggccct gtctcagata cagatatgga atatacaatt | 480 |
| gatgttttct ttcgacaaaa atggaaagat gaacgtttaa aatttaaagg tcctatgaat | 540 |
| atccttcgac taaacaattt aatggctagc aaaatctgga ctccagatac cttttttcac | 600 |
| aatgggaaga aatcagtagc tcataatatg acaatgccaa ataagttgct tcgaattcag | 660 |
| gatgatggga ctctgctgta taccatgagg cttacagttc aagctgaatg cccaatgcac | 720 |
| ttggaggatt tcccaatgga tgctcattca tgtcctctga aatttggcag ctatgcatat | 780 |
| acaacttcag aggtcactta tatttggact tacaatgcat ctgattcagt acaggttgct | 840 |
| cctgatggct ctaggttaaa tcaatatgac ctgctgggcc aatcaatcgg aaaggagaca | 900 |
| attaaatcca gtacaggtga atatactgta atgacagctc atttccacct gaaaagaaaa | 960 |
| attgggtatt ttgtgattca aacctatctg ccttgcatca tgactgtcat tctctcccaa | 1020 |
| gtttcattct ggcttaacag agaatctgtg cctgcaagaa ctgtgtttgg agtaacaact | 1080 |
| gtcctaacaa tgacaactct aagcatcagt gctcggaatt ctctccccaa agtggcttat | 1140 |
| gcaactgcca tggactggtt tattgctgtt tgttatgcat ttgtgttctc tgccctaatt | 1200 |
| gaatttgcaa ctgttaatta cttcaccaaa agaggatgga cttgggatgg aagagtgta | 1260 |
| gtaaatgaca agaaaaaaga aaggcttcc gttatgatac agaacaacgc ttatgcagtg | 1320 |
| gctgttgcca attatgcccc gaatctttca aaagatccag ttctctccac catctccaag | 1380 |
| agtgcaacca cgccagaacc caacaagaag ccagaaaaca agccagctga agcaaagaaa | 1440 |
| actttcaaca gtgttagcaa aattgacaga atgtccagaa tagttttttcc agttttgttt | 1500 |
| ggtaccttta atttagttta ctgggctaca tatttaaaca gagaacctgt attaggggtc | 1560 |
| agtccttgaa ttgagaccca tgttatcttt gggatgtata gcaacattaa atttggtttg | 1620 |
| ttttgctatg tacagtctga ctaataactg ctaatttgtg atccaacatg tacagtatgt | 1680 |
| atatagtgac atagcttacc agtagacctt taatggagac atgcatttgc taactcatgg | 1740 |
| aactgcagac agaaagcact ccatgcgaaa acagccattg ccttttttaa agatttaccc | 1800 |
| taggacctga tttaaagtga atttcaaatg acctgattaa tttcctattc ttccaaatga | 1860 |
| gatgaaaatg gggatcctgt acaacccttt gtggaccctt ttggtttagc tcttaagtag | 1920 |
| gggtattttc tactgttgct taattatgat ggaagataac attgtcattc ctagatgaat | 1980 |
| cctttgaagt aacaaacatt gtatctgaca tcagctctgt tcatgagtgc tcagagtccc | 2040 |
| tgctaatgta attggaagct tggtacacat aagaaaaact agagatttga aatctagcta | 2100 |
| tgaattactc tatatagtat ctatagccat gtacatatta cagcatgaca agctcgaaat | 2160 |
| aattatgagt cagcccgaaa gatgttaat | 2189 |

<210> SEQ ID NO 58
<211> LENGTH: 2352
<212> TYPE: DNA
<213> ORGANISM: Homo sapiens

<400> SEQUENCE: 58

| | |
|---|---|
| gaagatgctg ttgagggccc tggagaaact tcagcagaac agggcctctc cccttgcagg | 60 |
| ccgagccgcg gccctgcgcc ctcccccctcc gcccagctcg gccaagggcg catttgctga | 120 |
| gcgtctggcg gcctctaccg gagcacctct gcagagggcc gatcctccag cccagagacg | 180 |
| acatgtggcg ctcgggcgag tgccttgcag agagaggagt agcttgctgg ctttgaacgc | 240 |
| gtggcgtggc agatatttca gaaagcttca agaacaagct ggagaaggga agagttattc | 300 |

| | |
|---|---|
| ctccatattc acctgcttca actactattc ttattgggaa tggacaatgg aatgttctct | 360 |
| ggttttatca tgatcaaaaa cctccttctc ttttgtattt ccatgaactt atccagtcac | 420 |
| tttggctttt cacagatgcc aaccagttca gtgaaagatg agaccaatga caacatcacg | 480 |
| atatttacca ggatcttgga tgggctcttg gatggctacg acaacagact tcggcccggg | 540 |
| ctgggagagc gcatcactca ggtgaggacc gacatctacg tcaccagctt cggcccggtg | 600 |
| tccgacacgg aaatggagta caccatagac gtgttttttcc gacaaagctg aaagatgaa | 660 |
| aggcttcggt ttaaggggcc catgcagcgc ctccctctca caacctcct tgccagcaag | 720 |
| atctggaccc cagacacgtt cttccacaac gggaagaagt ccatcgctca acatgacc | 780 |
| acgcccaaca gctgctgcg gctggaggac gacggcaccc tgctctacac catgcgcttg | 840 |
| accatctctg cagagtgccc catgcagctt gggacttcc cgatggatgc gcacgcttgc | 900 |
| cctctgaaat ttggcagcta tgcgtaccct aattctgaag tcgtttacgt ctggaccaac | 960 |
| ggctccacca gtcggtggt ggtggcgaa gatggctcca gactgaacca gtaccacctg | 1020 |
| atggggcaga cggtgggcac tgagaacatc agcaccagca caggcgaata cacaatcatg | 1080 |
| acagctcact ccacctgaa aaggaagatt ggctactttg tcatccagac ctaccttccc | 1140 |
| tgcataatga ccgtgatctt atcacaggtg tccttttggc tgaaccggga atcagtccca | 1200 |
| gccaggacag tttttgggt caccacggtg ctgaccatga cgaccctcag catcagcgcc | 1260 |
| aggaactctc tgcccaaagt ggcctacgcc accgccatgg actggttcat agctgtgtgc | 1320 |
| tatgccttcg tcttctcggc gctgatagag tttgccacgg tcaattactt taccaagaga | 1380 |
| ggctgggcct gggatggcaa aaaagccttg gaagcagcca agatcaagaa aaagcgtgaa | 1440 |
| gtcatactaa ataagtcaac aaacgctttt acaactggga gatgtctca cccccaaac | 1500 |
| attccgaagg aacagacccc agcagggacg tcgaatacaa cctcagtctc agtaaaaccc | 1560 |
| tctgaagaga agacttctga aagcaaaaag acttacaaca gtatcagcaa aattgacaaa | 1620 |
| atgtcccgaa tcgtattccc agtcttgttc ggcacttttca acttagttta ctgggcaacg | 1680 |
| tatttgaata gggagccggt gataaaagga gccgcctctc caaaataacc ggccacactc | 1740 |
| ccaaactcca agacagccat acttccagcg aaatggtacc aaggagaggt tttgctcaca | 1800 |
| gggactctcc atatgtgagc actatctttc aggaatttt tgcatgttta ataatatgta | 1860 |
| caaataatat tgccttgatg tttctatatg taacttcaga tgtttccaag atgtcccatt | 1920 |
| gataattcga gcaaacaact ttctggaaaa acaggatacg atgactgaca ctcagatgcc | 1980 |
| cagtatcata cgttgatagt ttacaaacaa gatacgtata ttttttaactg cttcaagtgt | 2040 |
| tacctaacaa tgttttttat acttcaaatg tcatttcata caaatttttcc cagtgaataa | 2100 |
| atattttagg aaactctcca tgattattag aagaccaact atattgcgag aaacagagat | 2160 |
| cataaagagc acgttttcca ttatgaggaa acttggacat ttatgtacaa aatgaattgc | 2220 |
| ctttgataat tcttactgtt ctgaaattag gaaagtactt gcatgatctt acacgaagaa | 2280 |
| atagaatagg caaacttta tgtaggcaga ttaataacag aaatacatca tatgttagat | 2340 |
| acacaaaata tt | 2352 |

<210> SEQ ID NO 59
<211> LENGTH: 2352
<212> TYPE: DNA
<213> ORGANISM: Homo sapiens

<400> SEQUENCE: 59
gaagatgctg ttgagggccc tggagaaact tcagcagaac agggcctctc cccttgcagg          60

```
ccgagccggg gccctgcgcc ctcccctcc gcccagctcg gccaagggcg cgtttgctga      120
gcgtctggcg gcctctaccg gagcacctct gcagagggcc gatcctccag cccagagacg      180
acatgtggcg ctcgggcgag tgccttgcag agagaggagt agcttgctgg ctttgaacgc      240
gtggcgtggc agatatttca gaaagcttca agaacaagct ggagaaggga agagttattc      300
ctccatattc acctgcttca actactattc ttattgggaa tggacaatgg aatgttctct      360
ggttttatca tgatcaaaaa cctccttctc ttttgtattt ccatgaactt atccagtcac      420
tttggctttt cacagatgcc aaccagttca gtgaaagatg agaccaatga caacatcacg      480
atatttacca ggatcttgga tgggctcttg gatggctacg acaacagact tcggcccggg      540
ctgggagagc gcatcactca ggtgaggacc gacatctacg tcaccagctt cggcccggtg      600
tccgacacgg aaatggagta caccatagac gtgttttcc gacaaagctg aaagatgaa       660 aggcttcggt ttaaggggcc catgcagcgc ctccctctca caacctcct tgccagcaag      720 atctggaccc cagacacgtt cttccacaac gggaagaagt ccatcgctca caacatgacc      780
acgcccaaca agctgctgcg gctggaggac gacggcaccc tgctctacac catgcgcttg      840
accatctctg cagagtgccc catgcagctt gaggacttcc cgatggatgc gcacgcttgc      900
cctctgaaat ttggcagcta tgcgtaccct aattctgaag tcgtttacgt ctggaccaac      960
ggctccacca agtcggtggt ggtggcgaa gatggctcca gactgaacca gtaccacctg     1020
atggggcaga cggtgggcac tgagaacatc agcaccagca caggcgaata cacaatcatg     1080
acagctcact tccacctgaa aaggaagatt ggctactttg tcatccagac ctaccttccc     1140
tgcataatga ccgtgatctt atcacaggtg tccttttggc tgaaccggga atcagtccca     1200
gccaggacag ttttttgggt caccacggtg ctgaccatga cgaccctcag catcagcgcc     1260
aggaactctc tgcccaaagt ggcctacgcc accgccatgg actggttcat agctgtgtgc     1320
tatgccttcg tcttctcggc gctgatagag tttgccacgg tcaattactt taccaagaga     1380
ggctgggcct gggatggcaa aaaagccttg gaagcagcca gatcaagaa aaagcgtgaa      1440 gtcatactaa ataagtcaac aaacgctttt acaactggga gatgtctca cccccaaac      1500 attccgaagg aacagacccc agcagggacg tcgaatacaa cctcagtctc agtaaaaccc     1560
tctgaagaga agacttctga aagcaaaaag acttacaaca gtatcagcaa aattgacaaa     1620
atgtcccgaa tcgtattccc agtcttgttc ggcactttca acttagttta ctgggcaacg     1680
tatttgaata gggagccggt gataaaagga gccgcctctc caaaataacc ggccacactc     1740
ccaaactcca agacagccat acttccgcg aaatggtacc aaggagaggt tttgctcaca      1800
gggactctcc atatgtgagc actatctttc aggaaatttt tgcatgttta ataatatgta     1860
caaataatat tgccttgatg tttctatatg taacttcaga tgtttccaag atgtcccatt     1920
gataattcga gcaaacaact ttctggaaaa acaggatacg atgactgaca ctcagatgcc     1980
cagtatcata cgttgatagt ttacaaacaa gatacgtata tttttaactg cttcaagtgt     2040
tacctaacaa tgtttttat acttcaaatg tcatttcata caattttcc cagtgaataa       2100 atattttagg aaactctcca tgattattag aagaccaact atattgcgag aaacagagat     2160
cataaagagc acgtttcca ttatgaggaa acttggacat ttatgtacaa aatgaattgc      2220
ctttgataat tcttactgtt ctgaaattag gaaagtactt gcatgatctt acacgaagaa     2280
atagaatagg caaactttta tgtaggcaga ttaataacag aaatacatca tatgttagat     2340
acacaaaata tt                                                        2352
```

<210> SEQ ID NO 60

<211> LENGTH: 2373
<212> TYPE: DNA
<213> ORGANISM: Homo sapiens

<400> SEQUENCE: 60

```
gcgcgcggcc cggggcgcgg cgcggagcgg agctgcaggg cggcggcggg agcgcggggc      60
gcaagagccg ctccgccggg agtgccgggg aagttcgcgc tggcagcatg gggcggtgac     120
gccgcaccgg ccttccgcgc ctgccagccg ggcgagagca ggcggaggag aaggaggatg     180
catcctcacc gacggctcgc ctcccggggc ccgcgcgcag gtgccttgca gagagaggag     240
tagcttgctg gctttgaacg cgtggcgtgg cagatatttc agaaagcttc aagaacaagc     300
tggagaaggg aagagttatt cctccatatt cacctgcttc aactactatt cttattggga     360
atggacaatg gaatgttctc tggttttatc atgatcaaaa acctccttct cttttgtatt     420
tccatgaact tatccagtca ctttggcttt tcacagatgc caaccagttc agtgaaagat     480
gagaccaatg acaacatcac gatatttacc aggatcttgg atgggctctt ggatggctac     540
gacaacagac ttcggcccgg gctgggagag cgcatcactc aggtgaggac cgacatctac     600
gtcaccagct tcggcccggt gtccgacacg gaaatggagt acaccataga cgtgttttc      660
cgacaaagct ggaaagatga aaggcttcgg tttaaggggc ccatgcagcg cctccctctc     720
aacaacctcc ttgccagcaa gatctggacc ccagacacgt tcttccacaa cgggaagaag     780
tccatcgctc acaacatgac cacgcccaac aagctgctgc ggctggagga cgacggcacc     840
ctgctctaca ccatgcgctt gaccatctct gcagagtgcc ccatgcagct tgaggacttc     900
ccgatggatg cgcacgcttg ccctctgaaa tttggcagct atgcgtaccc taattctgaa     960
gtcgtttacg tctggaccaa cggctccacc aagtcggtgg tggtggcgga agatggctcc    1020
agactgaacc agtaccacct gatggggcag acggtgggca ctgagaacat cagcaccagc    1080
acaggcgaat acacaatcat gacagctcac ttccacctga aaggaagat tggctacttt    1140
gtcatccaga cctaccttcc ctgcataatg accgtgatct tatcacaggt gtccttttgg    1200
ctgaaccggg aatcagtccc agccaggaca gttttggggg tcaccacggt gctgaccatg    1260
acgaccctca gcatcagcgc caggaactct ctgcccaaag tggcctacgc caccgccatg    1320
gactggttca tagctgtgtg ctatgccttc gtcttctcgg cgctgataga gtttgccacg    1380
gtcaattact ttaccaagag aggctgggcc tgggatggca aaaaagcctt ggaagcagcc    1440
aagatcaaga aaaagcgtga agtcatacta ataagtcaa caaacgcttt tacaactggg    1500
aagatgtctc accccccaaa cattccgaag gaacagaccc cagcagggac gtcgaataca    1560
acctcagtct cagtaaaacc ctctgaagag aagacttctg aaagcaaaaa gacttacaac    1620
agtatcagca aaattgacaa aatgtcccga atcgtattcc cagtcttgtt cggcactttc    1680
aacttagttt actgggcaac gtatttgaat agggagccgg tgataaaagg agccgcctct    1740
ccaaaataac cggccacact cccaaactcc aagcagcca tacttccagc gaaatggtac    1800
caaggagagg ttttgctcac agggactctc catatgtgag cactatcttt caggaaattt    1860
ttgcatgttt aataatatgt acaaataata ttgccttgat gtttctatat gtaacttcag    1920
atgtttccaa gatgtcccat tgataattcg agcaaacaac tttctggaaa aacaggatac    1980
gatgactgac actcagatgc ccagtatcat acgttgatag tttacaaaca agatacgtat    2040
atttttaact gcttcaagtg ttacctaaca atgttttta tacttcaaat gtcatttcat    2100
acaaattttc ccagtgaata aatatttag gaaactctcc atgattatta gaagaccaac    2160
tatattgcga gaaacagaga tcataaagag cacgttttcc attatgagga aacttggaca    2220
```

```
tttatgtaca aaatgaattg cctttgataa ttcttactgt tctgaaatta ggaaagtact    2280
tgcatgatct tacacgaaga aatagaatag gcaaacttttt atgtaggcag attaataaca   2340
gaaatacatc atatgttaga tacacaaaat att                                2373
```

<210> SEQ ID NO 61
<211> LENGTH: 1974
<212> TYPE: DNA
<213> ORGANISM: Homo sapiens

<400> SEQUENCE: 61

```
cgcgcggga agggaagaag aggacgaggt ggcgcagaga ccgcgggaga acacagtgct     60
tccggaggaa atctgctcgg tccccggcag ccgcgcttcc cctttgatgt tttggtacgc   120
cgtggccatg cgcctcacat tagaattact gcactgggca gactaagttg gatctcctct   180
cttcagtgaa accctcaatt ccatcaaaaa ctaaagggat gtggagagtc cggaaaaggg   240
gctactttgg gatttggtcc ttccccttaa taatcgccgc tgtctgtgcg cagagtgtca   300
atgaccctag taatatgtcg ctggttaaag agacggtgga tagactcctg aaaggctatg   360
acattcgtct gagaccagat tttggaggtc ccccgtggc tgtggggatg aacattgaca    420
ttgccagcat cgatatggtt tctgaagtca atatggatta taccttgaca atgtactttc   480
aacaagcctg gagagataag aggctgtcct ataatgtaat acctttaaac ttgactctgg   540
acaacagagt ggcagaccag ctctgggtgc ctgatatccta tttcctgaac gataagaagt  600
catttgtgca cggagtgact gttaagaacc gcatgattcg cctgcatcct gatggcaccg   660
tcctttatgg actcagaatc acaaccacag ctgcctgcat gatggaccta aggaggtacc   720
cactggatga acaaaactgc accttggaaa ttgagagcta tggatacaca actgatgaca   780
ttgagtttta ctggcgtggc gatgataatg cagtaacagg agtaacgaaa attgaacttc   840
cacagttctc tattgtagat tacaaactta tcaccaagaa ggttgttttt tccacaggtt   900
cctatcccag gttatccctc agctttaagc ttaagagaaa cattggctac tttatcctgc   960
aaacatacat gccttccatc ctgattacca tcctctcctg ggtctccttc tggattaatt  1020
acgatgcttc agctgcaagg gtggcattag gaatcacaac tgtcctcaca atgaccacaa  1080
tcaacaccca cctccgggaa actctcccta aaatccccta tgtgaaggcc attgacatgt  1140
acctgatggg gtgctttgtc ttcgttttca tggcccttct ggaatatgcc ctagtcaact  1200
acatcttctt tgggagggg ccccaacgcc aaaagaaagc agctgagaag gctgccagtg   1260
ccaacaatga gaagatgcgc ctggatgtca acagatttttt ttataaagat attaaacaaa  1320
atgggaccca atatcgatcc ttgtgggacc ctactggaaa cctctcccca actagacgga  1380
ctaccaatta cgatttctct ctgtatacga tggacccccca tgagaacatc ttactgagca  1440
ctctcgagat aaaaaatgaa atggccacat ctgaggctgt gatgggactt ggagacccca  1500
gaagcacaat gctagcctat gatgcctcca gcatccagta tcgaaagct gggttgccca   1560 ggcatagttt tggccgaaat gctctggaac gacatgtggc gcaaaagaaa agtcgcctga   1620
ggagacgcgc ctcccaactg aaaatcacca tccctgactt gactgatgtg aatgccatag  1680
atcggtggtc ccgcatattc ttcccagtgg ttttttttcctt cttcaacatc gtctattggc  1740
tttactatgt gaactaaaca tggcctccca ctggaagcaa ggactagatt cctcctcaaa  1800
ccagttgtac agcctgatgt aggacttgga aaacacatca atccaggaca aaagtgacgc  1860
taaaatacct tagttgctgg cctatcctgt ggtccattttc ataccatttg ggttgcttct  1920
gctaagtaat gaatacacta aggtccttgt ggttttttccag ttaaaacgca agta        1974
```

<210> SEQ ID NO 62
<211> LENGTH: 1974
<212> TYPE: DNA
<213> ORGANISM: Homo sapiens

<400> SEQUENCE: 62

```
cgcgcgggga agggaagaag aggacgaggt ggcgcagaga ccgcgggaga acacagtgcc      60
tccggaggaa atctgctcgg tccccggcag ccgcgcttcc cctttgatgt tttggtacgc     120
cgtggccatg cgcctcacat tagaattact gcactgggca gactaagttg gatctcctct     180
cttcagtgaa accctcaatt ccatcaaaaa ctaaagggat gtggagagtc cggaaagggg     240
gctactttgg gatttggtcc ttcccccttaa taatcgccgc tgtctgtgcg cagagtgtca     300
atgaccctag taatatgtcg ctggttaaag agacggtgga tagactcctg aaaggctatg     360
acattcgtct gagaccagat tttggaggtc ccccgtggc tgtggggatg aacattgaca      420
ttgccagcat cgatatggtt tctgaagtca atatggatta taccttgaca atgtactttc     480
aacaagcctg gagagataag aggctgtcct ataatgtaat acctttaaac ttgactctgg     540
acaacagagt ggcagaccag ctctgggtgc ctgataccta tttcctgaac gataagaagt     600
catttgtgca cggagtgact gttaagaacc gcatgattcg cctgcatcct gatggcaccg     660
tcctttatgg actcagaatc acaaccacag ctgcctgcat gatggaccta aggaggtacc     720
cactggatga acaaaactgc accttggaaa ttgagagcta tggatacaca actgatgaca     780
ttgagttta ctggcgtggc gatgataatg cagtaacagg agtaacgaaa attgaacttc      840
cacagttctc tattgtagat tacaaactta tcaccaagaa ggttgttttt tccacaggtt     900
cctatcccag gttatccctc agctttaagc ttaagagaaa cattggctac tttatcctgc     960
aaacatacat gccttccatc ctgattacca tcctctcctg ggtctccttc tggattaatt    1020
acgatgcttc agctgcaagg gtggcattag gaatcacaac tgtcctcaca atgaccacaa    1080
tcaacaccca cctccgggaa actctcccta aaatcccccta tgtgaaggcc attgacatgt    1140
acctgatggg gtgctttgtc ttcgttttca tggcccttct ggaatatgcc ctagtcaact    1200
acatcttctt tgggagggggg cccccaacgcc aaaagaaagc agctgagaag gctgccagtg    1260
ccaacaatga aagatgcgc ctggatgtca acaagatttt ttataaagat attaaacaaa     1320
atgggaccca atatcgatcc ttgtgggacc ctactggaaa cctctccccca actagacgga    1380
ctaccaatta cgatttctct ctgtatacga tggaccccca tgagaacatc ttactgagca    1440
ctctcgagat aaaaaatgaa atggccacat ctgaggctgt gatgggactt ggagaccca     1500
gaagcacaat gctagcctat gatgcctcca gcatccagta tcggaaagct gggttgccca    1560
ggcatagttt tggccgaaat gctctggaac gacatgtggc gcaaaagaaa agtcgcctga    1620
ggagacgcgc ctcccaactg aaaatcacca tccctgactt gactgatgtg aatgccatag    1680
atcggtggtc ccgcatattc ttcccagtgg ttttttcctt cttcaacatc gtctattggc    1740
tttactatgt gaactaaaca tggcctccca ctggaagcaa ggactagatt cctcctcaaa    1800
ccagttgtac agcctgatgt aggacttgga aaacacatca atccaggaca aaagtgacgc    1860
taaaatacct tagttgctgg cctatcctgt ggtccatttc ataccatttg ggttgcttct    1920
gctaagtaat gaatacacta aggtccttgt ggttttccag ttaaaatgca agta           1974
```

<210> SEQ ID NO 63
<211> LENGTH: 3282
<212> TYPE: DNA
<213> ORGANISM: Homo sapiens

```
<400> SEQUENCE: 63
gggacagggc tgaggatgag gagaaccctg gggacccaga agaccgtgcc ttgcctggaa      60
gtcctgcctg taggcctgaa ggacttgccc taacagagcc tcaacaacta cctggtgatt     120
cctacttcag cccttggtg tgagcagctt ctcaacatga actacagcct ccacttggcc      180
ttcgtgtgtc tgagtctctt cactgagagg atgtgcatcc aggggagtca gttcaacgtc     240
gaggtcggca gaagtgacaa gctttccctg cctggctttg agaacctcac agcaggatat     300
aacaaatttc tcaggcccaa ttttggtgga gaacccgtac agatagcgct gactctggac     360
attgcaagta tctctagcat ttcagagagt aacatggact acacagccac catatacctc     420
cgacagcgct ggatggacca gcggctggtg tttgaaggca acaagagctt cactctggat     480
gcccgcctcg tggagttcct ctgggtgcca gatacttaca ttgtggagtc caagaagtcc     540
ttcctccatg aagtcactgt gggaaacagg ctcatccgcc tcttctccaa tggcacggtc     600
ctgtatgccc tcagaatcac gacaactgtt gcatgtaaca tggatctgtc taaatacccc     660
atggacacac agacatgcaa gttgcagctg gaaagctggg gctatgatgg aaatgatgtg     720
gagttcacct ggctgagagg gaacgactct gtgcgtggac tggaacacct gcggcttgct     780
cagtacacca tagagcggta tttcacctta gtcaccagat cgcagcagga gacaggaaat     840
tacactagat tggtcttaca gtttgagctt cggaggaatg ttctgtattt cattttggaa     900
acctacgttc cttccacttt cctggtggtg ttgtcctggg tttcattttg gatctctctc     960
gattcagtcc ctgcaagaac ctgcattgga gtgacgaccg tgttatcaat gaccacactg    1020
atgatcgggt cccgcacttc tcttcccaac accaactgct tcatcaaggc catcgatgtg    1080
tacctgggga tctgctttag cttgtgtttt gggccttgc tagaatatgc agttgctcac    1140
tacagttcct tacagcagat ggcagccaaa gataggggga caacaaagga agtagaagaa    1200
gtcagtatta ctaatatcat caacagctcc atctccagct ttaaacgaaa gatcagcttt    1260
gccagcattg aaatttccag cgacaacgtt gactacagtg acttgacaat gaaaaccagc    1320
gacaagttca gtttgtcttc cgagaaaag atgggcagga ttgttgatta tttcacaatt    1380 caaaaccca gtaatgttga tcactattcc aaactactgt ttcctttgat ttttatgcta    1440
gccaatgtat tttactgggc atactacatg tattttgag tcaatgttaa atttcttgca    1500
tgccataggt cttcaacagg acaagataat gatgtaaatg gtattttagg ccaagtgtgc    1560
acccacatcc aatggtgcta caagtgactg aaataatatt tgagtctttc tgctcaaaga    1620
atgaagctcc aaccattgtt ctaagctgtg tagaagtcct agcattatag gatcttgtaa    1680
tagaaacatc agtccattcc tctttcatct taatcaagga cattcccatg gagcccaaga    1740
ttacaaatgt actcagggct gtttattcgg tggctccctg gtttgcattt acctcatata    1800
aagaatggga aggagaccat tgggtaaccc tcaagtgtca gaagttgttt ctaaagtaac    1860
tatacatgtt ttttactaaa tctctgcagt gcttataaaa tacattgttg cctatttagg    1920
gagtaacatt ttctagtttt tgtttctggt taaaatgaaa tatgggctta tgtcaattca    1980
ttggaagtca atgcactaac tcaataccaa gatgagtttt taaataatga atattattta    2040
ataccacaac agaattatcc ccaatttcca ataagtccta tcattgaaaa ttcaaatata    2100
agtgaagaaa aaattagtag atcaacaatc taaacaaatc cctcggttct aagatacaat    2160
ggattcccca tactggaagg actctgaggc tttattcccc cactatgcat atcttatcat    2220
tttattatta tacacacatc catcctaaac tatactaaag ccctttttccc atgcatggat    2280 ggaaatggaa gatttttttg taacttgttc tagaagtctt aatatgggct gttgccatga    2340
```

-continued

| | |
|---|---|
| aggcttgcag aattgagtcc attttctagc tgcctttatt cacatagtga tggggtacta | 2400 |
| aaagtactgg gttgactcag agagtcgctg tcattctgtc attgctgcta ctctaacact | 2460 |
| gagcaacact ctcccagtgg cagatcccct gtatcattcc aagaggagca ttcatccctt | 2520 |
| tgctctaatg atcaggaatg atgcttatta gaaaacaaac tgcttgaccc aggaacaagt | 2580 |
| ggcttagctt aagtaaactt ggctttgctc agatccctga tccttccagc tggtctgctc | 2640 |
| tgagtggctt atcccgcatg agcaggagcg tgctggccct gagtactgaa ctttctgagt | 2700 |
| aacaatgaga cacgttacag aacctatgtt caggttgcgg gtgagctgcc ctctccaaat | 2760 |
| ccagccagag atgcacattc ctcggccagt ctcagccaac agtaccaaaa gtgattttg | 2820 |
| agtgtgccag ggtaaaggct tccagttcag cctcagttat tttagacaat ctcgccatct | 2880 |
| ttaatttctt agcttcctgt tctaataaat gcacggcttt accttcctg tcagaaataa | 2940 |
| accaaggctc taaagatga tttcccttct gtaactccct agagccacag gttctcattc | 3000 |
| cttttcccat tatacttctc acaattcagt ttctatgagt ttgatcacct gattttttta | 3060 |
| acaaaatatt tctaacggga atgggtggga gtgctggtga aaagagatga aatgtggttg | 3120 |
| tatgagccaa tcatatttgt gatttttaa aaaagttta aaggaaata tctgttctga | 3180 |
| aaccccactt aagcattgtt tttatataaa aacaatgata aagatgtgaa ctgtgaaata | 3240 |
| aatataccat attagctacc caccaaaaaa aaaaaaaaaa aa | 3282 |

<210> SEQ ID NO 64
<211> LENGTH: 270
<212> TYPE: DNA
<213> ORGANISM: Homo sapiens

<400> SEQUENCE: 64

| | |
|---|---|
| ggtccattcg ggaattactg cccagcagcc gactaagttg cattccttga atcttcgcag | 60 |
| aaaagacaat tcttttaatc agagttagta atgtggacag tacaaaatcg agagagtctg | 120 |
| gggcttctct ctttccctgt gatgattacc atggtctgtt gtgcacacag gtgagctgct | 180 |
| gttgttgaat ctcgctctct ctctctcttt ttttcttggt atgtttcttt ttacgtgtct | 240 |
| gctggatcat gtatcttgtt gtttgggggt | 270 |

<210> SEQ ID NO 65
<211> LENGTH: 238
<212> TYPE: DNA
<213> ORGANISM: Homo sapiens

<400> SEQUENCE: 65

| | |
|---|---|
| atggctatac cactgatgac attgaatttt actggaatgg aggagaaggg gcagtcactg | 60 |
| gtgttaataa aatcgaactt cctcaatttt caattgttga ctacaagatg gtgtctaaga | 120 |
| aggtggagtt cacaacaggt gaggttgttt cccccaaaat gtactagggg tgctgtgaaa | 180 |
| ggaagaagat ggttccaacc aaataatggg ctgattactt gtcttttgtt tctcaact | 238 |

<210> SEQ ID NO 66
<211> LENGTH: 345
<212> TYPE: DNA
<213> ORGANISM: Homo sapiens

<400> SEQUENCE: 66

| | |
|---|---|
| gcaccaataa ggaagtggca aatggcatct gtcctctcaa tcttgaaaaa ggaacttaat | 60 |
| agtggcgcct tcagctaagt gttgtctttc tctttcacag gaatcacgac agtgcttaca | 120 |
| atgacaacca tcagcaccca cctcagggag accctgccaa agatccctta tgtcaaagcg | 180 |

```
attgatattt atctgatggg ttgctttgtg tttgtgttcc tggctctgct ggagtatgcc      240
tttgtaaatt acatcttctt tgggaaaggc cctcagaaaa agggagctag caaacaagac      300
cagagtgcca atgagaagaa taaactggag atgaataaag tccag                      345
```

```
<210> SEQ ID NO 67
<211> LENGTH: 190
<212> TYPE: DNA
<213> ORGANISM: Homo sapiens

<400> SEQUENCE: 67
gggtgggccg gcgggcggcg ggcagggcgc ggggtgcgcg ggcgctggc ggctgagccg        60 cccctgaccc cgctctttgt gctccctgtc cctcccccag tgtgaacgat cccgggaaca     120
tgtcctttgt gaaggagacg gtggacaagc tgttgaaagg ctacgacatt cgcctaagac     180
ccgacttcgg                                                            190
```

```
<210> SEQ ID NO 68
<211> LENGTH: 253
<212> TYPE: DNA
<213> ORGANISM: Homo sapiens

<400> SEQUENCE: 68
gtgcctatcc tcgactgtca ctgagctttc ggttgaagag gaacattgga tacttcattc       60
ttcagactta tatgccctct atactgataa cgattctgtc gtgggtgtcc ttctggatca     120
attatgatgc atctgctgct agagttgccc tcggtatgtg ctattttaa gtgatattta     180 aatgtaaagt aaccgtatca ttacagtatt gagagttcaa aggctgtagt tcaactacca     240 tttttttgaca gcg                                                       253
```

```
<210> SEQ ID NO 69
<211> LENGTH: 288
<212> TYPE: DNA
<213> ORGANISM: Homo sapiens

<400> SEQUENCE: 69
acggttactc atcggaggac atcgtctact actggtcgga gagccaggag cacatccacg       60
ggctggacaa gctgcagctg gcgcagttca ccatcaccag ctaccgcttc accacggagc     120
tgatgaactt caagtccggt aacatatgcc cgccgcccct tccgcatgtg cccgccgccc     180
cttccgcgcg cgcccaccgc cccttccgcg gcgcccacc gccccttccg cgtgcgcccg      240
cctgtggttt tcatgctttt tagtcaagcc gcccgcaggc ccccaggg                  288
```

```
<210> SEQ ID NO 70
<211> LENGTH: 288
<212> TYPE: DNA
<213> ORGANISM: Homo sapiens

<400> SEQUENCE: 70
acggttactc atcggaggac atcgtctact actggtcgga gagccaggag cacatccacg       60
ggctggacaa gctgcagctg gcgcagttca ccatcaccag ctaccgcttc accacggagc     120
tgatgaactt caagtccggt aacatatgcc cgccgcccct tccgcatgtg cccgccgccc     180
cttccgcgcg cgcccaccgc cccttccgcg gcgcccacc gccccttccg cgtgcgcccg      240
cctgtggttt tcatgctttt tagtcaacgc gcccgcaggc ccccaggg                  288
```

```
<210> SEQ ID NO 71
<211> LENGTH: 288
<212> TYPE: DNA
```

<213> ORGANISM: Homo sapiens

<400> SEQUENCE: 71

```
acggttactc atcggaggac atcgtctact actggtcgga gagccaggag cacatccacg    60
ggctggacaa gctgcagctg gcgcagttca ccatccaccag ctaccgcttc accacggagc   120
tgatgaactt caagtccggt aacatatgcc cgccgcccct tccgcatgtg cccgccgccc   180
cttccgcgcg cgcccaccgc cccttccgcg tgcgcccgcc tgtggttttc atgcttttta   240
gtcaagcgcc cgcaggcccc cagggcctct ggggatgcag ctgggacg                288
```

<210> SEQ ID NO 72
<211> LENGTH: 170
<212> TYPE: DNA
<213> ORGANISM: Homo sapiens

<400> SEQUENCE: 72

```
accggtgatg tggcttggtt tagtcatacc ctaaagattg ctcttaagag tgatcttgga    60
tgcaaatgtt catgacagtt tcctagttat ttttcttct tttcttgtag ttactacatc    120
cagattcctc aagatggatt cctgagcgaa taagcctaca agccccttcc               170
```

<210> SEQ ID NO 73
<211> LENGTH: 221
<212> TYPE: PRT
<213> ORGANISM: Homo sapiens

<400> SEQUENCE: 73

```
Met Glu Gln Thr Val Leu Val Pro Pro Gly Pro Asp Ser Phe Asn Phe
 1               5                  10                  15
Phe Thr Arg Glu Ser Leu Ala Ala Ile Glu Arg Arg Ile Ala Glu Glu
                20                  25                  30
Lys Ala Lys Asn Pro Lys Pro Asp Lys Lys Asp Asp Asp Glu Asn Gly
            35                  40                  45
Pro Lys Pro Asn Ser Asp Leu Glu Ala Gly Lys Asn Leu Pro Phe Ile
        50                  55                  60
Tyr Gly Asp Ile Pro Pro Glu Met Val Ser Glu Pro Leu Glu Asp Leu
 65                  70                  75                  80
Asp Pro Tyr Tyr Ile Asn Lys Lys Thr Phe Ile Val Leu Asn Lys Leu
                85                  90                  95
Lys Ala Ile Phe Arg Phe Ser Ala Thr Ser Ala Leu Tyr Ile Leu Thr
           100                 105                 110
Pro Phe Asn Pro Leu Arg Lys Ile Ala Ile Lys Ile Leu Val His Ser
       115                 120                 125
Leu Phe Ser Met Leu Ile Met Cys Thr Ile Leu Thr Asn Cys Val Phe
   130                 135                 140
Met Thr Met Ser Asn Pro Pro Asp Trp Thr Lys Asn Val Glu Tyr Thr
145                 150                 155                 160
Phe Thr Gly Ile Tyr Thr Phe Glu Ser Leu Ile Lys Ile Ile Ala Arg
                165                 170                 175
Gly Phe Cys Leu Glu Asp Phe Thr Phe Leu Arg Asp Pro Trp Asn Trp
            180                 185                 190
Leu Asp Phe Thr Val Ile Thr Phe Ala Tyr Val Thr Glu Phe Val Asp
        195                 200                 205
Leu Gly Asn Val Ser Ala Leu Arg Thr Phe Arg Val Leu
    210                 215                 220
```

<210> SEQ ID NO 74

<211> LENGTH: 383
<212> TYPE: PRT
<213> ORGANISM: Homo sapiens

<400> SEQUENCE: 74

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe
370                 375                 380

<210> SEQ ID NO 75

```
<211> LENGTH: 2009
<212> TYPE: PRT
<213> ORGANISM: Homo sapiens

<400> SEQUENCE: 75

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Pro Gly Lys Thr Tyr Met
385                 390                 395                 400
```

```
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Gln Asn Gln Ala
            420                 425                 430
Thr Leu Glu Glu Ala Glu Gln Lys Glu Ala Glu Phe Gln Gln Met Ile
                435                 440                 445
Glu Gln Leu Lys Lys Gln Gln Glu Ala Ala Gln Ala Ala Thr Ala
        450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
                500                 505                 510
Glu Glu Lys Asp Glu Asp Glu Phe Gln Lys Ser Glu Ser Glu Asp Ser
                515                 520                 525
Ile Arg Arg Lys Gly Phe Arg Phe Ser Ile Glu Gly Asn Arg Leu Thr
        530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
                595                 600                 605
Phe Val Pro Arg Arg His Gly Glu Arg Arg Asn Ser Asn Leu Ser Gln
        610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
                660                 665                 670
Ile Asp Lys Pro Ala Thr Asp Asp Asn Gly Thr Thr Thr Glu Thr Glu
        675                 680                 685
Met Arg Lys Arg Arg Ser Ser Ser Phe His Val Ser Met Asp Phe Leu
        690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                725                 730                 735
Cys Trp Tyr Lys Phe Ser Asn Ile Phe Leu Ile Trp Asp Cys Ser Pro
                740                 745                 750
Tyr Trp Leu Lys Val Lys His Val Val Asn Leu Val Val Met Asp Pro
        755                 760                 765
Phe Val Asp Leu Ala Ile Thr Ile Cys Ile Val Leu Asn Thr Leu Phe
        770                 775                 780
Met Ala Met Glu His Tyr Pro Met Thr Asp His Phe Asn Asn Val Leu
785                 790                 795                 800
Thr Val Gly Asn Leu Val Phe Thr Gly Ile Phe Thr Ala Glu Met Phe
                805                 810                 815
Leu Lys Ile Ile Ala Met Asp Pro Tyr Tyr Tyr Phe Gln Glu Gly Trp
```

-continued

```
              820                 825                 830
Asn Ile Phe Asp Gly Phe Ile Val Thr Leu Ser Leu Val Glu Leu Gly
            835                 840                 845
Leu Ala Asn Val Glu Gly Leu Ser Val Leu Arg Ser Phe Arg Leu Leu
            850                 855                 860
Arg Val Phe Lys Leu Ala Lys Ser Trp Pro Thr Leu Asn Met Leu Ile
865                 870                 875                 880
Lys Ile Ile Gly Asn Ser Val Gly Ala Leu Gly Asn Leu Thr Leu Val
                885                 890                 895
Leu Ala Ile Ile Val Phe Ile Phe Ala Val Val Gly Met Gln Leu Phe
            900                 905                 910
Gly Lys Ser Tyr Lys Asp Cys Val Cys Lys Ile Ala Ser Asp Cys Gln
            915                 920                 925
Leu Pro Arg Trp His Met Asn Asp Phe Phe His Ser Phe Leu Ile Val
            930                 935                 940
Phe Arg Val Leu Cys Gly Glu Trp Ile Glu Thr Met Trp Asp Cys Met
945                 950                 955                 960
Glu Val Ala Gly Gln Ala Met Cys Leu Thr Val Phe Met Met Val Met
                965                 970                 975
Val Ile Gly Asn Leu Val Val Leu Asn Leu Phe Leu Ala Leu Leu Leu
                980                 985                 990
Ser Ser Phe Ser Ala Asp Asn Leu Ala Ala Thr Asp Asp Asp Asn Glu
            995                1000                1005
Met Asn Asn Leu Gln Ile Ala Val Asp Arg Met His Lys Gly Val
            1010                1015                1020
Ala Tyr Val Lys Arg Lys Ile Tyr Glu Phe Ile Gln Gln Ser Phe
            1025                1030                1035
Ile Arg Lys Gln Lys Ile Leu Asp Glu Ile Lys Pro Leu Asp Asp
            1040                1045                1050
Leu Asn Asn Lys Lys Asp Ser Cys Met Ser Asn His Thr Thr Glu
            1055                1060                1065
Ile Gly Lys Asp Leu Asp Tyr Leu Lys Asp Val Asn Gly Thr Thr
            1070                1075                1080
Ser Gly Ile Gly Thr Gly Ser Ser Val Glu Lys Tyr Ile Ile Asp
            1085                1090                1095
Glu Ser Asp Tyr Met Ser Phe Ile Asn Asn Pro Ser Leu Thr Val
            1100                1105                1110
Thr Val Pro Ile Ala Val Gly Glu Ser Asp Phe Glu Asn Leu Asn
            1115                1120                1125
Thr Glu Asp Phe Ser Ser Glu Ser Asp Leu Glu Glu Ser Lys Glu
            1130                1135                1140
Lys Leu Asn Glu Ser Ser Ser Ser Ser Glu Gly Ser Thr Val Asp
            1145                1150                1155
Ile Gly Ala Pro Val Glu Glu Gln Pro Val Val Glu Pro Glu Glu
            1160                1165                1170
Thr Leu Glu Pro Glu Ala Cys Phe Thr Glu Gly Cys Val Gln Arg
            1175                1180                1185
Phe Lys Cys Cys Gln Ile Asn Val Glu Glu Gly Arg Gly Lys Gln
            1190                1195                1200
Trp Trp Asn Leu Arg Arg Thr Cys Phe Arg Ile Val Glu His Asn
            1205                1210                1215
Trp Phe Glu Thr Phe Ile Val Phe Met Ile Leu Leu Ser Ser Gly
            1220                1225                1230
```

```
Ala Leu Ala Phe Glu Asp Ile Tyr Ile Asp Gln Arg Lys Thr Ile
1235                1240                1245

Lys Thr Met Leu Glu Tyr Ala Asp Lys Val Phe Thr Tyr Ile Phe
1250                1255                1260

Ile Leu Glu Met Leu Leu Lys Trp Val Ala Tyr Gly Tyr Gln Thr
1265                1270                1275

Tyr Phe Thr Asn Ala Trp Cys Trp Leu Asp Phe Leu Ile Val Asp
1280                1285                1290

Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Lys Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635
```

```
Arg Leu Ala Arg Ile Gly Arg Ile Leu Arg Leu Ile Lys Gly Ala
    1640            1645                1650

Lys Gly Ile Arg Thr Leu Leu Phe Ala Leu Met Met Ser Leu Pro
    1655            1660                1665

Ala Leu Phe Asn Ile Gly Leu Leu Leu Phe Leu Val Met Phe Ile
    1670            1675                1680

Tyr Ala Ile Phe Gly Met Ser Asn Phe Ala Tyr Val Lys Arg Glu
    1685            1690                1695

Val Gly Ile Asp Asp Met Phe Asn Phe Glu Thr Phe Gly Asn Ser
    1700            1705                1710

Met Ile Cys Leu Phe Gln Ile Thr Thr Ser Ala Gly Trp Asp Gly
    1715            1720                1725

Leu Leu Ala Pro Ile Leu Asn Ser Lys Pro Pro Asp Cys Asp Pro
    1730            1735                1740

Asn Lys Val Asn Pro Gly Ser Ser Val Lys Gly Asp Cys Gly Asn
    1745            1750                1755

Pro Ser Val Gly Ile Phe Phe Phe Val Ser Tyr Ile Ile Ile Ser
    1760            1765                1770

Phe Leu Val Val Val Asn Met Tyr Ile Ala Val Ile Leu Glu Asn
    1775            1780                1785

Phe Ser Val Ala Thr Glu Glu Ser Ala Glu Pro Leu Ser Glu Asp
    1790            1795                1800

Asp Phe Glu Met Phe Tyr Glu Val Trp Glu Lys Phe Asp Pro Asp
    1805            1810                1815

Ala Thr Gln Phe Met Glu Phe Glu Lys Leu Ser Gln Phe Ala Ala
    1820            1825                1830

Ala Leu Glu Pro Pro Leu Asn Leu Pro Gln Pro Asn Lys Leu Gln
    1835            1840                1845

Leu Ile Ala Met Asp Leu Pro Met Val Ser Gly Asp Arg Ile His
    1850            1855                1860

Cys Leu Asp Ile Leu Phe Ala Phe Thr Lys Arg Val Leu Gly Glu
    1865            1870                1875

Ser Gly Glu Met Asp Ala Leu Arg Ile Gln Met Glu Glu Arg Phe
    1880            1885                1890

Met Ala Ser Asn Pro Ser Lys Val Ser Tyr Gln Pro Ile Thr Thr
    1895            1900                1905

Thr Leu Lys Arg Lys Gln Glu Glu Val Ser Ala Val Ile Ile Gln
    1910            1915                1920

Arg Ala Tyr Arg Arg His Leu Leu Lys Arg Thr Val Lys Gln Ala
    1925            1930                1935

Ser Phe Thr Tyr Asn Lys Asn Lys Ile Lys Gly Gly Ala Asn Leu
    1940            1945                1950

Leu Ile Lys Glu Asp Met Ile Ile Asp Arg Ile Asn Glu Asn Ser
    1955            1960                1965

Ile Thr Glu Lys Thr Asp Leu Thr Met Ser Thr Ala Ala Cys Pro
    1970            1975                1980

Pro Ser Tyr Asp Arg Val Thr Lys Pro Ile Val Glu Lys His Glu
    1985            1990                1995

Gln Glu Gly Lys Asp Glu Lys Ala Lys Gly Lys
    2000            2005

<210> SEQ ID NO 76
<211> LENGTH: 2009
<212> TYPE: PRT
```

<213> ORGANISM: Homo sapiens

<400> SEQUENCE: 76

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Leu Val Leu Val Ile Phe Leu Gly Ser Phe Tyr Leu Ile Asn
```

```
                    405                 410                 415
Leu Ile Leu Ala Val Val Ala Met Ala Tyr Glu Glu Gln Asn Gln Ala
                420                 425                 430
Thr Leu Glu Glu Ala Glu Gln Lys Glu Ala Glu Phe Gln Gln Met Ile
            435                 440                 445
Glu Gln Leu Lys Lys Gln Gln Glu Ala Ala Gln Ala Ala Thr Ala
        450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
                500                 505                 510
Glu Glu Lys Asp Glu Asp Glu Phe Gln Lys Ser Glu Ser Glu Asp Ser
            515                 520                 525
Ile Arg Arg Lys Gly Phe Arg Phe Ser Ile Glu Gly Asn Arg Leu Thr
        530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
            595                 600                 605
Phe Val Pro Arg Arg His Gly Glu Arg Arg Asn Ser Asn Leu Ser Gln
        610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
            660                 665                 670
Ile Asp Lys Pro Ala Thr Asp Asp Asn Gly Thr Thr Thr Glu Thr Glu
        675                 680                 685
Met Arg Lys Arg Arg Ser Ser Ser Phe His Val Ser Met Asp Phe Leu
            690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                725                 730                 735
Cys Trp Tyr Lys Phe Ser Asn Ile Phe Leu Ile Trp Asp Cys Ser Pro
                740                 745                 750
Tyr Trp Leu Lys Val Lys His Val Val Asn Leu Val Val Met Asp Pro
            755                 760                 765
Phe Val Asp Leu Ala Ile Thr Ile Cys Ile Val Leu Asn Thr Leu Phe
        770                 775                 780
Met Ala Met Glu His Tyr Pro Met Thr Asp His Phe Asn Asn Val Leu
785                 790                 795                 800
Thr Val Gly Asn Leu Val Phe Thr Gly Ile Phe Thr Ala Glu Met Phe
                805                 810                 815
Leu Lys Ile Ile Ala Met Asp Pro Tyr Tyr Tyr Phe Gln Glu Gly Trp
            820                 825                 830
```

-continued

```
Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
        995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Thr Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245
```

```
Lys Thr Met Leu Glu Tyr Ala Asp Lys Val Phe Thr Tyr Ile Phe
1250                1255                1260

Ile Leu Glu Met Leu Leu Lys Trp Val Ala Tyr Gly Tyr Gln Thr
1265                1270                1275

Tyr Phe Thr Asn Ala Trp Cys Trp Leu Asp Phe Leu Ile Val Asp
1280                1285                1290

Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Lys Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635

Arg Leu Ala Arg Ile Gly Arg Ile Leu Arg Leu Ile Lys Gly Ala
```

```
                    1640                1645                1650
Lys Gly Ile Arg Thr Leu Leu Phe Ala Leu Met Met Ser Leu Pro
    1655                1660                1665
Ala Leu Phe Asn Ile Gly Leu Leu Leu Phe Leu Val Met Phe Ile
    1670                1675                1680
Tyr Ala Ile Phe Gly Met Ser Asn Phe Ala Tyr Val Lys Arg Glu
    1685                1690                1695
Val Gly Ile Asp Asp Met Phe Asn Phe Glu Thr Phe Gly Asn Ser
    1700                1705                1710
Met Ile Cys Leu Phe Gln Ile Thr Thr Ser Ala Gly Trp Asp Gly
    1715                1720                1725
Leu Leu Ala Pro Ile Leu Asn Ser Lys Pro Pro Asp Cys Asp Pro
    1730                1735                1740
Asn Lys Val Asn Pro Gly Ser Ser Val Lys Gly Asp Cys Gly Asn
    1745                1750                1755
Pro Ser Val Gly Ile Phe Phe Phe Val Ser Tyr Ile Ile Ile Ser
    1760                1765                1770
Phe Leu Val Val Val Asn Met Tyr Ile Ala Val Ile Leu Glu Asn
    1775                1780                1785
Phe Ser Val Ala Thr Glu Glu Ser Ala Glu Pro Leu Ser Glu Asp
    1790                1795                1800
Asp Phe Glu Met Phe Tyr Glu Val Trp Glu Lys Phe Asp Pro Asp
    1805                1810                1815
Ala Thr Gln Phe Met Glu Phe Glu Lys Leu Ser Gln Phe Ala Ala
    1820                1825                1830
Ala Leu Glu Pro Pro Leu Asn Leu Pro Gln Pro Asn Lys Leu Gln
    1835                1840                1845
Leu Ile Ala Met Asp Leu Pro Met Val Ser Gly Asp Arg Ile His
    1850                1855                1860
Cys Leu Asp Ile Leu Phe Ala Phe Thr Lys Arg Val Leu Gly Glu
    1865                1870                1875
Ser Gly Glu Met Asp Ala Leu Arg Ile Gln Met Glu Glu Arg Phe
    1880                1885                1890
Met Ala Ser Asn Pro Ser Lys Val Ser Tyr Gln Pro Ile Thr Thr
    1895                1900                1905
Thr Leu Lys Arg Lys Gln Glu Glu Val Ser Ala Val Ile Ile Gln
    1910                1915                1920
Arg Ala Tyr Arg Arg His Leu Leu Lys Arg Thr Val Lys Gln Ala
    1925                1930                1935
Ser Phe Thr Tyr Asn Lys Asn Lys Ile Lys Gly Gly Ala Asn Leu
    1940                1945                1950
Leu Ile Lys Glu Asp Met Ile Ile Asp Arg Ile Asn Glu Asn Ser
    1955                1960                1965
Ile Thr Glu Lys Thr Asp Leu Thr Met Ser Thr Ala Ala Cys Pro
    1970                1975                1980
Pro Ser Tyr Asp Arg Val Thr Lys Pro Ile Val Glu Lys His Glu
    1985                1990                1995
Gln Glu Gly Lys Asp Glu Lys Ala Lys Gly Lys
    2000                2005

<210> SEQ ID NO 77
<211> LENGTH: 2009
<212> TYPE: PRT
<213> ORGANISM: Homo sapiens
```

<400> SEQUENCE: 77

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Asn Leu Ile Asn
                405                 410                 415
```

```
Leu Ile Leu Ala Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Ala Ala Thr Ala
450                     455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Gln Lys Glu Gln Ser Gly Gly
                500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
            530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
            755                 760                 765

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
            835                 840                 845
```

```
Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
        930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
        995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Thr Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
```

-continued

```
          1250              1255              1260
Ile Leu Glu Met Leu Leu Lys Trp Val Ala Tyr Gly Tyr Gln Thr
    1265              1270              1275
Tyr Phe Thr Asn Ala Trp Cys Trp Leu Asp Phe Leu Ile Val Asp
    1280              1285              1290
Val Ser Leu Val Ser Leu Thr Ala Asn Ala Leu Gly Tyr Ser Glu
    1295              1300              1305
Leu Gly Ala Ile Lys Ser Leu Arg Thr Leu Arg Ala Leu Arg Pro
    1310              1315              1320
Leu Arg Ala Leu Ser Arg Phe Glu Gly Met Arg Val Val Val Asn
    1325              1330              1335
Ala Leu Leu Gly Ala Ile Pro Ser Ile Met Asn Val Leu Leu Val
    1340              1345              1350
Cys Leu Ile Phe Trp Leu Ile Phe Ser Ile Met Gly Val Asn Leu
    1355              1360              1365
Phe Ala Gly Lys Phe Tyr His Cys Ile Asn Thr Thr Thr Gly Asp
    1370              1375              1380
Arg Phe Asp Ile Glu Asp Val Asn Asn His Thr Asp Cys Leu Lys
    1385              1390              1395
Leu Ile Glu Arg Asn Glu Thr Ala Arg Trp Lys Asn Val Lys Val
    1400              1405              1410
Asn Phe Asp Asn Val Gly Phe Gly Tyr Leu Ser Leu Leu Gln Val
    1415              1420              1425
Ala Thr Phe Lys Gly Trp Met Asp Ile Met Tyr Ala Ala Val Asp
    1430              1435              1440
Ser Arg Asn Val Glu Leu Gln Pro Lys Tyr Glu Lys Ser Leu Tyr
    1445              1450              1455
Met Tyr Leu Tyr Phe Val Ile Phe Ile Ile Phe Gly Ser Phe Phe
    1460              1465              1470
Thr Leu Asn Leu Phe Ile Gly Val Ile Ile Asp Asn Phe Asn Gln
    1475              1480              1485
Gln Lys Lys Lys Phe Gly Gly Gln Asp Ile Phe Met Thr Glu Glu
    1490              1495              1500
Gln Lys Lys Tyr Tyr Asn Ala Met Lys Lys Leu Gly Ser Lys Lys
    1505              1510              1515
Pro Gln Lys Pro Ile Pro Arg Pro Gly Asn Lys Phe Gln Gly Met
    1520              1525              1530
Val Phe Asp Phe Val Thr Arg Gln Val Phe Asp Ile Ser Ile Met
    1535              1540              1545
Ile Leu Ile Cys Leu Asn Met Val Thr Met Met Val Glu Thr Asp
    1550              1555              1560
Asp Gln Ser Glu Tyr Val Thr Thr Ile Leu Ser Arg Ile Asn Leu
    1565              1570              1575
Val Phe Ile Val Leu Phe Thr Gly Glu Cys Val Leu Lys Leu Ile
    1580              1585              1590
Ser Leu Arg His Tyr Tyr Phe Thr Ile Gly Trp Asn Ile Phe Asp
    1595              1600              1605
Phe Val Val Val Ile Leu Ser Ile Val Gly Met Phe Leu Ala Glu
    1610              1615              1620
Leu Ile Glu Lys Tyr Phe Val Ser Pro Thr Leu Phe Arg Val Ile
    1625              1630              1635
Arg Leu Ala Arg Ile Gly Arg Ile Leu Arg Leu Ile Lys Gly Ala
    1640              1645              1650
```

Lys Gly Ile Arg Thr Leu Leu Phe Ala Leu Met Met Ser Leu Pro
1655               1660                1665

Ala Leu Phe Asn Ile Gly Leu Leu Phe Leu Val Met Phe Ile
1670               1675                1680

Tyr Ala Ile Phe Gly Met Ser Asn Phe Ala Tyr Val Lys Arg Glu
1685               1690                1695

Val Gly Ile Asp Asp Met Phe Asn Phe Glu Thr Phe Gly Asn Ser
1700               1705                1710

Met Ile Cys Leu Phe Gln Ile Thr Thr Ser Ala Gly Trp Asp Gly
1715               1720                1725

Leu Leu Ala Pro Ile Leu Asn Ser Lys Pro Pro Asp Cys Asp Pro
1730               1735                1740

Asn Lys Val Asn Pro Gly Ser Ser Val Lys Gly Asp Cys Gly Asn
1745               1750                1755

Pro Ser Val Gly Ile Phe Phe Phe Val Ser Tyr Ile Ile Ile Ser
1760               1765                1770

Phe Leu Val Val Val Asn Met Tyr Ile Ala Val Ile Leu Glu Asn
1775               1780                1785

Phe Ser Val Ala Thr Glu Glu Ser Ala Glu Pro Leu Ser Glu Asp
1790               1795                1800

Asp Phe Glu Met Phe Tyr Glu Val Trp Glu Lys Phe Asp Pro Asp
1805               1810                1815

Ala Thr Gln Phe Met Glu Phe Glu Lys Leu Ser Gln Phe Ala Ala
1820               1825                1830

Ala Leu Glu Pro Pro Leu Asn Leu Pro Gln Pro Asn Lys Leu Gln
1835               1840                1845

Leu Ile Ala Met Asp Leu Pro Met Val Ser Gly Asp Arg Ile His
1850               1855                1860

Cys Leu Asp Ile Leu Phe Ala Phe Thr Lys Arg Val Leu Gly Glu
1865               1870                1875

Ser Gly Glu Met Asp Ala Leu Arg Ile Gln Met Glu Glu Arg Phe
1880               1885                1890

Met Ala Ser Asn Pro Ser Lys Val Ser Tyr Gln Pro Ile Thr Thr
1895               1900                1905

Thr Leu Lys Arg Lys Gln Glu Glu Val Ser Ala Val Ile Ile Gln
1910               1915                1920

Arg Ala Tyr Arg Arg His Leu Leu Lys Arg Thr Val Lys Gln Ala
1925               1930                1935

Ser Phe Thr Tyr Asn Lys Asn Lys Ile Lys Gly Gly Ala Asn Leu
1940               1945                1950

Leu Ile Lys Glu Asp Met Ile Ile Asp Arg Ile Asn Glu Asn Ser
1955               1960                1965

Ile Thr Glu Lys Thr Asp Leu Thr Met Ser Thr Ala Ala Cys Pro
1970               1975                1980

Pro Ser Tyr Asp Arg Val Thr Lys Pro Ile Val Glu Lys His Glu
1985               1990                1995

Gln Glu Gly Lys Asp Glu Lys Ala Lys Gly Lys
2000               2005

<210> SEQ ID NO 78
<211> LENGTH: 2009
<212> TYPE: PRT
<213> ORGANISM: Homo sapiens

<400> SEQUENCE: 78

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Glu Ala Met Ala Tyr Glu Glu Gln Asn Gln Ala
            420                 425                 430
```

```
Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
                500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
        530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
                580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
        610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
        690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Val Asn Leu Val Val Met Asp Pro
            755                 760                 765

Phe Val Asp Leu Ala Ile Thr Ile Cys Ile Val Leu Asn Thr Leu Phe
        770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
```

```
              850             855             860
Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe Phe His Ser Phe Leu Ile Val
            930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
            995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Thr Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260
```

```
Ile Leu Glu Met Leu Leu Lys Trp Val Ala Tyr Gly Tyr Gln Thr
1265                 1270                1275

Tyr Phe Thr Asn Ala Trp Cys Trp Leu Asp Phe Leu Ile Val Asp
1280                 1285                1290

Val Ser Leu Val Ser Leu Thr Ala Asn Ala Leu Gly Tyr Ser Glu
1295                 1300                1305

Leu Gly Ala Ile Lys Ser Leu Arg Thr Leu Arg Ala Leu Arg Pro
1310                 1315                1320

Leu Arg Ala Leu Ser Arg Phe Glu Gly Met Arg Val Val Val Asn
1325                 1330                1335

Ala Leu Leu Gly Ala Ile Pro Ser Ile Met Asn Val Leu Leu Val
1340                 1345                1350

Cys Leu Ile Phe Trp Leu Ile Phe Ser Ile Met Gly Val Asn Leu
1355                 1360                1365

Phe Ala Gly Lys Phe Tyr His Cys Ile Asn Thr Thr Thr Gly Asp
1370                 1375                1380

Arg Phe Asp Ile Glu Asp Val Asn Asn His Thr Asp Cys Leu Lys
1385                 1390                1395

Leu Ile Glu Arg Asn Glu Thr Ala Arg Trp Lys Asn Val Lys Val
1400                 1405                1410

Asn Phe Asp Asn Val Gly Phe Gly Tyr Leu Ser Leu Leu Gln Val
1415                 1420                1425

Ala Thr Phe Lys Gly Trp Met Asp Ile Met Tyr Ala Ala Val Asp
1430                 1435                1440

Ser Arg Asn Val Glu Leu Gln Pro Lys Tyr Glu Lys Ser Leu Tyr
1445                 1450                1455

Met Tyr Leu Tyr Phe Val Ile Phe Ile Ile Phe Gly Ser Phe Phe
1460                 1465                1470

Thr Leu Asn Leu Phe Ile Gly Val Ile Ile Asp Asn Phe Asn Gln
1475                 1480                1485

Gln Lys Lys Lys Phe Gly Gly Gln Asp Ile Phe Met Thr Glu Glu
1490                 1495                1500

Gln Lys Lys Tyr Tyr Asn Ala Met Lys Lys Leu Gly Ser Lys Lys
1505                 1510                1515

Pro Gln Lys Pro Ile Pro Arg Pro Gly Asn Lys Phe Gln Gly Met
1520                 1525                1530

Val Phe Asp Phe Val Thr Arg Gln Val Phe Asp Ile Ser Ile Met
1535                 1540                1545

Ile Leu Ile Cys Leu Asn Met Val Thr Met Met Val Glu Thr Asp
1550                 1555                1560

Asp Gln Ser Glu Tyr Val Thr Thr Ile Leu Ser Arg Ile Asn Leu
1565                 1570                1575

Val Phe Ile Val Leu Phe Thr Gly Glu Cys Val Leu Lys Leu Ile
1580                 1585                1590

Ser Leu Arg His Tyr Tyr Phe Thr Ile Gly Trp Asn Ile Phe Asp
1595                 1600                1605

Phe Val Val Val Ile Leu Ser Ile Val Gly Met Phe Leu Ala Glu
1610                 1615                1620

Leu Ile Glu Lys Tyr Phe Val Ser Pro Thr Leu Phe Arg Val Ile
1625                 1630                1635

Arg Leu Ala Arg Ile Gly Arg Ile Leu Arg Leu Ile Lys Gly Ala
1640                 1645                1650

Lys Gly Ile Arg Thr Leu Leu Phe Ala Leu Met Met Ser Leu Pro
1655                 1660                1665
```

```
Ala Leu Phe Asn Ile Gly Leu Leu Leu Phe Leu Val Met Phe Ile
        1670             1675                 1680

Tyr Ala Ile Phe Gly Met Ser Asn Phe Ala Tyr Val Lys Arg Glu
    1685             1690                 1695

Val Gly Ile Asp Asp Met Phe Asn Phe Glu Thr Phe Gly Asn Ser
    1700             1705                 1710

Met Ile Cys Leu Phe Gln Ile Thr Thr Ser Ala Gly Trp Asp Gly
    1715             1720                 1725

Leu Leu Ala Pro Ile Leu Asn Ser Lys Pro Pro Asp Cys Asp Pro
        1730             1735                 1740

Asn Lys Val Asn Pro Gly Ser Ser Val Lys Gly Asp Cys Gly Asn
    1745             1750                 1755

Pro Ser Val Gly Ile Phe Phe Phe Val Ser Tyr Ile Ile Ile Ser
    1760             1765                 1770

Phe Leu Val Val Val Asn Met Tyr Ile Ala Val Ile Leu Glu Asn
    1775             1780                 1785

Phe Ser Val Ala Thr Glu Glu Ser Ala Glu Pro Leu Ser Glu Asp
    1790             1795                 1800

Asp Phe Glu Met Phe Tyr Glu Val Trp Glu Lys Phe Asp Pro Asp
    1805             1810                 1815

Ala Thr Gln Phe Met Glu Phe Glu Lys Leu Ser Gln Phe Ala Ala
    1820             1825                 1830

Ala Leu Glu Pro Pro Leu Asn Leu Pro Gln Pro Asn Lys Leu Gln
        1835             1840                 1845

Leu Ile Ala Met Asp Leu Pro Met Val Ser Gly Asp Arg Ile His
        1850             1855                 1860

Cys Leu Asp Ile Leu Phe Ala Phe Thr Lys Arg Val Leu Gly Glu
    1865             1870                 1875

Ser Gly Glu Met Asp Ala Leu Arg Ile Gln Met Glu Glu Arg Phe
    1880             1885                 1890

Met Ala Ser Asn Pro Ser Lys Val Ser Tyr Gln Pro Ile Thr Thr
    1895             1900                 1905

Thr Leu Lys Arg Lys Gln Glu Glu Val Ser Ala Val Ile Ile Gln
    1910             1915                 1920

Arg Ala Tyr Arg Arg His Leu Leu Lys Arg Thr Val Lys Gln Ala
    1925             1930                 1935

Ser Phe Thr Tyr Asn Lys Asn Lys Ile Lys Gly Gly Ala Asn Leu
    1940             1945                 1950

Leu Ile Lys Glu Asp Met Ile Ile Asp Arg Ile Asn Glu Asn Ser
    1955             1960                 1965

Ile Thr Glu Lys Thr Asp Leu Thr Met Ser Thr Ala Ala Cys Pro
    1970             1975                 1980

Pro Ser Tyr Asp Arg Val Thr Lys Pro Ile Val Glu Lys His Glu
    1985             1990                 1995

Gln Glu Gly Lys Asp Glu Lys Ala Lys Gly Lys
    2000             2005

<210> SEQ ID NO 79
<211> LENGTH: 1406
<212> TYPE: PRT
<213> ORGANISM: Homo sapiens

<400> SEQUENCE: 79

Met Glu Gln Thr Val Leu Val Pro Pro Gly Pro Asp Ser Phe Asn Phe
1               5                   10                  15
```

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Glu Asn Gly
        35                  40                  45

Pro Lys Pro Asn Ser Asp Leu Glu Ala Gly Lys Asn Leu Pro Phe Ile
 50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
            115                 120                 125

Leu Phe Ser Met Leu Ile Met Cys Thr Ile Leu Thr Asn Cys Val Phe
        130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
            195                 200                 205

Leu Gly Asn Val Ser Ala Leu Arg Thr Phe Arg Val Leu Arg Ala Leu
 210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
        290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
 370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile

```
              435                 440                 445
Glu Gln Leu Lys Lys Gln Gln Glu Ala Ala Gln Ala Ala Thr Ala
450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                        485                 490                 495
Arg Arg Asn Arg Arg Lys Lys Arg Lys Gln Lys Glu Gln Ser Gly Gly
                500                 505                 510
Glu Glu Lys Asp Glu Asp Glu Phe Gln Lys Ser Glu Ser Glu Asp Ser
        515                 520                 525
Ile Arg Arg Lys Gly Phe Arg Phe Ser Ile Glu Gly Asn Arg Leu Thr
530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
        595                 600                 605
Phe Val Pro Arg Arg His Gly Glu Arg Arg Asn Ser Asn Leu Ser Gln
610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
                660                 665                 670
Ile Asp Lys Pro Ala Thr Asp Asp Asn Gly Thr Thr Thr Glu Thr Glu
                675                 680                 685
Met Arg Lys Arg Arg Ser Ser Ser Phe His Val Ser Met Asp Phe Leu
        690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                725                 730                 735
Cys Trp Tyr Lys Phe Ser Asn Ile Phe Leu Ile Trp Asp Cys Ser Pro
                740                 745                 750
Tyr Trp Leu Lys Val Lys His Val Val Asn Leu Val Val Met Asp Pro
        755                 760                 765
Phe Val Asp Leu Ala Ile Thr Ile Cys Ile Val Leu Asn Thr Leu Phe
770                 775                 780
Met Ala Met Glu His Tyr Pro Met Thr Asp His Phe Asn Asn Val Leu
785                 790                 795                 800
Thr Val Gly Asn Leu Val Phe Thr Gly Ile Phe Thr Ala Glu Met Phe
                805                 810                 815
Leu Lys Ile Ile Ala Met Asp Pro Tyr Tyr Tyr Phe Gln Glu Gly Trp
                820                 825                 830
Asn Ile Phe Asp Gly Phe Ile Val Thr Leu Ser Leu Val Glu Leu Gly
        835                 840                 845
Leu Ala Asn Val Glu Gly Leu Ser Val Leu Arg Ser Phe Arg Leu Leu
850                 855                 860
```

-continued

```
Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
            885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe Phe His Ser Phe Leu Ile Val
        930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu Ala Ala Thr Asp Asp Asp Asn Glu
                995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Thr Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275
```

```
Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala
    1400                1405

<210> SEQ ID NO 80
<211> LENGTH: 2009
<212> TYPE: PRT
<213> ORGANISM: Homo sapiens

<400> SEQUENCE: 80

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240
```

```
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Ile Gln Trp Pro Pro Thr Asn Ala Ser Leu Glu
        275                 280                 285
Glu His Ser Ile Glu Lys Asn Ile Thr Val Asn Tyr Asn Gly Thr Leu
    290                 295                 300
Ile Asn Glu Thr Val Phe Glu Phe Asp Trp Lys Ser Tyr Ile Gln Asp
305                 310                 315                 320
Ser Arg Tyr His Tyr Phe Leu Glu Gly Phe Leu Asp Ala Leu Leu Cys
                325                 330                 335
Gly Asn Ser Ser Asp Ala Gly Gln Cys Pro Glu Gly Tyr Met Cys Val
            340                 345                 350
Lys Ala Gly Arg Asn Pro Asn Tyr Gly Tyr Thr Ser Phe Asp Thr Phe
        355                 360                 365
Ser Trp Ala Phe Leu Ser Leu Phe Arg Leu Met Thr Gln Asp Phe Trp
    370                 375                 380
Glu Asn Leu Tyr Gln Leu Thr Leu Arg Ala Ala Gly Lys Thr Tyr Met
385                 390                 395                 400
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Glu Gln Asn Gln Ala
            420                 425                 430
Thr Leu Glu Glu Ala Glu Gln Lys Glu Ala Glu Phe Gln Gln Met Ile
        435                 440                 445
Glu Gln Leu Lys Lys Gln Gln Glu Ala Ala Gln Ala Ala Thr Ala
    450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
            500                 505                 510
Glu Glu Lys Asp Glu Asp Glu Phe Gln Lys Ser Glu Ser Glu Asp Ser
        515                 520                 525
Ile Arg Arg Lys Gly Phe Arg Phe Ser Ile Glu Gly Asn Arg Leu Thr
    530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
            580                 585                 590
Asp Glu His Ser Thr Phe Glu Asp Asn Glu Ser Arg Arg Asp Ser Leu
        595                 600                 605
Phe Val Pro Arg Arg His Gly Glu Arg Arg Asn Ser Asn Leu Ser Gln
    610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
```

-continued

```
                  660                 665                 670
Ile Asp Lys Pro Ala Thr Asp Asn Gly Thr Thr Glu Thr Glu
                675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Val Asn Leu Val Val Met Asp Pro
                755                 760                 765

Phe Val Asp Leu Ala Ile Thr Ile Cys Ile Val Leu Asn Thr Leu Phe
                770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
                835                 840                 845

Leu Ala Asn Val Glu Gly Leu Ser Val Leu Arg Ser Phe Arg Leu Leu
                850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe Phe His Ser Phe Leu Ile Val
930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu Ala Ala Thr Asp Asp Asp Asn Glu
                995                 1000                1005

Met Asn Asn Leu Gln Ile Ala Val Asp Arg Met His Lys Gly Val
                1010                1015                1020

Ala Tyr Val Lys Arg Lys Ile Tyr Glu Phe Ile Gln Gln Ser Phe
                1025                1030                1035

Ile Arg Lys Gln Lys Ile Leu Asp Glu Ile Lys Pro Leu Asp Asp
                1040                1045                1050

Leu Asn Asn Lys Lys Asp Ser Cys Met Ser Asn His Thr Thr Glu
                1055                1060                1065

Ile Gly Lys Asp Leu Asp Tyr Leu Lys Asp Val Asn Gly Thr Thr
                1070                1075                1080
```

```
Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Glu Gly Ser Thr Val Asp
    1145                1150                1155

Ile Gly Ala Pro Val Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275

Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Lys Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485
```

```
Gln Lys Lys Lys Phe Gly Gly Gln Asp Ile Phe Met Thr Glu Glu
    1490            1495                1500

Gln Lys Lys Tyr Tyr Asn Ala Met Lys Lys Leu Gly Ser Lys Lys
    1505            1510                1515

Pro Gln Lys Pro Ile Pro Arg Pro Gly Asn Lys Phe Gln Gly Met
    1520            1525                1530

Val Phe Asp Phe Val Thr Arg Gln Val Phe Asp Ile Ser Ile Met
    1535            1540                1545

Ile Leu Ile Cys Leu Asn Met Val Thr Met Met Val Glu Thr Asp
    1550            1555                1560

Asp Gln Ser Glu Tyr Val Thr Thr Ile Leu Ser Arg Ile Asn Leu
    1565            1570                1575

Val Phe Ile Val Leu Phe Thr Gly Glu Cys Val Leu Lys Leu Ile
    1580            1585                1590

Ser Leu Arg His Tyr Tyr Phe Thr Ile Gly Trp Asn Ile Phe Asp
    1595            1600                1605

Phe Val Val Val Ile Leu Ser Ile Val Gly Met Phe Leu Ala Glu
    1610            1615                1620

Leu Ile Glu Lys Tyr Phe Val Ser Pro Thr Leu Phe Arg Val Ile
    1625            1630                1635

Arg Leu Ala Arg Ile Gly Arg Ile Leu Arg Leu Ile Lys Gly Ala
    1640            1645                1650

Lys Gly Ile Arg Thr Leu Leu Phe Ala Leu Met Met Ser Leu Pro
    1655            1660                1665

Ala Leu Phe Asn Ile Gly Leu Leu Leu Phe Leu Val Met Phe Ile
    1670            1675                1680

Tyr Ala Ile Phe Gly Met Ser Asn Phe Ala Tyr Val Lys Arg Glu
    1685            1690                1695

Val Gly Ile Asp Asp Met Phe Asn Phe Glu Thr Phe Gly Asn Ser
    1700            1705                1710

Met Ile Cys Leu Phe Gln Ile Thr Thr Ser Ala Gly Trp Asp Gly
    1715            1720                1725

Leu Leu Ala Pro Ile Leu Asn Ser Lys Pro Pro Asp Cys Asp Pro
    1730            1735                1740

Asn Lys Val Asn Pro Gly Ser Ser Val Lys Gly Asp Cys Gly Asn
    1745            1750                1755

Pro Ser Val Gly Ile Phe Phe Val Ser Tyr Ile Ile Ile Ser
    1760            1765                1770

Phe Leu Val Val Asn Thr Tyr Ile Ala Val Ile Leu Glu Asn
    1775            1780                1785

Phe Ser Val Ala Thr Glu Glu Ser Ala Glu Pro Leu Ser Glu Asp
    1790            1795                1800

Asp Phe Glu Met Phe Tyr Glu Val Trp Glu Lys Phe Asp Pro Asp
    1805            1810                1815

Ala Thr Gln Phe Met Glu Phe Glu Lys Leu Ser Gln Phe Ala Ala
    1820            1825                1830

Ala Leu Glu Pro Pro Leu Asn Leu Pro Gln Pro Asn Lys Leu Gln
    1835            1840                1845

Leu Ile Ala Met Asp Leu Pro Met Val Ser Gly Asp Arg Ile His
    1850            1855                1860

Cys Leu Asp Ile Leu Phe Ala Phe Thr Lys Arg Val Leu Gly Glu
    1865            1870                1875

Ser Gly Glu Met Asp Ala Leu Arg Ile Gln Met Glu Glu Arg Phe
```

```
                   1880           1885           1890
Met Ala Ser Asn Pro Ser Lys Val Ser Tyr Gln Pro Ile Thr Thr
   1895            1900           1905

Thr Leu Lys Arg Lys Gln Glu Glu Val Ser Ala Val Ile Ile Gln
   1910            1915           1920

Arg Ala Tyr Arg Arg His Leu Leu Lys Arg Thr Val Lys Gln Ala
   1925            1930           1935

Ser Phe Thr Tyr Asn Lys Asn Lys Ile Lys Gly Gly Ala Asn Leu
   1940            1945           1950

Leu Ile Lys Glu Asp Met Ile Ile Asp Arg Ile Asn Glu Asn Ser
   1955            1960           1965

Ile Thr Glu Lys Thr Asp Leu Thr Met Ser Thr Ala Ala Cys Pro
   1970            1975           1980

Pro Ser Tyr Asp Arg Val Thr Lys Pro Ile Val Glu Lys His Glu
   1985            1990           1995

Gln Glu Gly Lys Asp Glu Lys Ala Lys Gly Lys
   2000            2005

<210> SEQ ID NO 81
<211> LENGTH: 1891
<212> TYPE: PRT
<213> ORGANISM: Homo sapiens

<400> SEQUENCE: 81

Met Glu Gln Thr Val Leu Val Pro Pro Gly Pro Asp Ser Phe Asn Phe
 1               5                  10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Glu Asn Gly
            35                  40                  45

Pro Lys Pro Asn Ser Asp Leu Glu Ala Gly Lys Asn Leu Pro Phe Ile
        50                  55                  60

Tyr Gly Asp Ile Pro Pro Glu Met Val Ser Glu Pro Leu Glu Asp Leu
 65                 70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
```

```
                245                 250                 255
Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
            325                 330                 335

Gly Asn Ser Ser Asp Ala Gly Gln Cys Pro Glu Gly Tyr Met Cys Val
        340                 345                 350

Lys Ala Gly Arg Asn Pro Asn Tyr Gly Tyr Thr Ser Phe Asp Thr Phe
    355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
            405                 410                 415

Leu Ile Leu Ala Val Val Ala Met Ala Tyr Glu Glu Gln Asn Gln Ala
        420                 425                 430

Thr Leu Glu Glu Ala Glu Gln Lys Glu Ala Glu Phe Gln Gln Met Ile
    435                 440                 445

Glu Gln Leu Lys Lys Gln Gln Glu Ala Ala Gln Ala Ala Thr Ala
450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
            485                 490                 495

Arg Arg Asn Arg Arg Lys Lys Arg Lys Gln Lys Glu Gln Ser Gly Gly
        500                 505                 510

Glu Glu Lys Asp Glu Asp Glu Phe Gln Lys Ser Glu Ser Glu Asp Ser
    515                 520                 525

Ile Arg Arg Lys Gly Phe Arg Phe Ser Ile Glu Gly Asn Arg Leu Thr
530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
            565                 570                 575

Phe Arg Gly Arg Ala Lys Asp Val Gly Ser Glu Asn Asp Phe Ala Asp
        580                 585                 590

Asp Glu His Ser Thr Phe Glu Asp Asn Glu Ser Arg Arg Asp Ser Leu
    595                 600                 605

Phe Val Pro Arg Arg His Gly Glu Arg Arg Asn Ser Asn Leu Ser Gln
610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
            645                 650                 655

Pro Ser Val Pro Thr Ser Pro Val Gly Gln Leu Leu Pro Glu Val Ile
        660                 665                 670
```

```
Ile Asp Lys Pro Ala Thr Asp Asn Gly Thr Thr Thr Glu Thr Glu
        675                 680                 685

Met Arg Lys Arg Arg Ser Ser Ser Phe His Val Ser Met Asp Phe Leu
        690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Val Asn Leu Val Val Met Asp Pro
                755                 760                 765

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
                835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe His Ser Phe Leu Ile Val
930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu Ala Ala Thr Asp Asp Asp Asn Glu
        995                 1000                1005

Met Asn Asn Leu Gln Ile Ala Val Asp Arg Met His Lys Gly Val
        1010                1015                1020

Ala Tyr Val Lys Arg Lys Ile Tyr Glu Phe Ile Gln Gln Ser Phe
        1025                1030                1035

Ile Arg Lys Gln Lys Ile Leu Asp Glu Ile Lys Pro Leu Asp Asp
        1040                1045                1050

Leu Asn Asn Lys Lys Asp Ser Cys Met Ser Asn His Thr Thr Glu
        1055                1060                1065

Ile Gly Lys Asp Leu Asp Tyr Leu Lys Asp Val Asn Gly Thr Thr
        1070                1075                1080

Ser Gly Ile Gly Thr Gly Ser Ser Val Glu Lys Tyr Ile Ile Asp
        1085                1090                1095
```

-continued

```
Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275

Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Lys Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
```

-continued

```
                1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu
    1880                1885                1890
```

<210> SEQ ID NO 82
<211> LENGTH: 218
<212> TYPE: PRT
<213> ORGANISM: Homo sapiens

<400> SEQUENCE: 82

Met Gly Arg Leu Leu Ala Leu Val Val Gly Ala Ala Leu Val Ser Ser
1               5                   10                  15

Ala Cys Gly Gly Cys Val Glu Val Asp Ser Glu Thr Glu Ala Val Tyr
            20                  25                  30

Gly Met Thr Phe Lys Ile Leu Cys Ile Ser Cys Lys Arg Arg Ser Glu
        35                  40                  45

Thr Asn Ala Glu Thr Phe Thr Glu Trp Thr Phe Arg Gln Lys Gly Thr
    50                  55                  60

Glu Glu Phe Val Lys Ile Leu Arg Tyr Glu Asn Glu Val Leu Gln Leu
65                  70                  75                  80

Glu Glu Asp Glu His Phe Glu Gly Arg Val Val Trp Asn Gly Ser Arg
                85                  90                  95

Gly Thr Lys Asp Leu Gln Asp Leu Ser Ile Phe Ile Thr Asn Val Thr
            100                 105                 110

Tyr Asn His Ser Gly Asp Tyr Glu Cys His Val Tyr Arg Leu Leu Phe
        115                 120                 125

Phe Glu Asn Tyr Glu His Asn Thr Ser Val Val Lys Lys Ile His Ile
    130                 135                 140

Glu Val Asp Lys Ala Asn Arg Asp Met Ala Ser Ile Val Ser Glu
145                 150                 155                 160

Ile Met Met Tyr Val Leu Ile Val Val Leu Thr Ile Trp Leu Val Ala
                165                 170                 175

Glu Met Ile Tyr Cys Tyr Lys Lys Ile Ala Ala Thr Glu Thr Ala
            180                 185                 190

Ala Gln Glu Asn Ala Ser Glu Tyr Leu Ala Ile Thr Ser Glu Ser Lys
        195                 200                 205

Glu Asn Cys Thr Gly Val Gln Val Ala Glu
    210                 215

<210> SEQ ID NO 83
<211> LENGTH: 2005
<212> TYPE: PRT
<213> ORGANISM: Homo sapiens

<400> SEQUENCE: 83

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His

-continued

```
            115                 120                 125
Ser Leu Phe Asn Met Leu Ile Met Cys Thr Ile Leu Thr Asn Cys Val
130                 135                 140
Phe Met Thr Met Ser Asn Pro Pro Asp Trp Thr Lys Asn Val Glu Tyr
145                 150                 155                 160
Thr Phe Thr Gly Ile Tyr Thr Phe Glu Ser Leu Ile Lys Ile Leu Ala
                165                 170                 175
Arg Gly Phe Cys Leu Glu Asp Phe Thr Phe Leu Arg Asp Pro Trp Asn
                180                 185                 190
Trp Leu Asp Phe Thr Val Ile Thr Phe Ala Tyr Val Thr Glu Phe Val
                195                 200                 205
Asp Leu Gly Asn Val Ser Ala Leu Arg Thr Phe Arg Val Leu Gln Ala
210                 215                 220
Leu Lys Thr Ile Ser Val Ile Pro Gly Leu Lys Thr Ile Val Gly Ala
225                 230                 235                 240
Leu Ile Gln Ser Val Lys Lys Leu Ser Asp Val Met Ile Leu Thr Val
                245                 250                 255
Phe Cys Leu Ser Val Phe Ala Leu Ile Gly Leu Gln Leu Phe Met Gly
                260                 265                 270
Asn Leu Arg Asn Lys Cys Leu Gln Trp Pro Pro Asp Asn Ser Ser Phe
                275                 280                 285
Glu Ile Asn Ile Thr Ser Phe Phe Asn Asn Ser Leu Asp Gly Asn Gly
                290                 295                 300
Thr Thr Phe Asn Arg Thr Val Ser Ile Phe Asn Trp Asp Glu Tyr Ile
305                 310                 315                 320
Glu Asp Lys Ser His Phe Tyr Phe Leu Glu Gly Gln Asn Asp Ala Leu
                325                 330                 335
Leu Cys Gly Asn Ser Ser Asp Ala Gly Gln Cys Pro Glu Gly Tyr Ile
                340                 345                 350
Cys Val Lys Ala Gly Arg Asn Pro Asn Tyr Gly Tyr Thr Ser Phe Asp
                355                 360                 365
Thr Phe Ser Trp Ala Phe Leu Ser Leu Phe Arg Leu Met Thr Gln Asp
370                 375                 380
Phe Trp Glu Asn Leu Tyr Gln Leu Thr Leu Arg Ala Ala Gly Lys Thr
385                 390                 395                 400
Tyr Met Ile Phe Phe Val Leu Val Ile Phe Leu Gly Ser Phe Tyr Leu
                405                 410                 415
Ile Asn Leu Ile Leu Ala Val Val Ala Met Ala Tyr Glu Glu Gln Asn
                420                 425                 430
Gln Ala Thr Leu Glu Glu Ala Glu Gln Lys Glu Ala Glu Phe Gln Gln
                435                 440                 445
Met Leu Glu Gln Leu Lys Lys Gln Gln Glu Glu Ala Gln Ala Ala Ala
450                 455                 460
Ala Ala Ala Ser Ala Glu Ser Arg Asp Phe Ser Gly Ala Gly Gly Ile
465                 470                 475                 480
Gly Val Phe Ser Glu Ser Ser Val Ala Ser Lys Leu Ser Ser Lys
                485                 490                 495
Ser Glu Lys Glu Leu Lys Asn Arg Arg Lys Lys Lys Gln Lys Glu
                500                 505                 510
Gln Ser Gly Glu Glu Lys Asn Asp Arg Val Leu Lys Ser Glu Ser
                515                 520                 525
Glu Asp Ser Ile Arg Arg Lys Gly Phe Arg Phe Ser Leu Glu Gly Ser
530                 535                 540
```

```
Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Asn Ser Arg Ala Ser
            565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
            595                 600                 605

Asp Ser Leu Phe Val Pro His Arg His Gly Glu Arg Arg His Ser Asn
        610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Glu Thr Glu Ile Arg Lys Arg Arg Ser Ser Ser Tyr
        675                 680                 685

His Val Ser Met Asp Leu Leu Glu Asp Pro Thr Ser Arg Gln Arg Ala
        690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
        755                 760                 765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ala Met Asp Pro Tyr
            805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
        850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
        915                 920                 925

Phe His Ser Phe Leu Ile Val Phe Arg Val Leu Cys Gly Glu Trp Ile
        930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975
```

```
Leu Phe Leu Ala Leu Leu Leu Ser Ser Phe Ser Ser Asp Asn Leu Ala
            980                 985                 990

Ala Thr Asp Asp Asp Asn Glu Met Asn Asn Leu Gln Ile Ala Val Gly
            995                 1000                1005

Arg Met Gln Lys Gly Ile Asp Phe Val Lys Lys Ile Arg Glu
        1010                1015                1020

Phe Ile Gln Lys Ala Phe Val Arg Lys Gln Lys Ala Leu Asp Glu
        1025                1030                1035

Ile Lys Pro Leu Glu Asp Leu Asn Asn Lys Lys Asp Ser Cys Ile
        1040                1045                1050

Ser Asn His Thr Thr Ile Glu Ile Gly Lys Asp Leu Asn Tyr Leu
        1055                1060                1065

Lys Asp Gly Asn Gly Thr Thr Ser Gly Ile Gly Ser Ser Val Glu
        1070                1075                1080

Lys Tyr Val Val Asp Glu Ser Asp Tyr Met Ser Phe Ile Asn Asn
        1085                1090                1095

Pro Ser Leu Thr Val Thr Val Pro Ile Ala Val Gly Glu Ser Asp
        1100                1105                1110

Phe Glu Asn Leu Asn Thr Glu Glu Phe Ser Glu Ser Asp Met
        1115                1120                1125

Glu Glu Ser Lys Glu Lys Leu Asn Ala Thr Ser Ser Glu Gly
        1130                1135                1140

Ser Thr Val Asp Ile Gly Ala Pro Ala Glu Gly Glu Gln Pro Glu
        1145                1150                1155

Val Glu Pro Glu Glu Ser Leu Glu Pro Glu Ala Cys Phe Thr Glu
        1160                1165                1170

Asp Cys Val Arg Lys Phe Lys Cys Cys Gln Ile Ser Ile Glu Glu
        1175                1180                1185

Gly Lys Gly Lys Leu Trp Trp Asn Leu Arg Lys Thr Cys Tyr Lys
        1190                1195                1200

Ile Val Glu His Asn Trp Phe Glu Thr Phe Ile Val Phe Met Ile
        1205                1210                1215

Leu Leu Ser Ser Gly Ala Leu Ala Phe Glu Asp Ile Tyr Ile Glu
        1220                1225                1230

Gln Arg Lys Thr Ile Lys Thr Met Leu Glu Tyr Ala Asp Lys Val
        1235                1240                1245

Phe Thr Tyr Ile Phe Ile Leu Glu Met Leu Leu Lys Trp Val Ala
        1250                1255                1260

Tyr Gly Phe Gln Val Tyr Phe Thr Asn Ala Trp Cys Trp Leu Asp
        1265                1270                1275

Phe Leu Ile Val Asp Val Ser Leu Val Ser Leu Thr Ala Asn Ala
        1280                1285                1290

Leu Gly Tyr Ser Glu Leu Gly Ala Ile Lys Ser Leu Arg Thr Leu
        1295                1300                1305

Arg Ala Leu Arg Pro Leu Arg Ala Leu Ser Arg Phe Glu Gly Met
        1310                1315                1320

Arg Val Val Val Asn Ala Leu Leu Gly Ala Ile Pro Ser Ile Met
        1325                1330                1335

Asn Val Leu Leu Val Cys Leu Ile Phe Trp Leu Ile Phe Ser Ile
        1340                1345                1350

Met Gly Val Asn Leu Phe Ala Gly Lys Phe Tyr His Cys Ile Asn
        1355                1360                1365

Tyr Thr Thr Gly Glu Met Phe Asp Val Ser Val Val Asn Asn Tyr
```

```
        1370               1375               1380
Ser Glu Cys Lys Ala Leu Ile Glu Ser Asn Gln Thr Ala Arg Trp
    1385               1390               1395
Lys Asn Val Lys Val Asn Phe Asp Asn Val Gly Leu Gly Tyr Leu
    1400               1405               1410
Ser Leu Leu Gln Val Ala Thr Phe Lys Gly Trp Met Asp Ile Met
    1415               1420               1425
Tyr Ala Ala Val Asp Ser Arg Asn Val Glu Leu Gln Pro Lys Tyr
    1430               1435               1440
Glu Asp Asn Leu Tyr Met Tyr Leu Tyr Phe Val Ile Phe Ile Ile
    1445               1450               1455
Phe Gly Ser Phe Phe Thr Leu Asn Leu Phe Ile Gly Val Ile Ile
    1460               1465               1470
Asp Asn Phe Asn Gln Gln Lys Lys Lys Phe Gly Gly Gln Asp Ile
    1475               1480               1485
Phe Met Thr Glu Glu Gln Lys Lys Tyr Tyr Asn Ala Met Lys Lys
    1490               1495               1500
Leu Gly Ser Lys Lys Pro Gln Lys Pro Ile Pro Arg Pro Ala Asn
    1505               1510               1515
Lys Phe Gln Gly Met Val Phe Asp Phe Val Thr Lys Gln Val Phe
    1520               1525               1530
Asp Ile Ser Ile Met Ile Leu Ile Cys Leu Asn Met Val Thr Met
    1535               1540               1545
Met Val Glu Thr Asp Asp Gln Ser Gln Glu Met Thr Asn Ile Leu
    1550               1555               1560
Tyr Trp Ile Asn Leu Val Phe Ile Val Leu Phe Thr Gly Glu Cys
    1565               1570               1575
Val Leu Lys Leu Ile Ser Leu Arg Tyr Tyr Tyr Phe Thr Ile Gly
    1580               1585               1590
Trp Asn Ile Phe Asp Phe Val Val Val Ile Leu Ser Ile Val Gly
    1595               1600               1605
Met Phe Leu Ala Glu Leu Ile Glu Lys Tyr Phe Val Ser Pro Thr
    1610               1615               1620
Leu Phe Arg Val Ile Arg Leu Ala Arg Ile Gly Arg Ile Leu Arg
    1625               1630               1635
Leu Ile Lys Gly Ala Lys Gly Ile Arg Thr Leu Leu Phe Ala Leu
    1640               1645               1650
Met Met Ser Leu Pro Ala Leu Phe Asn Ile Gly Leu Leu Leu Phe
    1655               1660               1665
Leu Val Met Phe Ile Tyr Ala Ile Phe Gly Met Ser Asn Phe Ala
    1670               1675               1680
Tyr Val Lys Arg Glu Val Gly Ile Asp Asp Met Phe Asn Phe Glu
    1685               1690               1695
Thr Phe Gly Asn Ser Met Ile Cys Leu Phe Gln Ile Thr Thr Ser
    1700               1705               1710
Ala Gly Trp Asp Gly Leu Leu Ala Pro Ile Leu Asn Ser Gly Pro
    1715               1720               1725
Pro Asp Cys Asp Pro Asp Lys Asp His Pro Gly Ser Ser Val Lys
    1730               1735               1740
Gly Asp Cys Gly Asn Pro Ser Val Gly Ile Phe Phe Phe Val Ser
    1745               1750               1755
Tyr Ile Ile Ile Ser Phe Leu Val Val Leu Asn Met Tyr Ile Ala
    1760               1765               1770
```

```
Val Ile Leu Glu Asn Phe Ser Val Ala Thr Glu Glu Ser Ala Glu
    1775                1780                1785

Pro Leu Ser Glu Asp Asp Phe Glu Met Phe Tyr Glu Val Trp Glu
    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
    1865                1870                1875

Met Glu Glu Arg Phe Met Ala Ser Asn Pro Ser Lys Val Ser Tyr
    1880                1885                1890

Glu Pro Ile Thr Thr Thr Leu Lys Arg Lys Gln Glu Glu Val Ser
    1895                1900                1905

Ala Ile Ile Ile Gln Arg Ala Tyr Arg Arg Tyr Leu Leu Lys Gln
    1910                1915                1920

Lys Val Lys Lys Val Ser Ser Ile Tyr Lys Lys Asp Lys Gly Lys
    1925                1930                1935

Glu Cys Asp Gly Thr Pro Ile Lys Glu Asp Thr Leu Ile Asp Lys
    1940                1945                1950

Leu Asn Glu Asn Ser Thr Pro Glu Lys Thr Asp Met Thr Pro Ser
    1955                1960                1965

Thr Thr Ser Pro Pro Ser Tyr Asp Ser Val Thr Lys Pro Glu Lys
    1970                1975                1980

Glu Lys Phe Glu Lys Asp Lys Ser Glu Lys Glu Asp Lys Gly Lys
    1985                1990                1995

Asp Ile Arg Glu Ser Lys Lys
    2000                2005

<210> SEQ ID NO 84
<211> LENGTH: 2005
<212> TYPE: PRT
<213> ORGANISM: Homo sapiens

<400> SEQUENCE: 84

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125
```

-continued

```
Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asp Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
        275                 280                 285

Glu Ile Asn Ile Thr Ser Phe Phe Asn Asn Ser Leu Asp Gly Asn Gly
    290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
        355                 360                 365

Thr Phe Ser Trp Ala Phe Leu Ser Leu Phe Arg Leu Met Thr Gln Asp
    370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
        435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Val Ala Ser Lys Leu Ser Ser Lys
                485                 490                 495

Ser Glu Lys Glu Leu Lys Asn Arg Arg Lys Lys Lys Gln Lys Glu
            500                 505                 510

Gln Ser Gly Glu Glu Lys Asn Asp Arg Val Leu Lys Ser Glu Ser
        515                 520                 525

Glu Asp Ser Ile Arg Arg Lys Gly Phe Arg Phe Ser Leu Glu Gly Ser
    530                 535                 540

Arg Leu Thr Tyr Glu Lys Arg Phe Ser Ser Pro His Gln Ser Leu Leu
545                 550                 555                 560
```

```
Ser Ile Arg Gly Ser Leu Phe Ser Pro Arg Arg Asn Ser Arg Ala Ser
            565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
            595                 600                 605

Asp Ser Leu Phe Val Pro His Arg His Gly Glu Arg Arg His Ser Asn
            610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Pro Ser Thr Leu Thr Ser Ala Gly Gln Leu Leu Pro Glu
                660                 665                 670

Gly Thr Thr Thr Glu Thr Glu Ile Arg Lys Arg Ser Ser Ser Tyr
                675                 680                 685

His Val Ser Met Asp Leu Leu Glu Asp Pro Thr Ser Arg Gln Arg Ala
            690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
                740                 745                 750

Asn Leu Val Val Met Asp Pro Phe Val Asp Leu Ala Ile Thr Ile Cys
            755                 760                 765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
                820                 825                 830

Leu Ser Leu Met Glu Leu Gly Leu Ala Asn Val Glu Gly Leu Ser Val
                835                 840                 845

Leu Arg Ser Phe Arg Leu Leu Arg Val Phe Lys Leu Ala Lys Ser Trp
850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
            915                 920                 925

Phe His Ser Phe Leu Ile Val Phe Arg Val Leu Cys Gly Glu Trp Ile
            930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
```

-continued

```
                980             985             990
Ala Thr Asp Asp Asp Asn Glu Met  Asn Asn Leu Gln Ile  Ala Val Gly
            995             1000            1005
Arg Met Gln Lys Gly Ile Asp Phe  Val Lys Arg Lys Ile  Arg Glu
       1010            1015            1020
Phe Ile Gln Lys Ala Phe Val Arg  Lys Gln Lys Ala Leu  Asp Glu
       1025            1030            1035
Ile Lys Pro Leu Glu Asp Leu Asn  Asn Lys Lys Asp Ser  Cys Ile
       1040            1045            1050
Ser Asn His Thr Thr Ile Glu Ile  Gly Lys Asp Leu Asn  Tyr Leu
       1055            1060            1065
Lys Asp Gly Asn Gly Thr Thr Ser  Gly Ile Gly Ser Ser  Val Glu
       1070            1075            1080
Lys Tyr Val Val Asp Glu Ser Asp  Tyr Met Ser Phe Ile  Asn Asn
       1085            1090            1095
Pro Ser Leu Thr Val Thr Val Pro  Ile Ala Val Gly Glu  Ser Asp
       1100            1105            1110
Phe Glu Asn Leu Asn Thr Glu Glu  Phe Ser Ser Glu Ser  Asp Met
       1115            1120            1125
Glu Glu Ser Lys Glu Lys Leu Asn  Ala Thr Ser Ser Ser  Glu Gly
       1130            1135            1140
Ser Thr Val Asp Ile Gly Ala Pro  Ala Glu Gly Glu Gln  Pro Glu
       1145            1150            1155
Val Glu Pro Glu Glu Ser Leu Glu  Pro Glu Ala Cys Phe  Thr Glu
       1160            1165            1170
Asp Cys Val Arg Lys Phe Lys Cys  Cys Gln Ile Ser Ile  Glu Glu
       1175            1180            1185
Gly Lys Gly Lys Leu Trp Trp Asn  Leu Arg Lys Thr Cys  Tyr Lys
       1190            1195            1200
Ile Val Glu His Asn Trp Phe Glu  Thr Phe Ile Val Phe  Met Ile
       1205            1210            1215
Leu Leu Ser Ser Gly Ala Leu Ala  Phe Glu Asp Ile Tyr  Ile Glu
       1220            1225            1230
Gln Arg Lys Thr Ile Lys Thr Met  Leu Glu Tyr Ala Asp  Lys Val
       1235            1240            1245
Phe Thr Tyr Ile Phe Ile Leu Glu  Met Leu Leu Lys Trp  Val Ala
       1250            1255            1260
Tyr Gly Phe Gln Val Tyr Phe Thr  Asn Ala Trp Cys Trp  Leu Asp
       1265            1270            1275
Phe Leu Ile Val Asp Val Ser Leu  Val Ser Leu Thr Ala  Asn Ala
       1280            1285            1290
Leu Gly Tyr Ser Glu Leu Gly Ala  Ile Lys Ser Leu Arg  Thr Leu
       1295            1300            1305
Arg Ala Leu Arg Pro Leu Arg Ala  Leu Ser Arg Phe Glu  Gly Met
       1310            1315            1320
Arg Val Val Val Asn Ala Leu Leu  Gly Ala Ile Pro Ser  Ile Met
       1325            1330            1335
Asn Val Leu Leu Val Cys Leu Ile  Phe Trp Leu Ile Phe  Ser Ile
       1340            1345            1350
Met Gly Val Asn Leu Phe Ala Gly  Lys Phe Tyr His Cys  Ile Asn
       1355            1360            1365
Tyr Thr Thr Gly Glu Met Phe Asp  Val Ser Val Val Asn  Asn Tyr
       1370            1375            1380
```

-continued

Ser Glu Cys Lys Ala Leu Ile Glu Ser Asn Gln Thr Ala Arg Trp
1385                    1390                    1395

Lys Asn Val Lys Val Asn Phe Asp Asn Val Gly Leu Gly Tyr Leu
1400                    1405                    1410

Ser Leu Leu Gln Val Ala Thr Phe Lys Gly Trp Met Asp Ile Met
1415                    1420                    1425

Tyr Ala Ala Val Asp Ser Arg Asn Val Glu Leu Gln Pro Lys Tyr
1430                    1435                    1440

Glu Asp Asn Leu Tyr Met Tyr Leu Tyr Phe Val Ile Phe Ile Ile
1445                    1450                    1455

Phe Gly Ser Phe Phe Thr Leu Asn Leu Phe Ile Gly Val Ile Ile
1460                    1465                    1470

Asp Asn Phe Asn Gln Gln Lys Lys Lys Phe Gly Gly Gln Asp Ile
1475                    1480                    1485

Phe Met Thr Glu Glu Gln Lys Lys Tyr Tyr Asn Ala Met Lys Lys
1490                    1495                    1500

Leu Gly Ser Lys Lys Pro Gln Lys Pro Ile Pro Arg Pro Ala Asn
1505                    1510                    1515

Lys Phe Gln Gly Met Val Phe Asp Phe Val Thr Lys Gln Val Phe
1520                    1525                    1530

Asp Ile Ser Ile Met Ile Leu Ile Cys Leu Asn Met Val Thr Met
1535                    1540                    1545

Met Val Glu Thr Asp Asp Gln Ser Gln Glu Met Thr Asn Ile Leu
1550                    1555                    1560

Tyr Trp Ile Asn Leu Val Phe Ile Val Leu Phe Thr Gly Glu Cys
1565                    1570                    1575

Val Leu Lys Leu Ile Ser Leu Arg Tyr Tyr Tyr Phe Thr Ile Gly
1580                    1585                    1590

Trp Asn Ile Phe Asp Phe Val Val Val Ile Leu Ser Ile Val Gly
1595                    1600                    1605

Met Phe Leu Ala Glu Leu Ile Glu Lys Tyr Phe Val Ser Pro Thr
1610                    1615                    1620

Leu Phe Arg Val Ile Arg Leu Ala Arg Ile Gly Arg Ile Leu Arg
1625                    1630                    1635

Leu Ile Lys Gly Ala Lys Gly Ile Arg Thr Leu Leu Phe Ala Leu
1640                    1645                    1650

Met Met Ser Leu Pro Ala Leu Phe Asn Ile Gly Leu Leu Leu Phe
1655                    1660                    1665

Leu Val Met Phe Ile Tyr Ala Ile Phe Gly Met Ser Asn Phe Ala
1670                    1675                    1680

Tyr Val Lys Arg Glu Val Gly Ile Asp Asp Met Phe Asn Phe Glu
1685                    1690                    1695

Thr Phe Gly Asn Ser Met Ile Cys Leu Phe Gln Ile Thr Thr Ser
1700                    1705                    1710

Ala Gly Trp Asp Gly Leu Leu Ala Pro Ile Leu Asn Ser Gly Pro
1715                    1720                    1725

Pro Asp Cys Asp Pro Asp Lys Asp His Pro Gly Ser Ser Val Lys
1730                    1735                    1740

Gly Asp Cys Gly Asn Pro Ser Val Gly Ile Phe Phe Phe Val Ser
1745                    1750                    1755

Tyr Ile Ile Ile Ser Phe Leu Val Val Leu Asn Met Tyr Ile Ala
1760                    1765                    1770

Val Ile Leu Glu Asn Phe Ser Val Ala Thr Glu Glu Ser Ala Glu
1775                    1780                    1785

Pro Leu Ser Glu Asp Asp Phe Glu Met Phe Tyr Glu Val Trp Glu
    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
    1865                1870                1875

Met Glu Glu Arg Phe Met Ala Ser Asn Pro Ser Lys Val Ser Tyr
    1880                1885                1890

Glu Pro Ile Thr Thr Thr Leu Lys Arg Lys Gln Glu Glu Val Ser
    1895                1900                1905

Ala Ile Ile Ile Gln Arg Ala Tyr Arg Arg Tyr Leu Leu Lys Gln
    1910                1915                1920

Lys Val Lys Lys Val Ser Ser Ile Tyr Lys Lys Asp Lys Gly Lys
    1925                1930                1935

Glu Cys Asp Gly Thr Pro Ile Lys Glu Asp Thr Leu Ile Asp Lys
    1940                1945                1950

Leu Asn Glu Asn Ser Thr Pro Glu Lys Thr Asp Met Thr Pro Ser
    1955                1960                1965

Thr Thr Ser Pro Pro Ser Tyr Asp Ser Val Thr Lys Pro Glu Lys
    1970                1975                1980

Glu Lys Phe Glu Lys Asp Lys Ser Glu Lys Glu Asp Lys Gly Lys
    1985                1990                1995

Asp Ile Arg Glu Ser Lys Lys
    2000                2005

<210> SEQ ID NO 85
<211> LENGTH: 2005
<212> TYPE: PRT
<213> ORGANISM: Homo sapiens

<400> SEQUENCE: 85

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

-continued

```
Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asp Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
                260                 265                 270

Asn Leu Arg Asn Lys Cys Leu Gln Trp Pro Pro Asp Asn Ser Ser Phe
            275                 280                 285

Glu Ile Asn Ile Thr Ser Phe Phe Asn Asn Ser Leu Asp Gly Asn Gly
    290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
                340                 345                 350

Cys Val Lys Ala Gly Arg Asn Pro Asn Tyr Gly Tyr Thr Ser Phe Asp
            355                 360                 365

Thr Phe Ser Trp Ala Phe Leu Ser Leu Phe Arg Leu Met Thr Gln Asp
        370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
                420                 425                 430

Gln Ala Thr Leu Glu Glu Ala Glu Gln Lys Glu Ala Glu Phe Gln Gln
            435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Gln Lys Glu
                500                 505                 510

Gln Ser Gly Glu Glu Glu Lys Asn Asp Arg Val Leu Lys Ser Glu Ser
            515                 520                 525

Glu Asp Ser Ile Arg Arg Lys Gly Phe Arg Phe Ser Leu Glu Gly Ser
    530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
```

```
                        565                 570                 575
Leu Phe Ser Phe Arg Gly Arg Ala Lys Asp Ile Gly Ser Glu Asn Asp
                580                 585                 590

Phe Ala Asp Asp Glu His Ser Thr Phe Glu Asp Asn Asp Ser Arg Arg
            595                 600                 605

Asp Ser Leu Phe Val Pro His Arg His Gly Glu Arg Arg His Ser Asn
        610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
        675                 680                 685

His Val Ser Met Asp Leu Leu Glu Asp Pro Thr Ser Arg Gln Arg Ala
    690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
        755                 760                 765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
    850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
        915                 920                 925

Phe His Ser Phe Leu Ile Val Phe Arg Val Leu Cys Gly Glu Trp Ile
930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990
```

```
Ala Thr Asp Asp Asp Asn Glu Met   Asn Asn Ile Gln Ile  Ala Val Gly
        995                 1000                1005

Arg Met Gln Lys Gly Ile Asp Phe   Val Lys Arg Lys  Ile  Arg Glu
    1010                1015                1020

Phe Ile Gln Lys Ala Phe Val Arg   Lys Gln Lys Ala  Leu  Asp Glu
    1025                1030                1035

Ile Lys Pro Leu Glu Asp Leu Asn   Asn Lys Lys Asp  Ser  Cys Ile
    1040                1045                1050

Ser Asn His Thr Thr Ile Glu Ile   Gly Lys Asp Leu  Asn  Tyr Leu
    1055                1060                1065

Lys Asp Gly Asn Gly Thr Thr Ser   Gly Ile Gly Ser  Ser  Val Glu
    1070                1075                1080

Lys Tyr Val Val Asp Glu Ser Asp   Tyr Met Ser Phe  Ile  Asn Asn
    1085                1090                1095

Pro Ser Leu Thr Val Thr Val Pro   Ile Ala Val Gly  Glu  Ser Asp
    1100                1105                1110

Phe Glu Asn Leu Asn Thr Glu Glu   Phe Ser Ser Glu  Ser  Asp Met
    1115                1120                1125

Glu Glu Ser Lys Glu Lys Leu Asn   Ala Thr Ser Ser  Ser  Glu Gly
    1130                1135                1140

Ser Thr Val Asp Ile Gly Ala Pro   Ala Glu Gly Glu  Gln  Pro Glu
    1145                1150                1155

Val Glu Pro Glu Glu Ser Leu Glu   Pro Glu Ala Cys  Phe  Thr Glu
    1160                1165                1170

Asp Cys Val Arg Lys Phe Lys Cys   Cys Gln Ile Ser  Ile  Glu Glu
    1175                1180                1185

Gly Lys Gly Lys Leu Trp Trp Asn   Leu Arg Lys Thr  Cys  Tyr Lys
    1190                1195                1200

Ile Val Glu His Asn Trp Phe Glu   Thr Phe Ile Val  Phe  Met Ile
    1205                1210                1215

Leu Leu Ser Ser Gly Ala Leu Ala   Phe Glu Asp Ile  Tyr  Ile Glu
    1220                1225                1230

Gln Arg Lys Thr Ile Lys Thr Met   Leu Glu Tyr Ala  Asp  Lys Val
    1235                1240                1245

Phe Thr Tyr Ile Phe Ile Leu Glu   Met Leu Leu Lys  Trp  Val Ala
    1250                1255                1260

Tyr Gly Phe Gln Val Tyr Phe Thr   Asn Ala Trp Cys  Trp  Leu Asp
    1265                1270                1275

Phe Leu Ile Val Asp Val Ser Leu   Val Ser Leu Thr  Ala  Asn Ala
    1280                1285                1290

Leu Gly Tyr Ser Glu Leu Gly Ala   Ile Lys Ser Leu  Arg  Thr Leu
    1295                1300                1305

Arg Ala Leu Arg Pro Leu Arg Ala   Leu Ser Arg Phe  Glu  Gly Met
    1310                1315                1320

Arg Val Val Val Asn Ala Leu Leu   Gly Ala Ile Pro  Ser  Ile Met
    1325                1330                1335

Asn Val Leu Leu Val Cys Leu Ile   Phe Trp Leu Ile  Phe  Ser Ile
    1340                1345                1350

Met Gly Val Asn Leu Phe Ala Gly   Lys Phe Tyr His  Cys  Ile Asn
    1355                1360                1365

Tyr Thr Thr Gly Glu Met Phe Asp   Val Ser Val Val  Asn  Asn Tyr
    1370                1375                1380

Ser Glu Cys Lys Ala Leu Ile Glu   Ser Asn Gln Thr  Ala  Arg Trp
    1385                1390                1395
```

| | | | | | | | | | |
|---|---|---|---|---|---|---|---|---|---|
|Lys|Asn|Val|Lys|Val|Asn|Phe|Asp|Asn|Val|Gly|Leu|Gly|Tyr|Leu|

Lys Asn Val Lys Val Asn Phe Asp Asn Val Gly Leu Gly Tyr Leu
    1400            1405            1410

Ser Leu Leu Gln Val Ala Thr Phe Lys Gly Trp Met Asp Ile Met
    1415            1420            1425

Tyr Ala Ala Val Asp Ser Arg Asn Val Glu Leu Gln Pro Lys Tyr
    1430            1435            1440

Glu Asp Asn Leu Tyr Met Tyr Leu Tyr Phe Val Ile Phe Ile Ile
    1445            1450            1455

Phe Gly Ser Phe Phe Thr Leu Asn Leu Phe Ile Gly Val Ile Ile
    1460            1465            1470

Asp Asn Phe Asn Gln Gln Lys Lys Lys Phe Gly Gly Gln Asp Ile
    1475            1480            1485

Phe Met Thr Glu Glu Gln Lys Lys Tyr Tyr Asn Ala Met Lys Lys
    1490            1495            1500

Leu Gly Ser Lys Lys Pro Gln Lys Pro Ile Pro Arg Pro Ala Asn
    1505            1510            1515

Lys Phe Gln Gly Met Val Phe Asp Phe Val Thr Lys Gln Val Phe
    1520            1525            1530

Asp Ile Ser Ile Met Ile Leu Ile Cys Leu Asn Met Val Thr Met
    1535            1540            1545

Met Val Glu Thr Asp Asp Gln Ser Gln Glu Met Thr Asn Ile Leu
    1550            1555            1560

Tyr Trp Ile Asn Leu Val Phe Ile Val Leu Phe Thr Gly Glu Cys
    1565            1570            1575

Val Leu Lys Leu Ile Ser Leu Arg Tyr Tyr Tyr Phe Thr Ile Gly
    1580            1585            1590

Trp Asn Ile Phe Asp Phe Val Val Val Ile Leu Ser Ile Val Gly
    1595            1600            1605

Met Phe Leu Ala Glu Leu Ile Glu Lys Tyr Phe Val Ser Pro Thr
    1610            1615            1620

Leu Phe Arg Val Ile Arg Leu Ala Arg Ile Gly Arg Ile Leu Arg
    1625            1630            1635

Leu Ile Lys Gly Ala Lys Gly Ile Arg Thr Leu Leu Phe Ala Leu
    1640            1645            1650

Met Met Ser Leu Pro Ala Leu Phe Asn Ile Gly Leu Leu Leu Phe
    1655            1660            1665

Leu Val Met Phe Ile Tyr Ala Ile Phe Gly Met Ser Asn Phe Ala
    1670            1675            1680

Tyr Val Lys Arg Glu Val Gly Ile Asp Asp Met Phe Asn Phe Glu
    1685            1690            1695

Thr Phe Gly Asn Ser Met Ile Cys Leu Phe Gln Ile Thr Thr Ser
    1700            1705            1710

Ala Gly Trp Asp Gly Leu Leu Ala Pro Ile Leu Asn Ser Gly Pro
    1715            1720            1725

Pro Asp Cys Asp Pro Asp Lys Asp His Pro Gly Ser Ser Val Lys
    1730            1735            1740

Gly Asp Cys Gly Asn Pro Ser Val Gly Ile Phe Phe Phe Val Ser
    1745            1750            1755

Tyr Ile Ile Ile Ser Phe Leu Val Val Leu Asn Met Tyr Ile Ala
    1760            1765            1770

Val Ile Leu Glu Asn Phe Ser Val Ala Thr Glu Glu Ser Ala Glu
    1775            1780            1785

Pro Leu Ser Glu Asp Asp Phe Glu Met Phe Tyr Glu Val Trp Glu

-continued

```
                    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
    1865                1870                1875

Met Glu Glu Arg Phe Met Ala Ser Asn Pro Ser Lys Val Ser Tyr
    1880                1885                1890

Glu Pro Ile Thr Thr Thr Leu Lys Arg Lys Gln Glu Glu Val Ser
    1895                1900                1905

Ala Ile Ile Ile Gln Arg Ala Tyr Arg Arg Tyr Leu Leu Lys Gln
    1910                1915                1920

Lys Val Lys Lys Val Ser Ser Ile Tyr Lys Lys Asp Lys Gly Lys
    1925                1930                1935

Glu Cys Asp Gly Thr Pro Ile Lys Glu Asp Thr Leu Ile Asp Lys
    1940                1945                1950

Leu Asn Glu Asn Ser Thr Pro Glu Lys Thr Asp Met Thr Pro Ser
    1955                1960                1965

Thr Thr Ser Pro Pro Ser Tyr Asp Ser Val Thr Lys Pro Glu Lys
    1970                1975                1980

Glu Lys Phe Glu Lys Asp Lys Ser Glu Lys Glu Asp Lys Gly Lys
    1985                1990                1995

Asp Ile Arg Glu Ser Lys Lys
    2000                2005

<210> SEQ ID NO 86
<211> LENGTH: 2005
<212> TYPE: PRT
<213> ORGANISM: Homo sapiens

<400> SEQUENCE: 86

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
                20                  25                  30

Lys Ala Lys Arg Pro Lys Gln Glu Arg Lys Asp Glu Asp Asp Glu Asn
            35                  40                  45

Gly Pro Lys Pro Asn Ser Asp Leu Glu Ala Gly Lys Ser Leu Pro Phe
        50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
```

-continued

```
              145                 150                 155                 160
        Thr Phe Thr Gly Ile Tyr Thr Phe Glu Ser Leu Ile Lys Ile Leu Ala
                        165                 170                 175

Arg Gly Phe Cys Leu Glu Asp Phe Thr Phe Leu Arg Asp Pro Trp Asn
                        180                 185                 190

Trp Leu Asp Phe Thr Val Ile Thr Phe Ala Tyr Val Thr Glu Phe Val
                        195                 200                 205

Asp Leu Gly Asn Val Ser Ala Leu Arg Thr Phe Arg Val Leu Arg Ala
                        210                 215                 220

Leu Lys Thr Ile Ser Val Ile Pro Gly Leu Lys Thr Ile Val Gly Ala
        225                 230                 235                 240

Leu Ile Gln Ser Val Lys Lys Leu Ser Asp Val Met Ile Leu Thr Val
                        245                 250                 255

Phe Cys Leu Ser Val Phe Ala Leu Ile Gly Leu Gln Leu Phe Met Gly
                        260                 265                 270

Asn Leu Arg Asn Lys Cys Leu Gln Trp Pro Pro Asp Asn Ser Ser Phe
                        275                 280                 285

Glu Ile Asn Ile Thr Ser Phe Phe Asn Asn Ser Leu Asp Gly Asn Gly
                        290                 295                 300

Thr Thr Phe Asn Arg Thr Val Ser Ile Phe Asn Trp Asp Glu Tyr Ile
        305                 310                 315                 320

Glu Asp Lys Ser His Phe Tyr Phe Leu Glu Gly Gln Asn Asp Ala Leu
                        325                 330                 335

Leu Cys Gly Asn Ser Ser Asp Ala Gly Gln Cys Pro Glu Gly Tyr Ile
                        340                 345                 350

Cys Val Lys Ala Gly Arg Asn Pro Asn Tyr Gly Tyr Thr Ser Phe Asp
                        355                 360                 365

Thr Phe Ser Trp Ala Phe Leu Ser Leu Phe Arg Leu Met Thr Gln Asp
                        370                 375                 380

Phe Trp Glu Asn Leu Tyr Gln Leu Thr Leu Arg Ala Ala Gly Lys Thr
        385                 390                 395                 400

Tyr Met Ile Phe Phe Val Leu Val Ile Phe Leu Gly Ser Phe Tyr Leu
                        405                 410                 415

Ile Asn Leu Ile Leu Ala Val Val Ala Met Ala Tyr Glu Glu Gln Asn
                        420                 425                 430

Gln Ala Thr Leu Glu Glu Ala Glu Gln Lys Glu Ala Glu Phe Gln Gln
                        435                 440                 445

Met Leu Glu Gln Leu Lys Lys Gln Gln Glu Glu Ala Gln Ala Ala Ala
                        450                 455                 460

Ala Ala Ala Ser Ala Glu Ser Arg Asp Phe Ser Gly Ala Gly Gly Ile
        465                 470                 475                 480

Gly Val Phe Ser Glu Ser Ser Val Ala Ser Lys Leu Ser Ser Lys
                        485                 490                 495

Ser Glu Lys Glu Leu Lys Asn Arg Arg Lys Lys Lys Gln Lys Glu
                        500                 505                 510

Gln Ser Gly Glu Glu Lys Asn Asp Arg Val Leu Lys Ser Glu Ser
                        515                 520                 525

Glu Asp Ser Ile Arg Arg Lys Gly Phe Arg Phe Ser Leu Glu Gly Ser
                        530                 535                 540

Arg Leu Thr Tyr Glu Lys Arg Phe Ser Ser Pro His Gln Ser Leu Leu
        545                 550                 555                 560

Ser Ile Arg Gly Ser Leu Phe Ser Pro Arg Arg Asn Ser Arg Ala Ser
                        565                 570                 575
```

```
Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg His Ser Asn
    610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Pro Ser Thr Leu Thr Ser Ala Gly Gln Leu Leu Pro Glu
                660                 665                 670

Gly Thr Thr Thr Glu Thr Glu Ile Arg Lys Arg Arg Ser Ser Ser Tyr
            675                 680                 685

His Val Ser Met Asp Leu Leu Glu Asp Pro Thr Ser Arg Gln Arg Ala
        690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
                740                 745                 750

Asn Leu Val Val Met Asp Pro Phe Val Asp Leu Ala Ile Thr Ile Cys
            755                 760                 765

Ile Val Leu Asn Thr Leu Phe Met Ala Met Glu His Tyr Pro Met Thr
        770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
        915                 920                 925

Phe His Ser Phe Leu Ile Val Phe Arg Val Leu Cys Gly Glu Trp Ile
    930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990

Ala Thr Asp Asp Asp Asn Glu Met Asn Asn Leu Gln Ile Ala Val Gly
        995                 1000                1005
```

```
Arg Met Gln Lys Gly Ile Asp Phe Val Lys Arg Lys Ile Arg Glu
    1010                1015                1020

Phe Ile Gln Lys Ala Phe Val Arg Lys Gln Lys Ala Leu Asp Glu
    1025                1030                1035

Ile Lys Pro Leu Glu Asp Leu Asn Asn Lys Lys Asp Ser Cys Ile
    1040                1045                1050

Ser Asn His Thr Thr Ile Glu Ile Gly Lys Asp Leu Asn Tyr Leu
    1055                1060                1065

Lys Asp Gly Asn Gly Thr Thr Ser Gly Ile Gly Ser Ser Val Glu
    1070                1075                1080

Lys Tyr Val Val Asp Glu Ser Asp Tyr Met Ser Phe Ile Asn Asn
    1085                1090                1095

Pro Ser Leu Thr Val Thr Val Pro Ile Ala Val Gly Glu Ser Asp
    1100                1105                1110

Phe Glu Asn Leu Asn Thr Glu Glu Phe Ser Ser Glu Ser Asp Met
    1115                1120                1125

Glu Glu Ser Lys Glu Lys Leu Asn Ala Thr Ser Ser Ser Glu Gly
    1130                1135                1140

Ser Thr Val Asp Ile Gly Ala Pro Ala Glu Gly Glu Gln Pro Glu
    1145                1150                1155

Val Glu Pro Glu Glu Ser Leu Glu Pro Glu Ala Cys Phe Thr Glu
    1160                1165                1170

Asp Cys Val Arg Lys Phe Lys Cys Cys Gln Ile Ser Ile Glu Glu
    1175                1180                1185

Gly Lys Gly Lys Leu Trp Trp Asn Leu Arg Lys Ala Cys Tyr Lys
    1190                1195                1200

Ile Val Glu His Asn Trp Phe Glu Thr Phe Ile Val Phe Met Ile
    1205                1210                1215

Leu Leu Ser Ser Gly Ala Leu Ala Phe Glu Asp Ile Tyr Ile Glu
    1220                1225                1230

Gln Arg Lys Thr Ile Lys Thr Met Leu Glu Tyr Ala Asp Lys Val
    1235                1240                1245

Phe Thr Tyr Ile Phe Ile Leu Glu Met Leu Leu Lys Trp Val Ala
    1250                1255                1260

Tyr Gly Phe Gln Val Tyr Phe Thr Asn Ala Trp Cys Trp Leu Asp
    1265                1270                1275

Phe Leu Ile Val Asp Val Ser Leu Val Ser Leu Thr Ala Asn Ala
    1280                1285                1290

Leu Gly Tyr Ser Glu Leu Gly Ala Ile Lys Ser Leu Arg Thr Leu
    1295                1300                1305

Arg Ala Leu Arg Pro Leu Arg Ala Leu Ser Arg Phe Glu Gly Met
    1310                1315                1320

Arg Val Val Val Asn Ala Leu Leu Gly Ala Ile Pro Ser Ile Met
    1325                1330                1335

Asn Val Leu Leu Val Cys Leu Ile Phe Trp Leu Ile Phe Ser Ile
    1340                1345                1350

Met Gly Val Asn Leu Phe Ala Gly Lys Phe Tyr His Cys Ile Asn
    1355                1360                1365

Tyr Thr Thr Gly Glu Met Phe Asp Val Ser Val Val Asn Asn Tyr
    1370                1375                1380

Ser Glu Cys Lys Ala Leu Ile Glu Ser Asn Gln Thr Ala Arg Trp
    1385                1390                1395

Lys Asn Val Lys Val Asn Phe Asp Asn Val Gly Leu Gly Tyr Leu
```

-continued

```
                1400                1405                1410
Ser Leu Leu Gln Val Ala Thr Phe Lys Gly Trp Met Asp Ile Met
    1415                1420                1425

Tyr Ala Ala Val Asp Ser Arg Asn Val Glu Leu Gln Pro Lys Tyr
    1430                1435                1440

Glu Asp Asn Leu Tyr Met Tyr Leu Tyr Phe Val Ile Phe Ile Ile
    1445                1450                1455

Phe Gly Ser Phe Phe Thr Leu Asn Leu Phe Ile Gly Val Ile Ile
    1460                1465                1470

Asp Asn Phe Asn Gln Gln Lys Lys Lys Phe Gly Gly Gln Asp Ile
    1475                1480                1485

Phe Met Thr Glu Glu Gln Lys Lys Tyr Tyr Asn Ala Met Lys Lys
    1490                1495                1500

Leu Gly Ser Lys Lys Pro Gln Lys Pro Ile Pro Arg Pro Ala Asn
    1505                1510                1515

Lys Phe Gln Gly Met Val Phe Asp Phe Val Thr Lys Gln Val Phe
    1520                1525                1530

Asp Ile Ser Ile Met Ile Leu Ile Cys Leu Asn Met Val Thr Met
    1535                1540                1545

Met Val Glu Thr Asp Asp Gln Ser Gln Glu Met Thr Asn Ile Leu
    1550                1555                1560

Tyr Trp Ile Asn Leu Val Phe Ile Val Leu Phe Thr Gly Glu Cys
    1565                1570                1575

Val Leu Lys Leu Ile Ser Leu Arg Tyr Tyr Tyr Phe Thr Ile Gly
    1580                1585                1590

Trp Asn Ile Phe Asp Phe Val Val Val Ile Leu Ser Ile Val Gly
    1595                1600                1605

Met Phe Leu Ala Glu Leu Ile Glu Lys Tyr Phe Val Ser Pro Thr
    1610                1615                1620

Leu Phe Arg Val Ile Arg Leu Ala Arg Ile Gly Arg Ile Leu Arg
    1625                1630                1635

Leu Ile Lys Gly Ala Lys Gly Ile Arg Thr Leu Leu Phe Ala Leu
    1640                1645                1650

Met Met Ser Leu Pro Ala Leu Phe Asn Ile Gly Leu Leu Leu Phe
    1655                1660                1665

Leu Val Met Phe Ile Tyr Ala Ile Phe Gly Met Ser Asn Phe Ala
    1670                1675                1680

Tyr Val Lys Arg Glu Val Gly Ile Asp Asp Met Phe Asn Phe Glu
    1685                1690                1695

Thr Phe Gly Asn Ser Met Ile Cys Leu Phe Gln Ile Thr Thr Ser
    1700                1705                1710

Ala Gly Trp Asp Gly Leu Leu Ala Pro Ile Leu Asn Ser Gly Pro
    1715                1720                1725

Pro Asp Cys Asp Pro Asp Lys Asp His Pro Gly Ser Ser Val Lys
    1730                1735                1740

Gly Asp Cys Gly Asn Pro Ser Val Gly Ile Phe Phe Phe Val Ser
    1745                1750                1755

Tyr Ile Ile Ile Ser Phe Leu Val Val Leu Asn Met Tyr Ile Ala
    1760                1765                1770

Val Ile Leu Glu Asn Phe Ser Val Ala Thr Glu Glu Ser Ala Glu
    1775                1780                1785

Pro Leu Ser Glu Asp Asp Phe Glu Met Phe Tyr Glu Val Trp Glu
    1790                1795                1800
```

```
Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
    1865                1870                1875

Met Glu Glu Arg Phe Met Ala Ser Asn Pro Ser Lys Val Ser Tyr
    1880                1885                1890

Glu Pro Ile Thr Thr Thr Leu Lys Arg Lys Gln Glu Glu Val Ser
    1895                1900                1905

Ala Ile Ile Ile Gln Arg Ala Tyr Arg Arg Tyr Leu Leu Lys Gln
    1910                1915                1920

Lys Val Lys Lys Val Ser Ser Ile Tyr Lys Lys Asp Lys Gly Lys
    1925                1930                1935

Glu Cys Asp Gly Thr Pro Ile Lys Glu Asp Thr Leu Ile Asp Lys
    1940                1945                1950

Leu Asn Glu Asn Ser Thr Pro Glu Lys Thr Asp Met Thr Pro Ser
    1955                1960                1965

Thr Thr Ser Pro Pro Ser Tyr Asp Ser Val Thr Lys Pro Glu Lys
    1970                1975                1980

Glu Lys Phe Glu Lys Asp Lys Ser Glu Lys Glu Asp Lys Gly Lys
    1985                1990                1995

Asp Ile Arg Glu Ser Lys Lys
    2000                2005

<210> SEQ ID NO 87
<211> LENGTH: 2005
<212> TYPE: PRT
<213> ORGANISM: Homo sapiens

<400> SEQUENCE: 87

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
                20                  25                  30

Lys Ala Lys Arg Pro Lys Gln Glu Arg Lys Asp Glu Asp Asp Glu Asn
            35                  40                  45

Gly Pro Lys Pro Asn Ser Asp Leu Glu Ala Gly Lys Ser Leu Pro Phe
        50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160
```

```
Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
            195                 200                 205

Asp Leu Gly Asn Val Ser Ala Leu Arg Thr Phe Arg Val Leu Arg Ala
            210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
            275                 280                 285

Glu Ile Asn Ile Thr Ser Phe Phe Asn Asn Ser Leu Asp Gly Asn Gly
            290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
            355                 360                 365

Thr Phe Ser Trp Ala Phe Leu Ser Leu Phe Arg Leu Met Thr Gln Asp
370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
            435                 440                 445

Met Leu Glu Gln Leu Lys Lys Gln Gln Glu Glu Ala Gln Ala Ala Ala
450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Gln Lys Glu
            500                 505                 510

Gln Ser Gly Glu Glu Glu Lys Asn Asp Arg Val Leu Lys Ser Glu Ser
            515                 520                 525

Glu Asp Ser Ile Arg Arg Lys Gly Phe Arg Phe Ser Leu Glu Gly Ser
            530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590
```

```
Phe Ala Asp Asp Glu His Ser Thr Phe Glu Asp Asn Asp Ser Arg Arg
            595                 600                 605

Asp Ser Leu Phe Val Pro His Arg His Gly Glu Arg Arg His Ser Asn
            610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
            675                 680                 685

His Val Ser Met Asp Leu Leu Glu Asp Pro Thr Ser Arg Gln Arg Ala
            690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
                740                 745                 750

Asn Leu Val Val Met Asp Pro Phe Val Asp Leu Ala Ile Thr Ile Cys
                755                 760                 765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
                820                 825                 830

Leu Ser Leu Met Glu Leu Gly Leu Ala Asn Val Glu Gly Leu Ser Val
            835                 840                 845

Leu Arg Ser Phe Arg Leu Leu Arg Val Phe Lys Leu Ala Lys Ser Trp
            850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
            915                 920                 925

Phe His Ser Phe Leu Ile Val Phe Arg Val Leu Cys Gly Glu Trp Ile
            930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
                980                 985                 990

Ala Thr Asp Asp Asp Asn Glu Met  Asn Asn Leu Gln Ile  Ala Val Gly
            995                 1000                1005

Arg Met  Gln Lys Gly Ile Asp  Phe Val Lys Arg Lys  Ile Arg Glu
```

```
             1010                1015                1020

Phe Ile Gln Lys Ala Phe Val Arg Lys Gln Lys Ala Leu Asp Glu
    1025                1030                1035

Ile Lys Pro Leu Glu Asp Leu Asn Asn Lys Lys Asp Ser Cys Ile
    1040                1045                1050

Ser Asn His Thr Thr Ile Glu Ile Gly Lys Asp Leu Asn Tyr Leu
    1055                1060                1065

Lys Asp Gly Asn Gly Thr Thr Ser Gly Ile Gly Ser Ser Val Glu
    1070                1075                1080

Lys Tyr Val Val Asp Glu Ser Asp Tyr Met Ser Phe Ile Asn Asn
    1085                1090                1095

Pro Ser Leu Thr Val Thr Val Pro Ile Ala Val Gly Glu Ser Asp
    1100                1105                1110

Phe Glu Asn Leu Asn Thr Glu Glu Phe Ser Ser Glu Ser Asp Met
    1115                1120                1125

Glu Glu Ser Lys Glu Lys Leu Asn Ala Thr Ser Ser Ser Glu Gly
    1130                1135                1140

Ser Thr Val Asp Ile Gly Ala Pro Ala Glu Gly Glu Gln Pro Glu
    1145                1150                1155

Val Glu Pro Glu Glu Ser Leu Glu Pro Glu Ala Cys Phe Thr Glu
    1160                1165                1170

Asp Cys Val Arg Lys Phe Lys Cys Cys Gln Ile Ser Ile Glu Glu
    1175                1180                1185

Gly Lys Gly Lys Leu Trp Trp Asn Leu Arg Lys Thr Cys Tyr Lys
    1190                1195                1200

Ile Val Glu His Asn Trp Phe Glu Thr Phe Ile Val Phe Met Ile
    1205                1210                1215

Leu Leu Ser Ser Gly Ala Leu Ala Phe Glu Asp Ile Tyr Ile Glu
    1220                1225                1230

Gln Arg Lys Thr Ile Lys Thr Met Leu Glu Tyr Ala Asp Lys Val
    1235                1240                1245

Phe Thr Tyr Ile Phe Ile Leu Glu Met Leu Leu Lys Trp Val Ala
    1250                1255                1260

Tyr Gly Phe Gln Val Tyr Phe Thr Asn Ala Trp Cys Trp Leu Asp
    1265                1270                1275

Phe Leu Ile Val Asp Val Ser Leu Val Ser Leu Thr Ala Asn Ala
    1280                1285                1290

Leu Gly Tyr Ser Glu Leu Gly Ala Ile Lys Ser Leu Arg Thr Leu
    1295                1300                1305

Arg Ala Leu Arg Pro Leu Arg Ala Leu Ser Gln Phe Glu Gly Met
    1310                1315                1320

Arg Val Val Val Asn Ala Leu Leu Gly Ala Ile Pro Ser Ile Met
    1325                1330                1335

Asn Val Leu Leu Val Cys Leu Ile Phe Trp Leu Ile Phe Ser Ile
    1340                1345                1350

Met Gly Val Asn Leu Phe Ala Gly Lys Phe Tyr His Cys Ile Asn
    1355                1360                1365

Tyr Thr Thr Gly Glu Met Phe Asp Val Ser Val Val Asn Asn Tyr
    1370                1375                1380

Ser Glu Cys Lys Ala Leu Ile Glu Ser Asn Gln Thr Ala Arg Trp
    1385                1390                1395

Lys Asn Val Lys Val Asn Phe Asp Asn Val Gly Leu Gly Tyr Leu
    1400                1405                1410
```

-continued

Ser Leu Leu Gln Val Ala Thr Phe Lys Gly Trp Met Asp Ile Met
1415                1420                1425

Tyr Ala Ala Val Asp Ser Arg Asn Val Glu Leu Gln Pro Lys Tyr
1430                1435                1440

Glu Asp Asn Leu Tyr Met Tyr Leu Tyr Phe Val Ile Phe Ile Ile
1445                1450                1455

Phe Gly Ser Phe Phe Thr Leu Asn Leu Phe Ile Gly Val Ile Ile
1460                1465                1470

Asp Asn Phe Asn Gln Gln Lys Lys Lys Phe Gly Gly Gln Asp Ile
1475                1480                1485

Phe Met Thr Glu Glu Gln Lys Lys Tyr Tyr Asn Ala Met Lys Lys
1490                1495                1500

Leu Gly Ser Lys Lys Pro Gln Lys Pro Ile Pro Arg Pro Ala Asn
1505                1510                1515

Lys Phe Gln Gly Met Val Phe Asp Phe Val Thr Lys Gln Val Phe
1520                1525                1530

Asp Ile Ser Ile Met Ile Leu Ile Cys Leu Asn Met Val Thr Met
1535                1540                1545

Met Val Glu Thr Asp Asp Gln Ser Gln Glu Met Thr Asn Ile Leu
1550                1555                1560

Tyr Trp Ile Asn Leu Val Phe Ile Val Leu Phe Thr Gly Glu Cys
1565                1570                1575

Val Leu Lys Leu Ile Ser Leu Arg Tyr Tyr Tyr Phe Thr Ile Gly
1580                1585                1590

Trp Asn Ile Phe Asp Phe Val Val Val Ile Leu Ser Ile Val Gly
1595                1600                1605

Met Phe Leu Ala Glu Leu Ile Glu Lys Tyr Phe Val Ser Pro Thr
1610                1615                1620

Leu Phe Arg Val Ile Arg Leu Ala Arg Ile Gly Arg Ile Leu Arg
1625                1630                1635

Leu Ile Lys Gly Ala Lys Gly Ile Arg Thr Leu Leu Phe Ala Leu
1640                1645                1650

Met Met Ser Leu Pro Ala Leu Phe Asn Ile Gly Leu Leu Leu Phe
1655                1660                1665

Leu Val Met Phe Ile Tyr Ala Ile Phe Gly Met Ser Asn Phe Ala
1670                1675                1680

Tyr Val Lys Arg Glu Val Gly Ile Asp Asp Met Phe Asn Phe Glu
1685                1690                1695

Thr Phe Gly Asn Ser Met Ile Cys Leu Phe Gln Ile Thr Thr Ser
1700                1705                1710

Ala Gly Trp Asp Gly Leu Leu Ala Pro Ile Leu Asn Ser Gly Pro
1715                1720                1725

Pro Asp Cys Asp Pro Asp Lys Asp His Pro Gly Ser Ser Val Lys
1730                1735                1740

Gly Asp Cys Gly Asn Pro Ser Val Gly Ile Phe Phe Phe Val Ser
1745                1750                1755

Tyr Ile Ile Ile Ser Phe Leu Val Val Leu Asn Met Tyr Ile Ala
1760                1765                1770

Val Ile Leu Glu Asn Phe Ser Val Ala Thr Glu Glu Ser Ala Glu
1775                1780                1785

Pro Leu Ser Glu Asp Asp Phe Glu Met Phe Tyr Glu Val Trp Glu
1790                1795                1800

Lys Phe Asp Pro Asp Ala Thr Gln Phe Ile Glu Phe Ala Lys Leu
1805                1810                1815

Ser Asp Phe Ala Asp Ala Leu Asp Pro Pro Leu Leu Ile Ala Lys
    1820            1825            1830

Pro Asn Lys Val Gln Leu Ile Ala Met Asp Leu Pro Met Val Ser
    1835            1840            1845

Gly Asp Arg Ile His Cys Leu Asp Ile Leu Phe Ala Phe Thr Lys
    1850            1855            1860

Arg Val Leu Gly Glu Ser Gly Glu Met Asp Ala Leu Arg Ile Gln
    1865            1870            1875

Met Glu Glu Arg Phe Met Ala Ser Asn Pro Ser Lys Val Ser Tyr
    1880            1885            1890

Glu Pro Ile Thr Thr Thr Leu Lys Arg Lys Gln Glu Glu Val Ser
    1895            1900            1905

Ala Ile Ile Ile Gln Arg Ala Tyr Arg Arg Tyr Leu Leu Lys Gln
    1910            1915            1920

Lys Val Lys Lys Val Ser Ser Ile Tyr Lys Lys Asp Lys Gly Lys
    1925            1930            1935

Glu Cys Asp Gly Thr Pro Ile Lys Glu Asp Thr Leu Ile Asp Lys
    1940            1945            1950

Leu Asn Glu Asn Ser Thr Pro Glu Lys Thr Asp Met Thr Pro Ser
    1955            1960            1965

Thr Thr Ser Pro Pro Ser Tyr Asp Ser Val Thr Lys Pro Glu Lys
    1970            1975            1980

Glu Lys Phe Glu Lys Asp Lys Ser Glu Lys Glu Asp Lys Gly Lys
    1985            1990            1995

Asp Ile Arg Glu Ser Lys Lys
    2000            2005

<210> SEQ ID NO 88
<211> LENGTH: 468
<212> TYPE: PRT
<213> ORGANISM: Homo sapiens

<400> SEQUENCE: 88

Met Ala Ala Arg Gly Ser Gly Pro Arg Ala Leu Arg Leu Leu Leu
1               5                   10                  15

Val Gln Leu Val Ala Gly Ala Leu Arg Ser Ser Arg Ala Arg Ala
                20                  25                  30

Ala Arg Arg Gly Leu Ser Glu Pro Ser Ser Ile Ala Lys His Glu Asp
            35                  40                  45

Ser Leu Leu Lys Asp Leu Phe Gln Asp Tyr Glu Arg Trp Val Arg Pro
    50                  55                  60

Val Glu His Leu Asn Asp Lys Ile Lys Ile Lys Phe Gly Leu Ala Ile
65                  70                  75                  80

Ser Gln Leu Val Asp Val Asp Glu Lys Asn Gln Leu Met Thr Thr Asn
                85                  90                  95

Val Trp Leu Lys Gln Glu Trp Ile Asp Val Lys Leu Arg Trp Asn Pro
                100                 105                 110

Asp Asp Tyr Gly Gly Ile Lys Val Ile Arg Val Pro Ser Asp Ser Ser
            115                 120                 125

Trp Thr Pro Asp Ile Ile Leu Phe Asp Asn Ala Asp Gly Arg Phe Glu
    130                 135                 140

Gly Thr Ser Thr Lys Thr Val Ile Arg Tyr Asn Gly Thr Val Thr Trp
145                 150                 155                 160

Thr Pro Pro Ala Asn Tyr Lys Ser Ser Cys Thr Ile Asp Val Thr Phe
                165                 170                 175

```
Phe Pro Phe Asp Leu Gln Asn Cys Ser Met Lys Phe Gly Ser Trp Thr
            180                 185                 190

Tyr Asp Gly Ser Gln Val Asp Ile Ile Leu Glu Asp Gln Asp Val Asp
        195                 200                 205

Lys Arg Asp Phe Phe Asp Asn Gly Glu Trp Glu Ile Val Ser Ala Thr
    210                 215                 220

Gly Ser Lys Gly Asn Arg Thr Asp Ser Cys Cys Trp Tyr Pro Tyr Val
225                 230                 235                 240

Thr Tyr Ser Phe Val Ile Lys Arg Leu Pro Leu Phe Tyr Thr Leu Phe
            245                 250                 255

Leu Ile Ile Pro Cys Ile Gly Leu Ser Phe Leu Thr Val Leu Val Phe
            260                 265                 270

Tyr Leu Pro Ser Asn Glu Gly Glu Lys Ile Cys Leu Cys Thr Ser Val
            275                 280                 285

Leu Val Ser Leu Thr Val Phe Leu Leu Val Ile Glu Glu Ile Ile Pro
        290                 295                 300

Ser Ser Ser Lys Val Ile Pro Leu Ile Gly Glu Tyr Leu Val Phe Thr
305                 310                 315                 320

Met Ile Phe Val Thr Leu Ser Ile Met Val Thr Val Phe Ala Ile Asn
            325                 330                 335

Ile His His Arg Ser Ser Ser Thr His Asn Ala Met Ala Pro Leu Val
            340                 345                 350

Arg Lys Ile Phe Leu His Thr Leu Pro Lys Leu Leu Ser Met Arg Ser
            355                 360                 365

His Val Asp Arg Tyr Phe Thr Gln Lys Glu Glu Thr Glu Ser Gly Ser
        370                 375                 380

Gly Pro Lys Ser Ser Arg Asn Thr Leu Glu Ala Ala Leu Asp Ser Ile
385                 390                 395                 400

Arg Tyr Ile Thr Thr His Ile Met Lys Glu Asn Asp Val Arg Glu Val
            405                 410                 415

Val Glu Asp Trp Lys Phe Ile Ala Gln Val Leu Asp Arg Met Phe Leu
            420                 425                 430

Trp Thr Phe Leu Phe Val Ser Ile Val Gly Ser Leu Gly Leu Phe Val
        435                 440                 445

Pro Val Ile Tyr Lys Trp Ala Asn Ile Leu Ile Pro Val His Ile Gly
    450                 455                 460

Asn Ala Asn Lys
465

<210> SEQ ID NO 89
<211> LENGTH: 529
<212> TYPE: PRT
<213> ORGANISM: Homo sapiens

<400> SEQUENCE: 89

Met Gly Pro Ser Cys Pro Val Phe Leu Ser Phe Thr Lys Leu Ser Leu
1               5                   10                  15

Trp Trp Leu Leu Leu Thr Pro Ala Gly Gly Glu Glu Ala Lys Arg Pro
            20                  25                  30

Pro Pro Arg Ala Pro Gly Asp Pro Leu Ser Ser Pro Ser Pro Thr Ala
        35                  40                  45

Leu Pro Gln Gly Gly Ser His Thr Glu Thr Glu Asp Arg Leu Phe Lys
    50                  55                  60

His Leu Phe Arg Gly Tyr Asn Arg Trp Ala Arg Pro Val Pro Asn Thr
65                  70                  75                  80
```

```
Ser Asp Val Val Ile Val Arg Phe Gly Leu Ser Ile Ala Gln Leu Ile
            85                  90                  95

Asp Val Asp Glu Lys Asn Gln Met Met Thr Thr Asn Val Trp Leu Lys
            100                 105                 110

Gln Glu Trp Ser Asp Tyr Lys Leu Arg Trp Asn Pro Thr Asp Phe Gly
            115                 120                 125

Asn Ile Thr Ser Leu Arg Val Pro Ser Glu Met Ile Trp Ile Pro Asp
            130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
                180                 185                 190

Asp Gln Gln Asn Cys Lys Met Lys Phe Gly Ser Trp Thr Tyr Asp Lys
            195                 200                 205

Ala Lys Ile Asp Leu Glu Gln Met Glu Gln Thr Val Asp Leu Lys Asp
            210                 215                 220

Tyr Trp Glu Ser Gly Glu Trp Ala Ile Val Asn Ala Thr Gly Thr Tyr
225                 230                 235                 240

Asn Ser Lys Lys Tyr Asp Cys Cys Ala Glu Ile Tyr Pro Asp Val Thr
                245                 250                 255

Tyr Ala Phe Val Ile Arg Arg Leu Pro Leu Phe Tyr Thr Ile Asn Leu
                260                 265                 270

Ile Ile Pro Cys Leu Leu Ile Ser Cys Leu Thr Val Leu Val Phe Tyr
            275                 280                 285

Leu Pro Ser Asp Cys Gly Glu Lys Ile Thr Leu Cys Ile Ser Val Leu
            290                 295                 300

Leu Ser Leu Thr Val Phe Leu Leu Leu Ile Thr Glu Ile Ile Pro Ser
305                 310                 315                 320

Thr Ser Leu Val Ile Pro Leu Ile Gly Glu Tyr Leu Leu Phe Thr Met
                325                 330                 335

Ile Phe Val Thr Leu Ser Ile Val Ile Thr Val Phe Val Leu Asn Val
                340                 345                 350

His His Arg Ser Pro Ser Thr His Thr Met Pro His Trp Val Arg Gly
            355                 360                 365

Ala Leu Leu Gly Cys Val Pro Arg Trp Leu Leu Met Asn Arg Pro Pro
370                 375                 380

Pro Pro Val Glu Leu Cys His Pro Leu Arg Leu Lys Leu Ser Pro Ser
385                 390                 395                 400

Tyr His Trp Leu Glu Ser Asn Val Asp Ala Glu Glu Arg Glu Val Val
                405                 410                 415

Val Glu Glu Glu Asp Arg Trp Ala Cys Ala Gly His Val Ala Pro Ser
            420                 425                 430

Val Gly Thr Leu Cys Ser His Gly His Leu His Ser Gly Ala Ser Gly
            435                 440                 445

Pro Lys Ala Glu Ala Leu Leu Gln Glu Gly Glu Leu Leu Leu Ser Pro
450                 455                 460

His Met Gln Lys Ala Leu Glu Gly Val His Tyr Ile Ala Asp His Leu
465                 470                 475                 480

Arg Ser Glu Asp Ala Asp Ser Ser Val Lys Glu Asp Trp Lys Tyr Val
                485                 490                 495

Ala Met Val Ile Asp Arg Ile Phe Leu Trp Leu Phe Ile Ile Val Cys
```

```
                    500              505                  510
Phe Leu Gly Thr Ile Gly Leu Phe Leu Pro Pro Phe Leu Ala Gly Met
            515                  520                  525

Ile

<210> SEQ ID NO 90
<211> LENGTH: 505
<212> TYPE: PRT
<213> ORGANISM: Homo sapiens

<400> SEQUENCE: 90

Met Gly Ser Gly Pro Leu Ser Leu Pro Leu Ala Leu Ser Pro Pro Arg
1               5                   10                  15

Leu Leu Leu Leu Leu Leu Leu Ser Leu Leu Pro Val Ala Arg Ala Ser
            20                  25                  30

Glu Ala Glu His His Leu Phe Glu Arg Leu Phe Glu Asp Tyr Asn Glu
        35                  40                  45

Ile Ile Arg Pro Val Ala Asn Val Ser Asp Pro Val Ile His Phe
    50                  55                  60

Glu Val Ser Met Ser Gln Leu Val Lys Val Asp Glu Val Asn Gln Ile
65                  70                  75                  80

Met Glu Thr Asn Leu Trp Leu Lys Gln Ile Trp Asn Asp Tyr Lys Leu
                85                  90                  95

Lys Trp Asn Pro Ser Asp Tyr Gly Gly Ala Glu Phe Met Arg Val Pro
            100                 105                 110

Ala Gln Lys Ile Trp Lys Pro Asp Ile Val Leu Tyr Asn Asn Ala Val
        115                 120                 125

Gly Asp Phe Gln Val Asp Asp Lys Thr Lys Ala Leu Leu Lys Tyr Thr
    130                 135                 140

Gly Glu Val Thr Trp Ile Pro Pro Ala Ile Phe Lys Ser Ser Cys Lys
145                 150                 155                 160

Ile Asp Val Thr Tyr Phe Pro Phe Asp Tyr Gln Asn Cys Thr Met Lys
                165                 170                 175

Phe Gly Ser Trp Ser Tyr Asp Lys Ala Lys Ile Asp Leu Val Leu Ile
            180                 185                 190

Gly Ser Ser Met Asn Leu Lys Asp Tyr Trp Glu Ser Gly Glu Trp Ala
        195                 200                 205

Ile Ile Lys Ala Pro Gly Tyr Lys His Asp Ile Lys Tyr Asn Cys Cys
    210                 215                 220

Glu Glu Ile Tyr Pro Asp Ile Thr Tyr Ser Leu Tyr Ile Arg Arg Leu
225                 230                 235                 240

Pro Leu Phe Tyr Thr Ile Asn Leu Ile Ile Pro Cys Leu Leu Ile Ser
                245                 250                 255

Phe Leu Thr Val Leu Val Phe Tyr Leu Pro Ser Asp Cys Gly Glu Lys
            260                 265                 270

Val Thr Leu Cys Ile Ser Val Leu Leu Ser Leu Thr Val Phe Leu Leu
        275                 280                 285

Val Ile Thr Glu Thr Ile Pro Ser Thr Ser Leu Val Ile Pro Leu Ile
    290                 295                 300

Gly Glu Tyr Leu Leu Phe Thr Met Ile Phe Val Thr Leu Ser Ile Val
305                 310                 315                 320

Ile Thr Val Phe Val Leu Asn Val His Tyr Arg Thr Pro Thr Thr His
                325                 330                 335

Thr Met Pro Ser Trp Val Lys Val Phe Leu Asn Leu Leu Pro Arg
            340                 345                 350
```

Val Met Phe Met Thr Arg Pro Thr Ser Asn Glu Gly Asn Ala Gln Lys
            355                 360                 365

Pro Arg Pro Leu Tyr Gly Ala Glu Leu Ser Asn Leu Asn Cys Phe Ser
    370                 375                 380

Arg Ala Glu Ser Lys Gly Cys Lys Glu Gly Tyr Pro Cys Gln Asp Gly
385                 390                 395                 400

Met Cys Gly Tyr Cys His His Arg Arg Ile Lys Ile Ser Asn Phe Ser
                405                 410                 415

Ala Asn Leu Thr Arg Ser Ser Ser Glu Ser Val Asp Ala Val Leu
            420                 425                 430

Ser Leu Ser Ala Leu Ser Pro Glu Ile Lys Glu Ala Ile Gln Ser Val
            435                 440                 445

Lys Tyr Ile Ala Glu Asn Met Lys Ala Gln Asn Glu Ala Lys Glu Ile
            450                 455                 460

Gln Asp Asp Trp Lys Tyr Val Ala Met Val Ile Asp Arg Ile Phe Leu
465                 470                 475                 480

Trp Val Phe Thr Leu Val Cys Ile Leu Gly Thr Ala Gly Leu Phe Leu
                485                 490                 495

Gln Pro Leu Met Ala Arg Glu Asp Ala
            500                 505

<210> SEQ ID NO 91
<211> LENGTH: 118
<212> TYPE: PRT
<213> ORGANISM: Homo sapiens

<400> SEQUENCE: 91

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
            35                  40                  45

Lys Arg Gly Ser Ile Leu Ser Lys Pro Arg Ala Gly Ala Gly Ala
        50                  55                  60

Gly Lys Pro Pro Gln Ala Gln Arg Leu Leu Pro Gln Ala Ala Glu Phe
65                  70                  75                  80

Pro Leu Gln Arg Ala Gly Ala Ala Arg Leu Gly Val His Leu Pro
                85                  90                  95

Arg Leu Arg Val Pro Pro Gly Phe Leu Leu Pro Arg Ala Val Cys Val
                100                 105                 110

Phe His His Gln Gly Val
        115

<210> SEQ ID NO 92
<211> LENGTH: 854
<212> TYPE: PRT
<213> ORGANISM: Homo sapiens

<400> SEQUENCE: 92

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
            35                  40                  45

```
Lys Arg Gly Ser Ile Leu Ser Lys Pro Arg Ala Gly Ala Gly Ala
 50                  55                  60

Gly Lys Pro Pro Lys Arg Asn Ala Phe Tyr Arg Lys Leu Gln Asn Phe
 65                  70                  75                  80

Leu Tyr Asn Val Leu Glu Arg Pro Arg Gly Trp Ala Phe Ile Tyr His
                 85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Phe Gly Val Glu Tyr Phe Val Arg
130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
        290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Gly Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Gln Lys Val Ser Leu Lys Asp Arg Val Phe Ser Ser Pro Arg Gly Val
            420                 425                 430

Ala Ala Lys Gly Lys Gly Ser Pro Gln Ala Gln Thr Val Arg Arg Ser
        435                 440                 445

Pro Ser Ala Asp Gln Ser Leu Glu Asp Ser Pro Ser Lys Val Pro Lys
        450                 455                 460

Ser Trp Ser Phe Gly Asp Arg Ser Arg Ala Arg Gln Ala Phe Arg Ile
465                 470                 475                 480
```

```
Lys Gly Ala Ala Ser Arg Gln Asn Ser Glu Glu Ala Ser Leu Pro Gly
            485                 490                 495

Glu Asp Ile Val Asp Asp Lys Ser Cys Pro Cys Glu Phe Val Thr Glu
        500                 505                 510

Asp Leu Thr Pro Gly Leu Lys Val Ser Ile Arg Ala Val Cys Val Met
        515                 520                 525

Arg Phe Leu Val Ser Lys Arg Lys Phe Lys Glu Ser Leu Arg Pro Tyr
530                 535                 540

Asp Val Met Asp Val Ile Glu Gln Tyr Ser Ala Gly His Leu Asp Met
545                 550                 555                 560

Leu Ser Arg Ile Lys Ser Leu Gln Ser Arg Val Asp Gln Ile Val Gly
                565                 570                 575

Arg Gly Pro Ala Ile Thr Asp Lys Asp Arg Thr Lys Gly Pro Ala Glu
                580                 585                 590

Ala Glu Leu Pro Glu Asp Pro Ser Met Met Gly Arg Leu Gly Lys Val
                595                 600                 605

Glu Lys Gln Val Leu Ser Met Glu Lys Lys Leu Asp Phe Leu Val Asn
610                 615                 620

Ile Tyr Met Gln Arg Met Gly Ile Pro Pro Thr Glu Thr Glu Ala Tyr
625                 630                 635                 640

Phe Gly Ala Lys Glu Pro Glu Pro Ala Pro Tyr His Ser Pro Glu
                645                 650                 655

Asp Ser Arg Glu His Val Asp Arg His Gly Cys Ile Val Lys Ile Val
                660                 665                 670

Arg Ser Ser Ser Ser Thr Gly Gln Lys Asn Phe Ser Ala Pro Pro Ala
                675                 680                 685

Ala Pro Pro Val Gln Cys Pro Pro Ser Thr Ser Trp Gln Pro Gln Ser
                690                 695                 700

His Pro Arg Gln Gly His Gly Thr Ser Pro Val Gly Asp His Gly Ser
705                 710                 715                 720

Leu Val Arg Ile Pro Pro Pro Ala His Glu Arg Ser Leu Ser Ala
                725                 730                 735

Tyr Gly Gly Gly Asn Arg Ala Ser Met Glu Phe Leu Arg Gln Glu Asp
                740                 745                 750

Thr Pro Gly Cys Arg Pro Pro Glu Gly Thr Leu Arg Asp Ser Asp Thr
                755                 760                 765

Ser Ile Ser Ile Pro Ser Val Asp His Glu Glu Leu Glu Arg Ser Phe
        770                 775                 780

Ser Gly Phe Ser Ile Ser Gln Ser Lys Glu Asn Leu Asp Ala Leu Asn
785                 790                 795                 800

Ser Cys Tyr Ala Ala Val Ala Pro Cys Ala Lys Val Arg Pro Tyr Ile
                805                 810                 815

Ala Glu Gly Glu Ser Asp Thr Asp Ser Asp Leu Cys Thr Pro Cys Gly
                820                 825                 830

Pro Pro Pro Arg Ser Ala Thr Gly Glu Gly Pro Phe Gly Asp Val Gly
                835                 840                 845

Trp Ala Gly Pro Arg Lys
        850

<210> SEQ ID NO 93
<211> LENGTH: 429
<212> TYPE: PRT
<213> ORGANISM: Homo sapiens

<400> SEQUENCE: 93
```

```
Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
                100                 105                 110

Ser Thr Ile Lys Glu Tyr Glu Lys Ser Ser Glu Gly Ala Leu Tyr Ile
                115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
                180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
                260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
        340                 345                 350

Arg Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
        370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser Ser
                405                 410                 415

Gln Lys Val Ser Leu Lys Asp Arg Val Phe Ser Ser Pro
```

-continued

```
             420             425

<210> SEQ ID NO 94
<211> LENGTH: 854
<212> TYPE: PRT
<213> ORGANISM: Homo sapiens

<400> SEQUENCE: 94

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
                20                  25                  30

Asp Ser Thr Arg Asp Gly Ala Leu Leu Ile Ala Gly Ser Glu Ala Pro
            35                  40                  45

Lys Arg Gly Ser Ile Leu Ser Lys Pro Arg Ala Gly Gly Ala Gly Ala
50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
```

```
              370                 375                 380
Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Gln Lys Val Ser Leu Lys Asp Arg Val Phe Ser Ser Pro Arg Gly Val
                420                 425                 430

Ala Ala Lys Gly Lys Gly Ser Pro Gln Ala Gln Thr Val Arg Arg Ser
                435                 440                 445

Pro Ser Ala Asp Gln Ser Leu Glu Asp Ser Pro Ser Lys Val Pro Lys
450                 455                 460

Ser Trp Ser Phe Gly Asp Arg Ser Arg Ala Arg Gln Ala Phe Arg Ile
465                 470                 475                 480

Lys Gly Ala Ala Ser Arg Gln Asn Ser Glu Glu Ala Ser Leu Pro Gly
                485                 490                 495

Glu Asp Ile Val Asp Lys Ser Cys Pro Cys Glu Phe Val Thr Glu
                500                 505                 510

Asp Leu Thr Pro Gly Leu Lys Val Ser Ile Arg Ala Val Cys Val Met
                515                 520                 525

Arg Phe Leu Val Ser Lys Arg Lys Phe Lys Glu Ser Leu Arg Pro Tyr
530                 535                 540

Asp Val Met Asp Val Ile Glu Gln Tyr Ser Ala Gly His Leu Asp Met
545                 550                 555                 560

Leu Ser Arg Ile Lys Ser Leu Gln Ser Ser Val Asp Gln Ile Val Gly
                565                 570                 575

Arg Gly Pro Ala Ile Thr Asp Lys Asp Arg Thr Lys Gly Pro Ala Glu
                580                 585                 590

Ala Glu Leu Pro Glu Asp Pro Ser Met Met Gly Arg Leu Gly Lys Val
                595                 600                 605

Glu Lys Gln Val Leu Ser Met Glu Lys Lys Leu Asp Phe Leu Val Asn
                610                 615                 620

Ile Tyr Met Gln Arg Met Gly Ile Pro Pro Thr Glu Thr Glu Ala Tyr
625                 630                 635                 640

Phe Gly Ala Lys Glu Pro Glu Pro Ala Pro Pro Tyr His Ser Pro Glu
                645                 650                 655

Asp Ser Arg Glu His Val Asp Arg His Gly Cys Ile Val Lys Ile Val
                660                 665                 670

Arg Ser Ser Ser Thr Gly Gln Lys Asn Phe Ser Ala Pro Pro Ala
                675                 680                 685

Ala Pro Pro Val Gln Cys Pro Pro Ser Thr Ser Trp Gln Pro Gln Ser
                690                 695                 700

His Pro Arg Gln Gly His Gly Thr Ser Pro Val Gly Asp His Gly Ser
705                 710                 715                 720

Leu Val Arg Ile Pro Pro Pro Ala His Glu Arg Ser Leu Ser Ala
                725                 730                 735

Tyr Gly Gly Asn Arg Ala Ser Met Glu Phe Leu Arg Gln Glu Asp
                740                 745                 750

Thr Pro Gly Cys Arg Pro Pro Glu Gly Thr Leu Arg Asp Ser Asp Thr
                755                 760                 765

Ser Ile Ser Ile Pro Ser Val Asp His Glu Glu Leu Glu Arg Ser Phe
                770                 775                 780

Ser Gly Phe Ser Ile Ser Gln Ser Lys Glu Asn Leu Asp Ala Leu Asn
785                 790                 795                 800
```

```
Ser Cys Tyr Ala Ala Val Ala Pro Cys Ala Lys Val Arg Pro Tyr Ile
                805                 810                 815

Ala Glu Gly Glu Ser Asp Thr Asp Ser Asp Leu Cys Thr Pro Cys Gly
            820                 825                 830

Pro Pro Pro Arg Ser Ala Thr Gly Glu Gly Pro Phe Gly Asp Val Gly
            835                 840                 845

Trp Ala Gly Pro Arg Lys
        850

<210> SEQ ID NO 95
<211> LENGTH: 854
<212> TYPE: PRT
<213> ORGANISM: Homo sapiens

<400> SEQUENCE: 95

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Gly Ala Gly Ala
50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320
```

-continued

```
Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
    370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Gln Lys Val Ser Leu Lys Asp Arg Val Phe Ser Ser Pro Arg Gly Val
                420                 425                 430

Ala Ala Lys Gly Lys Gly Ser Pro Gln Ala Gln Thr Val Arg Arg Ser
            435                 440                 445

Pro Ser Ala Asp Gln Ser Leu Glu Asp Ser Pro Ser Lys Val Pro Lys
        450                 455                 460

Ser Trp Ser Phe Gly Asp Arg Ser Arg Ala Arg Gln Ala Phe Arg Ile
465                 470                 475                 480

Lys Gly Ala Ala Ser Arg Gln Asn Ser Glu Glu Ala Ser Leu Pro Gly
                485                 490                 495

Glu Asp Ile Val Asp Asp Lys Ser Cys Pro Cys Glu Phe Val Thr Glu
                500                 505                 510

Asp Leu Thr Pro Gly Leu Lys Val Ser Ile Arg Ala Val Cys Val Met
            515                 520                 525

Arg Phe Leu Val Ser Lys Arg Lys Phe Lys Glu Ser Leu Arg Pro Tyr
        530                 535                 540

Asp Val Met Asp Val Ile Glu Gln Tyr Ser Ala Gly His Leu Asp Met
545                 550                 555                 560

Leu Ser Arg Ile Lys Ser Leu Gln Ser Arg Val Asp Gln Ile Val Gly
                565                 570                 575

Arg Gly Pro Ala Ile Thr Asp Lys Asp Arg Thr Lys Gly Pro Ala Glu
            580                 585                 590

Ala Glu Leu Pro Glu Asp Pro Ser Met Met Gly Arg Leu Gly Lys Val
        595                 600                 605

Glu Lys Gln Val Leu Ser Met Glu Lys Lys Arg Asp Phe Leu Val Asn
    610                 615                 620

Ile Tyr Met Gln Arg Met Gly Ile Pro Pro Thr Glu Thr Glu Ala Tyr
625                 630                 635                 640

Phe Gly Ala Lys Glu Pro Glu Pro Ala Pro Pro Tyr His Ser Pro Glu
                645                 650                 655

Asp Ser Arg Glu His Val Asp Arg His Gly Cys Ile Val Lys Ile Val
                660                 665                 670

Arg Ser Ser Ser Ser Thr Gly Gln Lys Asn Phe Ser Ala Pro Pro Ala
            675                 680                 685

Ala Pro Pro Val Gln Cys Pro Pro Ser Thr Ser Trp Gln Pro Gln Ser
        690                 695                 700

His Pro Arg Gln Gly His Gly Thr Ser Pro Val Gly Asp His Gly Ser
705                 710                 715                 720

Leu Val Arg Ile Pro Pro Pro Ala His Glu Arg Ser Leu Ser Ala
                725                 730                 735

Tyr Gly Gly Gly Asn Arg Ala Ser Met Glu Phe Leu Arg Gln Glu Asp
                740                 745                 750
```

```
Thr Pro Gly Cys Arg Pro Pro Glu Gly Thr Leu Arg Asp Ser Asp Thr
        755                 760                 765

Ser Ile Ser Ile Pro Ser Val Asp His Glu Glu Leu Glu Arg Ser Phe
    770                 775                 780

Ser Gly Phe Ser Ile Ser Gln Ser Lys Glu Asn Leu Asp Ala Leu Asn
785                 790                 795                 800

Ser Cys Tyr Ala Ala Val Ala Pro Cys Ala Lys Val Arg Pro Tyr Ile
                805                 810                 815

Ala Glu Gly Glu Ser Asp Thr Asp Ser Asp Leu Cys Thr Pro Cys Gly
                820                 825                 830

Pro Pro Pro Arg Ser Ala Thr Gly Glu Gly Pro Phe Gly Asp Val Gly
            835                 840                 845

Trp Ala Gly Pro Arg Lys
        850

<210> SEQ ID NO 96
<211> LENGTH: 6030
<212> TYPE: DNA
<213> ORGANISM: Homo sapiens
<220> FEATURE:
<221> NAME/KEY: CDS
<222> LOCATION: (1)..(6030)

<400> SEQUENCE: 96
```

| | | | | | | | | | | | | | | | | |
|---|---|---|---|---|---|---|---|---|---|---|---|---|---|---|---|---|
| atg gag caa aca gtg ctt gta cca cca gga cct gac agc ttc aac ttc | | | | | | | | | | | | | | | | 48 |
| Met Glu Gln Thr Val Leu Val Pro Pro Gly Pro Asp Ser Phe Asn Phe | | | | | | | | | | | | | | | | |
| 1             5                   10                  15        | | | | | | | | | | | | | | | | |
| ttc acc aga gaa tct ctt gcg gct att gaa aga cgc att gca gaa gaa | | | | | | | | | | | | | | | | 96 |
| Phe Thr Arg Glu Ser Leu Ala Ala Ile Glu Arg Arg Ile Ala Glu Glu | | | | | | | | | | | | | | | | |
|                 20                  25                  30       | | | | | | | | | | | | | | | | |
| aag gca aag aat ccc aaa cca gac aaa aaa gat gac gac gaa aat ggc | | | | | | | | | | | | | | | | 144 |
| Lys Ala Lys Asn Pro Lys Pro Asp Lys Lys Asp Asp Asp Glu Asn Gly | | | | | | | | | | | | | | | | |
|         35                  40                  45              | | | | | | | | | | | | | | | | |
| cca aag cca aat agt gac ttg gaa gct gga aag aac ctt cca ttt att | | | | | | | | | | | | | | | | 192 |
| Pro Lys Pro Asn Ser Asp Leu Glu Ala Gly Lys Asn Leu Pro Phe Ile | | | | | | | | | | | | | | | | |
|     50                  55                  60                  | | | | | | | | | | | | | | | | |
| tat gga gac att cct cca gag atg gtg tca gag ccc ctg gag gac ctg | | | | | | | | | | | | | | | | 240 |
| Tyr Gly Asp Ile Pro Pro Glu Met Val Ser Glu Pro Leu Glu Asp Leu | | | | | | | | | | | | | | | | |
| 65                  70                  75                  80  | | | | | | | | | | | | | | | | |
| gac ccc tac tat atc aat aag aaa act ttt ata gta ttg aat aaa ttg | | | | | | | | | | | | | | | | 288 |
| Asp Pro Tyr Tyr Ile Asn Lys Lys Thr Phe Ile Val Leu Asn Lys Leu | | | | | | | | | | | | | | | | |
|                 85                  90                  95       | | | | | | | | | | | | | | | | |
| aag gcc atc ttc cgg ttc agt gcc acc tct gcc ctg tac att tta act | | | | | | | | | | | | | | | | 336 |
| Lys Ala Ile Phe Arg Phe Ser Ala Thr Ser Ala Leu Tyr Ile Leu Thr | | | | | | | | | | | | | | | | |
|         100                 105                 110             | | | | | | | | | | | | | | | | |
| ccc ttc aat cct ctt agg aaa ata gct att aag att ttg gta cat tca | | | | | | | | | | | | | | | | 384 |
| Pro Phe Asn Pro Leu Arg Lys Ile Ala Ile Lys Ile Leu Val His Ser | | | | | | | | | | | | | | | | |
|     115                 120                 125                 | | | | | | | | | | | | | | | | |
| tta ttc agc atg cta att atg tgc act att ttg aca aac tgt gtg ttt | | | | | | | | | | | | | | | | 432 |
| Leu Phe Ser Met Leu Ile Met Cys Thr Ile Leu Thr Asn Cys Val Phe | | | | | | | | | | | | | | | | |
| 130                 135                 140                     | | | | | | | | | | | | | | | | |
| atg aca atg agt aac cct cct gat tgg aca aag aat gta gaa tac acc | | | | | | | | | | | | | | | | 480 |
| Met Thr Met Ser Asn Pro Pro Asp Trp Thr Lys Asn Val Glu Tyr Thr | | | | | | | | | | | | | | | | |
| 145                 150                 155                 160 | | | | | | | | | | | | | | | | |
| ttc aca gga ata tat act ttt gaa tca ctt ata aaa att att gca agg | | | | | | | | | | | | | | | | 528 |
| Phe Thr Gly Ile Tyr Thr Phe Glu Ser Leu Ile Lys Ile Ile Ala Arg | | | | | | | | | | | | | | | | |
|                 165                 170                 175     | | | | | | | | | | | | | | | | |
| gga ttc tgt tta gaa gat ttt act ttc ctt cgg gat cca tgg aac tgg | | | | | | | | | | | | | | | | 576 |
| Gly Phe Cys Leu Glu Asp Phe Thr Phe Leu Arg Asp Pro Trp Asn Trp | | | | | | | | | | | | | | | | |
|         180                 185                 190             | | | | | | | | | | | | | | | | |

-continued

| | | |
|---|---|---|
| ctc gat ttc act gtc att aca ttt gcg tac gtc aca gag ttt gtg gac<br>Leu Asp Phe Thr Val Ile Thr Phe Ala Tyr Val Thr Glu Phe Val Asp<br>     195                   200                205 | 624 |
| ctg ggc aat gtc tcg gca ttg aga aca ttc aga gtt ctc cga gca ttg<br>Leu Gly Asn Val Ser Ala Leu Arg Thr Phe Arg Val Leu Arg Ala Leu<br>210                   215                   220 | 672 |
| aag acg att tca gtc att cca ggc ctg aaa acc att gtg gga gcc ctg<br>Lys Thr Ile Ser Val Ile Pro Gly Leu Lys Thr Ile Val Gly Ala Leu<br>225                     230                 235              240 | 720 |
| atc cag tct gtg aag aag ctc tca gat gta atg atc ctg act gtg ttc<br>Ile Gln Ser Val Lys Lys Leu Ser Asp Val Met Ile Leu Thr Val Phe<br>               245                 250              255 | 768 |
| tgt ctg agc gta ttt gct cta att ggg ctg cag ctg ttc atg ggc aac<br>Cys Leu Ser Val Phe Ala Leu Ile Gly Leu Gln Leu Phe Met Gly Asn<br>           260                   265              270 | 816 |
| ctg agg aat aaa tgt ata caa tgg cct ccc acc aat gct tcc ttg gag<br>Leu Arg Asn Lys Cys Ile Gln Trp Pro Pro Thr Asn Ala Ser Leu Glu<br>     275                   280                   285 | 864 |
| gaa cat agt ata gaa aag aat ata act gtg aat tat aat ggt aca ctt<br>Glu His Ser Ile Glu Lys Asn Ile Thr Val Asn Tyr Asn Gly Thr Leu<br>290                   295                   300 | 912 |
| ata aat gaa act gtc ttt gag ttt gac tgg aag tca tat att caa gat<br>Ile Asn Glu Thr Val Phe Glu Phe Asp Trp Lys Ser Tyr Ile Gln Asp<br>305                   310                 315              320 | 960 |
| tca aga tat cat tat ttc ctg gag ggt ttt tta gat gca cta cta tgt<br>Ser Arg Tyr His Tyr Phe Leu Glu Gly Phe Leu Asp Ala Leu Leu Cys<br>               325                 330              335 | 1008 |
| gga aat agc tct gat gca ggc caa tgt cca gag gga tat atg tgt gtg<br>Gly Asn Ser Ser Asp Ala Gly Gln Cys Pro Glu Gly Tyr Met Cys Val<br>           340                   345              350 | 1056 |
| aaa gct ggt aga aat ccc aat tat ggc tac aca agc ttt gat acc ttc<br>Lys Ala Gly Arg Asn Pro Asn Tyr Gly Tyr Thr Ser Phe Asp Thr Phe<br>     355                   360                   365 | 1104 |
| agt tgg gct ttt ttg tcc ttg ttt cga cta atg act cag gac ttc tgg<br>Ser Trp Ala Phe Leu Ser Leu Phe Arg Leu Met Thr Gln Asp Phe Trp<br>370                     375                   380 | 1152 |
| gaa aat ctt tat caa ctg aca tta cgt gct gct ggg aaa acg tac atg<br>Glu Asn Leu Tyr Gln Leu Thr Leu Arg Ala Ala Gly Lys Thr Tyr Met<br>385                   390                 395              400 | 1200 |
| ata ttt ttt gta ttg gtc att ttc ttg ggc tca ttc tac cta ata aat<br>Ile Phe Phe Val Leu Val Ile Phe Leu Gly Ser Phe Tyr Leu Ile Asn<br>               405                 410              415 | 1248 |
| ttg atc ctg gct gtg gtg gcc atg gcc tac gag gaa cag aat cag gcc<br>Leu Ile Leu Ala Val Val Ala Met Ala Tyr Glu Glu Gln Asn Gln Ala<br>           420                   425              430 | 1296 |
| acc ttg gaa gaa gca gaa cag aaa gag gcc gaa ttt cag cag atg att<br>Thr Leu Glu Glu Ala Glu Gln Lys Glu Ala Glu Phe Gln Gln Met Ile<br>     435                   440                   445 | 1344 |
| gaa cag ctt aaa aag caa cag gag gca gct cag cag gca gca acg gca<br>Glu Gln Leu Lys Lys Gln Gln Glu Ala Ala Gln Gln Ala Ala Thr Ala<br>450                   455                   460 | 1392 |
| act gcc tca gaa cat tcc aga gag ccc agt gca gca ggc agg ctc tca<br>Thr Ala Ser Glu His Ser Arg Glu Pro Ser Ala Ala Gly Arg Leu Ser<br>465                   470                 475              480 | 1440 |
| gac agc tca tct gaa gcc tct aag ttg agt tcc aag agt gct aag gaa<br>Asp Ser Ser Ser Glu Ala Ser Lys Leu Ser Ser Lys Ser Ala Lys Glu<br>               485                 490              495 | 1488 |
| aga aga aat cgg agg aag aaa aga aaa cag aaa gag cag tct ggt ggg<br>Arg Arg Asn Arg Arg Lys Lys Arg Lys Gln Lys Glu Gln Ser Gly Gly<br>           500                   505              510 | 1536 |

```
gaa gag aaa gat gag gat gaa ttc caa aaa tct gaa tct gag gac agc        1584
Glu Glu Lys Asp Glu Asp Glu Phe Gln Lys Ser Glu Ser Glu Asp Ser
        515                 520                 525 atc agg agg aaa ggt ttt cgc ttc tcc att gaa ggg aac cga ttg aca        1632
Ile Arg Arg Lys Gly Phe Arg Phe Ser Ile Glu Gly Asn Arg Leu Thr
530                 535                 540 tat gaa aag agg tac tcc tcc cca cac cag tct ttg ttg agc atc cgt        1680
Tyr Glu Lys Arg Tyr Ser Ser Pro His Gln Ser Leu Leu Ser Ile Arg
545                 550                 555                 560 ggc tcc cta ttt tca cca agg cga aat agc aga aca agc ctt ttc agc        1728
Gly Ser Leu Phe Ser Pro Arg Arg Asn Ser Arg Thr Ser Leu Phe Ser
                565                 570                 575 ttt aga ggg cga gca aag gat gtg gga tct gag aac gac ttc gca gat        1776
Phe Arg Gly Arg Ala Lys Asp Val Gly Ser Glu Asn Asp Phe Ala Asp
            580                 585                 590 gat gag cac agc acc ttt gag gat aac gag agc cgt aga gat tcc ttg        1824
Asp Glu His Ser Thr Phe Glu Asp Asn Glu Ser Arg Arg Asp Ser Leu
        595                 600                 605 ttt gtg ccc cga cga cac gga gag aga cgc aac agc aac ctg agt cag        1872
Phe Val Pro Arg Arg His Gly Glu Arg Arg Asn Ser Asn Leu Ser Gln
610                 615                 620 acc agt agg tca tcc cgg atg ctg gca gtg ttt cca gcg aat ggg aag        1920
Thr Ser Arg Ser Ser Arg Met Leu Ala Val Phe Pro Ala Asn Gly Lys
625                 630                 635                 640 atg cac agc act gtg gat tgc aat ggt gtg gtt tcc ttg gtt ggt gga        1968
Met His Ser Thr Val Asp Cys Asn Gly Val Val Ser Leu Val Gly Gly
                645                 650                 655 cct tca gtt cct aca tcg cct gtt gga cag ctt ctg cca gag gtg ata        2016
Pro Ser Val Pro Thr Ser Pro Val Gly Gln Leu Leu Pro Glu Val Ile
            660                 665                 670 ata gat aag cca gct act gat gac aat gga aca acc act gaa act gaa        2064
Ile Asp Lys Pro Ala Thr Asp Asp Asn Gly Thr Thr Thr Glu Thr Glu
        675                 680                 685 atg aga aag aga agg tca agt tct ttc cac gtt tcc atg gac ttt cta        2112
Met Arg Lys Arg Arg Ser Ser Ser Phe His Val Ser Met Asp Phe Leu
690                 695                 700 gaa gat cct tcc caa agg caa cga gca atg agt ata gcc agc att cta        2160
Glu Asp Pro Ser Gln Arg Gln Arg Ala Met Ser Ile Ala Ser Ile Leu
705                 710                 715                 720 aca aat aca gta gaa gaa ctt gaa gaa tcc agg cag aaa tgc cca ccc        2208
Thr Asn Thr Val Glu Glu Leu Glu Glu Ser Arg Gln Lys Cys Pro Pro
                725                 730                 735 tgt tgg tat aaa ttt tcc aac ata ttc tta atc tgg gac tgt tct cca        2256
Cys Trp Tyr Lys Phe Ser Asn Ile Phe Leu Ile Trp Asp Cys Ser Pro
            740                 745                 750 tat tgg tta aaa gtg aaa cat gtt gtc aac ctg gtt gtg atg gac cca        2304
Tyr Trp Leu Lys Val Lys His Val Val Asn Leu Val Val Met Asp Pro
        755                 760                 765 ttt gtt gac ctg gcc atc acc atc tgt att gtc tta aat act ctt ttc        2352
Phe Val Asp Leu Ala Ile Thr Ile Cys Ile Val Leu Asn Thr Leu Phe
770                 775                 780 atg gcc atg gag cac tat cca atg acg gac cat ttc aat aat gtg ctt        2400
Met Ala Met Glu His Tyr Pro Met Thr Asp His Phe Asn Asn Val Leu
785                 790                 795                 800 aca gta gga aac ttg gtt ttc act ggg atc ttt aca gca gaa atg ttt        2448
Thr Val Gly Asn Leu Val Phe Thr Gly Ile Phe Thr Ala Glu Met Phe
                805                 810                 815 ctg aaa att att gcc atg gat cct tac tat tat ttc caa gaa ggc tgg        2496
Leu Lys Ile Ile Ala Met Asp Pro Tyr Tyr Tyr Phe Gln Glu Gly Trp
            820                 825                 830
```

```
aat atc ttt gac ggt ttt att gtg acg ctt agc ctg gta gaa ctt gga    2544
Asn Ile Phe Asp Gly Phe Ile Val Thr Leu Ser Leu Val Glu Leu Gly
    835                 840                 845 ctc gcc aat gtg gaa gga tta tct gtt ctc cgt tca ttt cga ttg ctg    2592
Leu Ala Asn Val Glu Gly Leu Ser Val Leu Arg Ser Phe Arg Leu Leu
850                 855                 860 cga gtt ttc aag ttg gca aaa tct tgg cca acg tta aat atg cta ata    2640
Arg Val Phe Lys Leu Ala Lys Ser Trp Pro Thr Leu Asn Met Leu Ile
865                 870                 875                 880 aag atc atc ggc aat tcc gtg ggg gct ctg gga aat tta acc ctc gtc    2688
Lys Ile Ile Gly Asn Ser Val Gly Ala Leu Gly Asn Leu Thr Leu Val
                885                 890                 895 ttg gcc atc atc gtc ttc att ttt gcc gtg gtc ggc atg cag ctc ttt    2736
Leu Ala Ile Ile Val Phe Ile Phe Ala Val Val Gly Met Gln Leu Phe
            900                 905                 910 ggt aaa agc tac aaa gat tgt gtc tgc aag atc gcc agt gat tgt caa    2784
Gly Lys Ser Tyr Lys Asp Cys Val Cys Lys Ile Ala Ser Asp Cys Gln
        915                 920                 925 ctc cca cgc tgg cac atg aat gac ttc ttc cac tcc ttc ctg att gtg    2832
Leu Pro Arg Trp His Met Asn Asp Phe Phe His Ser Phe Leu Ile Val
930                 935                 940 ttc cgc gtg ctg tgt ggg gag tgg ata gag acc atg tgg gac tgt atg    2880
Phe Arg Val Leu Cys Gly Glu Trp Ile Glu Thr Met Trp Asp Cys Met
945                 950                 955                 960 gag gtt gct ggt caa gcc atg tgc ctt act gtc ttc atg atg gtc atg    2928
Glu Val Ala Gly Gln Ala Met Cys Leu Thr Val Phe Met Met Val Met
                965                 970                 975 gtg att gga aac cta gtg gtc ctg aat ctc ttt ctg gcc ttg ctt ctg    2976
Val Ile Gly Asn Leu Val Val Leu Asn Leu Phe Leu Ala Leu Leu Leu
            980                 985                 990 agc tca ttt agt gca gac aac ctt gca gcc act gat gat gat aat gaa    3024
Ser Ser Phe Ser Ala Asp Asn Leu Ala Ala Thr Asp Asp Asp Asn Glu
        995                 1000                1005 atg aat aat ctc caa att gct gtg gat agg atg cac aaa gga gta        3069
Met Asn Asn Leu Gln Ile Ala Val Asp Arg Met His Lys Gly Val
    1010                1015                1020 gct tat gtg aaa aga aaa ata tat gaa ttt att caa cag tcc ttc        3114
Ala Tyr Val Lys Arg Lys Ile Tyr Glu Phe Ile Gln Gln Ser Phe
1025                1030                1035 att agg aaa caa aag att tta gat gaa att aaa cca ctt gat gat        3159
Ile Arg Lys Gln Lys Ile Leu Asp Glu Ile Lys Pro Leu Asp Asp
1040                1045                1050 cta aac aac aag aaa gac agt tgt atg tcc aat cat aca aca gaa        3204
Leu Asn Asn Lys Lys Asp Ser Cys Met Ser Asn His Thr Thr Glu
    1055                1060                1065 att ggg aaa gat ctt gac tat ctt aaa gat gta aat gga act aca        3249
Ile Gly Lys Asp Leu Asp Tyr Leu Lys Asp Val Asn Gly Thr Thr
1070                1075                1080 agt ggt ata gga act ggc agc agt gtt gaa aaa tac att att gat        3294
Ser Gly Ile Gly Thr Gly Ser Ser Val Glu Lys Tyr Ile Ile Asp
1085                1090                1095 gaa agt gat tac atg tca ttc ata aac aac ccc agt ctt act gtg        3339
Glu Ser Asp Tyr Met Ser Phe Ile Asn Asn Pro Ser Leu Thr Val
    1100                1105                1110 act gta cca att gct gta gga gaa tct gac ttt gaa aat tta aac        3384
Thr Val Pro Ile Ala Val Gly Glu Ser Asp Phe Glu Asn Leu Asn
1115                1120                1125 acg gaa gac ttt agt agt gaa tcg gat ctg gaa gaa agc aaa gag        3429
Thr Glu Asp Phe Ser Ser Glu Ser Asp Leu Glu Glu Ser Lys Glu
1130                1135                1140
```

```
aaa ctg aat gaa agc agt agc tca tca gaa ggt agc act gtg gac      3474
Lys Leu Asn Glu Ser Ser Ser Ser Ser Glu Gly Ser Thr Val Asp
    1145            1150                1155 atc ggc gca cct gta gaa gaa cag ccc gta gtg gaa cct gaa gaa      3519
Ile Gly Ala Pro Val Glu Glu Gln Pro Val Val Glu Pro Glu Glu
    1160            1165                1170 act ctt gaa cca gaa gct tgt ttc act gaa ggc tgt gta caa aga      3564
Thr Leu Glu Pro Glu Ala Cys Phe Thr Glu Gly Cys Val Gln Arg
    1175            1180                1185 ttc aag tgt tgt caa atc aat gtg gaa gaa ggc aga gga aaa caa      3609
Phe Lys Cys Cys Gln Ile Asn Val Glu Glu Gly Arg Gly Lys Gln
    1190            1195                1200 tgg tgg aac ctg aga agg acg tgt ttc cga ata gtt gaa cat aac      3654
Trp Trp Asn Leu Arg Arg Thr Cys Phe Arg Ile Val Glu His Asn
    1205            1210                1215 tgg ttt gag acc ttc att gtt ttc atg att ctc ctt agt agt ggt      3699
Trp Phe Glu Thr Phe Ile Val Phe Met Ile Leu Leu Ser Ser Gly
    1220            1225                1230 gct ctg gca ttt gaa gat ata tat att gat cag cga aag acg att      3744
Ala Leu Ala Phe Glu Asp Ile Tyr Ile Asp Gln Arg Lys Thr Ile
    1235            1240                1245 aag acg atg ttg gaa tat gct gac aag gtt ttc act tac att ttc      3789
Lys Thr Met Leu Glu Tyr Ala Asp Lys Val Phe Thr Tyr Ile Phe
    1250            1255                1260 att ctg gaa atg ctt cta aaa tgg gtg gca tat ggc tat caa aca      3834
Ile Leu Glu Met Leu Leu Lys Trp Val Ala Tyr Gly Tyr Gln Thr
    1265            1270                1275 tat ttc acc aat gcc tgg tgt tgg ctg gac ttc tta att gtt gat      3879
Tyr Phe Thr Asn Ala Trp Cys Trp Leu Asp Phe Leu Ile Val Asp
    1280            1285                1290 gtt tca ttg gtc agt tta aca gca aat gcc ttg ggt tac tca gaa      3924
Val Ser Leu Val Ser Leu Thr Ala Asn Ala Leu Gly Tyr Ser Glu
    1295            1300                1305 ctt gga gcc atc aaa tct ctc agg aca cta aga gct ctg aga cct      3969
Leu Gly Ala Ile Lys Ser Leu Arg Thr Leu Arg Ala Leu Arg Pro
    1310            1315                1320 cta aga gcc tta tct cga ttt gaa ggg atg agg gtg gtt gtg aat      4014
Leu Arg Ala Leu Ser Arg Phe Glu Gly Met Arg Val Val Val Asn
    1325            1330                1335 gcc ctt tta gga gca att cca tcc atc atg aat gtg ctt ctg gtt      4059
Ala Leu Leu Gly Ala Ile Pro Ser Ile Met Asn Val Leu Leu Val
    1340            1345                1350 tgt ctt ata ttc tgg cta att ttc agc atc atg ggc gta aat ttg      4104
Cys Leu Ile Phe Trp Leu Ile Phe Ser Ile Met Gly Val Asn Leu
    1355            1360                1365 ttt gct ggc aaa ttc tac cac tgt att aac acc aca act ggt gac      4149
Phe Ala Gly Lys Phe Tyr His Cys Ile Asn Thr Thr Thr Gly Asp
    1370            1375                1380 agg ttt gac atc gaa gac gtg aat aat cat act gat tgc cta aaa      4194
Arg Phe Asp Ile Glu Asp Val Asn Asn His Thr Asp Cys Leu Lys
    1385            1390                1395 cta ata gaa aga aat gag act gct cga tgg aaa aat gtg aaa gta      4239
Leu Ile Glu Arg Asn Glu Thr Ala Arg Trp Lys Asn Val Lys Val
    1400            1405                1410 aac ttt gat aat gta gga ttt ggg tat ctc tct ttg ctt caa gtt      4284
Asn Phe Asp Asn Val Gly Phe Gly Tyr Leu Ser Leu Leu Gln Val
    1415            1420                1425 gcc aca ttc aaa gga tgg atg gat ata atg tat gca gca gtt gat      4329
Ala Thr Phe Lys Gly Trp Met Asp Ile Met Tyr Ala Ala Val Asp
    1430            1435                1440
```

```
tcc aga aat gtg gaa ctc cag cct aag tat gaa aaa agt ctg tac    4374
Ser Arg Asn Val Glu Leu Gln Pro Lys Tyr Glu Lys Ser Leu Tyr
    1445                1450                1455 atg tat ctt tac ttt gtt att ttc atc atc ttt ggg tcc ttc ttc    4419
Met Tyr Leu Tyr Phe Val Ile Phe Ile Ile Phe Gly Ser Phe Phe
1460                1465                1470 acc ttg aac ctg ttt att ggt gtc atc ata gat aat ttc aac cag    4464
Thr Leu Asn Leu Phe Ile Gly Val Ile Ile Asp Asn Phe Asn Gln
    1475                1480                1485 cag aaa aag aag ttt gga ggt caa gac atc ttt atg aca gaa gaa    4509
Gln Lys Lys Lys Phe Gly Gly Gln Asp Ile Phe Met Thr Glu Glu
1490                1495                1500 cag aag aaa tac tat aat gca atg aaa aaa tta gga tcg aaa aaa    4554
Gln Lys Lys Tyr Tyr Asn Ala Met Lys Lys Leu Gly Ser Lys Lys
    1505                1510                1515 ccg caa aag cct ata cct cga cca gga aac aaa ttt caa gga atg    4599
Pro Gln Lys Pro Ile Pro Arg Pro Gly Asn Lys Phe Gln Gly Met
1520                1525                1530 gtc ttt gac ttc gta acc aga caa gtt ttt gac ata agc atc atg    4644
Val Phe Asp Phe Val Thr Arg Gln Val Phe Asp Ile Ser Ile Met
    1535                1540                1545 att ctc atc tgt ctt aac atg gtc aca atg atg gtg gaa aca gat    4689
Ile Leu Ile Cys Leu Asn Met Val Thr Met Met Val Glu Thr Asp
1550                1555                1560 gac cag agt gaa tat gtg act acc att ttg tca cgc atc aat ctg    4734
Asp Gln Ser Glu Tyr Val Thr Thr Ile Leu Ser Arg Ile Asn Leu
    1565                1570                1575 gtg ttc att gtg cta ttt act gga gag tgt gta ctg aaa ctc atc    4779
Val Phe Ile Val Leu Phe Thr Gly Glu Cys Val Leu Lys Leu Ile
1580                1585                1590 tct cta cgc cat tat tat ttt acc att gga tgg aat att ttt gat    4824
Ser Leu Arg His Tyr Tyr Phe Thr Ile Gly Trp Asn Ile Phe Asp
    1595                1600                1605 ttt gtg gtt gtc att ctc tcc att gta ggt atg ttt ctt gcc gag    4869
Phe Val Val Val Ile Leu Ser Ile Val Gly Met Phe Leu Ala Glu
1610                1615                1620 ctg ata gaa aag tat ttc gtg tcc cct acc ctg ttc cga gtg atc    4914
Leu Ile Glu Lys Tyr Phe Val Ser Pro Thr Leu Phe Arg Val Ile
    1625                1630                1635 cgt ctt gct agg att ggc cga atc cta cgt ctg atc aaa gga gca    4959
Arg Leu Ala Arg Ile Gly Arg Ile Leu Arg Leu Ile Lys Gly Ala
1640                1645                1650 aag ggg atc cgc acg ctg ctc ttt gct ttg atg atg tcc ctt cct    5004
Lys Gly Ile Arg Thr Leu Leu Phe Ala Leu Met Met Ser Leu Pro
    1655                1660                1665 gcg ttg ttt aac atc ggc ctc cta ctc ttc cta gtc atg ttc atc    5049
Ala Leu Phe Asn Ile Gly Leu Leu Leu Phe Leu Val Met Phe Ile
1670                1675                1680 tac gcc atc ttt ggg atg tcc aac ttt gcc tat gtt aag agg gaa    5094
Tyr Ala Ile Phe Gly Met Ser Asn Phe Ala Tyr Val Lys Arg Glu
    1685                1690                1695 gtt ggg atc gat gac atg ttc aac ttt gag acc ttt ggc aac agc    5139
Val Gly Ile Asp Asp Met Phe Asn Phe Glu Thr Phe Gly Asn Ser
1700                1705                1710 atg atc tgc cta ttc caa att aca acc tct gct ggc tgg gat gga    5184
Met Ile Cys Leu Phe Gln Ile Thr Thr Ser Ala Gly Trp Asp Gly
    1715                1720                1725 ttg cta gca ccc att ctc aac agt aag cca ccc gac tgt gac cct    5229
Leu Leu Ala Pro Ile Leu Asn Ser Lys Pro Pro Asp Cys Asp Pro
1730                1735                1740
```

| | | | | | | | | | | | | |
|---|---|---|---|---|---|---|---|---|---|---|---|---|
| aat | aaa | gtt | aac | cct | gga | agc | tca | gtt | aag | gga | gac | tgt | ggg | aac | 5274 |
| Asn | Lys | Val | Asn | Pro | Gly | Ser | Ser | Val | Lys | Gly | Asp | Cys | Gly | Asn | |
| | 1745 | | | | 1750 | | | | | 1755 | | | | | |

| | | | | | | | | | | | | | | | |
|---|---|---|---|---|---|---|---|---|---|---|---|---|---|---|---|
| cca | tct | gtt | gga | att | ttc | ttt | ttt | gtc | agt | tac | atc | atc | ata | tcc | 5319 |
| Pro | Ser | Val | Gly | Ile | Phe | Phe | Phe | Val | Ser | Tyr | Ile | Ile | Ile | Ser | |
| 1760 | | | | | 1765 | | | | | 1770 | | | | | |

| | | | | | | | | | | | | | | | |
|---|---|---|---|---|---|---|---|---|---|---|---|---|---|---|---|
| ttc | ctg | gtt | gtg | gtg | aac | atg | tac | atc | gcg | gtc | atc | ctg | gag | aac | 5364 |
| Phe | Leu | Val | Val | Val | Asn | Met | Tyr | Ile | Ala | Val | Ile | Leu | Glu | Asn | |
| 1775 | | | | | 1780 | | | | | 1785 | | | | | |

| | | | | | | | | | | | | | | | |
|---|---|---|---|---|---|---|---|---|---|---|---|---|---|---|---|
| ttc | agt | gtt | gct | act | gaa | gaa | agt | gca | gag | cct | ctg | agt | gag | gat | 5409 |
| Phe | Ser | Val | Ala | Thr | Glu | Glu | Ser | Ala | Glu | Pro | Leu | Ser | Glu | Asp | |
| 1790 | | | | | 1795 | | | | | 1800 | | | | | |

| | | | | | | | | | | | | | | | |
|---|---|---|---|---|---|---|---|---|---|---|---|---|---|---|---|
| gac | ttt | gag | atg | ttc | tat | gag | gtt | tgg | gag | aag | ttt | gat | ccc | gat | 5454 |
| Asp | Phe | Glu | Met | Phe | Tyr | Glu | Val | Trp | Glu | Lys | Phe | Asp | Pro | Asp | |
| 1805 | | | | | 1810 | | | | | 1815 | | | | | |

| | | | | | | | | | | | | | | | |
|---|---|---|---|---|---|---|---|---|---|---|---|---|---|---|---|
| gca | act | cag | ttc | atg | gaa | ttt | gaa | aaa | tta | tct | cag | ttt | gca | gct | 5499 |
| Ala | Thr | Gln | Phe | Met | Glu | Phe | Glu | Lys | Leu | Ser | Gln | Phe | Ala | Ala | |
| 1820 | | | | | 1825 | | | | | 1830 | | | | | |

| | | | | | | | | | | | | | | | |
|---|---|---|---|---|---|---|---|---|---|---|---|---|---|---|---|
| gcg | ctt | gaa | ccg | cct | ctc | aat | ctg | cca | caa | cca | aac | aaa | ctc | cag | 5544 |
| Ala | Leu | Glu | Pro | Pro | Leu | Asn | Leu | Pro | Gln | Pro | Asn | Lys | Leu | Gln | |
| 1835 | | | | | 1840 | | | | | 1845 | | | | | |

| | | | | | | | | | | | | | | | |
|---|---|---|---|---|---|---|---|---|---|---|---|---|---|---|---|
| ctc | att | gcc | atg | gat | ttg | ccc | atg | gtg | agt | ggt | gac | cgg | atc | cac | 5589 |
| Leu | Ile | Ala | Met | Asp | Leu | Pro | Met | Val | Ser | Gly | Asp | Arg | Ile | His | |
| 1850 | | | | | 1855 | | | | | 1860 | | | | | |

| | | | | | | | | | | | | | | | |
|---|---|---|---|---|---|---|---|---|---|---|---|---|---|---|---|
| tgt | ctt | gat | atc | tta | ttt | gct | ttt | aca | aag | cgg | gtt | cta | gga | gag | 5634 |
| Cys | Leu | Asp | Ile | Leu | Phe | Ala | Phe | Thr | Lys | Arg | Val | Leu | Gly | Glu | |
| 1865 | | | | | 1870 | | | | | 1875 | | | | | |

| | | | | | | | | | | | | | | | |
|---|---|---|---|---|---|---|---|---|---|---|---|---|---|---|---|
| agt | gga | gag | atg | gat | gct | cta | cga | ata | cag | atg | gaa | gag | cga | ttc | 5679 |
| Ser | Gly | Glu | Met | Asp | Ala | Leu | Arg | Ile | Gln | Met | Glu | Glu | Arg | Phe | |
| 1880 | | | | | 1885 | | | | | 1890 | | | | | |

| | | | | | | | | | | | | | | | |
|---|---|---|---|---|---|---|---|---|---|---|---|---|---|---|---|
| atg | gct | tcc | aat | cct | tcc | aag | gtc | tcc | tat | cag | cca | atc | act | act | 5724 |
| Met | Ala | Ser | Asn | Pro | Ser | Lys | Val | Ser | Tyr | Gln | Pro | Ile | Thr | Thr | |
| 1895 | | | | | 1900 | | | | | 1905 | | | | | |

| | | | | | | | | | | | | | | | |
|---|---|---|---|---|---|---|---|---|---|---|---|---|---|---|---|
| act | tta | aaa | cga | aaa | caa | gag | gaa | gta | tct | gct | gtc | att | att | cag | 5769 |
| Thr | Leu | Lys | Arg | Lys | Gln | Glu | Glu | Val | Ser | Ala | Val | Ile | Ile | Gln | |
| 1910 | | | | | 1915 | | | | | 1920 | | | | | |

| | | | | | | | | | | | | | | | |
|---|---|---|---|---|---|---|---|---|---|---|---|---|---|---|---|
| cgt | gct | tac | aga | cgc | cac | ctt | tta | aag | cga | act | gta | aaa | caa | gct | 5814 |
| Arg | Ala | Tyr | Arg | Arg | His | Leu | Leu | Lys | Arg | Thr | Val | Lys | Gln | Ala | |
| 1925 | | | | | 1930 | | | | | 1935 | | | | | |

| | | | | | | | | | | | | | | | |
|---|---|---|---|---|---|---|---|---|---|---|---|---|---|---|---|
| tcc | ttt | acg | tac | aat | aaa | aac | aaa | atc | aaa | ggt | ggg | gct | aat | ctt | 5859 |
| Ser | Phe | Thr | Tyr | Asn | Lys | Asn | Lys | Ile | Lys | Gly | Gly | Ala | Asn | Leu | |
| 1940 | | | | | 1945 | | | | | 1950 | | | | | |

| | | | | | | | | | | | | | | | |
|---|---|---|---|---|---|---|---|---|---|---|---|---|---|---|---|
| ctt | ata | aaa | gaa | gac | atg | ata | att | gac | aga | ata | aat | gaa | aac | tct | 5904 |
| Leu | Ile | Lys | Glu | Asp | Met | Ile | Ile | Asp | Arg | Ile | Asn | Glu | Asn | Ser | |
| 1955 | | | | | 1960 | | | | | 1965 | | | | | |

| | | | | | | | | | | | | | | | |
|---|---|---|---|---|---|---|---|---|---|---|---|---|---|---|---|
| att | aca | gaa | aaa | act | gat | ctg | acc | atg | tcc | act | gca | gct | tgt | cca | 5949 |
| Ile | Thr | Glu | Lys | Thr | Asp | Leu | Thr | Met | Ser | Thr | Ala | Ala | Cys | Pro | |
| 1970 | | | | | 1975 | | | | | 1980 | | | | | |

| | | | | | | | | | | | | | | | |
|---|---|---|---|---|---|---|---|---|---|---|---|---|---|---|---|
| cct | tcc | tat | gac | cgg | gtg | aca | aag | cca | att | gtg | gaa | aaa | cat | gag | 5994 |
| Pro | Ser | Tyr | Asp | Arg | Val | Thr | Lys | Pro | Ile | Val | Glu | Lys | His | Glu | |
| 1985 | | | | | 1990 | | | | | 1995 | | | | | |

| | | | | | | | | | | |
|---|---|---|---|---|---|---|---|---|---|---|
| caa | gaa | ggc | aaa | gat | gaa | aaa | gcc | aaa | ggg | aaa | taa | 6030 |
| Gln | Glu | Gly | Lys | Asp | Glu | Lys | Ala | Lys | Gly | Lys | | |
| | 2000 | | | | | 2005 | | | | | | |

<210> SEQ ID NO 97
<211> LENGTH: 2009
<212> TYPE: PRT
<213> ORGANISM: Homo sapiens

<400> SEQUENCE: 97

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Asp Asp Glu Asn Gly
            35                  40                  45

Pro Lys Pro Asn Ser Asp Leu Glu Ala Gly Lys Asn Leu Pro Phe Ile
            50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
            115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
    195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
    275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
```

-continued

```
               420             425             430
Thr Leu Glu Glu Ala Glu Gln Lys Glu Ala Glu Phe Gln Gln Met Ile
        435                 440                 445
Glu Gln Leu Lys Lys Gln Gln Glu Ala Ala Gln Ala Ala Thr Ala
        450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
            500                 505                 510
Glu Glu Lys Asp Glu Asp Glu Phe Gln Lys Ser Glu Ser Glu Asp Ser
            515                 520                 525
Ile Arg Arg Lys Gly Phe Arg Phe Ser Ile Glu Gly Asn Arg Leu Thr
            530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
                595                 600                 605
Phe Val Pro Arg Arg His Gly Glu Arg Arg Asn Ser Asn Leu Ser Gln
            610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
                660                 665                 670
Ile Asp Lys Pro Ala Thr Asp Asp Asn Gly Thr Thr Thr Glu Thr Glu
            675                 680                 685
Met Arg Lys Arg Arg Ser Ser Ser Phe His Val Ser Met Asp Phe Leu
            690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                725                 730                 735
Cys Trp Tyr Lys Phe Ser Asn Ile Phe Leu Ile Trp Asp Cys Ser Pro
                740                 745                 750
Tyr Trp Leu Lys Val Lys His Val Val Asn Leu Val Val Met Asp Pro
                755                 760                 765
Phe Val Asp Leu Ala Ile Thr Ile Cys Ile Val Leu Asn Thr Leu Phe
            770                 775                 780
Met Ala Met Glu His Tyr Pro Met Thr Asp His Phe Asn Asn Val Leu
785                 790                 795                 800
Thr Val Gly Asn Leu Val Phe Thr Gly Ile Phe Thr Ala Glu Met Phe
                805                 810                 815
Leu Lys Ile Ile Ala Met Asp Pro Tyr Tyr Phe Gln Glu Gly Trp
            820                 825                 830
Asn Ile Phe Asp Gly Phe Ile Val Thr Leu Ser Leu Val Glu Leu Gly
            835                 840                 845
```

```
Leu Ala Asn Val Glu Gly Leu Ser Val Leu Arg Ser Phe Arg Leu Leu
850                 855                 860
Arg Val Phe Lys Leu Ala Lys Ser Trp Pro Thr Leu Asn Met Leu Ile
865                 870                 875                 880
Lys Ile Ile Gly Asn Ser Val Gly Ala Leu Gly Asn Leu Thr Leu Val
                885                 890                 895
Leu Ala Ile Ile Val Phe Ile Phe Ala Val Val Gly Met Gln Leu Phe
                900                 905                 910
Gly Lys Ser Tyr Lys Asp Cys Val Cys Lys Ile Ala Ser Asp Cys Gln
                915                 920                 925
Leu Pro Arg Trp His Met Asn Asp Phe Phe His Ser Phe Leu Ile Val
930                 935                 940
Phe Arg Val Leu Cys Gly Glu Trp Ile Glu Thr Met Trp Asp Cys Met
945                 950                 955                 960
Glu Val Ala Gly Gln Ala Met Cys Leu Thr Val Phe Met Met Val Met
                965                 970                 975
Val Ile Gly Asn Leu Val Val Leu Asn Leu Phe Leu Ala Leu Leu Leu
                980                 985                 990
Ser Ser Phe Ser Ala Asp Asn Leu Ala Ala Thr Asp Asp Asp Asn Glu
                995                 1000                1005
Met Asn Asn Leu Gln Ile Ala Val Asp Arg Met His Lys Gly Val
        1010                1015                1020
Ala Tyr Val Lys Arg Lys Ile Tyr Glu Phe Ile Gln Gln Ser Phe
        1025                1030                1035
Ile Arg Lys Gln Lys Ile Leu Asp Glu Ile Lys Pro Leu Asp Asp
        1040                1045                1050
Leu Asn Asn Lys Lys Asp Ser Cys Met Ser Asn His Thr Thr Glu
        1055                1060                1065
Ile Gly Lys Asp Leu Asp Tyr Leu Lys Asp Val Asn Gly Thr Thr
        1070                1075                1080
Ser Gly Ile Gly Thr Gly Ser Ser Val Glu Lys Tyr Ile Ile Asp
        1085                1090                1095
Glu Ser Asp Tyr Met Ser Phe Ile Asn Asn Pro Ser Leu Thr Val
        1100                1105                1110
Thr Val Pro Ile Ala Val Gly Glu Ser Asp Phe Glu Asn Leu Asn
        1115                1120                1125
Thr Glu Asp Phe Ser Ser Glu Ser Asp Leu Glu Glu Ser Lys Glu
        1130                1135                1140
Lys Leu Asn Glu Ser Ser Ser Ser Ser Glu Gly Ser Thr Val Asp
        1145                1150                1155
Ile Gly Ala Pro Val Glu Glu Gln Pro Val Val Glu Pro Glu Glu
        1160                1165                1170
Thr Leu Glu Pro Glu Ala Cys Phe Thr Glu Gly Cys Val Gln Arg
        1175                1180                1185
Phe Lys Cys Cys Gln Ile Asn Val Glu Glu Gly Arg Gly Lys Gln
        1190                1195                1200
Trp Trp Asn Leu Arg Arg Thr Cys Phe Arg Ile Val Glu His Asn
        1205                1210                1215
Trp Phe Glu Thr Phe Ile Val Phe Met Ile Leu Leu Ser Ser Gly
        1220                1225                1230
Ala Leu Ala Phe Glu Asp Ile Tyr Ile Asp Gln Arg Lys Thr Ile
        1235                1240                1245
Lys Thr Met Leu Glu Tyr Ala Asp Lys Val Phe Thr Tyr Ile Phe
        1250                1255                1260
```

-continued

```
Ile Leu Glu Met Leu Leu Lys Trp Val Ala Tyr Gly Tyr Gln Thr
1265                1270                1275

Tyr Phe Thr Asn Ala Trp Cys Trp Leu Asp Phe Leu Ile Val Asp
1280                1285                1290

Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Lys Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635

Arg Leu Ala Arg Ile Gly Arg Ile Leu Arg Leu Ile Lys Gly Ala
1640                1645                1650

Lys Gly Ile Arg Thr Leu Leu Phe Ala Leu Met Met Ser Leu Pro
```

```
                  1655           1660            1665
Ala Leu Phe Asn Ile Gly Leu Leu Leu Phe Leu Val Met Phe Ile
    1670            1675            1680

Tyr Ala Ile Phe Gly Met Ser Asn Phe Ala Tyr Val Lys Arg Glu
    1685            1690            1695

Val Gly Ile Asp Asp Met Phe Asn Phe Glu Thr Phe Gly Asn Ser
    1700            1705            1710

Met Ile Cys Leu Phe Gln Ile Thr Thr Ser Ala Gly Trp Asp Gly
    1715            1720            1725

Leu Leu Ala Pro Ile Leu Asn Ser Lys Pro Pro Asp Cys Asp Pro
    1730            1735            1740

Asn Lys Val Asn Pro Gly Ser Ser Val Lys Gly Asp Cys Gly Asn
    1745            1750            1755

Pro Ser Val Gly Ile Phe Phe Phe Val Ser Tyr Ile Ile Ile Ser
    1760            1765            1770

Phe Leu Val Val Val Asn Met Tyr Ile Ala Val Ile Leu Glu Asn
    1775            1780            1785

Phe Ser Val Ala Thr Glu Glu Ser Ala Glu Pro Leu Ser Glu Asp
    1790            1795            1800

Asp Phe Glu Met Phe Tyr Glu Val Trp Glu Lys Phe Asp Pro Asp
    1805            1810            1815

Ala Thr Gln Phe Met Glu Phe Glu Lys Leu Ser Gln Phe Ala Ala
    1820            1825            1830

Ala Leu Glu Pro Pro Leu Asn Leu Pro Gln Pro Asn Lys Leu Gln
    1835            1840            1845

Leu Ile Ala Met Asp Leu Pro Met Val Ser Gly Asp Arg Ile His
    1850            1855            1860

Cys Leu Asp Ile Leu Phe Ala Phe Thr Lys Arg Val Leu Gly Glu
    1865            1870            1875

Ser Gly Glu Met Asp Ala Leu Arg Ile Gln Met Glu Glu Arg Phe
    1880            1885            1890

Met Ala Ser Asn Pro Ser Lys Val Ser Tyr Gln Pro Ile Thr Thr
    1895            1900            1905

Thr Leu Lys Arg Lys Gln Glu Glu Val Ser Ala Val Ile Ile Gln
    1910            1915            1920

Arg Ala Tyr Arg Arg His Leu Leu Lys Arg Thr Val Lys Gln Ala
    1925            1930            1935

Ser Phe Thr Tyr Asn Lys Asn Lys Ile Lys Gly Gly Ala Asn Leu
    1940            1945            1950

Leu Ile Lys Glu Asp Met Ile Ile Asp Arg Ile Asn Glu Asn Ser
    1955            1960            1965

Ile Thr Glu Lys Thr Asp Leu Thr Met Ser Thr Ala Ala Cys Pro
    1970            1975            1980

Pro Ser Tyr Asp Arg Val Thr Lys Pro Ile Val Glu Lys His Glu
    1985            1990            1995

Gln Glu Gly Lys Asp Glu Lys Ala Lys Gly Lys
    2000            2005
```

MUTATIONS IN ION CHANNELS

TECHNICAL FIELD

The present invention is concerned with mutations in proteins having biological functions as ion channels and, more particularly, with such mutations where they are associated with diseases such as epilepsy and disorders associated with ion channel dysfunction including, but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness.

BACKGROUND ART

Epilepsies constitute a diverse collection of brain disorders that affect about 3% of the population at some time in their lives (Annegers, 1996). An epileptic seizure can be defined as an episodic change in behaviour caused by the disordered firing of populations of neurons in the central nervous system. This results in varying degrees of involuntary muscle contraction and often a loss of consciousness. Epilepsy syndromes have been classified into more than 40 distinct types based upon characteristic symptoms, types of seizure, cause, age of onset and EEG patterns (Commission on Classification and Terminology of the International League Against Epilepsy, 1989). However the single feature that is common to all syndromes is the persistent increase in neuronal excitability that is both occasionally and unpredictably expressed as a seizure.

A genetic contribution to the aetiology of epilepsy has been estimated to be present in approximately 40% of affected individuals (Gardiner, 2000). As epileptic seizures may be the end-point of a number of molecular aberrations that ultimately disturb neuronal synchrony, the genetic basis for epilepsy is likely to be heterogeneous. There are over 200 Mendelian diseases which include epilepsy as part of the phenotype. In these diseases, seizures are symptomatic of underlying neurological involvement such as disturbances, in brain structure or function. In contrast, there are also a number of "pure" epilepsy syndromes in which epilepsy is the sole manifestation in the affected individuals. These are termed idiopathic and account for over 60% of all epilepsy cases.

Idiopathic epilepsies have been further divided into partial and generalized sub-types. Partial (focal or local) epileptic fits arise from localized cortical discharges, so that only certain groups of muscles are involved and consciousness may be retained. However, in generalized epilepsy, EEG discharge shows no focus such that all subcortical regions of the brain are involved. Although the observation that generalized epilepsies are frequently inherited is understandable, the mechanism by which genetic defects, presumably expressed constitutively in the brain, give rise to partial seizures is less clear.

The molecular genetic era has resulted in spectacular advances in classification, diagnosis and biological understanding of numerous inherited neurological disorders including muscular dystrophies, familial neuropathies and spinocerebellar degenerations. These disorders are all uncommon or rare and have simple Mendelian inheritance. In contrast, common neurological diseases like epilepsy, have complex inheritance where they are determined by multiple genes sometimes interacting with environmental influences. Molecular genetic advances in disorders with complex inheritance have been far more modest to date (Todd, 1999).

Most of the molecular genetic advances have occurred by a sequential three stage process. First a clinically homogeneous disorder is identified and its mode of inheritance determined. Second, linkage analysis is performed on carefully characterized clinical populations with the disorder. Linkage analysis is a process where the chromosomal localization of a particular disorder is narrowed down to approximately 0.5% of the total genome. Knowledge of linkage imparts no intrinsic biological insights other than the important clue as to where to look in the genome for the abnormal gene. Third, strategies such as positional cloning or the positional candidate approach are used to identify the aberrant gene and its specific mutations within the linked region (Collins, 1995).

Linkage studies in disorders with complex inheritance have been bedevilled by negative results and by failure to replicate positive findings. A sense of frustration permeates current literature in the genetics of complex disorders. Carefully performed, large scale studies involving hundreds of sibpairs in disorders including multiple sclerosis and diabetes have been essentially negative (Bell and Lathrop, 1996; Lernmark and Ott, 1998). An emerging view is that such disorders are due to the summation of many genes of small effect and that identification of these genes may only be possible with very large-scale association studies. Such studies on a genome-wide basis are currently impossible due to incomplete marker sets and computational limitations.

The idiopathic generalized epilepsies (IGE) are the most common group of inherited human epilepsy and do not have simple inheritance. Like other complex disorders, linkage studies in IGE have generated controversial and conflicting claims. Previous authors have suggested the possibility of multifactorial, polygenic, oligogenic or two locus models for the disease (Andermann, 1982; Doose and Baier, 1989; Greenberg et al., 1988a; 1992; Janz et al., 1992).

Two broad groups of IGE are now known—the classical idiopathic generalized epilepsies (Commission on Classification and Terminology of the International League Against Epilepsy, 1989) and the newly recognized genetic syndrome of generalized epilepsy with febrile seizures plus (GEFS$^+$) (Scheffer and Berkovic, 1997; Singh et al., 1999).

The classical IGEs are divided into a number of clinically recognizable but overlapping sub-syndromes including childhood absence epilepsy, juvenile absence epilepsy, juvenile myoclonic epilepsy etc (Commission on Classification and Terminology of the International League Against Epilepsy, 1989; Roger et al., 1992). The sub-syndromes are identified by age of onset and the pattern of seizure types (absence, myoclonus and tonic-clonic) Some patients, particularly those with tonic-clonic seizures alone do not fit a specifically recognized sub-syndrome. Arguments for regarding these as separate syndromes, yet recognizing that they are part of a neurobiological continuum, have been presented previously (Berkovic et al. 1987; 1994; Reutens and Berkovic, 1995).

GEFS$^+$ was originally recognized through large multi-generation families and comprises a variety of sub-syndromes. Febrile seizures plus (FS$^+$) is a sub-syndrome where children have febrile seizures occurring outside the age range of 3 months to 6 years, or have associated febrile tonic-clonic seizures. Many family members have a phenotype indistinguishable from the classical febrile convulsion syndrome and some have FS$^+$ with additional absence, myoclonic, atonic, or complex partial seizures. The severe end of the GEFS$^+$ spectrum includes myoclonic-astatic epilepsy.

The cumulative incidence for epilepsy by age 30 years (proportion suffering from epilepsy at some time) is 1.5% (Hauser et al., 1993). Accurate estimates for the cumulative incidence of the IGEs are unavailable. In epidemiological studies where attempts are made to subclassify epilepsies, rather few cases of IGE are diagnosed, and many cases are unclassified. This is probably because cases are rarely directly examined by epileptologists. In clinic- or office-based series seen by experts, most cases are classifiable and IGEs account for about 25% of cases. This suggests that about 0.3% of the population suffer from IGE at some time.

In outbred populations many patients with classical IGE appear to be sporadic as siblings and parents are usually unaffected. Systematic EEG studies on clinically unaffected family members show an increase in age-dependent occurrence of generalized epileptiform discharges compared to controls. In addition, to the approximate 0.3% of the population with clinical IGE, systematic EEG studies suggest that about 1% of healthy children have generalized epileptiform discharges while awake (Cavazzuti et al., 1980; Okubo et al., 1994).

Approximately 5-10% of first degree relatives of classical IGE probands have seizures with affected relatives usually having IGE phenotypes or febrile seizures. While nuclear families with 2-4 affected individuals are well recognized and 3 generation families or grandparent-grandchild pairs are occasionally observed (Italian League Against Epilepsy Genetic Collaborative Group, 1993), families with multiple affected individuals extending over 4 or more generations are exceptionally rare.

For GEFS$^+$, however, a number of large multi-generation families showing autosomal dominant inheritance with incomplete penetrance are known. Similar to classical IGE, analysis of sporadic cases and small families with GEFS$^+$ phenotypes does not suggest simple Mendelian inheritance. Indeed, bilineal inheritance, where there is a history of epilepsy on maternal and paternal sides, is observed in both GEFS$^+$ and classical IGE families (Singh et al., 1999; Italian League Against Epilepsy Genetic Collaborative Group, 1993).

Within single families with classical IGE or GEFS$^+$, affected individuals often have different sub-syndromes. The closer an affected relative is to the proband, the more similar are their sub-syndromes, and siblings often have similar sub-syndromes (Italian League Against Epilepsy Genetic Collaborative Group, 1993). Less commonly, families are observed where most, or all, known affected individuals have one classical IGE sub-syndrome such as childhood absence epilepsy or juvenile myoclonic epilepsy (Italian League Against Epilepsy Genetic Collaborative Group, 1993).

Importantly, sub-syndromes are identical in affected monozygous twins with IGE. In contrast, affected dizygous twins, may have the same or different sub-syndromes. Classical IGE and GEFS$^+$ sub-syndromes tend to segregate separately (Singh et al., 1999).

In some inbred communities, pedigree analysis strongly suggests recessive inheritance for juvenile myoclonic epilepsy and other forms of IGE (Panayiotopoulos and Obeid, 1989; Berkovic et al., 2000). In such families, sub-syndromes are much more similar in affected siblings than in affected sib-pairs from outbred families. Recently, a family with an infantile form of IGE with autosomal recessive inheritance, confirmed by linkage analysis, was described in Italy (Zara et al., 2000).

Most work on the molecular genetics of classical IGEs has been done on the sub-syndrome of juvenile myoclonic epilepsy where a locus in proximity or within the HLA region on chromosome 6p was first reported in 1988 (Greenberg et al., 1988b). This finding was supported by two collaborating laboratories, in separate patient samples, and subsequently three groups provided further evidence for a 6p locus for juvenile myoclonic epilepsy in some, but not all, of their families. However, genetic defects have not been found and the exact locus of the gene or genes, in relationship to the HLA region, remains controversial. Strong evidence for linkage to chromosome 6 also comes from a study of a single large family with juvenile myoclonic epilepsy, but in this pedigree the locus is well outside the HLA region. A locus on chromosome 15q has also been suggested for juvenile myoclonic epilepsy, but was not confirmed by two other studies.

In general, the results of studies of the putative chromosomal 6p locus in the HLA region in patients with absence epilepsies or other forms of idiopathic generalized epilepsies have been negative. The major exception is that study of probands with tonic-clonic seizures on awakening, a sub-syndrome closely related to juvenile myoclonic epilepsy, suggests linkage to 6p.

Linkage for classical remitting childhood absence epilepsy remains elusive, but in a family with persisting absence evolving into a juvenile myoclonic epilepsy phenotype, linkage to chromosome 1p has been claimed. An Indian pedigree with persisting absence and tonic-clonic seizures may link to 8q24. Linkage to this region was also suggested by a non-parametric analysis in IGE, irrespective of subsyndrome, but was not confirmed in another study. Other loci for IGEs that have been reported in single studies include 3p14, 8p, 18 and possibly 5p. The unusual example of recessively inherited infantile onset IGE described in Italy maps to 16p in a single family.

Thus, like most disorders with complex inheritance, the literature on genetics of classical IGEs is confusing and contradictory. Some, and perhaps much, of this confusion is due to heterogeneity, with the likelihood of a number of loci for IGEs. The studies reviewed above were principally performed on multiple small families, so heterogeneity within and between samples is probable. Whether all, some, or none of the linkages reported above will be found to harbour relevant genes for IGE remains to be determined. Most of the studies reviewed above used analysis methods assuming Mendelian inheritance, an assumption that is not correct for outbred communities. Some studies used multiple models (autosomal recessive, autosomal dominant). Although parametric linkage analysis may be reliable in some circumstance of analyzing complex disease, it can lead to spurious findings as highlighted by the literature on linkage in major psychoses (Risch and Botstein, 1996).

In so far as GEFS$^+$ is concerned, linkage analysis on rare multi-generation large families with clinical evidence of a major autosomal dominant gene have demonstrated loci on chromosomes 19q and 2q. Both the 19q and 2q GEFS$^+$ loci have been confirmed in independently ascertained large families, and genetic defects have been identified. Families linked to 19q are known and a mutation in the gene for the β1 subunit of the neuronal sodium channel (SCN1B) has been identified (Wallace et al., 1998). This mutation results in the loss of a critical disulphide bridge of this regulatory subunit and causes a loss of function in vitro. Families linked to 2q are also known and mutations in the pore-forming α subunit of the neuronal sodium channel (SCN1A) have been identified (PCT/AU01/01648; Wallace et al., 2001b; Escayg et al., 2000). Studies on the more common small families with GEFS$^+$ have not revealed these or other mutations to date.

In addition to the SCN1B and SCN1A mutations in GEFS$^+$, four other gene defects have been discovered for human idiopathic epilepsies through the study of large families. Mutations in the alpha-4 subunit of the neuronal nicotinic acetylcholine receptor (CHRNA4) occur in the focal epilepsy syndrome of autosomal dominant nocturnal frontal lobe epilepsy (Australian patent AU-B-56247/96; Steinlein et al., 1995). Mutations in the gamma-2 subunit of the GABAA receptor (GABRG2) have been identified in childhood absence epilepsy, febrile seizures (including febrile seizures plus) and myoclonic epilepsy (PCT/AU01/00729; Wallace et al., 2001a). Finally, mutations in two potassium channel genes (KCNQ2 and KCNQ3) were identified in benign familial neonatal convulsions (Singh et al., 1998; Biervert et al., 1998; Charlier et al., 1998). Although initially regarded as a special form of IGE, this unusual syndrome is probably a form of inherited focal epilepsy.

Further to these studies, mutations in other genes have been identified to be causative of epilepsy. These include mutations in the beta-2 subunit (CHRNB2) of the neuronal nicotinic acetylcholine receptor (PCT/AU01/00541; Phillips et al., 2001) and the delta subunit (GABRD) of the GABAA receptor (PCT/AU01/00729).

A number of mouse models approximating human IGE are known. These mice mutants have ataxia in addition to generalized spike-and-wave discharges with absences or tonic-clonic seizures. Recessive mutations in calcium channel subunit genes have been found in lethargic (CACNB4), tottering/leaner (CACNA1A), and stargazer (CACNG2) mutants. The slow-wave epilepsy mouse mutant has a mutation in the sodium/hydrogen exchanger gene, which may have important downstream effects on pH-sensitive ion channels.

The human and mouse literature is now suggesting that the idiopathic epilepsies comprise a family of channelopathies with mutations in ion channel subunits of voltage-gated (eg SCN1A, SCN1B, KCNQ2, KCNQ3) or ligand-gated (eg CHRNA4, CHRNB2, GABRG2, GABRD) types. These channels are typically comprised of a number of subunits, specified by genes on different chromosomes. The stoichiometry and conformation of ion channel subunits are not yet well understood, but many have multiple subunits in a variety of combinations.

The involvement of ion channels in other neuro/physiological disorders has also been observed (reviewed in Dworakowska and Dolowy, 2000). Mutations in voltage-gated sodium, potassium, calcium and chloride channels as well as ligand-gated channels such as the acetylcholine and GABA receptors may lead to physiological disorders such as hyper- and hypo-kalemic periodic paralysis, myotonias, malignant hyperthermia, myasthenia and cardiac arrhythmias. Neurological disorders other than epilepsy that are associated with ion channel mutations include episodic ataxia, migraine, Alzheimer's disease, Parkinson's disease, schizophrenia, hyperekplexia, anxiety, depression, phobic obsessive symptoms, as well as neuropathic pain, inflammatory pain and chronic/acute pain. Some kidney disorders such as Bartter's syndrome, polycystic kidney disease and Dent's disease, secretion disorders such as hyperinsulinemic hypoglycemia of infancy and cystic fibrosis, and vision disorders such as congenital stationary night blindness and total colour-blindness may also be linked to mutations in ion channels.

DISCLOSURE OF THE INVENTION

In a new genetic model for the idiopathic generalised epilepsies (IGEs) described in PCT/AU01/00872 (the disclosure of which is incorporated herein by reference) it has been postulated that most classical IGE and GEFS$^+$ cases are due to the combination of two mutations in multi-subunit ion channels. These are typically point mutations resulting in a subtle change of function. The critical postulate is that two mutations, usually, but not exclusively, in different subunit alleles ("digenic model"), are required for clinical expression of IGE. It was further proposed that a) A number of different mutated subunit pairs can be responsible for IGE. Combinations of two mutated subunits lead to an IGE genotype with ~30% penetrance.

b) The total allele frequency of mutated subunits is ~8%. It was calculated that approximately 15% of the population has one or more mutated subunit genes and 1% have two or more mutated subunits.

c) Sub-syndromes are principally determined by the specific combination of mutated subunit pairs, although one or more other genes, including ion channel subunits, of smaller effect may modify the phenotype.

d) Mutated subunit combinations that cause classical IGEs are largely separate from those that cause GEFS$^+$, although some subunits may be involved in both syndromes.

e) Individuals with single 'change of function' mutations would not have IGE, but such mutations may contribute to simple febrile seizures, which are observed with increased frequency in relatives of IGE probands.

The model also proposes that subunit mutations with more severe functional consequences (eg breaking a disulphide bridge in SCN1B or amino acid substitution in the pore forming regions of SCN1A for GEFS$^+$) cause autosomal dominant generalized epilepsies with a penetrance of 60-90%. The precise sub-syndromes in GEFS$^+$ are determined by minor allelic variation or mutations in other ion channel subunits. Such "severe" mutations are rare (allele frequency <0.01%) and are infrequent causes of GEFS$^+$. They very rarely, or perhaps never, cause classical IGE.

The identification of molecular changes in ion channel subunits is therefore a significant step towards the elucidation of genetic variants that alone or in combination (based on the digenic model) give rise to an epilepsy phenotype, and to other neuro/physiological disorders associated with ion channel dysfunction.

The present inventors have identified a number of novel mutations or variants in genes encoding subunits of ion channels in individuals with epilepsy. It will be appreciated that for each molecular defect one can provide an isolated nucleic acid molecule coding for a protein having a biological function as part of an ion channel in a mammal, wherein a mutation event selected from the group consisting of point mutations, deletions, insertions and rearrangements has occurred so as to affect the functioning of the ion channel. In some instances this single mutation alone will produce a phenotype of epilepsy or other neuro/physiological disorders associated with ion channel dysfunction.

In the case where a single mutation alone does not produce, say, an epilepsy phenotype, there would be provided one or more additional isolated nucleic acid molecules coding for proteins having a biological function as part of an ion channel in a mammal, wherein a mutation event selected from the group consisting of point mutations, deletions, insertions and rearrangements has occurred so as to affect the functioning of the ion channel. The cumulative effect of the mutations in each isolated nucleic acid molecule in vivo is to produce a epilepsy or another neuro/physiological disorders in said mammal. The mutations may be in nucleic acid molecules coding for protein subunits belonging to the same ion channel or may be in nucleic acid molecules coding for protein subunits that belong to different ion channels.

Typically such mutations are point mutations and the ion channels are voltage-gated channels such as a sodium, potassium, calcium or chloride channels or are ligand-gated channels such as members of the nAChR/GABA super family of receptors, or a functional fragment or homologue thereof.

Mutations may include those in non-coding regions of the ion channel subunits (eg mutations in the promoter region which affect the level of expression of the subunit gene, mutations in intronic sequences which affect the correct splicing of the subunit during mRNA processing, or mutations in the 5' or 3' untranslated regions that can affect translation or stability of the mRNA). Mutations may also and more preferably will be in coding regions of the ion channel subunits (eg nucleotide mutations may give rise to an amino acid change in the encoded protein or nucleotide mutations that do not give rise to an amino acid change but may affect the stability of the mRNA).

Mutation combinations may be selected from, but are not restricted to, those identified in Table 1.

Accordingly in one aspect of the present invention there is provided a method of identifying a subject predisposed to a disorder associated with ion channel dysfunction, comprising ascertaining whether at least one of the genes encoding ion channel subunits in said subject has undergone a mutation event selected from the group consisting of the mutation events set forth in the following Table:

| Subunit Gene | Exon/Intron | DNA Mutation |
|---|---|---|
| SCN1A | Exon 5 | c664C→T |
| SCN1A | Exon 8 | c1152G→A |
| SCN1A | Exon 9 | c1183G→C |
| SCN1A | Exon 9 | c1207T→C |
| SCN1A | Exon 9 | c1237T→A |
| SCN1A | Exon 9 | c1265T→A |
| SCN1A | Exon 21 | c4219C→T |
| SCN1A | Exon 26 | c5339T→C |
| SCN1A | Exon 26 | c5674C→T |
| SCN1B | Exon 3 | c254G→A |
| SCN2A | Exon 6A | c668G→A |
| SCN2A | Exon 16 | c2674G→A |
| SCN2A | Exon 17 | c3007C→A |
| SCN2A | Exon 19 | c3598A→G |
| SCN2A | Exon 20 | c3956G→A |
| SCN2A | Exon 12 | c1785T→C |
| SCN2A | Exon 27 | c4919T→A |
| SCN1A | Intron 9 | IVS9-1G→A |
| SCN1A | Intron 23 | IVS23+33G→A |
| SCN2A | Intron 7 | IVS7+61T→A |
| SCN2A | Intron 19 | IVS19-55A→G |
| SCN2A | Intron 22 | IVS22-31A→G |
| SCN2A | Intron 2 | IVS2-28G→A |
| SCN2A | Intron 8 | IVS8-3T→C |
| SCN2A | Intron 11 | IVS11+49A→G |
| SCN2A | Intron 11 | IVS11-16C→T |
| SCN2A | Intron 17 | IVS17-71C→T |
| SCN2A | Intron 17 | IVS17-74delG |
| SCN2A | Intron 17 | IVS17-74insG |
| CHRNA5 | Exon 4 | c400G→A |
| CHRNA2 | Exon 4 | c373G→A |
| CHRNA3 | Exon 2 | c110G→A |
| CHRNA2 | Exon 4 | c351C→T |
| CHRNA2 | Exon 5 | c771C→T |
| CHRNA3 | Exon 2 | c159A→G |
| CHRNA3 | Exon 4 | c291G→A |
| CHRNA3 | Exon 4 | c345G→A |
| CHRNA2 | Intron 3 | IVS3-16C→T |
| CHRNA3 | Intron 3 | IVS3-5T→C |
| CHRNA3 | Intron 4 | IVS4+8G→C |
| KCNQ2 | Exon 1 | c204-c205insC |
| KCNQ2 | Exon 1 | c1A→G |
| KCNQ2 | Exon 1 | c2T→C |
| KCNQ2 | Exon 8 | c1057C→G |
| KCNQ2 | Exon 11 | c1288C→T |
| KCNQ2 | Exon 14 | c1710A→T |
| KCNQ2 | Exon 15 | c1856T→G |
| KCNQ2 | Intron 9 | IVS9+(46-48)delCCT |
| KCNQ3 | Intron 11 | IVS11+43G→A |
| KCNQ3 | Intron 12 | IVS12+29G→A |
| GABRB1 | Exon 5 | c508C→T |
| GABRB1 | Exon 9 | c1329G→A |
| GABRB1 | Exon 8 | c975C→T |
| GABRG3 | Exon 8 | c995T→C |
| GABRA1 | 5' UTR | c-142A→G |
| GABRA1 | 5' UTR | c-31C→T |
| GABRA2 | 3' UTR | c1615G→A |
| GABRA5 | 5' UTR | c-271G→C |
| GABRA5 | 5' UTR | c-228A→G |
| GABRA5 | 5' UTR | c-149G→C |
| GABRB2 | 5' UTR | c-159C→T |
| GABRB2 | 3' UTR | c1749C→T |
| GABRPi | 5' UTR | c-101C→T |
| GABRB1 | Intron 1 | IVS1+24T→G |
| GABRB1 | Intron 6 | IVS6+72T→G |
| GABRB1 | Intron 7 | IVS7-34A→G |
| GABRB3 | Intron 1 | IVS1-14C→T |
| GABRB3 | Intron 7 | IVS7+58delAA |
| GABRD | Intron 6 | IVS6+132insC |
| GABRD | Intron 6 | IVS6+130insC |
| GABRD | Intron 6 | IVS6+73delCGCGCCCACCGCCCCTTCCGCG |
| GABRG3 | Intron 8 | IVS8-102C→T |

In a further aspect there is provided a method of identifying a subject predisposed to a disorder associated with ion channel dysfunction, comprising ascertaining whether at least one of the genes encoding ion channel subunits in said subject has undergone a mutation event as set forth in one of SEQ ID Numbers: 1-72.

In another aspect of the present invention there is provided an isolated nucleic acid molecule encoding a mutant or variant ion channel subunit wherein a mutation event selected from the group consisting of the mutation events set forth in the following Table:

| Subunit Gene | Exon/Intron | DNA Mutation |
|---|---|---|
| SCN1A | Exon 5 | c664C→T |
| SCN1A | Exon 8 | c1152G→A |
| SCN1A | Exon 9 | c1183G→C |
| SCN1A | Exon 9 | c1207T→C |
| SCN1A | Exon 9 | c1237T→A |
| SCN1A | Exon 9 | c1265T→A |
| SCN1A | Exon 21 | c4219C→T |
| SCN1A | Exon 26 | c5339T→C |
| SCN1A | Exon 26 | c5674C→T |
| SCN1B | Exon 3 | c254G→A |
| SCN2A | Exon 6A | c668G→A |
| SCN2A | Exon 16 | c2674G→A |
| SCN2A | Exon 17 | c3007C→A |
| SCN2A | Exon 19 | c3598A→G |
| SCN2A | Exon 20 | c3956G→A |
| SCN2A | Exon 12 | c1785T→C |
| SCN2A | Exon 27 | c4919T→A |
| SCN1A | Intron 9 | IVS9-1G→A |
| SCN1A | Intron 23 | IVS23+33G→A |
| SCN2A | Intron 7 | IVS7+61T→A |
| SCN2A | Intron 19 | IVS19-55A→G |
| SCN2A | Intron 22 | IVS22-31A→G |
| SCN2A | Intron 2 | IVS2-28G→A |
| SCN2A | Intron 8 | IVS8-3T→C |
| SCN2A | Intron 11 | IVS11+49A→G |
| SCN2A | Intron 11 | IVS11-16C→T |

-continued

| Subunit Gene | Exon/Intron | DNA Mutation |
|---|---|---|
| SCN2A | Intron 17 | IVS17-71C→T |
| SCN2A | Intron 17 | IVS17-74delG |
| SCN2A | Intron 17 | IVS17-74insG |
| CHRNA5 | Exon 4 | c400G→A |
| CHRNA2 | Exon 4 | c373G→A |
| CHRNA3 | Exon 2 | c110G→A |
| CHRNA2 | Exon 4 | c351C→T |
| CHRNA2 | Exon 5 | c771C→T |
| CHRNA3 | Exon 2 | c159A→G |
| CHRNA3 | Exon 4 | c291G→A |
| CHRNA3 | Exon 4 | c345G→A |
| CHRNA2 | Intron 3 | IVS3-16C→T |
| CHRNA3 | Intron 3 | IVS3-5T→C |
| CHRNA3 | Intron 4 | IVS4+8G→C |
| KCNQ2 | Exon 1 | c204-c205insC |
| KCNQ2 | Exon 1 | c1A→G |
| KCNQ2 | Exon 1 | c2T→C |
| KCNQ2 | Exon 8 | c1057C→G |
| KCNQ2 | Exon 11 | c1288C→T |
| KCNQ2 | Exon 14 | c1710A→T |
| KCNQ2 | Exon 15 | c1856T→G |
| KCNQ2 | Intron 9 | IVS9+(46-48)delCCT |
| KCNQ3 | Intron 11 | IVS11+43G→A |
| KCNQ3 | Intron 12 | IVS12+29G→A |
| GABRB1 | Exon 5 | c508C→T |
| GABRB1 | Exon 9 | c1329G→A |
| GABRB1 | Exon 8 | c975C→T |
| GABRG3 | Exon 8 | c995T→C |
| GABRA1 | 5' UTR | c-142A→G |
| GABRA1 | 5' UTR | c-31C→T |
| GABRA2 | 3' UTR | c1615G→A |
| GABRA5 | 5' UTR | c-271G→C |
| GABRA5 | 5' UTR | c-228A→G |
| GABRB1 | 5' UTR | c-149G→C |
| GABRB2 | 5' UTR | c-159C→T |
| GABRB2 | 3' UTR | c1749C→T |
| GABRPi | 5' UTR | c-101C→T |
| GABRB1 | Intron 1 | IVS1+24T→G |
| GABRB1 | Intron 6 | IVS6+72T→G |
| GABRB1 | Intron 7 | IVS7-34A→G |
| GABRB3 | Intron 1 | IVS1-14C→T |
| GABRB3 | Intron 7 | IVS7+58delAA |
| GABRD | Intron 6 | IVS6+132insC |
| GABRD | Intron 6 | IVS6+130insC |
| GABRD | Intron 6 | IVS6+73delCGCGCCCACCGCCCCTTCCGCG |
| GABRG3 | Intron 8 | IVS8-102C→T | has occurred.

In still another aspect of the present invention there is provided an isolated nucleic acid molecule encoding a mutant or variant ion channel subunit wherein a mutation event has occurred as set forth in one of SEQ ID Numbers: 1-72.

The mutation event disrupts the functioning of an ion channel so as to produce a phenotype of epilepsy, and/or one or more other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness, either alone or in combination with one or more additional mutations or variations in the ion channel subunit genes.

In another aspect of the present invention there is provided an isolated nucleic acid molecule encoding a mutant KCNQ2 subunit, wherein the mutation event has occurred in the C-terminal domain of the KCNQ2 subunit and leads to a disturbance in the calmodulin binding affinity of the subunit, so as to produce an epilepsy phenotype.

In one form of the invention, the mutations are in exon 8 or exon 15 of the KCNQ2 subunit and result in the replacement of an arginine residue with a glycine residue at amino acid position 353, or the replacement of a leucine residue with an arginine at amino acid position 619. The R353G mutation occurs as a result of a C to G nucleotide substitution at position 1057 of the KCNQ2 coding sequence as shown in SEQ ID NO: 44. The L619R mutation occurs as a result of a T to G nucleotide substitution at position 1856 of the KCNQ2 coding sequence as shown in SEQ ID NO: 47.

In a further form of the invention, the mutations are in exon 11 or exon 14 of the KCNQ2 subunit and result in the replacement of an arginine residue with a stop codon at amino acid position 430, or the replacement of an arginine residue with a serine at amino acid position 570. The R430X mutation occurs as a result of a C to T nucleotide substitution at position 1288 of the KCNQ2 coding sequence as shown in SEQ ID NO: 45. The R570S mutation occurs as a result of an A to T nucleotide substitution at position 1710 of the KCNQ2 coding sequence as shown in SEQ ID NO: 46.

Preferably these mutations create a phenotype of benign familial neonatal seizures (BFNS).

In a further aspect of the present invention there is provided a combination of two or more isolated nucleic acid molecules each having a novel mutation event as laid out in Table 1. The cumulative effect of the mutations in each isolated nucleic acid molecule in vivo is to produce an epilepsy or another disorder associated with ion channel dysfunction as described above in said mammal.

In a particularly preferred embodiment of the present invention, the isolated nucleic acid molecules have a nucleotide sequence as shown in any one of SEQ ID Numbers: 1-72. The sequences correspond to the novel DNA mutations or variants laid out in Table 1.

In another aspect of the present invention there is provided an isolated nucleic acid molecule comprising any one of the nucleotide sequences set forth in SEQ ID Numbers: 1-72.

In another aspect of the present invention there is provided an isolated nucleic acid molecule consisting of any one of the nucleotide sequences set forth in SEQ ID Numbers: 1-72.

The nucleotide sequences of the present invention can be engineered using methods accepted in the art for a variety of purposes. These include, but are not limited to, modification of the cloning, processing, and/or expression of the gene product. PCR reassembly of gene fragments and the use of synthetic oligonucleotides allow the engineering of the nucleotide sequences of the present invention. For example, oligonucleotide-mediated site-directed mutagenesis can introduce further mutations that create new restriction sites, alter expression patterns and produce splice variants etc.

As a result of the degeneracy of the genetic code, a number of polynucleotide sequences, some that may have minimal similarity to the polynucleotide sequences of any known and naturally occurring gene, may be produced. Thus, the invention includes each and every possible variation of a polynucleotide sequence that could be made by selecting combinations based on possible codon choices. These combinations are made in accordance with the standard triplet genetic code as applied to the polynucleotide sequences of the present invention, and all such variations are to be considered as being specifically disclosed.

The nucleic acid molecules of this invention are typically DNA molecules, and include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences possessing a substantially different codon usage than that of the polynucleotide sequences of the present invention. For example, codons may be selected to increase the rate of expression of the peptide in a particular prokaryotic or eukaryotic host corresponding with the frequency that particular codons are utilized by the host. Other reasons to alter the nucleotide sequence without altering the encoded amino acid sequences include the production of RNA transcripts having more desirable properties, such as a greater half-life, than transcripts produced from the naturally occurring mutated sequence.

The invention also encompasses production of nucleic acid sequences of the present invention entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 3' untranslated regions and specific initiation signals (such as an ATG initiation codon and Kozak consensus sequence) which allow more efficient translation of sequences encoding the polypeptides of the present invention. In cases where the complete coding sequence, including the initiation codon and upstream regulatory sequences, are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The invention also includes nucleic acid molecules that are the complements of the sequences described herein.

The present invention allows for the preparation of purified polypeptide or protein from the polynucleotides of the present invention, or variants thereof. In order to do this, host cells may be transformed with a novel nucleic acid molecule as described above, or with nucleic acid molecules encoding two or more mutant ion channel subunits. If the mutant subunits form a part of the same ion channel a receptor protein containing two or more mutant subunits may be isolated. If the mutant subunits are subunits of different ion channels the host cells will express two or more mutant receptor proteins. Typically said host cells are transfected with an expression vector comprising a DNA molecule according to the invention or, in particular, DNA molecules encoding two or more mutant ion channel subunits. A variety of expression vector/host systems may be utilized to contain and express sequences encoding polypeptides of the invention. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can also be used to express a protein using a vaccinia virus expression system. The invention is not limited by the host cell or vector employed.

The polynucleotide sequences, or variants thereof, of the present invention can be stably expressed in cell lines to allow long term production of recombinant proteins in mammalian systems. Sequences encoding the polypeptides of the present invention can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

The protein produced by a transformed cell may be secreted or retained intracellularly depending on the sequence and/or the vector used. As will be understood by those of skill in the art, expression vectors containing polynucleotides which encode a protein may be designed to contain signal sequences which direct secretion of the protein through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

When large quantities of the protein product of the gene are needed, such as for antibody production, vectors which direct high levels of expression of this protein may be used, such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate cDNA sequence is inserted into a vector which contains a nucleotide sequence encoding another peptide (for example, glutathionine succinyl transferase). The fusion protein is expressed and recovered from prokaryotic or eukaryotic cells. The fusion protein can then be purified by affinity chromatography based upon the fusion vector sequence. The desired protein is then obtained by enzymatic cleavage of the fusion protein.

Fragments of the polypeptides of the present invention may also be produced by direct peptide synthesis using solid-phase techniques. Automated synthesis may be achieved by using the ABI 431A Peptide Synthesizer (Perkin-Elmer). Various fragments of this protein may be synthesized separately and then combined to produce the full-length molecule.

The present invention is also concerned with polypeptides having a biological function as an ion channel in a mammal, wherein a mutation event selected from the group consisting of substitutions, deletions, truncations, insertions and rearrangements has occurred so as to affect the functioning of the ion channel. In some instances this single mutation alone will produce an epilepsy phenotype or other neuro/physiological disorders associated with ion channel dysfunction.

In the case where a single mutation alone does not produce, say, an epilepsy phenotype, there would be provided one or more additional isolated mammalian polypeptides having biological functions as part of an ion channel in a mammal, wherein a mutation event selected from the group consisting of substitutions, deletions, truncations, insertions and rearrangements has occurred so as to affect the functioning of the ion channel. The cumulative effect of the mutations in each isolated mammalian polypeptide in vivo being to produce epilepsy or another neuro/physiological disorder in said mammal. The mutations may be in polypeptide subunits belonging to the same ion channel as described above, but may also be in polypeptide subunits that belong to different ion channels.

Typically the mutation is an amino acid substitution and the ion channel is a voltage-gated channel such as a sodium, potassium, calcium or chloride channel or a ligand-gated channel such as a member of the nAChR/GABA super family of receptors, or a functional fragment or homologue thereof.

Mutation combinations may be selected from, but are not restricted to, those represented in Table 1.

Accordingly, in a further aspect of the present invention there is provided an isolated polypeptide, said polypeptide being a mutant or variant ion channel subunit wherein a mutation event selected from the group consisting of the mutation events set forth in the following Table:

| Subunit Gene | Amino Acid Change |
| --- | --- |
| SCN1A | R222X |
| SCN1A | W384X |
| SCN1A | A395P |
| SCN1A | F403L |
| SCN1A | Y413N |
| SCN1A | V422E |
| SCN1A | R1407X |
| SCN1A | M1780T |
| SCN1A | R1892X |
| SCN1B | R85H |
| SCN2A | R223Q |
| SCN2A | V892I |
| SCN2A | L1003I |
| SCN2A | T1200A |
| SCN2A | R1319Q |
| CHRNA5 | V134I |
| CHRNA2 | A125T |
| CHRNA3 | R37H |
| KCNQ2 | K69fsX119 |
| KCNQ2 | M1V |
| KCNQ2 | M1T |
| KCNQ2 | R353G |
| KCNQ2 | R430X |
| KCNQ2 | R570S |
| KCNQ2 | L619R | has occurred.

In a further aspect of the invention there is provided an isolated polypeptide, said polypeptide being a mutant or variant ion channel subunit wherein a mutation event has occurred such that the polypeptide has the amino acid sequence set forth in one of SEQ ID Numbers: 73-95. The mutation event disrupts the functioning of an ion channel so as to produce a phenotype of epilepsy, and/or one or more other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness.

In a particularly preferred embodiment of the present invention, the isolated polypeptide has an amino acid sequence as shown in any one of SEQ ID Numbers: 73-95. The sequences correspond to the novel amino acid changes laid out in Table 1 for those instances where the DNA mutation results in an amino acid change.

According to still another aspect of the present invention there is provided an isolated polypeptide, said polypeptide being a mutant KCNQ2 subunit, wherein the mutation event has occurred in the C-terminal domain of the KCNQ2 subunit and leads to a disturbance in the calmodulin binding affinity of the subunit, so as to produce an epilepsy phenotype.

In one form of the invention the mutations are substitutions in which an arginine residue is replaced with a glycine residue, or a leucine residue is replaced with an arginine. Preferably the substitutions are R353G and L619R transitions as illustrated by SEQ ID NOS: 92 and 95 respectively.

In a further form of the invention the mutations result in the replacement of an arginine for a stop codon, or an arginine is replaced with a serine. Preferably the mutations are R430X and R570S transitions as illustrated by SEQ ID NOS: 93 and 94 respectively.

In a still further aspect of the present invention there is provided a combination of two or more isolated polypeptides each having a novel mutation event as laid out in Table 1. The cumulative effect of the mutations in each isolated polypeptide molecule in vivo is to produce an epilepsy or another disorder associated with ion channel dysfunction as described above in said mammal.

In a particularly preferred embodiment of the present invention, the isolated polypeptides have an amino acid sequence as shown in any one of SEQ ID Numbers: 73-95. The sequences correspond to the novel amino acid changes laid out in Table 1.

According to still another aspect of the present invention there is provided an isolated polypeptide comprising the amino acid sequence set forth in any one of SEQ ID Numbers: 73-95.

According to still another aspect of the present invention there is provided a polypeptide consisting of the amino acid sequence set forth in any one of SEQ ID Numbers: 73-95.

According to still another aspect of the present invention there is provided a method of preparing a polypeptide, comprising the steps of:

(1) culturing host cells transfected with an expression vector comprising a nucleic acid molecule as described above under conditions effective for polypeptide production; and (2) harvesting the mutant ion channel subunit.

The mutant ion channel subunit may be allowed to assemble with other subunits constituting the channel that are either wild-type or themselves mutant subunits, whereby the assembled ion channel is harvested.

According to still another aspect of the invention there is provided a polypeptide which is the product of the process described above.

Substantially purified protein or fragments thereof can then be used in further biochemical analyses to establish secondary and tertiary structure. Such methodology is known in the art and includes, but is not restricted to, X-ray crystallography of crystals of the proteins or of the assembled ion channel incorporating the proteins or by nuclear magnetic resonance (NMR). Determination of structure allows for the rational design of pharmaceuticals to interact with the ion channel as a whole or through interaction with a specific subunit protein (see drug screening below), alter the overall ion channel protein charge configuration or charge interaction with other proteins, or to alter its function in the cell.

It will be appreciated that the mutant ion channel subunits included as part of the present invention will be useful in further applications which include a variety of hybridisation and immunological assays to screen for and detect the presence of either a normal or mutated gene or gene product. The invention enables therapeutic methods for the treatment of epilepsy as well as other disorders associated with ion channel dysfunction and also enables methods for the diagnosis or prognosis of epilepsy as well as other disorders associated with ion channel dysfunction.

Therapeutic Applications

According to still another aspect of the invention there is provided a method of treating epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, comprising administering a selective antagonist, agonist or modulator of an ion channel or ion channel subunit, when the ion channel contains a mutation in a subunit comprising the channel, as described above, to a subject in need of such treatment. Said mutation event may be causative of the disorder when expressed alone or when expressed in combination with one or more additional mutations in subunits of the same or different ion channels, which are typically those identified in Table 1.

In still another aspect of the invention there is provided the use of a selective antagonist, agonist or modulator of an ion channel or ion channel subunit when the ion channel contains a mutation in a subunit comprising the channel, as described above, said mutation being causative of epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, when expressed alone or when expressed in combination with a second mutation in a subunit of the same or different ion channel, as described above, in the manufacture of a medicament for the treatment of the disorder.

In one aspect, a suitable antagonist, agonist or modulator will restore wild-type function to the ion channel or channels containing the mutations of the present invention, or will negate the effects the mutant channel or channels have on cell function.

Using methods well known in the art, a mutant ion channel may be used to produce antibodies specific for the mutant channel that is causative of the disease or to screen libraries of pharmaceutical agents to identify those that bind the mutant ion channel.

In one aspect, an antibody, which specifically binds to a mutant ion channel or mutant ion channel subunit of the invention, may be used directly as an agonist, antagonist or modulator, or indirectly as a targeting or delivery mechanism for bringing a pharmaceutical agent to cells or tissues that express the mutant ion channel.

In a still further aspect of the invention there is provided an antibody which is immunologically reactive with a polypeptide as described above, but not with a wild-type ion channel or ion channel subunit thereof.

In particular, there is provided an antibody to an assembled ion channel containing a mutation in a subunit comprising the channel, which is causative of epilepsy or another disorder associated with ion channel dysfunction when expressed alone or when expressed in combination with one or more other mutations in subunits of the same or different ion channels. Such antibodies may include, but are not limited to, polyclonal, monoclonal, chimeric, and single chain antibodies as would be understood by the person skilled in the art.

For the production of antibodies, various hosts including rabbits, rats, goats, mice, humans, and others may be immunized by injection with a polypeptide as described above or with any fragment or oligopeptide thereof which has immunogenic properties. Various adjuvants may be used to increase immunological response and include, but are not limited to, Freund's, mineral gels such as aluminium hydroxide, and surface-active substances such as lysolecithin. Adjuvants used in humans include BCG (bacilli Calmette-Guérin) and *Corynebacterium parvum*.

It is preferred that the oligopeptides, peptides, or fragments used to induce antibodies to the mutant ion channel have an amino acid sequence consisting of at least amino acids, and, more preferably, of at least 10 amino acids. It is also preferable that these oligopeptides, peptides, or fragments are identical to a portion of the amino acid sequence of the natural protein and contain the entire amino acid sequence of a small, naturally occurring molecule. Short stretches of ion channel amino acids may be fused with those of another protein, such as KLH, and antibodies to the chimeric molecule may be produced.

Monoclonal antibodies to a mutant ion channel may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler et al., 1975; Kozbor et al., 1985; Cote et al., 1983; Cole et al., 1984).

Monoclonal antibodies produced may include, but are not limited to, mouse-derived antibodies, humanised antibodies and fully human antibodies.

Antibodies may also be produced by inducing in vivo production in the lymphocyte population or by screening immunoglobulin libraries or panels of highly specific binding reagents as disclosed in the literature. (For example, see Orlandi et al., 1989; Winter and Milstein, 1991).

Antibody fragments which contain specific binding sites for a mutant ion channel may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between an ion channel and its specific antibody. A two-site, monoclonal-based immunoassay utilizing antibodies reactive to two non-interfering ion channel epitopes is preferred, but a competitive binding assay may also be employed.

In a further aspect of the invention there is provided a method of treating epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, comprising administering an isolated nucleic acid molecule which is the complement (antisense) of any one of the nucleic acid molecules described above and which encodes an RNA molecule that hybridizes with the mRNA encoding a mutant ion channel subunit of the invention, to a subject in need of such treatment.

In a still further aspect of the invention there is provided the use of an isolated nucleic acid molecule which is the complement (antisense) of a nucleic acid molecule of the invention and which encodes an RNA molecule that hybridizes with the mRNA encoding a mutant ion channel subunit of the invention, in the manufacture of a medicament for the treatment of epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness.

Typically, a vector expressing the complement (antisense) of the polynucleotides of the invention may be administered to a subject in need of such treatment. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

Additional antisense or gene-targeted silencing strategies may include, but are not limited to, the use of antisense oligonucleotides, injection of antisense RNA, transfection of antisense RNA expression vectors, and the use of RNA interference (RNAi) or short interfering RNAs (siRNA). Still further, catalytic nucleic acid molecules such as DNAzymes and ribozymes may be used for gene silencing (Breaker and Joyce, 1994; Haseloff and Gerlach, 1988). These molecules function by cleaving their target mRNA molecule rather than merely binding to it as in traditional antisense approaches.

In a further aspect, a suitable agonist, antagonist or modulator may include peptides, phosphopeptide's or small organic or inorganic compounds that can restore wild-type activity of ion channels containing mutations in the subunits which comprise the channels as described above.

Peptides, phosphopeptides or small organic or inorganic compounds suitable for therapeutic applications may be identified using nucleic acids and peptides of the invention in drug screening applications as described below. Molecules identified from these screens may also be of therapeutic application in affected individuals carrying other ion channel subunit gene mutations if the molecule is able to correct the common underlying functional deficit imposed by these mutations and those of the invention.

There is therefore provided a method of treating epilepsy as well as other disorders associated with ion channel dysfunction comprising administering a compound that is a suitable agonist, antagonist or modulator of an ion channel and that has been identified using the mutant ion channel subunits of the invention.

In some instances, an appropriate approach for treatment may be combination therapy. This may involve the administering an antibody or complement (antisense) to a mutant ion channel or ion channel subunit of the invention to inhibit its functional effect, combined with administration of wild-type ion channel subunits which may restore levels of wild-type ion channel formation to normal levels. Wild-type ion channel subunits of the invention can be administered using gene therapy approaches as described above for complement administration.

There is therefore provided a method of treating epilepsy as well as other disorders associated with ion channel dysfunction comprising administration of an antibody or complement to a mutant ion channel or ion channel subunit of the invention in combination with administration of wild-type ion channel subunits.

In still another aspect of the invention there is provided the use of an antibody or complement to a mutant ion channel or ion channel subunit of the invention in combination with the use of wild-type ion channel subunits, in the manufacture of a medicament for the treatment of epilepsy as well as other disorders associated with ion channel dysfunction.

In further embodiments, any of the agonists, antagonists, modulators, antibodies, complementary sequences or vectors of the invention may be administered in combination with other appropriate therapeutic agents. Selection of the appropriate agents may be made by those skilled in the art, according to conventional pharmaceutical principles. The combination of therapeutic agents may act synergistically to effect the treatment or prevention of the various disorders described above. Using this approach, therapeutic efficacy with lower dosages of each agent may be possible, thus reducing the potential for adverse side effects.

Any of the therapeutic methods described above may be applied to any subject in need of such therapy, including, for example, mammals such as dogs, cats, cows, horses, rabbits, monkeys, and most preferably, humans.

Drug Screening

According to still another aspect of the invention, nucleic acid molecules of the invention as well as peptides of the invention, particularly purified mutant ion channel subunit polypeptide and cells expressing these, are useful for the screening of candidate pharmaceutical agents for the treatment of epilepsy as well as other as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness.

Still further, it provides the use of a polypeptide complex for the screening of candidate pharmaceutical compounds.

Still further, it provides the use wherein high throughput screening techniques are employed.

Compounds that can be screened in accordance with the invention include, but are not limited to peptides (such as soluble peptides), phosphopeptides and small organic or inorganic molecules (such as natural product or synthetic chemical libraries and peptidomimetics).

In one embodiment, a screening assay may include a cell-based assay utilising eukaryotic or prokaryotic host cells that are stably transformed with recombinant molecules expressing the polypeptides or fragments of the invention, in competitive binding assays. Binding assays will measure the formation of complexes between a specific mutant ion channel subunit polypeptide or ion channel incorporating a mutant ion channel subunit polypeptide, and the compound being tested, or will measure the degree to which a compound being tested will inhibit or restore the formation of a complex between a specific mutant ion channel subunit polypeptide or ion channel incorporating a mutant ion channel subunit polypeptide, and its interactor or ligand.

The invention is particularly useful for screening compounds by using the polypeptides of the invention in transformed cells, transfected or injected oocytes, or animal models bearing mutated ion channel subunits such as transgenic animals or gene targeted (knock-in) animals (see transformed hosts). Drug candidates can be added to cultured cells that express a single mutant ion channel subunit or combination of mutant ion channel subunits (appropriate wild-type ion channel subunits should also be expressed for receptor assembly), can be added to oocytes transfected or injected with either a mutant ion channel subunit or combination of mutant ion channel subunits (appropriate wild-type ion channel subunits must also be injected for receptor assembly), or can be administered to an animal model containing a mutant ion channel or combination of mutant ion channels. Determining the ability of the test compound to modulate mutant ion channel activity can be accomplished by a number of techniques known in the art. These include for example measuring the effect on the current of the channel (e.g. calcium-, chloride-, sodium-, potassium-ion flux) as compared to the current of a cell or animal containing wild-type ion channels. Current in cells can be measured by a number of approaches including the patch-clamp technique (methods described in Hamill et al, 1981) or using fluorescence based assays as are known in the art (see Gonzalez et al. 1999). Drug candidates that alter the current to a more normal level are useful for treating or preventing epilepsy as well as other disorders associated with ion channel dysfunction.

Non cell-based assays may also be used for identifying compounds that can inhibit or restore binding between the polypeptides of the invention or ion channels incorporating the polypeptides of the invention, and their interactors. Such assays are known in the art and include for example AlphaScreen technology (PerkinElmer Life Sciences, MA, USA). This application relies on the use of beads such that each interaction partner is bound to a separate bead via an antibody. Interaction of each partner will bring the beads into proximity, such that laser excitation initiates a number of chemical reactions ultimately leading to fluorophores emitting a light signal. Candidate compounds that inhibit the binding of the mutant ion channel subunit, or ion channel incorporating the mutant subunit, with its interactor will result in loss of light emission, while candidate compounds that restore the binding of the mutant ion channel subunit, or ion channel incorporating the mutant subunit, with its interactor will result in positive light emission. These assays ultimately enable identification and isolation of the candidate compounds.

High-throughput drug screening techniques may also employ methods as described in WO84/03564. Small peptide test compounds synthesised on a solid substrate can be assayed for mutant ion channel subunit polypeptide or mutant ion channel binding. Bound mutant ion channel or mutant ion channel subunit polypeptide is then detected by methods well known in the art. In a variation of this technique, purified polypeptides of the invention can be coated directly onto plates to identify interacting test compounds.

The invention also contemplates the use of competition drug screening assays in which neutralizing antibodies capable of specifically binding the mutant ion channel compete with a test compound for binding thereto. In this manner, the antibodies can be used to detect the presence of any peptide that shares one or more antigenic determinants of the mutant ion channel.

The polypeptides of the present invention may also be used for screening compounds developed as a result of combinatorial library technology. This provides a way to test a large number of different substances for their ability to modulate activity of a polypeptide. A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in viva or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original receptor. The anti-id could then be used to isolate peptides from chemically or biologically produced peptide banks.

Another alternative method for drug screening relies on structure-based rational drug design. Determination of the three dimensional structure of the polypeptides of the invention, or the three dimensional structure of the ion channels which incorporate these polypeptides allows for structure-based drug design to identify biologically active lead compounds.

Three dimensional structural models can be generated by a number of applications, some of which include experimental models such as x-ray crystallography and NMR and/or from in silico studies of structural databases such as the Protein Databank (PDB). In addition, three dimensional structural models can be determined using a number of known protein structure prediction techniques based on the primary sequences of the polypeptides (e.g. SYBYL—Tripos Associated, St. Louis, Mo.), de novo protein structure design programs (e.g. MODELER—MSI Inc., San Diego, Calif., or MOE—Chemical Computing Group, Montreal, Canada) or ab initio methods (e.g. see U.S. Pat. Nos. 5,331,573 and 5,579,250).

Once the three dimensional structure of a polypeptide or polypeptide complex has been determined, structure-based drug discovery techniques can be employed to design biologically-active compounds based on these three dimensional structures. Such techniques are known in the art and include examples such as DOCK (University of California, San Francisco) or AUTODOCK (Scripps Research Institute, La Jolla, Calif.). A computational docking protocol will identify the active site or sites that are deemed important for protein activity based on a predicted protein model. Molecular databases, such as the Available Chemicals Directory (ACD) are then screened for molecules that complement the protein model.

Using methods such as these, potential clinical drug candidates can be identified and computationally ranked in order to reduce the time and expense associated with typical 'wet lab' drug screening methodologies.

Compounds identified through screening procedures as described above, and which are based on the use of the mutant nucleic acid and polypeptides of the invention, can also be tested for their effect on correcting the functional deficit imposed by other gene mutations in affected individuals including other ion channel subunit mutations.

Such compounds form a part of the present invention, as do pharmaceutical compositions containing these and a pharmaceutically acceptable carrier.

Pharmaceutical Preparations

Compounds identified from screening assays and shown to restore ion channel wild-type activity can be administered to a patient at a therapeutically effective dose to treat or ameliorate epilepsy as well as other disorders associated with ion channel dysfunction, as described above. A therapeutically effective dose refers to that amount of the compound sufficient to result in amelioration of symptoms of the disorder.

Toxicity and therapeutic efficacy of such compounds can be determined by standard pharmaceutical procedures in cell cultures or experimental animals. The data obtained from these studies can then be used in the formulation of a range of dosages for use in humans.

Pharmaceutical compositions for use in accordance with the present invention can be formulated in a conventional manner using one or more physiological acceptable carriers, excipients or stabilisers which are well, known. Acceptable carriers, excipients or stabilizers are non-toxic at the dosages and concentrations employed, and include buffers such as phosphate, citrate, and other organic acids; antioxidants including absorbic acid; low molecular weight (less than about 10 residues) polypeptides; proteins, such as serum albumin, gelatin, or immunoglobulins; binding agents including hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween, Pluronics or polyethylene glycol (PEG).

The formulation of pharmaceutical compositions for use in accordance with the present invention will be based on the proposed route of administration. Routes of administration may include, but are not limited to, inhalation, insufflation (either through the mouth or nose), oral, buccal, rectal or parental administration.

Diagnostic and Prognostic Applications

Polynucleotide sequences encoding an ion channel subunit may be used for the diagnosis or prognosis of epilepsy, as well as other as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, and the use of the nucleic acid molecules incorporated as part of the invention in diagnosis or prognosis of these disorders, or a predisposition to these disorders, is therefore contemplated. The nucleic acid molecules incorporating the novel mutation events laid out in Table 1 may be used for this purpose.

The polynucleotides that may be used for diagnostic or prognostic purposes include oligonucleotide sequences, genomic DNA and complementary RNA and DNA molecules. The polynucleotides may be used to detect and quantitate gene expression in biological samples. Genomic DNA used for the diagnosis or prognosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, hybridisation using specific oligonucleotides, restriction enzyme digest and mapping, PCR mapping, RNAse protection, and various other methods may be employed. Oligonucleotides specific to particular sequences can be chemically synthesized and labelled radioactively or nonradioactively and hybridised to individual samples immobilized on membranes or other solid-supports or in solution. The presence, absence or excess expression of any one of the mutant ion channel genes of the invention may then be visualized using methods such as autoradiography, fluorometry, or colorimetry.

In a further diagnostic or prognostic approach, the nucleotide sequences of the invention may be useful in assays that detect the presence of associated disorders, particularly those mentioned previously. The nucleotide sequences may be labelled by standard methods and added to a fluid or tissue sample from a patient under conditions suitable for the formation of hybridisation complexes. After a suitable incubation period, the sample is washed and the signal is quantitated and compared with a standard value. If the amount of signal in the patient sample is significantly altered in comparison to a control sample then the presence of altered levels of nucleotide sequences in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis or prognosis of epilepsy and other disorders as described above, which are associated with the ion channel subunit mutations or variants of the invention, the nucleotide sequence of each gene can be compared between normal tissue and diseased tissue in order to establish whether the patient expresses a mutant gene.

In order to provide a basis for the diagnosis or prognosis of a disorder associated with abnormal expression of an ion channel subunit gene of the invention, a normal or standard profile for expression is established. This may be accomplished by combining body fluids or cell extracts taken from normal subjects, either animal or human, with a sequence, or a fragment thereof, encoding the relevant ion channel subunit gene, under conditions suitable for hybridisation or amplification. Standard hybridisation may be quantified by comparing the values obtained from normal subjects with values from an experiment in which a known amount of a substantially purified polynucleotide is used. Another method to identify a normal or standard profile for expression of an ion channel subunit gene is through quantitative RT-PCR studies. RNA isolated from body cells of a normal individual is reverse transcribed and real-time PCR using oligonucleotides specific for the relevant gene is conducted to establish a normal level of expression of the gene. Standard values obtained in both these examples may be compared with values obtained from samples from patients who are symptomatic for a disorder. Deviation from standard values is used to establish the presence of a disorder.

Once the presence of a disorder is established and a treatment protocol is initiated, hybridisation assays or quantitative RT-PCR studies may be repeated on a regular basis to determine if the level of expression in the patient begins to approximate that which is observed in the normal subject. The results obtained from successive assays may be used to show the efficacy of treatment over a period ranging from several days to months.

According to a further aspect of the invention there is provided the use of a polypeptide as described above in the diagnosis or prognosis of epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness.

When a diagnostic or prognostic assay is to be based upon proteins constituting an ion channel, a variety of approaches are possible. For example, diagnosis or prognosis can be achieved by monitoring differences in the electrophoretic mobility of normal and mutant proteins that form the ion channel. Such an approach will be particularly useful in identifying mutants in which charge substitutions are present, or in which insertions, deletions or substitutions have resulted in a significant change in the electrophoretic migration of the resultant protein. Alternatively, diagnosis or prognosis may be based upon differences in the proteolytic cleavage patterns of normal and mutant proteins, differences in molar ratios of the various amino acid residues, or by functional assays demonstrating altered function of the gene products.

In another aspect, antibodies that specifically bind mutant ion channels may be used for the diagnosis or prognosis of a disorder, or in assays to monitor patients being treated with a complete ion channel or agonists, antagonists, modulators or inhibitors of an ion channel. Antibodies useful for diagnostic or prognostic purposes may be prepared in the same manner as described above for therapeutics. Diagnostic or prognostic assays for ion channels include methods that utilize the antibody and a label to detect a mutant ion channel in human body fluids or in extracts of cells or tissues. The antibodies may be used with or without modification, and may be labelled by covalent or non-covalent attachment of a reporter molecule.

A variety of protocols for measuring the presence of mutant ion channels, including but not restricted to, ELISAs, RIAs, and FACS, are known in the art and provide a basis for diagnosing or prognosing a disorder. The expression of a mutant ion channel or combination of mutant ion channels is established by combining body fluids or cell extracts taken from test mammalian subjects, preferably human, with antibody to the ion channel or channels under conditions suitable for complex formation. The amount of complex formation may be quantitated by various methods, preferably by photometric means. Antibodies specific for the mutant ion channels will only bind to individuals expressing the said mutant ion channels and not to individuals expressing only wild-type channels (ie normal individuals). This establishes the basis for diagnosing the disorder.

Once an individual has been diagnosed or prognosed with a disorder, effective treatments can be initiated as described above. Treatments can be directed to amend the combination of ion channel subunit mutations or may be directed to one mutation.

Microarray

In further embodiments, complete cDNAs, oligonucleotides or longer fragments derived from any of the polynucleotide sequences described herein may be used as probes in a microarray. The microarray can be used to diagnose or prognose epilepsy, as well as other disorders associated with ion channel dysfunction, through the identification of genetic variants, mutations, and polymorphisms in the ion channel subunits that form part of the invention, to understand the genetic basis of a disorder, or can be used to develop and monitor the activities of therapeutic agents.

According to a further aspect of the present invention, tissue material obtained from genetically modified non-human animal models generated as a result of the identification of specific ion channel subunit human mutations (see below), particularly those disclosed in the present invention, can be used in microarray experiments. These experiments can be conducted to identify the level of expression of specific ion channel subunits, or the level of expression of any cDNA clone from whole-tissue libraries, in diseased tissue as opposed to normal control tissue. Variations in the expression level of genes, including ion channel subunits, between the two tissues indicates their possible involvement in the disease process either as a cause or consequence of the original ion channel subunit mutation present in the animal model. These experiments may be used to determine gene function, to understand the genetic basis of a disorder, to diagnose or prognose a disorder, and to develop and monitor the activities of therapeutic agents. Microarrays may be prepared, used, and analyzed using methods known in the art. (For example, see Schena et al., 1996; Heller et al., 1997).

Transformed Hosts

The present invention also provides for the production of genetically modified (knock-out, knock-in and transgenic), non-human animal models comprising nucleic acid molecules containing the novel ion channel mutations or variants as laid out in Table 1. These animals are useful for the study of the function of ion channels, to study the mechanisms by which combinations of mutations in ion channel subunits interact to give rise to disease and the effects of these mutations on tissue development, for the screening of candidate pharmaceutical compounds, for the creation of explanted mammalian cell cultures which express mutant ion channels or combinations of mutant ion channels, and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to the relative ease in generating knock-in, knock-out or transgenics of these animals, their ease of maintenance and their shorter life spans. For certain studies, transgenic yeast or invertebrates may be suitable and preferred because they allow for rapid screening and provide for much easier handling. For longer term studies, non-human primates may be desired due to their similarity with humans.

To create an animal model for a mutated ion channel, or an animal model incorporating a combination of mutations, several methods can be employed. These include, but are not limited to, generation of a specific mutation in a homologous animal gene, insertion of a wild type human gene and/or a humanized animal gene by homologous recombination, insertion of a mutant (single or multiple) human gene as genomic or minigene cDNA constructs using wild type or mutant or artificial promoter elements, or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create transgenic mice in order to study gain of gene function in vivo, any mutant ion channel subunit gene of the invention can be inserted into a mouse germ line using standard techniques such as oocyte microinjection. Gain of gene function can mean the over-expression of a gene and its protein product, or the genetic complementation of a mutation of the gene under investigation. For oocyte injection, one or more copies of the mutant gene can be inserted into the pronucleus of a just-fertilized mouse oocyte. This oocyte is then reimplanted into a pseudo-pregnant foster mother. The live-born mice can then be screened for integrants using analysis of tail DNA for the presence of the relevant human ion channel subunit gene sequence. The transgene can be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

To generate knock-out mice or knock-in mice, gene targeting through homologous recombination in mouse embryonic stem (ES) cells may be applied. Knock-out mice are generated to study loss of gene function in vivo while knock-in mice (which are preferred) allow the study of gain of function or to study the effect of specific gene mutations. Knock-in mice are similar to transgenic mice however the integration site and copy number are defined in the former.

For knock-out mouse generation, gene targeting vectors can be designed such that they delete (knock-out) the protein coding sequence of the relevant ion channel subunit gene in the mouse genome. In contrast, knock-in mice can be produced whereby a gene targeting vector containing the relevant ion channel subunit gene can integrate into a defined genetic locus in the mouse genome. For both applications, homologous recombination is catalysed by specific DNA repair enzymes that recognise homologous DNA sequences and exchange them via double crossover.

Gene targeting vectors are usually introduced into ES cells using electroporation. ES cell integrants are then isolated via an antibiotic resistance gene present on the targeting vector and are subsequently genotyped to identify those ES cell clones in which the gene under investigation has integrated into the locus of interest. The appropriate ES cells are then transmitted through the germline to produce a novel mouse strain.

In instances where gene ablation results in early embryonic lethality, conditional gene targeting may be employed. This allows genes to be deleted in a temporally and spatially controlled fashion. As above, appropriate ES cells are transmitted through the germline to produce a novel mouse strain, however the actual deletion of the gene is performed in the adult mouse in a tissue specific or time controlled manner. Conditional gene targeting is most commonly achieved by use of the cre/lox system. The enzyme cre is able to recognise the 34 base pair loxp sequence such that loxp flanked (or floxed) DNA is recognised and excised by cre. Tissue specific cre expression in transgenic mice enables the generation of tissue specific knock-out mice by mating gene targeted floxed mice with cre transgenic mice. Knock-out can be conducted in every tissue (Schwenk et al., 1995) using the 'deleter' mouse or using transgenic mice with an inducible cre gene (such as those with tetracycline inducible cre genes), or knock-out can be tissue specific for example through the use of the CD19-cre mouse (Rickert et al., 1997).

Once knock-in animals have been produced which contain a specific mutation in a particular ion channel subunit, mating combinations may be initiated between such animals so as to produce progeny containing combinations of two or more ion channel mutations. These animals effectively mimic combinations of mutations that are proposed to cause human IGE cases. These animal models can subsequently be used to study the extent and mechanisms of disease as related to the mutated ion channel combinations, as well as for the screening of candidate therapeutic compounds.

According to still another aspect of the invention there is provided the use of genetically modified non-human animals as described above for the screening of candidate pharmaceutical compounds (see drug screening above). These animals are also useful for the evaluation (eg therapeutic efficacy, toxicity, metabolism) of candidate pharmaceutical compounds, including those identified from the invention as described above, for the treatment of epilepsy as well as other as other disorders associated with ion channel dysfunction as described above.

It will be clearly understood that, although a number of prior art publications are referred to herein, this reference does not constitute an admission that any of these documents forms part of the common general knowledge in the art, in Australia or in any other country.

Throughout this specification and the claims, the words "comprise", "comprises" and "comprising" are used in a non-exclusive sense, except where the context requires otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

BRIEF DESCRIPTION OF THE DRAWINGS

Preferred forms of the invention will now be described, by way of example only, with reference to the following examples and the accompanying drawings, in which:

FIG. 1A: A typical channel may have five subunits of three different types.

FIG. 1B: In outbred populations complex diseases such as idiopathic generalized epilepsies may be due to mutations in two (or more) different subunit genes. Because only one allele of each subunit gene is abnormal, half the expressed subunits will have the mutation.

FIG. 1C: In inbred populations, both alleles of a single subunit gene will be affected, so all expressed subunits will be mutated.

FIG. 1D: Autosomal dominant disorders can be attributed to single ion channel subunit mutations that give rise to severe functional consequences.

MODES FOR PERFORMING THE INVENTION

Figure 1:
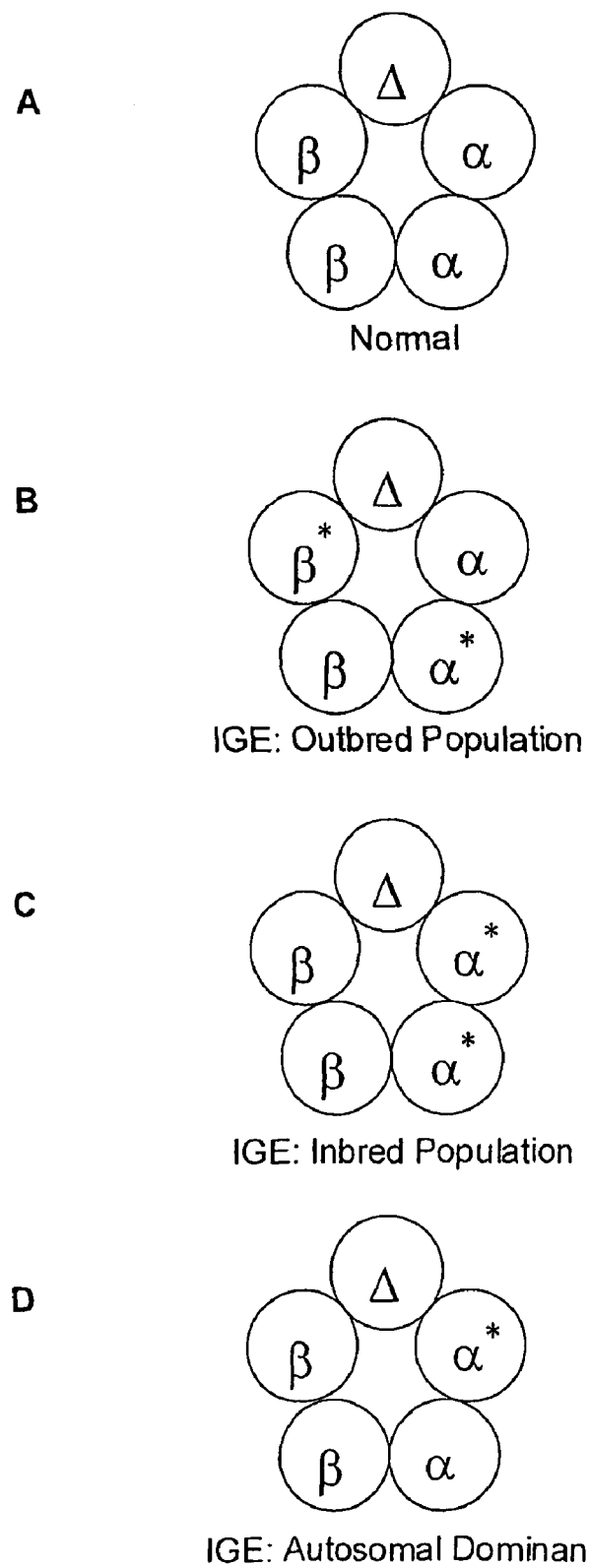
FIG. 1 provides an example of ion channel subunit stoichiometry and the effect of multiple versus single ion channel subunit mutations.

Potassium channels are the most diverse class of ion channel. The *C. elegans* genome encodes about 80 different potassium channel genes and there are probably more in mammals. About ten potassium channel genes are known to be mutated in human disease and include four members of the KCNQ gene sub-family of potassium channels. KCNQ proteins have six transmembrane domains, a single P-loop that forms the selectivity filter of the pore, a positively charged fourth transmembrane domain that probably acts as a voltage sensor, and intracellular amino and carboxy termini. The C-terminus is long and contains a conserved "A domain" followed by a short stretch thought to be involved in subunit assembly.

Four KCNQ subunits are thought to combine to form a functional potassium channel. All five known KCNQ proteins can form homomeric channels in vitro and the formation of heteromers appears to be restricted to certain combinations. For instance KCNQ2 and KCNQ3, which are predominantly expressed in the central nervous system, form a heteromultimeric channel that mediates the neuronal muscarinic-regulated current (M-current), also known as the M-channel (or M-type $K^+$ channel). The M-current is a slowly activating, non-inactivating potassium conductance known to regulate neuronal excitability by determining the firing properties of neurons and their responsiveness to synaptic input (Wang et al., 1998). Because it is the only current active at voltages near the threshold for action potential initiation, the M-current has a major impact on neuronal excitability.

Sodium (the alpha subunit) and calcium channels are thought to have evolved from the potassium channel subunit, and they each consist of four domains covalently linked as the one molecule, each domain being equivalent to one of the subunits that associate to form the potassium channel. Each of the four domains of the sodium and calcium channels are comprised of six transmembrane segments.

Voltage-gated sodium channels are required to generate the electrical excitation in neurones, heart and skeletal muscle fibres, which express tissue specific isoforms. Sodium channels are heteromers of a pore forming alpha subunit and a modulatory beta-1 subunit, with an additional beta-2 subunit in neuronal channels. Ten genes encoding sodium channel alpha subunits and 3 genes encoding different beta subunits have so far been identified. The beta subunits of the sodium channels do not associate with the alpha subunits to form any part of the pore, they do however affect the way the alpha pore forming subunit functions.

As with sodium channels, calcium channels consist of a single pore forming alpha subunit, of which at least six types have been identified to date, and several accessory subunits including four beta, one gamma and one alpha2-delta gene. Many of these subunits also encode multiple splice variants adding to the diversity of receptor subunits of this family of ion channels.

The ion channels in the nAChR/GABA super family show a theoretical pentameric channel. Gamma-Aminobutyric acid (GABA) is the most abundant inhibitory neurotransmitter in the central nervous system. GABA-ergic inhibition is mediated by two major classes of receptors, type A (GABA-A) and type B (GABA-B). GABA-B receptors are members of the class of receptors coupled to G-proteins and mediate a variety of inhibitory effects via secondary messenger cascades. GABA-A receptors are ligand-gated chloride channels that mediate rapid inhibition.

The GABA-A channel has 16 separate, but related, genes encoding subunits. These are grouped on the basis of sequence identity into alpha, beta, gamma, delta, epsilon, theta and pi subunits. There are six alpha subunits ($\alpha 1$-$\alpha 6$), three beta subunits ($\beta 1$-$\beta 3$) and three gamma subunits ($\gamma 1$-$\gamma 3$). Each GABA-A receptor comprises five subunits which may, at least in theory, be selected from any of these subunits.

Neuronal nicotinic acetylcholine receptors (nAChRs) consist of heterologous pentamers comprising various combinations of alpha subunits or alpha and beta subunits ($\alpha 2$-$\alpha 9$; $\beta 2$-$\beta 4$). The alpha subunits are characterised by adjacent cysteine residues at amino acid positions 192 and 193, and the beta subunits by the lack of these cysteine residues. They are ligand-gated ion channels differentially expressed throughout the brain to form physiologically and pharmacologically distinct receptors hypothesised to mediate fast, excitatory transmission between neurons of the central nervous system or to modulate neurotransmission from their presynaptic position.

In chicken and rat, the predominant nAChR subtype is composed of alpha-4 and beta-2 subunits. The transmembrane 2 (M2) segments of the subunits are arranged as alpha helices and contribute to the walls of the neurotransmitter-gated ion channel. The alpha helices appear to be kinked and orientated in such a way that the side chains of the highly conserved M2-leucine residues project inwards when the channel is closed. ACh is thought to cause a conformational change by altering the association of the amino acid residues of M2. The opening of the channel seems to be due to rotations of the gate forming side chains of the amino acid residues; the conserved polar serines and threonines may form the critical gate in the open channel.

EXAMPLE 1

Identification of Mutations in Ion Channels

Previous studies by reference (Wallace et al., 1998; PCT/AU01/00581; Wallace et al., 2001b; Australian patent AU-B-56247/96; Steinlein et al., 1995; PCT/AU01/00541; Phillips et al., 2001; PCT/AU01/00729; PCT/AU01/01648; PCT/AU02/00910; Wallace et al., 2001a, the disclosures of which are incorporated herein by reference) have identified mutations in a number of ion channel subunits associated with epilepsy. These include ion channel subunits of voltage-gated (eg SCN1A, SCN1B, KCNQ2, KCNQ3) or ligand-gated (eg CHRNA4, CHRNB2, GABRG2, GABRD) types. To identify further mutations in ion channel genes, subunits which comprise the ion channels were screened for molecular defects in epilepsy patients.

Human genomic sequence available from the Human Genome Project was used to characterize the genomic organisation for each subunit gene. Each gene was subsequently screened for sequence changes using single strand conformation polymorphism (SSCP) analysis in a large sample of epileptics with common sporadic IGE subtypes eg juvenile myoclonic epilepsy (JME), childhood absence epilepsy (CAE), juvenile absence epilepsy (JAE) and epilepsy with generalized tonic-clonic seizures (TCS). Clinical observations can then be compared to the molecular defects characterized in order to establish the combinations of mutant subunits involved in the various disease states, and therefore to provide validated drug targets for each of these disease states. This will provide a basis for novel drug treatments directed at the genetic defects present in each patient.

The coding sequence for each of the ion channel subunits was aligned with human genomic sequence present in available databases at the National Centre for Biotechnology Information (NCBI). The BLASTN algorithm was typically used for sequence alignment and resulted in the genomic organisation (intron-exon structure) of each gene being determined. Where genomic sequence for an ion channel subunit was not available, BACs or PACs containing the relevant ion channel subunit were identified through screening of high density filters containing these clones and were subsequently sequenced.

Availability of entire genomic sequence for each ion channel subunit facilitated the design of intronic primers spanning each exon. These primers were used for both high throughput SSCP screening and direct DNA sequencing.

EXAMPLE 2

Sample Preparation for SSCP Screening

A large collection of individuals affected with epilepsy have undergone careful clinical phenotyping and additional data regarding their family history has been collated. Informed consent was obtained from each individual for blood collection and its use in subsequent experimental procedures. Clinical phenotypes incorporated classical IGE cases as well as GEFS+ and febrile seizure cases.

DNA was extracted from collected blood using the QIAamp DNA Blood Maxi kit (Qiagen) according to manufacturers specifications or through procedures adapted from Wyman and White (1980). Stock DNA samples were kept at a concentration of 1 ug/ul.

In preparation for SSCP analysis, samples to be screened were formatted into 96-well plates at a concentration of 30 ng/ul. These master plates were subsequently used to prepare exon specific PCR reactions in the 96-well format.

EXAMPLE 3

Identification of Sequence Alterations in Ion Channel Genes

SSCP analysis of specific ion channel exons followed by sequencing of SSCP bandshifts was performed on individuals constituting the 96-well plates to identify sequence alterations.

Primers used for SSCP were labelled at their 5' end with HEX and typical PCR reactions were performed in a total volume of 10 µl. All PCR reactions contained 67 mM Tris-HCl (pH 8.8); 16.5 mM $(NH_4)_2SO_4$; 6.5 µM EDTA; 1.5 mM $MgCl_2$; 200 µM each DNTP; 10% DMSO; 0.17 mg/ml BSA; 10 mM β-mercaptoethanol; 5 µg/ml each primer and 100 U/ml Taq DNA polymerase. PCR reactions were typically performed using 10 cycles of 94° C. for 30 seconds, 60° C. for 30 seconds, and 72° C. for 30 seconds followed by 25 cycles of 94° C. for 30 seconds, 55° C. for 30 seconds, and 72° C. for 30 seconds. A final extension reaction for 10 minutes at 72° C. followed.

Ten to twenty µl of loading dye comprising 50% (v/v) formamide, 12.5 mM EDTA and 0.02% (w/v) bromophenol blue were added to completed reactions which were subsequently run on non-denaturing 4% polyacrylamide gels with a cross-linking ratio of 35:1 (acrylamide:bis-acrylamide) and containing 2% glycerol. Gel thickness was 100 µm, width 168 mm and length 1600 mm. Gels were run at 1200 volts and approximately 20 mA, at 18° C. and analysed on the GelScan 2000 system (Corbett Research, Australia) according to manufacturers specifications.

PCR products showing a conformational change were subsequently sequenced. This first involved re-amplification of the amplicon from the relevant individual (primers used in this instance did not contain 5' HEX labels) followed by purification of the PCR amplified templates for sequencing using QiaQuick PCR preps (Qiagen) based on manufacturers procedures. The primers used to sequence the purified amplicons were identical to those used for the initial amplification step. For each sequencing reaction, 25 ng of primer and 100 ng of purified PCR template were used. The BigDye sequencing kit (ABI) was used for all sequencing reactions according to the manufacturers specifications. The products were run on an ABI 377 Sequencer and analysed using the EditView program.

Table 1 shows the novel sequence changes identified in the ion channel subunits screened.

EXAMPLE 4

Digenic Model Examples

In some instances a single mutation in an ion channel alone is insufficient to give rise to an epilepsy phenotype. However combinations of mutations each conferring a subtle change of function to an ion channel, as proposed by the digenic model (PCT/AU01/00872), may be sufficient to produce an epilepsy phenotype.

Using mutations and variations in ion channel subunits previously identified, the digenic model may be validated through a parametric analysis of large families in which two abnormal alleles co-segregate by chance to identify mutations which act co-operatively to give an epilepsy phenotype. It is envisaged that the strategy of careful, clinical phenotyping in these large families, together with a linkage analysis based on the digenic hypothesis will allow identification of the mutations in ion channels associated with IGEs. If molecular genetic studies in IGE are successful using the digenic hypothesis, such an approach might serve as a model for other disorders with complex inheritance.

The digenic hypothesis predicts that the closer the genetic relationship between affected individuals, the more similar the sub-syndromes, consistent with published data (Italian League Against Epilepsy Genetic Collaborative Group, 1993). This is because more distant relatives are less likely to share the same combinations of mutated subunits.

Identical twins have the same pair of mutated subunits and the same minor alleles so the sub-syndromes are identical. Affected sib-pairs, including dizygous twins, with the same sub-syndrome would also have the same pair of mutated subunits, but differences in minor alleles would lead to less similarity than with monozygous twins. Some sib-pairs and dizygous twins, have quite different sub-syndromes; this would be due to different combinations of mutated subunits, when the parents have more than two mutated alleles between them.

A special situation exists in inbred communities that parallels observations on autosomal recessive mouse models. Here the two mutated alleles of the digenic model are the same and thus result in a true autosomal recessive disorder. Because all affected individuals have the same pair of mutated alleles, and a similar genetic background, the phenotypes are very similar.

In outbred communities approximately 1% of the population would have IGE genotypes (2 mutated alleles) and 0.3% would clinically express IGE. Most of these would have mutations in two different channel subunits. In such communities most cases would appear "sporadic" as the risk to first degree relatives would be less than 10%.

For example, let there be three IGE loci (A,B,C) and let the frequency of abnormal alleles (a*,b*,c*) at each locus be 0.027 and of normal alleles (a, b, c) be 0.973. Then, the distribution of genotypes aa*, a*a, a*a* and aa at locus A will be 0.0263 (0.027×0.973), 0.0263, 0.0007 and 0.9467 respectively, and similarly for loci B and C. In this population 0.8485 will have no mutated alleles ($0.9467^3$), 0.1413 will have one mutated allele (a* or b* or c*; $0.0263×0.9467^2×6$), 0.0098 will have two mutated alleles (0.0020 two same abnormal alleles, 0.0078, two different abnormal alleles) and 0.00037 will have more than two abnormal alleles. Thus in this population 0.01, or 1%, will have two or more abnormal alleles (IGE genotype), and the total abnormal allele frequency will be 0.08 (3×0.027).

To determine the familial risks and allele patterns in affected pairs, the frequency distribution of population matings and the percentage of children with 2 or more abnormal alleles must be determined. The frequency of matings with no abnormal alleles (0×0) is 0.72 ($0.8485^2$), for 1×0 and 0×1 matings 0.24 (2×0.8485×0.1413), for a 1×1 mating 0.020, and for 2×0 and 0×2 matings 0.0166 etc. From this distribution of matings the frequency of children with 2 or more abnormal alleles can be shown to be 0.01. For example, the 0×2 and 2×0 matings contribute 0.0033 of this 0.01 frequency (0.0166 [mating frequency]×0.2 [chance of that mating producing a child with 2 or more abnormal alleles]).

To determine parental risk it can be shown that of children with 2 abnormal alleles (IGE genotype), 0.49 derive from 1×1 matings where no parent is affected, 0.33 derive from a 2×0 and 0×2 matings etc. For the 2×0 and 0×2 matings, half the parents have IGE genotypes and contribute 0.16 (0.33/2) to the parental risk with the total parental risk of an IGE genotype being 0.258. The other matings that contribute to affected parent-child pairs are 2×1, 1×2, 3×0, 0×3 etc.

The sibling risk of an IGE genotype is 0.305. For example 2×0 and 0×2 matings contributed 0.08 to the sibling risk (0.33[fraction of children with 2 abnormal alleles]×0.25[the chance of that mating producing a child with 2 or more abnormal alleles]). Similarly the offspring risk was determined to be 0.248 by mating individuals with 2 abnormal alleles with the general population. Thus at 30% penetrance the risk for IGE phenotype for parents of a proband is 0.077, for siblings 0.091, and for offspring 0.074.

It can be shown that affected sib pairs share the same abnormal allele pair in 85% of cases. This is because of all affected sib pairs 44% derive from 1×1 matings and 23% from 0×2 and 2×0 matings where all affected siblings have the same genotype. In contrast, 24% derive from 1×2 matings and 9% from 3×1 and 2×2 matings etc where affected sibling genotypes sometimes differ.

For affected parent-child pairs, genotypes are identical in only 58%. Of affected parent child pairs, 43% derive from 0×2 matings where genotypes are identical, whereas 38% derive from 0×3 and 17% from 1×2 where the majority of crosses yield different affected genotypes.

Based on the digenic model it has been postulated that most classical IGE and GEFS+ cases are due to the combination of two mutations in multi-subunit ion channels. These are typically point mutations resulting in a subtle change of function. The critical postulate is that two mutations, usually, but not exclusively, in different subunit alleles ("digenic model"), are required for clinical expression of IGE.

The hypothesis that, similar phenotypes can be caused by the combination of mutations in two (or more) different subunits (outbred communities), or by the same mutation in two (or more) alleles of the same subunit (inbred communities), may seem implausible. However, applying the digenic hypothesis to the theoretical pentameric channel shown in FIG. 1, in outbred communities IGE will be due to subunit combinations such as $\alpha^*\alpha\beta^*\beta\Delta$, $\alpha^*\alpha^*\beta\beta\Delta$ or $\alpha\alpha\beta^*\beta\Delta^*$ (mutated subunits indicated by *). In inbred communities $\alpha^*\alpha^*\beta\beta\Delta$ or $\alpha\alpha\beta^*\beta^*\Delta$ combinations might cause IGE phenotypes. We assume that the mutations will not cause reduced expression of the alleles and that the altered ion channel excitability, and consequent IGE phenotype, caused by mutations in two different alleles is similar to that caused by the same mutation in both alleles of one subunit. Finally, subunit mutations with more severe functional consequences (eg breaking a disulphide bridge in SCN1B or amino acid substitution in the pore forming regions of SCN1A for GEFS+) cause autosomal dominant generalized epilepsies with a penetrance of 60-90%. Such "severe" mutations are rare (allele frequency <0.01%) and are infrequent causes of GEFS+. They very rarely, or perhaps never, cause classical IGE.

The relative separate segregation of classical IGE and GEFS+ phenotypes is an anecdotal clinical observation of ours (Singh et al., 1999), although the separation is not absolute. The separation is supported by previous family and EEG studies of Doose and colleagues who described "type A" and "type B" liabilities which we may approximate the GEFS+ and classical IGE groupings respectively (Doose and Baier, 1987).

The digenic model predicts that affected sib pairs will share the same genes in 85% of cases whereas they will have at least one different allele in the remaining 15%. In contrast, only 58% of parent-child pairs share the same alleles in a 3 locus model. Thus there should be greater similarity of syndromes between sibling pairs than parent-child pairs. This would be most objectively measured by age of onset and seizure types.

Estimates for the risk of febrile seizures or IGE in relatives vary. The estimates range from 5%-10% for siblings, 4%-6% for offspring, 3%-6% for parents, and 2-3% for grandparents. Underestimation may occur because IGE manifest in youth, and parents and particularly grandparents may be unaware of seizures in themselves in younger years. This is particularly true where there was stigma associated with epilepsy and where the epilepsy may have been mild and unrecognized. Underestimation of sibling and offspring risks occurs when unaffected young children are counted, some of whom will develop IGE in adolescence. Overestimation may occur with misdiagnosis of seizures or inclusion of seizures unrelated to IGE (e.g. due to trauma or tumors)

In autosomal dominant models the risk to affected relatives reduces proportionally (50% for first degree relatives, 25% for second degree etc). For all oligogenic or polygenic models the risk decreases more quickly. For a digenic model with three loci, the risks are 9.1% for siblings, 7.4% for offspring, 7.7% for parents. Rigorous measurement of the familial recurrence rates, with careful phenotyping and age-corrected risk estimates could be compared with the predictions from the digenic model, and it is proposed to do this.

There is a small amount of information on IGE families regarding haplotype distribution. For example, there is some evidence for a locus on 8q as determined by parametric linkage in a single family (Fong et al., 1998) and by non-parametric analysis in multiple small families (Zara et al., 1995). Interestingly, in the latter study the 8q haplotype not infrequently came from the unaffected parent. This would be quite compatible with the digenic model and evaluation of other data sets in this manner could be used to test the hypothesis, and it is proposed to do this.

Following the analysis of one large family with epilepsy where the two main phenotypes were childhood absence epilepsy (CAE) and febrile seizures (FS), the inheritance of FS was found to be autosomal dominant and the penetrance 75%. However the inheritance of CAE in this family was not simple Mendelian, but suggestive of complex inheritance with the involvement of more than one gene. The power of this large family was used to explore the complex genetics of CAE further.

Linkage analysis on this family in which individuals with CAE, FS and FS+ were deemed affected led to the detection of linkage on chromosome 5q and identification of a mutation in the GABRG2 gene (R43Q) which is localised to this region (Wallace et al., 2001a; PCT/AU01/00729). All 10 tested individuals with FS alone in this family had this mutation and 7 CAE affected individuals in this family also had the mutation. To test the digenic model of IGEs in the CAE affected individuals, the whole genome screen of this family was reanalysed with only individuals with CAE considered affected. Linkage analysis was performed using FASTLINK v4.0, two-point lod scores were calculated assuming 50% penetrance and a 2% phenocopy rate and individuals with FS or FS+ were coded as unknown. Markers producing a lod score greater than 1 were reanalysed without a phenocopy rate and at the observed penetrance for CAE in this family (30%). Results from the analysis revealed significant linkage to chromosome 14q22-q23 (lod 3.4). This provides strong evidence for a second locus segregating with CAE affected individuals in this family. While the GABRG2 mutation is sufficient to cause FS, the CAE phenotype is thought to be due to both the GABRG2 mutation and a mutation occurring in a gene mapping to the 14q locus, as proposed by the digenic model.

Figure 2:
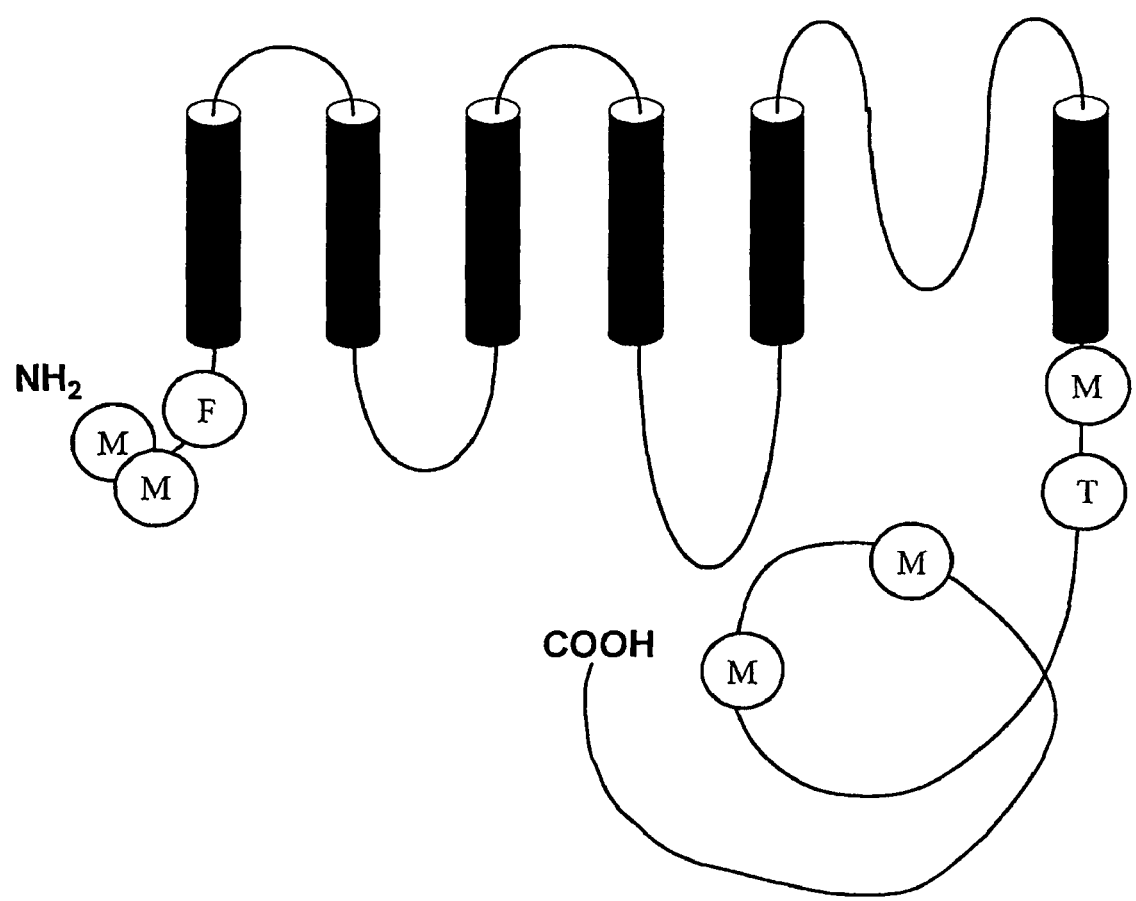
FIG. 2 represents the location of mutations identified in the KCNQ2 ion channel subunit constituting the potassium channel. M: Missense mutation; T: Truncation mutation; F: Frameshift mutation; S: Splice site mutation.

For the application of the digenic model to sporadic cases of IGE and affected individuals belonging to smaller families in which genotyping and linkage analysis is not a feasible approach to disease gene identification, direct mutation analysis of ion channel genes in these individuals has been carried out as described above. In Table 1 there is provided an indication of novel genetic alterations so far identified through mutation analysis screening of these individuals. FIG. 2 provides an example to indicate where some of these mutations have occurred with respect to the potassium channel KCNQ2 gene.

Figure 3:
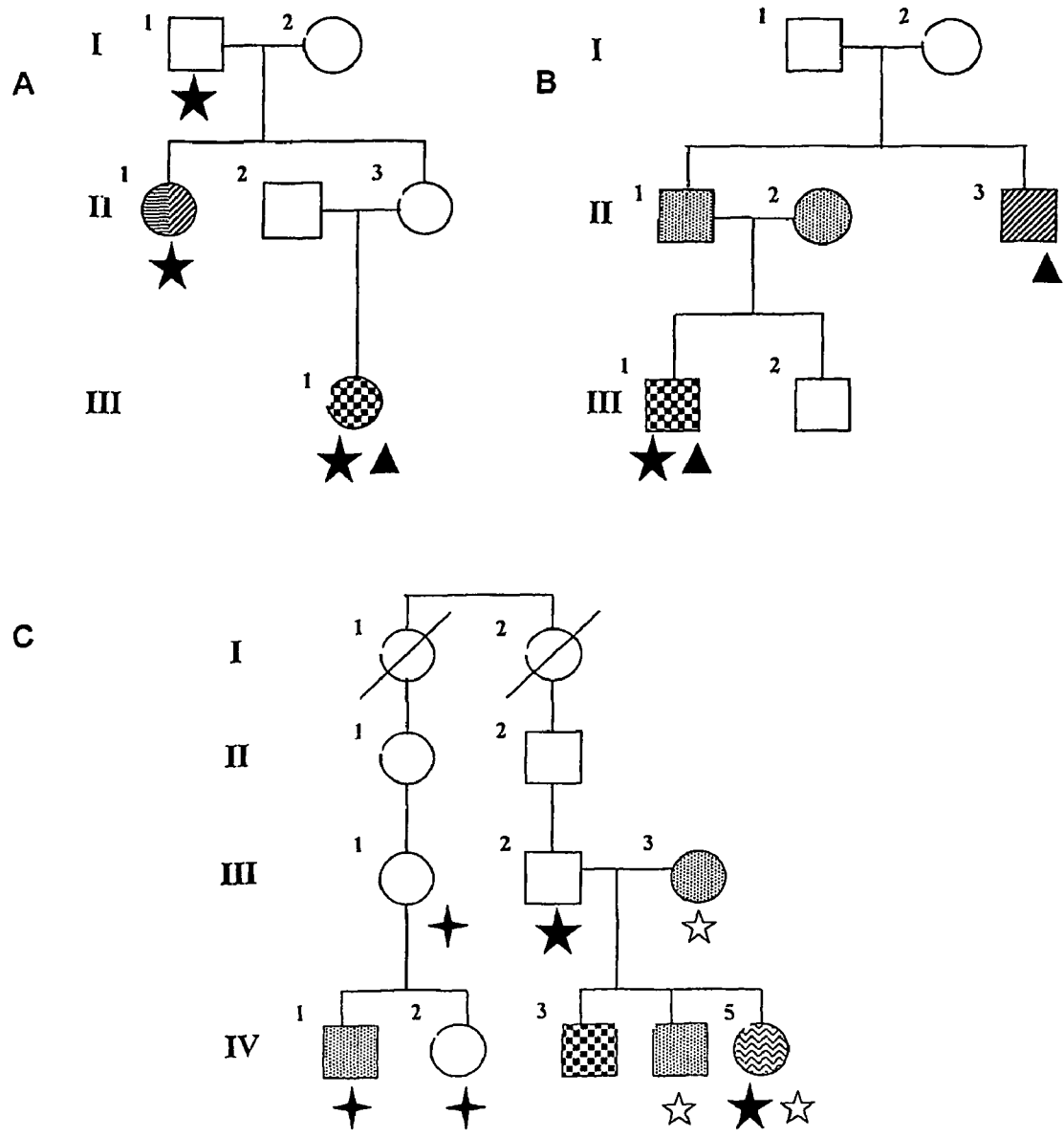
FIG. 3 provides examples of epilepsy pedigrees where mutation profiles of ion channel subunits for individuals constituting the pedigree have begun to be determined. These examples have been used to illustrate how the identification of novel ion channel subunit mutations and variations in IGE individuals can combine to give rise to the disorder.

The identification of novel mutations and variations in ion channel subunits in IGE individuals provides resources to further test the digenic hypothesis and mutation profiles are starting to accumulate for a number of subunit changes that are observed in the same individuals. FIG. 3 provides results from some of these profiles.

FIG. 3A shows a 3 generation family in which individual III-1 has myoclonic astatic epilepsy and contains a N43del mutation in the SCN3A gene as well as an A1067T mutation in the SCN1A gene. Individual I-1 also has the SCN3A mutation but alone this mutation is not sufficient to cause epilepsy in this individual. The SCN3A mutation has likely been inherited from the grandfather through the mother, while the SCN1A mutation is likely to arise from the father. Both parents are unaffected but have yet to be screened for the presence of the mutations in these subunits. Individual II-1 is likely to contain an as yet-unidentified ion channel subunit mutation acting in co-operation with the SCN3A mutation already identified in this individual.

FIG. 3B is another 3 generation family in which individual III-1 has myoclonic astatic epilepsy due to a combination of the same SCN3A and SCN1A mutations as above. However, in this family both parents have febrile seizures most likely due to the presence of just one of the mutations in each parent, as proposed by the model. This is in contrast to individuals II-2 and II-3 in FIG. 4A who also contain one of the mutations in these genes each. These individuals are phenotypically normal most likely due to incomplete penetrance of these mutations in each case.

FIG. 3C shows a larger multi-generation family in which individual IV-5 has a mutation in both the SCN3A and GABRG2 subunits. In combination, these give rise to severe myoclonic epilepsy of infancy but alone either cause febrile seizures (GABRG2 mutation in III-3 and IV-4) or are without an effect (SCN3A mutation in III-2) as proposed by the model.

These examples therefore illustrate the digenic model as determined from mutation analysis studies of ion channel subunits in affected individuals and highlight the need to identify genetic alterations in the genes encoding ion channel subunits.

EXAMPLE 5

Analysis of Ion Channels and Ion Channel Subunits

The structure and function of the mutant ion channels and mutant ion channel subunits of the present invention can be determined using a variety of molecular biological studies. These studies may provide clues as to the mechanisms by which mutations in ion channel subunits effect the functioning of the ion channel. For instance the identification of proteins that interact with mutant ion channels (or whose interaction is impeded by a mutation in an ion channel subunit) may help determine the molecular mechanisms that are disrupted as a result of a mutation. Procedures such as the yeast two-hybrid system can be used to discover and identify such interacting proteins.

The principle behind the yeast two-hybrid procedure is that many eukaryotic transcriptional activators, including those in yeast, consist of two discrete modular domains. The first is a DNA-binding domain that binds to a specific promoter sequence and the second is an activation domain that directs the RNA polymerase II complex to transcribe the gene downstream of the DNA binding site. Both domains are required for transcriptional activation as neither domain can activate transcription on its own. In the yeast two-hybrid procedure, the gene of interest or parts thereof (BAIT), is cloned in such a way that it is expressed as a fusion to a peptide that has a DNA binding domain. A second gene, or number of genes, such as those from a cDNA library (TARGET), is cloned so that it is expressed as a fusion to an activation domain. Interaction of the protein of interest with its binding partner brings the DNA-binding peptide together with the activation domain and initiates transcription of the reporter genes. The first reporter gene will select for yeast cells that contain interacting proteins (this reporter is usually a nutritional gene required for growth on selective media). The second reporter is used for confirmation and while being expressed in response to interacting proteins it is usually not required for growth.

KCNQ2 Interactors

Despite the identification of a number of KCNQ2 mutations responsible for epilepsy, including those of the present study, the underlying biological mechanisms responsible for the epilepsy remains largely uncharacterized. Towards identifying these mechanisms, the large intracellular C-terminal region of KCNQ2 was screened for interactions with other proteins using the yeast-two hybrid procedure. The C-terminus accounts for 63% of the KCNQ2 protein and, in common with other KCNQ subunits, contains a conserved 'A domain' (Jentsch, 2000; Schwake et al., 2000) thought to be involved in subunit interactions as well as another distal short conserved region that has been associated with subunit assembly, at least in KCNQ1 (Jentsch, 2000; Schmitt et al., 2000).

A) Yeast-two Hybrid Analysis

A yeast two-hybrid screen was carried out using the proQuest™ Two-Hybrid System with Gateway™ Technology (Invitrogen™) according to manufacturer's directions. A KCNQ2 C-terminal entry (BAIT) clone was generated using the pENTR Directional TOPO® Cloning Kit (Invitrogen™) The following primers were designed to amplify the intracellular C-terminal region of KCNQ2 based on the sequence of human KCNQ2 (Genbank accession number NM_172107): KCNQ2F: 5,—CACCAAGGTTCAGGAGCAGCACAGG-3' and KCNQ2R: 5'-TCACTTCCTGGGCCCGGC-CCAGCC-3'. The 1611 base pair cloned fragment included exon 10a (found in all our amplified clones), corresponding to amino acid 373-382 of the KCNQ2 protein. The extra 30 base pairs (10 amino acids) were included in our numbering. The PCR-product was cloned into the pENTR/D-TOPO® vector (Invitrogen™) via the TOPO® Cloning reaction according to the manufacturer's instructions. Following sequence verification, the KCNQ2 cDNA fragment was then subcloned into pDEST™32, the DNA Binding domain (DB) Gateway™ Destination Vector (Invitrogen™).

The ProQuest™ Two-Hybrid human brain cDNA Library (TARGET) with Gateway™ technology (ResGen™, Invitrogen™ Corporation) was amplified according to the manufacturer's instructions. Plasmid DNA was purified from the cell pellet using the HiSpeed Plasmid Maxi Kit (Qiagen) according to the manufacturer's instructions.

Both the DBLeu (empty bait vector) and DB-KCNQ2 wild-type (wt) C-term BAITS were transformed into the yeast strain May 203 and plated onto minimal selective media lacking leucine. A duplicate was carried out where the empty library TARGET (pAD) vector was co-transformed in addition to each BAIT and plated onto minimal selective media lacking leucine (-leu) and tryptophan (-tryp). Yeast control strains (Invitrogen™) were included on all plates. Control 1, used as a negative control, contained empty plasmids pPC97 and pPC86. Control 2 had pPC97-RB and pPC86-E2F1, which express a relatively weak interaction. Control 3 contained plasmids encoding the *Drosophila* DP (pPC97) and E2F (pPC86) domains that have a moderately strong interaction, and provide a control for plasmid shuffling. Control 4 contained pPC97-Fos and pPC86-Jun which express a relatively strong interaction, and control 5 had a pCL1 plasmid encoding full-length GAL4p and empty pPC86 and was used as a positive control.

The constructs were tested for self-activation of the his and β-gal reporter genes according to Invitrogen™ instructions.

For the yeast-two hybrid screen, competent yeast cells were prepared for each BAIT (DB-KCNQ2 wt C-term construct) to be screened, transformed with 31 µg of ProQuest™ Two-Hybrid human brain AD (activation domain)-cDNA Library and plated onto minimal selective media lacking leucine (-leu), tryptophan (-tryp) and histidine (-his) and containing 3-aminotriazole (+3AT). Positive colonies from each screen were PCR-amplified and re-introduced into fresh yeast cells containing the BAIT to re-test for two-hybrid interaction phenotypes. Those giving rise to more than one PCR product or that failed to re-test positively were systematically eliminated. Positives that re-tested were sequenced using the ABI PRISM® BigDyex Terminators v3.0 technology. Once identified, the sequence of the potential interactor was checked to verify it was in the same translational frame as the Gal4p-AD encoding sequence of the prey construct.

Approximately $3 \times 10^6$ clones from the ProQuest™ Two-Hybrid human brain cDNA Library were screened for interaction with the DB-Q2C wt bait. Among 1039 positive AD-cDNAs recovered, re-tested and subsequently sequenced all were identified as the CALM2 gene, encoding the ubiquitous, $Ca^{2+}$-binding protein, Calmodulin (CaM).

The interaction between the C-terminal region of KCNQ2 and CaM has also been reported by other studies (Wen and Levitan, 2002; Yus-Najera et al., 2002; Gamper and Shapiro, 2003). In mammals, the CaM protein is coded by a multigene family consisting of three bona fide members, CALM1, CALM2 and CALM3. Within the non-coding regions of the CaM transcripts, no striking homology is observed, and codon usage is maximally divergent amongst the three CaM mRNAs that encode an identical protein. It has been hypothesised that the existence of a multigene family provides a tight and complex level of regulatory control at the level of gene expression (Palfi et al., 2002). CaM genes are differentially expressed in the CNS during development and differential regulation of the CaM genes appears necessary to maintain the temporal and spatial fidelity of the CaM protein levels in all subcellular domains. Besides the fundamental housekeeping functions associated with CaM, it is also involved in specialized neuronal functions, such as the synthesis and release of neurotransmitters, neurite extension, long-term potentiation and axonal transport (Palfi et al., 2002).

B) Effect of Epilepsy-associated KCNQ2 Mutations on the CaM-KCNQ2 Interaction

To assess the effect that the C-terminus mutations of the present invention had on CaM binding, two of the identified mutations (R353G and L619R) were introduced into the DB-Q2C construct by mutagenesis and were re-analysed for an interaction with CaM using the yeast two-hybrid procedure.

The following primers were used to incorporate the c1057C→G (R353G) and c1856T→G (L619R) changes into the pDEST™32-KCNQ2 C-terminal bait construct.

```
R353G F
5'-CGCCACCAACCTCTCGGGCACAGACCTGCACTC-3'

R353G R
5'-GAGTGCAGGTCTGTGCCCGAGAGGTTGGTGGCG-3'

L619R F
5'-CTTGTCCATGGAGAAGAAGCGGGACTTCCTGGTGAATATC-3'

L619R R
5'-GATATTCACCAGGAAGTCCCGCTTCTTCTCCATGGACAAG-3'
```

Overlapping PCR products were generated using the ToPO® cloning compatible KCNQ2F primer from the initial cloning and the mutagenesis reverse primers, and the KCNQ2R primer from the initial cloning with the mutagenesis forward primers. Products were gel extracted and purified before a second round of PCR using the initial KCNQ2 F&R primers. These products were also gel extracted before cloning into the pDEST™32 bait vector via the TOPO® system (as described above). Mutant baits were sequence verified.

The interaction between each DB-Q2C mutant and CaM was then tested by the yeast two-hybrid assay and compared to the interaction with DB-Q2 wt. Three different PCR-amplified CaM positive clones from the initial screen were re-introduced by gap-repair[20] into the prey vector (pPC86) in the yeast strain expressing either DB-Q2C wt, DB-Q2C mutants or the empty DBLeu vector, used as negative control.

CaM interaction with the DB-Q2C wt and mutants was then assessed by expression of the HIS3 and LacZ reporter genes.

The Q2C R353G mutant did not interact with CaM, as seen by no growth on HIS3 selective plate (FIG. 4C) and no blue readout in the LacZ filter assay (seen as dark squares in FIG. 4D-F). On the other hand, the DB-Q2C L619R mutant was shown to still interact with CaM, as seen by growth on HIS3 selective plate (FIG. 4C) and the blue readout in the LacZ filter assay. Interestingly, the DB-Q2C L6.19R mutant showed an even greater growth level on HIS3 selective plate than the DB-Q2C wt and also appeared to stain faster and more intensely blue in the LacZ filter assay, suggesting a stronger interaction between CaM and this mutant.

In order to better quantify β-gal activity, a second assay was carried out using the high sensitivity substrate Chlorophenol Red-β-D-Galactopyranoside (CPRG) in liquid culture. The affinity of the DB-Q2C/AD-CaM interaction was measured in terms of units of β-gal activity, with a zero value indicating no expression of the LacZ reporter gene, and hence no interaction.

In the CPRG assay, a value of 0.05 units β-gal activity (FIG. 5) was significantly different from the empty bait vector replicate (P<0.01, Student's t test), confirming the interaction of the DB-Q2C wt with CaM.

Figure 4:
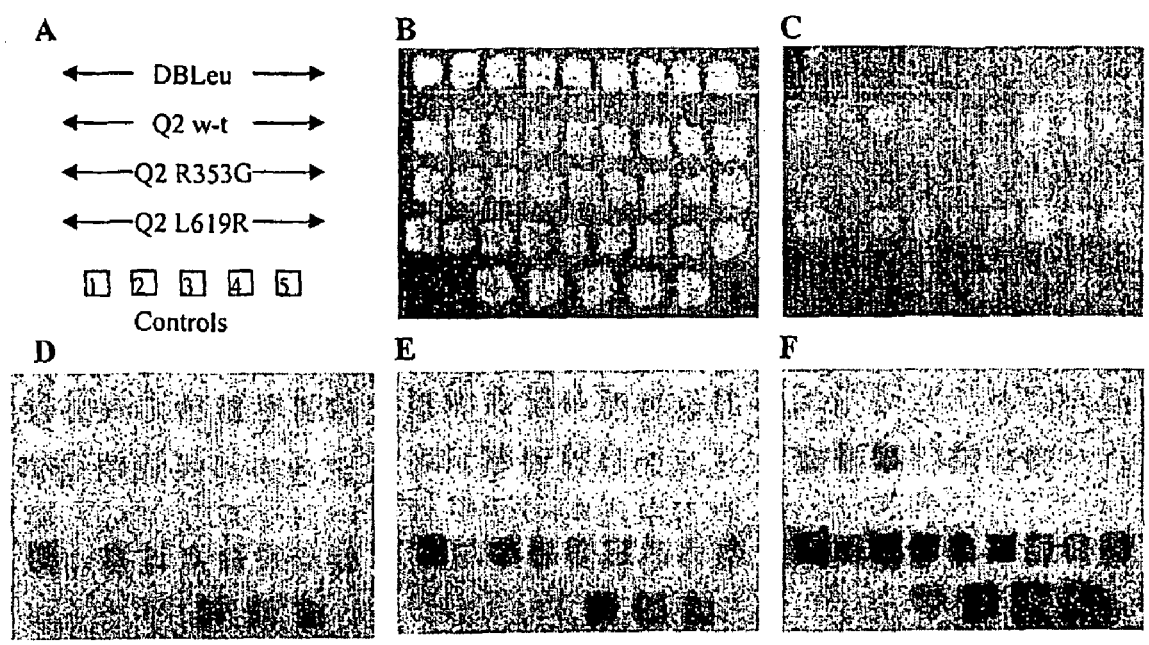
FIG. 4 shows the results of yeast two-hybrid analysis of R353G and L619R KCNQ2 mutants. Yeast were transformed with the empty DB (BAIT) plasmid (DBLeu), DB-Q2C wt, DB-Q2C R353G mutant or the DB-Q2 L619R mutant as indicated in A and the AD-CaM (TARGET) vector was introduced by gap-repair. Yeast control strains (Invitrogen™) were included on all plates for comparison. Control 1 has no interaction. Control 2 has a weak interaction. Control 3 has a moderately strong interaction. Control 4 has a strong interaction and control 5 has a very strong interaction. B. Growth of transformed yeast and controls on -leu -tryp selection. Yeast can grow on -leu if they contain the DB plasmid, and -tryp if they have AD plasmid. C. Growth of transformed yeast and controls on -leu -tryp -his+40 mM 3AT after 48 hrs. Yeast can grow on -his+3AT if the his reporter gene is activated by interaction between the BAIT and TARGET plasmids. D-F. LacZ Filter assay for interaction between BAIT and TARGET plasmids, photos taken after 2 hrs (D), 7 hrs (E) and 24 hrs (F). Activation of the β-galactosidase reporter gene by interaction of the BAIT and TARGET plasmids leads to the dark appearance of colonies.

As observed in the LacZ filter assay, the CPRG assay showed a significant difference in the interaction between the Q2C R353G mutant and CaM as compared to the wt replicate (P<0.01, Student's t test, FIG. 4).

These results suggest that the R353G mutation alters the structural conformation of the KCNQ2 C-terminal domain such that it is no longer able to bind to CaM and that this single point mutation is sufficient to abolish the interaction. By abolishing CaM binding, the R353G mutation could lead to an impairment of M-current in vivo due to decreased opening of the channel.

Figure 5:
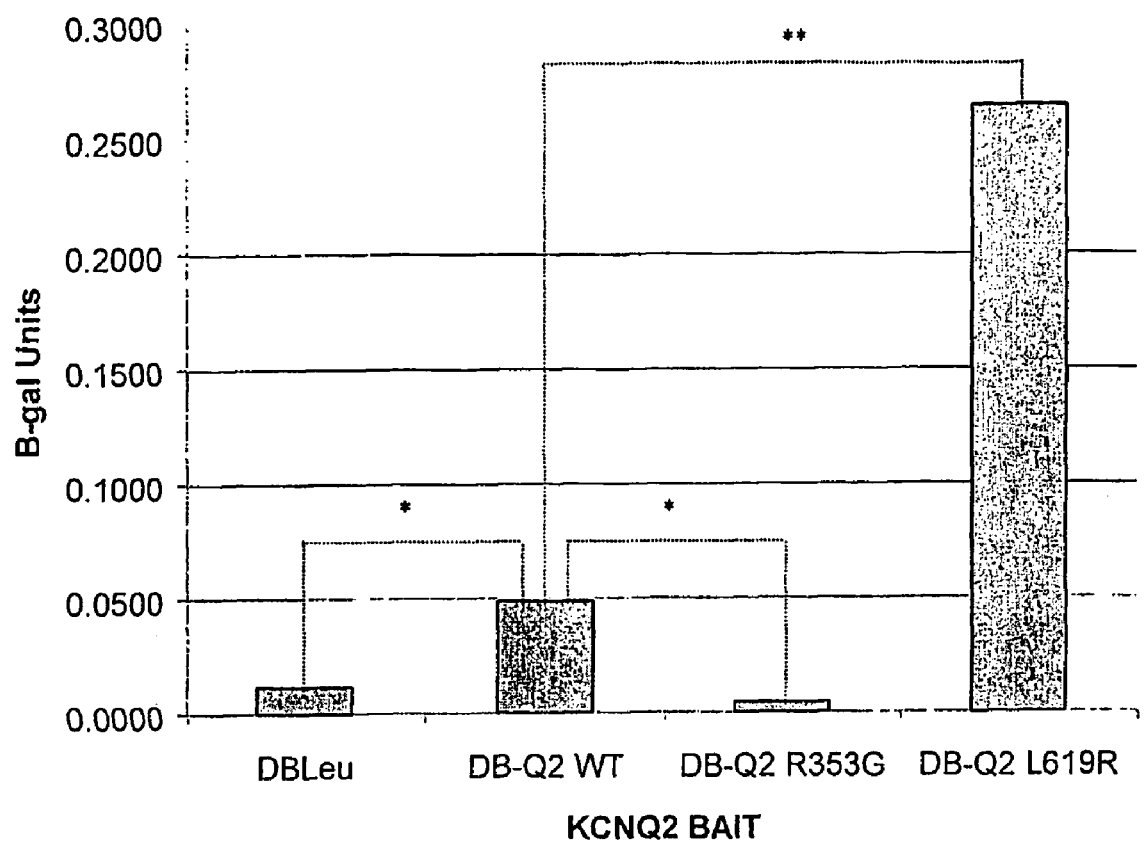
FIG. 5 shows the results of CaM affinity experiments with the R353G and L619R KCNQ2 mutants. The chart below shows the values from the CPRG assay for β-galactosidase activity as a measure of KCNQ2C-CaM binding efficiency. The area of each bar in the chart equates to the CaM binding efficiency of the BAIT. Broken lines indicate statistical comparison by Student's t test *P<0.01, ** P<0.001.

In contrast, the CPRG assay for the L619R Q2C mutant showed a significantly higher level of β-gal activity units (0.26 units) than the wt replicate (P<0.001, Student's t test, FIG. 5). This finding indicates that the L619R mutation alters the conformation of the protein in a manner that increases CaM binding affinity for the KCNQ2 C-terminal domain by approximately 5-fold. The increased affinity for CaM may affect the ability of the complex to change conformation normally in response to calcium signalling. Alternatively, the marked increase in binding of CaM to the KCNQ2 L619R mutant channel may be detrimental to the M-channel function via disruption of the normal neuronal inhibitory/excitatory balance, therefore causing the seizures associated with epilepsy, particularly BFNS. CaM is known to be involved in both the excitatory and inhibitory neurotransmission pathways (Ohya and Botstein, 1994) and it has been proposed that the temporal and spatial restrictions on CaM itself could enable the tight control of these opposing reactions (Toutenhoofd and Strehler, 2000). Hence, the KCNQ2 L619R mutation could lead to a disruption of the local CaM pool consequently disturbing the finely balanced excitatory and inhibitory neurotransmission systems.

These results implicate CaM in the pathogenesis of epilepsy and specifically in the BFNS syndrome. Whilst further work will be required to fully elucidate the involvement of the KCNQ2-CaM interaction in neuronal excitability and its correlation with idiopathic epilepsy, these data suggest that dysfunction of this interaction leads to aberrant neuronal excitability in some BFNS patients.

The calmodulin gene (and other ion channel interacting genes) may therefore be a target for mutation in epilepsy as well as other disorders associated with ion channel dysfunction. A mutation in an ion channel interacting gene when expressed alone, or when expressed in combination with one or more other ion channel mutations or ion channel interacting gene mutations (based on the digenic model), may give rise to the disorder. The nature of the ion channel interacting genes and proteins can be studied such that these partners can also be targets for drug discovery.

INDUSTRIAL APPLICABILITY

The mutant ion channel receptor subunits of the invention are useful in the diagnosis and treatment of diseases such as epilepsy and disorders associated with ion channel dysfunction including, but not limited to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness.

TABLE 1

Examples of mutations and variations identified in ion channel subunit genes

| Subunit Gene | Exon/Intron | DNA Mutation | Amino Acid Change | SEQ ID NOS |
|---|---|---|---|---|
| *Sodium Channel Subunits* | | | | |
| *Coding exonic variants - amino acid change* | | | | |
| SCN1A$^r$ | Exon 5 | c664C→T | R222X | 1, 73 |
| SCN1A$^r$ | Exon 8 | c1152G→A | W384X | 2, 74 |
| SCN1A$^r$ | Exon 9 | c1183G→C | A395P | 3, 75 |
| SCN1A$^r$ | Exon 9 | c1207T→C | F403L | 4, 76 |
| SCN1A$^r$ | Exon 9 | c1237T→A | Y413N | 5, 77 |
| SCN1A$^r$ | Exon 9 | c1265T→A | V422E | 6, 78 |
| SCN1A$^r$ | Exon 21 | c4219C→T | R1407X | 7, 79 |
| SCN1A$^r$ | Exon 26 | c5339T→C | M1780T | 8, 80 |
| SCN1A$^r$ | Exon 26 | c5674C→T | R1892X | 9, 81 |
| SCN1B$^r$ | Exon 3 | c254G→A | R85H | 10, 82 |
| SCN2A$^r$ | Exon 6A | c668G→A | R223Q | 11, 83 |
| SCN2A$^r$ | Exon 16 | c2674G→A | V892I | 12, 84 |
| SCN2A$^r$ | Exon 17 | c3007C→A | L1003I | 13, 85 |
| SCN2A$^r$ | Exon 19 | c3598A→G | T1200A | 14, 86 |
| SCN2A$^r$ | Exon 20 | c3956G→A | R1319Q | 15, 87 |
| *Coding exonic variants - no amino acid change* | | | | |
| SCN2A$^c$ | Exon 12 | c1785T→C | — | 16 |
| SCN2A$^c$ | Exon 27 | c4919T→A | — | 17 |
| *Non-coding variants* | | | | |
| SCN1A$^r$ | Intron 9 | IVS9−1G→A | — | 18 |
| SCN1A$^c$ | Intron 23 | IVS23+33G→A | — | 19 |
| SCN2A$^r$ | Intron 7 | IVS7+61T→A | — | 20 |
| SCN2A$^r$ | Intron 19 | IVS19−55A→G | — | 21 |
| SCN2A$^r$ | Intron 22 | IVS22−31A→G | — | 22 |
| SCN2A$^c$ | Intron 2 | IVS2−28G→A | — | 23 |
| SCN2A$^c$ | Intron 8 | IVS8−3T→C | — | 24 |
| SCN2A$^c$ | Intron 11 | IVS11+49A→G | — | 25 |
| SCN2A$^c$ | Intron 11 | IVS11−16C→T | — | 26 |
| SCN2A$^c$ | Intron 17 | IVS17−71C→T | — | 27 |
| SCN2A$^c$ | Intron 17 | IVS17−74delG | — | 28 |
| SCN2A$^c$ | Intron 17 | IVS17−74insG | — | 29 |
| *Nicotinic Acetylcholine Receptor Subunits* | | | | |
| *Coding exonic variants - amino acid change* | | | | |
| CHRNA5$^r$ | Exon 4 | c400G→A | V134I | 30, 88 |
| CHRNA2$^c$ | Exon 4 | c373G→A | A125T | 31, 89 |
| CHRNA3$^c$ | Exon 2 | c110G→A | R37H | 32, 90 |
| *Coding variants - no amino acid change* | | | | |
| CHRNA2$^c$ | Exon 4 | c351C→T | — | 33 |
| CHRNA2$^c$ | Exon 5 | c771C→T | — | 34 |
| CHRNA3$^c$ | Exon 2 | c159A→G | — | 35 |
| CHRNA3$^c$ | Exon 4 | c291G→A | — | 36 |
| CHRNA3$^c$ | Exon 4 | c345G→A | — | 37 |
| *Non-coding variants* | | | | |
| CHRNA2$^c$ | Intron 3 | IVS3−16C→T | — | 38 |
| CHRNA3$^c$ | Intron 3 | IVS3−5T→C | — | 39 |
| CHRNA3$^c$ | Intron 4 | IVS4+8G→C | — | 40 |
| *Potassium Channel Subunits* | | | | |
| *Coding exonic variants - amino acid change* | | | | |
| KCNQ2$^r$ | Exon 1 | c204-c205insC | K69fsX119 | 41, 91 |
| KCNQ2$^r$ | Exon 1 | c1A→G | M1V | 42 |
| KCNQ2$^r$ | Exon 1 | c2T→C | M1T | 43 |
| KCNQ2$^r$ | Exon 8 | c1057C→G | R353G | 44, 92 |
| KCNQ2$^r$ | Exon 11 | c1288C→T | R430X | 45, 93 |
| KCNQ2$^r$ | Exon 14 | c1710A→T | R570S | 46, 94 |
| KCNQ2$^r$ | Exon 15 | c1856T→G | L619R | 47, 95 |
| *Non-coding variants* | | | | |
| KCNQ2$^r$ | Intron 9 | IVS9+(46-48)delCCT | — | 48 |
| KCNQ3$^r$ | Intron 11 | IVS11+43G→A | — | 49 |

TABLE 1-continued

Examples of mutations and variations identified in ion channel subunit genes

| Subunit Gene | Exon/Intron | DNA Mutation | Amino Acid Change | SEQ ID NOS |
|---|---|---|---|---|
| KCNQ3[c] | Intron 12 | IVS12+29G→A | — | 50 |
| GABA Receptor Subunits | | | | |
| Coding exonic variants - no amino acid change | | | | |
| GABRB1[r] | Exon 5 | c508C→T | — | 51 |
| GABRB1[r] | Exon 9 | c1329G→A | — | 52 |
| GABRB1[c] | Exon 8 | c975C→T | — | 53 |
| GABRG3[c] | Exon 8 | c995T→C | — | 54 |
| Non-coding variants | | | | |
| GABRA1[c] | 5' UTR | c-142A→G | — | 55 |
| GABRA1[c] | 5' UTR | c-31C→T | — | 56 |
| GABRA2[c] | 3' UTR | c1615G→A | — | 57 |
| GABRA5[c] | 5' UTR | c-271G→C | — | 58 |
| GABRA5[c] | 5' UTR | c-228A→G | — | 59 |
| GABRA5[c] | 5' UTR | c-149G→C | — | 60 |
| GABRB2[b] | 5' UTR | c-159C→T | — | 61 |
| GABRB2[c] | 3' UTR | c1749C→T | — | 62 |
| GABRPi[c] | 5' UTR | c-101C→T | — | 63 |
| GABRB1[c] | Intron 1 | IVS1+24T→G | — | 64 |
| GABRB1[c] | Intron 5 | IVS6+72T→G | — | 65 |
| GABRB1[c] | Intron 7 | IVS7-34A→G | — | 66 |
| GABRB3[r] | Intron 1 | IVS1-14C→T | — | 67 |
| GABRB3[r] | Intron 7 | IVS7+58delAA | — | 68 |
| GABRD[r] | Intron 6 | IVS6+132insC | — | 69 |
| GABRD[r] | Intron 6 | IVS6+130insC | — | 70 |
| GABRD[r] | Intron 6 | IVS6+73del CGCGCCCACCGCCCCTTCCGCG | — | 71 |
| GABRG3[c] | Intron 8 | IVS8-102C→T | — | 72 |

Note:
[r]Mutations or variations only occurring in individuals with epilepsy;
[b]Variant seen only in normal control samples;
[c]Mutations or variants seen in individuals with epilepsy as well as normal control samples. The KCNQ2 numbering is based on the large isoform (inclusion of exon 10a). The numbering of exons and introns for SCN2A is based on the publication of Kasai et al., 2001.

REFERENCES

References cited herein are listed on the following pages, and are incorporated herein by this reference.

Andermann, E. (1982). In: *Genetic basis of the epilepsies*. Anderson, V E. Hauser, W A. Penry, J K. and Singh, C F. (Editors). New York, Raven Press. 355-374.

Annegers, J F. (1996). *The treatment of epilepsy: Principles and practice*. Second Edition. (Wyllie E (Ed) Williams and Wilkins).

Bell, J I. and Lathrop, M. (1996). *Nature Genet.* 13: 377-378.

Berkovic, S F. Andermann, F. Andermann, E. and Gloor, P. (1987). *Neurology* 37: 993-1000.

Berkovic, S F. Reutens, D C. Andermann, E. and Andermann, F. (1994). In: *Epileptic seizures and syndromes*. Wolf, P. (Editor). London: John Libbey. 25-37.

Berkovic, S F. Mazarib, A. Neufeld, M. et al. (2000). *Neurology* (Supplement 3). 54: A356.

Biervert, C. Schroeder, B C. Kubisch, C. Berkovic, S F. Propping, P. Jentsch, T J. and Steinlein, O K. (1998). *Science* 279: 403-406.

Breaker, R R. and Joyce, G F. (1995). *Chem. Biol.* 2: 655-600.

Cavazzuti, G B. Capella, L. and Nalin, A. (1980). *Epilepsia* 21: 43-55.

Charlier, C. Singh, N A. Ryan, S G. Lewis, T B. Reus, B E. Leach, R J. and Leppert, M. (1998). *Nature Genet.* 18: 53-55.

Cole, S P. Campling, B G. Atlaw, T. Kozbor, D. and Roder, J C. (1984). *Mol. Cell. Biochem.* 62: 109-120.

Collins, F S. (1995). *Nature Genet.* 9: 347-350.

Commission on Classification and Terminology of the International League against Epilepsy. (1989). *Epilepsia* 30: 389-399.

Cote, R J. Morrissey, D M. Houghton, A N. Beattie, E J Jr. Oettgen, H F. and Old, L J. (1983). *Proc. Natl. Acad. Sci. USA* 80: 2026-2030.

Doose, H. and Baier, W K. (1987). *Neuropediatrics* 18 (Supplement 1): 1-64.

Doose, H. and Baier, W. (1989). *Clev. Clin. J. Med.* 56 (Supplement): 5105-s110.

Dworakowska, B. and Dolowy, K. (2000). *Acta Biochim. Pol.* 47: 685-703.

Escayg, A. MacDonald, B T. Meisler, M H. Baulac, S. Huberfeld, G. An-Gourfinkel, I. Brice, A. LeGuern, E. Moulard, B. Chaigne, D. Buresi, C. and Malafosse, A. (2000). *Nature Genet.* 24: 343-345.

Fong, G C. Shah, P U. Gee, M N. Serratosa, J M. Castroviejo, I P. Khan, S. Ravat, S H. Mani, J. Huang, Y. Zhao, H Z. Medina, M T. Treiman, L J. Pineda, G. and Delgado-Escueta, A V. (1998). *Am. J. Hum. Genet.* 63: 1117-1129.

Gamper, N. and Shapiro, M S. (2003). *J. Gen. Physiol.* 122: 17-31.

Gardiner, M. (2000). *J. Neurol.* 247: 327-334.

Goldman, C K. Soroceanu, L. Smith, N. Gillespie, G Y. Shaw, W. Burgess, S. Bilbao, G. and Curiel, D T. (1997). *Nature Biotechnology* 15: 462-466.

Gonzalez, J E. et al. (1999). *Drug. Discov. Today* 4: 431-439.

Greenberg, D A. Delgado-Escueta, A V. Maldonado, H M. and Widellitz, H. (1988a). *Genet Epidem.* 5: 81-94.

Greenberg, D A. Delgado-Escueta, A V. Widelitz, H. Sparkes, R S. Treiman, L. Maldonado, H M. Park, M S. and Terasaki, P I. (1988b). *Am. J. Med. Genet.* 31: 185-192.

Greenberg, D A. Durner, M. and Delgado-Escueta, A V. (1992). *Neurology* 42 (Suppl 5): 56-62.

Hamill, O P. et al. (1981). *Pflugers Arch.* 391: 85-100.

Haseloff, J. and Gerlach, W L. (1988). *Nature* 334: 585-591.

Hauser, W A. Annegers, J F. and Kurland, L T. (1993). *Epilepsia* 34: 453-468.

Heller, R A. Schena, M. Chai, A. Shalon, D. Bedilion, T. Gilmore, J. Woolley, D E. and Davis R W. (1997). *Proc. Natl. Acad. Sci. USA* 94: 2150-2155.

Huse, W D. Sastry, L. Iverson, S A. Kang, A S. Alting-Mees, M. Burton, D R. Benkovic, S J. and Lerner, R A. (1989). *Science* 246: 1275-1281.

Italian League Against Epilepsy Genetic Collaborative Group. (1993). *Epilepsia* 34: 819-26.

Janz, D. Beck-Mannagetta, G. and Sander, T. (1992). *Neurology* 42 (Suppl 5): 48-55.

Jentsch, T J. (2000). *Nature Rev. Neurosci.* 1: 21-29.

Kasai, N. Fukushima, K. Ueki, Y. Prasad, S. Nosakowski, J. Sugata, K. Sugata, A. Nishizaki, K. Meyer, N C. and Smith, R J. (2001). *Gene* 264: 113-122.

Kohler, G. and Milstein, C. (1975). *Nature* 256: 495-497.

Kozbor, D. Abramow-Newerly, W. Tripputi, P. Cole, S P. Weibel, J. Roder, J C. and Croce, C M. (1985). *J. Immunol. Methods* 81:31-42.

Lernmark, A. and Ott, J. (1998). *Nature Genet.* 19: 213-214.

Ohya, Y. and Botstein; D. (1994). *Science* 263: 963-966.

Okubo, Y. Matsuura, M. Asai, T. Asai, K. Kato, M. Kojima, T. and Toru, M. (1994). *Epilepsia* 35: 832-841.

Orlandi, R. Gussow, D H. Jones, P T. and Winter, G. (1989). *Proc. Natl. Acad. Sci. USA* 86: 3833-3837.

Palfi, A. Kortvely, E. Fekete, E. Kovacs, B. Varszegi, S. and Gulya, K. (2002). *Life Sciences* 70: 2829-2855.

Panayiotopoulos, C P. and Obeid, T. (1989). *Ann. Neurol.* 25: 440-443.

Phillips, H A. Favre, I. Kirkpatrick, M. Zuberi, S M. Goudie, D. Heron, S E. Scheffer, I E. Sutherland, G R. Berkovic, S F. Bertrand, D. and Mulley, J C. (2001). *Am. J. Hum. Genet.* 68: 225-231.

Reutens, D C. and Berkovic, S F. (1995). *Neurology* 45: 1469-1476.

Rickert, R C. Roes, J. and Rajewsky, K. (1997). *Nucleic Acids Res.* 25: 1317-1318.

Risch, N. and Botstein, D. (1996). *Nature Genet.* 12: 351-353.

Roger, J. Bureau, M. Dravet, C. Dreifuss, F E. Perret, A. and Wolf, P. (1992). *Epileptic syndromes in infancy, childhood and adolescence.* 2nd Edition. London, John Libbey.

Scharf, K D. Materna, T. Treuter, E. and Nover, L. (1994). *Results Probl. Cell Differ.* 20: 125-162.

Scheffer, I E. and Berkovic, S F. (1997). *Brain* 120: 479-90.

Schena, M. Shalon, D. Heller, R. Chai, A. Brown, P O. and Davis, R W. (1996). *Proc. Natl. Acad. Sci. USA* 93: 10614-10619.

Schmitt, N. Schwarz, M. Peretz, A. Abitbol, I. Attali, B. and Pongs, O. (2000). *Embo J.* 19: 332-340.

Schwake, M. Pusch, M. Kharkovets, T. and Jentsch, T J. (2000). *J. Biol. Chem.* 275: 13343-13348.

Schwenk, F. Baron, U. and Rajewsky, K. (1995). *Nucleic Acids Res.* 23: 5080-5081.

Singh, N A. Charlie, C. Stauffer, D. DuPont, B R. Leach, R J. Melis, R. Ronen, G M. Bjerre, I. Quattlebaum, T. Murphy, J V. McHarg, M L. Gagnon, D. Rosales, T O. Peiffer, A. Anderson, V E. and Leppert, M. (1998). *Nature Genet.* 18: 25-29.

Singh, R. Scheffer, I E. Crossland, K. and Berkovic, S F. (1999). *Ann. Neurol.* 45: 75-81.

Steinlein, O K. Mulley, J C. Propping, P. Wallace, R H. Phillips, H A. Sutherland, G R. Scheffer, I E. and Berkovic, S F. (1995). *Nature Genet.* 11: 201-203.

Todd, J A. (1999). *Lancet* 354 (Supplement 1): 15-16.

Toutenhoofd, S L. and Strehler, E E. (2000). *Cell Calcium* 28: 83-96.

Wallace, R H. Marini, C. Petrou, S. Harkin, L A. Bowser, D N. Panchal, R G. Williams, D A. Sutherland, G R. Mulley, J C. Scheffer, I E. and Berkovic, S F. (2001a). *Nature Genet.* 28: 49-52.

Wallace, R H. Scheffer, I E. Barnett, S. Richards, M. Dibbens, L. Desai, R R. Lerman-Sagie, T. Lev, D. Mazarib, A. Brand, N. Ben-Zeev, B. Goikhman, I. Singh, R. Kremmidiotis, G. Gardner, A. Sutherland, G R. George, A L Jr. Mulley, J C. and Berkovic, S F. (2001b). *Am. J. Hum. Genet.* 68: 859-865.

Wallace, R H. Wang, D W. Singh, R. Scheffer, I. George, A. Phillips, H. Saar, K. Reis, A. Johnson, E. Sutherland, G. Berkovic, S, and Mulley, J. (1998). *Nature Genet.* 19: 366-370.

Wen, H. and Levitan, I B. (2002). *J. Neurosci.* 22: 7991-8001.

Winter, G. and Milstein, C. (1991). *Nature* 349: 293-299.

Wyman, A R. and White, R. (1980). *Proc. Natl. Acad. Sci.* 77: 6754-6758.

Yus-Najera, E. Santana-Castro, I. and Villarroel, A. (2002). *J. Biol. Chem.* 277: 28545-28553.

Zara, F. Bianchi, A. Avanzini, G. Di Donato, S. Castellotti, B. Patel, P I. and Pandolfo, M. (1995). *Hum. Mol. Genet.* 4: 1201-1207.

Zara, F. Gennaro, E. Stabile, M. Carbone, I. Malacarne, M. Majello, L. Santangelo, R. de Falco, F A. and Bricarelli, F D. (2000). *Am. J. Hum. Genet.* 66: 1552-1557.

---

The invention claimed is:

1. An isolated nucleic acid molecule encoding a mutant or variant sodium channel, voltage gated, type 1, alpha subunit (SCN1A) polypeptide, wherein the nucleic acid comprises a sequence selected from the group consisting of:
  A) SEQ ID NO:2, which carries a c. 1152G→A mutation,
  B) SEQ ID NO:3, which carries a c. 1183G→C mutation,
  C) SEQ ID NO:4, which carries a c. 1207T→C mutation,
  D) SEQ ID NO:5, which carries a c. 1237T→A mutation, and
  E) SEQ ID NO:6, which carries a c. 1265T→A mutation, the nucleotide positions being numbered according to SEQ ID NO:96.

2. The isolated nucleic acid molecule of claim 1, wherein a cDNA derived therefrom consists of the sequence set forth in any one of SEQ ID NOs.: 2-6.

3. The isolated nucleic acid molecule of claim 1, wherein said mutation event disrupts the functioning of an assembled ion channel so as to produce an epilepsy phenotype.

4. The isolated nucleic acid molecule of claim 1, wherein said mutation event disrupts the functioning of an assembled ion channel so as to produce an epilepsy phenotype when expressed in combination with one or more additional mutations or variations in an ion channel subunit gene.

5. An expression vector comprising the isolated nucleic acid molecule of claim 1.

6. A cell comprising at least one expression vector of claim 5.

7. The cell of claim 6, wherein the cell comprises two or more expression vectors of claim 5.

8. A method of preparing a polypeptide, the method comprising:
    (1) culturing the cell of claim 6 under conditions effective for expressing the polypeptide encoded by the expression vector; and
    (2) harvesting the polypeptide encoded by the expression vector.

9. An isolated nucleic acid molecule comprising the nucleotide sequences as set forth in any of SEQ ID NOs.: 2-6.

10. An isolated nucleic acid molecule consisting of the nucleotide sequences as set forth in any of SEQ ID NOs.: 2-6.

11. An isolated cell comprising at least one mutant sodium channel, voltage gated, type 1, alpha subunit (SCN1A) polypeptide, wherein the amino acid sequence is selected from the group consisting of:
    A) a sequence consisting of SEQ ID NO:74, which comprises a W384X mutation,
    B) a sequence comprising SEQ ID NO:75, which comprises a A395P mutation,
    C) a sequence comprising SEQ ID NO:76, which comprises a F403L mutation,
    D) a sequence comprising SEQ ID NO:77, which comprises a Y413N mutation, and
    E) a sequence comprising SEQ ID NO:78, which comprises a V422E mutation,
the amino acid residues being numbered according to SEQ ID NO:97.

12. The isolated cell of claim 11, wherein the isolated cell comprises two or more mutant SCN1A polypeptides.

13. The isolated cell of claim 12, wherein the two or more mutant SCN1A polypeptides are present in two or more ion channel types.

14. A polypeptide prepared by the method of claim 8.

15. An isolated polypeptide encoded by the isolated nucleic acid molecule of claim 1.

* * * * *